US011001804B2

(12) United States Patent
Chen et al.

(10) Patent No.: US 11,001,804 B2
(45) Date of Patent: May 11, 2021

(54) METHODS FOR THE PRODUCTION OF THERAPEUTIC, DIAGNOSTIC, OR RESEARCH ANTIBODIES

(71) Applicant: WAYNE STATE UNIVERSITY, Detroit, MI (US)

(72) Inventors: Kang Chen, Detroit, MI (US); Bo Pei, San Diego, CA (US)

(73) Assignee: Wayne State University, Detroit, MI (US)

( * ) Notice: Subject to any disclaimer, the term of this patent is extended or adjusted under 35 U.S.C. 154(b) by 248 days.

(21) Appl. No.: 16/118,090

(22) Filed: Aug. 30, 2018

(65) Prior Publication Data

US 2019/0062705 A1 Feb. 28, 2019

Related U.S. Application Data

(60) Provisional application No. 62/552,292, filed on Aug. 30, 2017.

(51) Int. Cl.

| | |
|---|---|
| ***C12N 5/0781*** | (2010.01) |
| ***C07K 14/54*** | (2006.01) |
| ***C07K 14/495*** | (2006.01) |
| ***C07K 16/06*** | (2006.01) |
| ***C12N 15/62*** | (2006.01) |
| ***C07K 14/705*** | (2006.01) |
| ***C07K 14/57*** | (2006.01) |
| ***C07K 14/47*** | (2006.01) |

(52) U.S. Cl.

CPC ........ *C12N 5/0635* (2013.01); *C07K 14/4702* (2013.01); *C07K 14/495* (2013.01); *C07K 14/5406* (2013.01); *C07K 14/57* (2013.01); *C07K 14/70578* (2013.01); *C07K 16/06* (2013.01); *C07K 16/065* (2013.01); *C12N 15/62* (2013.01); *C07K 2317/565* (2013.01); *C07K 2319/21* (2013.01); *C07K 2319/41* (2013.01); *C07K 2319/43* (2013.01); *C12N 2310/20* (2017.05)

(58) Field of Classification Search

CPC .......................... C12N 5/0635; C12N 2310/20

See application file for complete search history.

(56) References Cited

FOREIGN PATENT DOCUMENTS

WO WO-2011029126 A1 * 3/2011 ............. C07K 16/18

OTHER PUBLICATIONS

Trager et al., PLoS One. 2012;7(4):e35005 (Year: 2012).*

Akiyama, et al., "The Tumor Necrosis Factor Family Receptors RANK and CD40 Cooperatively Establish the Thymic Medullary Microenvironment and Self-Tolerance," Immunity, vol. 29, No. 3, 2008, pp. 423-437.

Anderson, et al., "Projection of an Immunological Self Shadow Within the Thymus by the Aire Protein," Science, vol. 298, No. 5597, 2002, pp. 1395-1401.

Casellas, et al., "Mutations, Kataegis and Translocations in B Cells: Understanding AID Promiscuous Activity," Nat. Rev. Immunol., vol. 16, No. 3, 2016, pp. 164-176.

Chen, et al., "Immunoglobulin D Enhances Immune Surveillance by Activating Antimicrobial, Proinflammatory and B Cell-Stimulating Programs in Basophils," Nat. Immunol., vol. 10, No. 8, 2009, pp. 889-898.

Durandy, et al., "Hyper-Immunoglobulin M Syndromes Caused by Intrinsic B-Lymphocyte Defects," Immunol. Rev., vol. 203, No. 1, 2005, pp. 67-79.

Finnish-German, "An Autoimmune Disease, APECED, Caused by Mutations in a Novel Gene Featuring Two PHD-Type Zinc-Finger Domains," Nat. Genet., vol. 17, No. 4, 1997, pp. 399-403.

Gardner, et al., "Deletional Tolerance Mediated by Extrathymic Aire-Expressing Cells," Science, vol. 321, No. 5890, 2008, pp. 843-847.

Kisand, et al., "Chronic Mucocutaneous Candidiasis in APECED or Thymoma Patients Correlates with Autoimmunity to Th17-Associated Cytokines," J. Exp. Med., vol. 207, No. 2, 2010, pp. 299-308.

Liu, et al., "Mechanism of Antigen-Driven Selection in Germinal Centres," Nature, vol. 342, No. 6252, 1989, pp. 929-931.

Malchow, et al., "Aire-Dependent Thymic Development of Tumor-Associated Regulatory T Cells," Science, vol. 339, No. 6124, 2013, pp. 1219-1224.

Maul, et al., "Uracil Residues Dependent on the Deaminase AID in Immunoglobulin Gene Variable and Switch Regions," Nat. Immunol., vol. 12, No. 1, 2011, pp. 70-76.

Meyer, et al., "Aire-Deficient Patients Harbor Unique High-Affinity Disease-Ameliorating Autoantibodies," Cell., vol. 166, No. 3, 2016, pp. 582-595.

Muramatsu, et al., "Class Switch Recombination and Hypermutation Require Activation-Induced Cytidine Deaminase (AID), a Potential RNA Editing Enzyme," Cell, vol. 102, No. 5, 2000, pp. 553-563.

Nagamine, et al., "Positional Cloning of the APECED Gene," Nat. Genet., vol. 17, No. 4, 1997, pp. 393-398.

Oven, et al., "Aire Recruits P-TEFb for Transcriptional Elongation of Target Genes in Medullary Thymic Epithelial Cells," Mol. Cell. Biol., vol. 27, No. 24, 2007, pp. 8815-8823.

(Continued)

*Primary Examiner* — Daniel C Gamett

(74) *Attorney, Agent, or Firm* — Tanya M. Harding

(57) ABSTRACT

Down-regulating autoimmune regulator (AIRE) function in B cells to produce antibodies is described. The antibodies can be class-switched, high affinity, and neutralizing, and have a high degree of somatic hypermutations, even in the framework region, as compared to antibodies produced in the absence of AIRE downregulation.

6 Claims, 65 Drawing Sheets

(46 of 65 Drawing Sheet(s) Filed in Color)

Specification includes a Sequence Listing.

(56) References Cited

OTHER PUBLICATIONS

Patenaude, et al., "Active Nuclear Import and Cytoplasmic Retention of Activation-Induced Deaminase," Nat. Struct. Mol. Biol., vol. 16, No. 5, 2009, pp. 517-527.
Pavri, et al., "Activation-Induced Cytidine Deaminase Targets DNA at Sites of RNA Polymerase II Stalling by Interaction With Spt5," Cell., vol. 143, No. 1, 2010, pp. 122-133.
Peterlin & Price, "Controlling the Elongation Phase of Transcription With P-TEFb," Mol. Cell., vol. 23, No. 3, 2006, pp. 297-305.
Puel, et al., "Autoantibodies Against IL-17A, IL-17F, and IL-22 in Patients With Chronic Mucocutaneous Candidiasis and Autoimmune Polyendocrine Syndrome Type I," J. Exp. Med., vol. 207, No. 2, 2010, pp. 291-297.
Revy, et al., "Activation-Induced Cytidine Deaminase (AID) Deficiency Causes the Autosomal Recessive Form of the Hyper-IgM Syndrome (HIGM2)," Cell., vol. 102, No. 5, 2000, pp. 565-575.
Rosenspire & Chen, "Anergic B Cells: Precarious On-Call Warriors at the Nexus of Autoimmunity and False-Flagged Pathogens," Front. Immunol., vol. 6, No. 580, 2015, pp. 1-5.
Sale & Neuberger, "TdT-Accessible Breaks are Scattered Over the Immunoglobulin V Domain in a Constitutively Hypermutating B Cell Line," Immunity, vol. 9, No. 6, 1998, pp. 859-869.
Schroeder, et al., "Breaching Peripheral Tolerance Promotes the Production of HIV-1-Neutralizing Antibodies," J. Exp. Med., vol. 214, No. 8, 2017, pp. 2283-2302.
Vinuesa, et al., "Dysregulation of Germinal Centres in Autoimmune Disease," Nat. Rev. Immunol., vol. 9, No. 12, 2009 pp. 845-857.
Vuong, et al., "Specific Recruitment of Protein Kinase A to the Immunoglobulin Locus Regulates Class-Switch Recombination," Nat. Immunol., vol. 10, No. 4, 2009, pp. 420-426.
Wei, et al., "Mice Carrying a Knock-In Mutation of Aicda Resulting in a Defect in Somatic Hypermutation Have Impaired Gut Homeostasis and Compromised Mucosal Defense," Nat. Immunol., vol. 12, No. 3, 2011, pp. 264-270.
Yamano, et al., "Thymic B Cells Are Licensed to Present Self Antigens for Central T Cell Tolerance Induction," Immunity, vol. 42, No. 6, 2015, pp. 1048-1061.
Yeh, et al., "A Pathway for Tumor Necrosis Factor-Alpha-Induced Bcl10 Nuclear Translocation. Bcl10 is Up-Regulated by NF-kappaB and Phosphorylated by Akt1 and Then Complexes With Bcl3 to Enter the Nucleus," J. Biol. Chem., vol. 281, No. 1, 2006, pp. 167-175.

* cited by examiner

FIG. 3C
HIGM3 tonsil
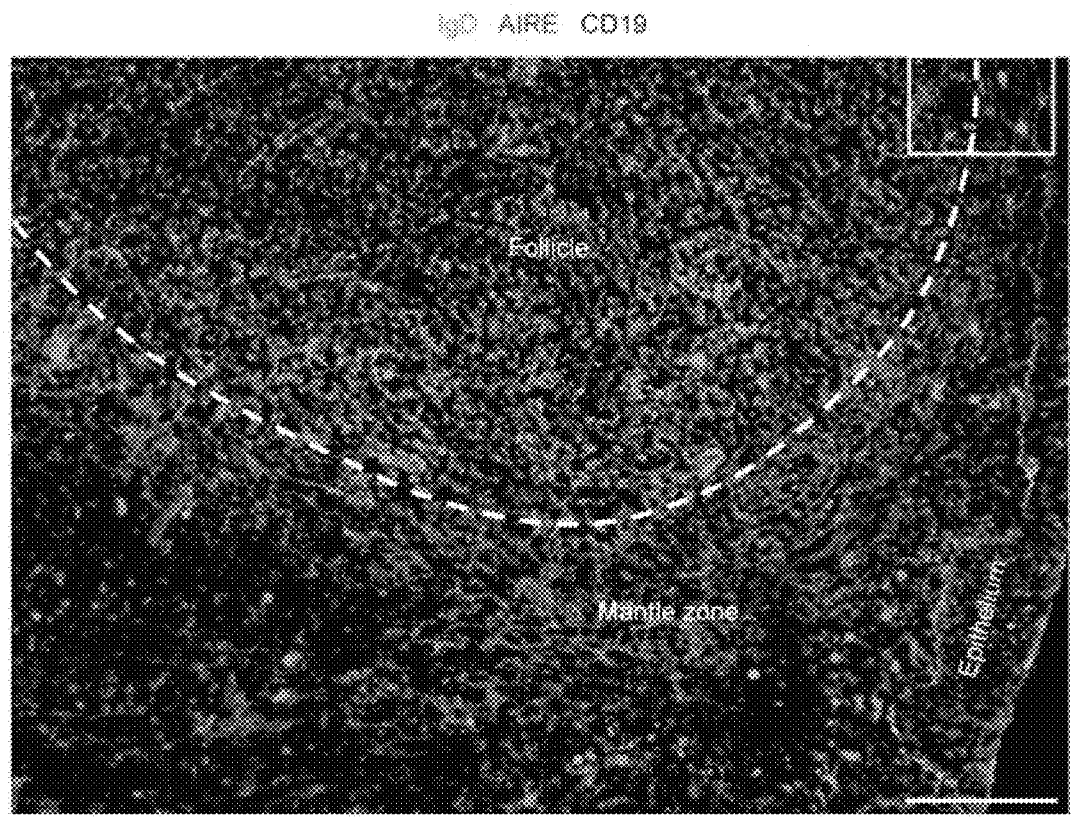
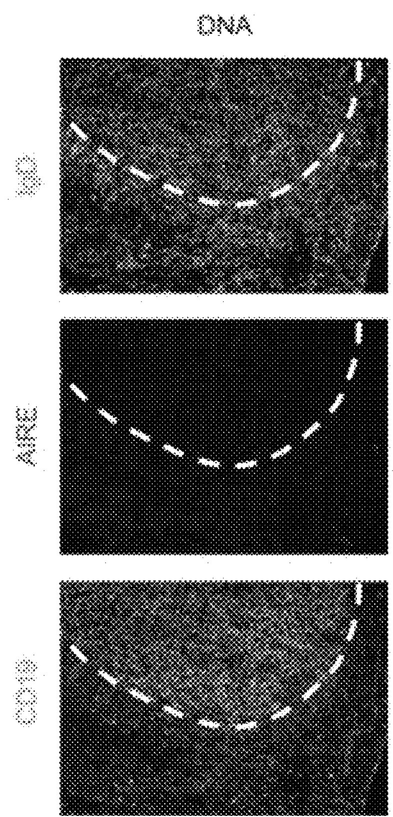

FIG. 7A

CH12$^{KO}$ clone 43, allele 1

Aire exon 3

Aire exon 4

FIG. 7A (cont'd)

CH12KO clone 43, allele 2

Aire exon 3

Aire exon 4

Sequence deleted here

FIG. 7B (cont'd)

CH12$^{KO}$ clone 53, allele 2

*Aire* exon 3

*Aire* exon 4

Sequence deleted here

FIG. 12A

| Name | Description | Remaining region | MW with tag (kDa) | Primer name and sequence (5'-3') |
| --- | --- | --- | --- | --- |
| a, Primers for cloning human AIRE constructs into pcDNA3.1(−)/Myc-His | | | | |
| WT | Full length | 1-545 | 60.7 | – |
| M1 | ΔPHD2 | 1-430 | 48.8 | D430_R AGGAGCCAGGTTCTGCTGACC<br>Hind-Myc_F GAAAGCTTTCTAGAACAAAAACTCATCTCA |
| M2 | ΔPHD1, PHD2 | 1-298 | 35 | D298_R CTCGTCCTCATTCTTCTGGTGGAG<br>Hind-Myc_F GAAAGCTTTCTAGAACAAAAACTCATCTCA |
| M3 | ΔSAND, PHD1, PHD2 | 1-181 | 23 | D181_R AATCCCGTTCCCGAGTGGAAG<br>Hind-Myc_F GAAAGCTTTCTAGAACAAAAACTCATCTCA |
| M4 | ΔCARD | 101-545 | 49 | EcoRV-ATG_R CATGGTGAATTCTGCAGATATCCAGC<br>D101_F CCCAAAGATGTGGACCTCAGCC |
| M5 | ΔCARD, ΔNLS | 181-545 | 41 | EcoRV-ATG_R CATGGTGAATTCTGCAGATATCCAGC<br>D181_F ATTCAGACCATGTCAGCTTCAGTCCA |
| M6 | ΔNLS | 1-100, 181-545 | 52.5 | D100_R GAAGCTGTCCAGGATGGGCTG<br>D181_F ATTCAGACCATGTCAGCTTCAGTCCA |
| M7 | NLS only | 101-181 | 12 | D181_R AATCCCGTTCCCGAGTGGAAG<br>Hind-Myc_F GAAAGCTTTCTAGAACAAAAACTCATCTCA |

FIG. 12B

| Name | Description | Remaining region | MW with tag (kDa) | Primer name and sequence (5'-3') |
|---|---|---|---|---|
| b, Primers for cloning human AID constructs into pFLAG-CMV2 | | | | |
| WT | Full length | 1-198 | 26.3 | AID_F ATGGACAGCCTCTTGATGAACCG<br>AID_R AAGTCCCAAAGTACGAAATGCGTC |
| M1 | E58A | 1-198 | 26.3 | AID_F ATGGACAGCCTCTTGATGAACCG<br>AID_R AAGTCCCAAAGTACGAAATGCGTC |
| M2 | NLS of AID replaced with NLS of nucleoplasmin | 1-198 | 26.3 | npNLS_top<br>AAAAGGCCGGCGGCCACGAAAAAGGCCGGCCAGGCAAAAAAGAAAAAG<br>npNLS_bottom<br>CTTTTTCTTTTTTGCCTGGCCGGCCTTTTTCGTGGCCGCCGGCCTTTT<br>(npNLS_top and npNLS_bottom were annealed together before ligation with the PCR product of the primer pair AID8-R and AID27-F.) |
| M3 | ΔCatalytic domain | 1-54, 95-198 | 21.4 | AID54_R GCCGTTCTTATTGCGAAGATAACCA<br>AID95_F GCCGACTTTCTGCGAGGGA |
| M4 | ΔAPOBEC-like and ΔNES domains | 1-94 | 13.8 | AID94_R CACATGTCGGGCACAGTCGTAG<br>TAG_F TAGACTGAAACTTTTTGGGGGAGGG |
| M5 | ΔNLS | 1-8, 27-198 | 24 | AID8_R CCGGTTCATCAAGAGGCTGTCC<br>AID27_F ACCTACCTGTGCTACGTAGTGAAGAGGC |
| M6 | G23S | 1-198 | 26.3 | AID22_R CTTAGCCCAGCGGACATTTTTGA<br>AIDS23_F AGTCGGCGTGAGACCTACCTGTG |

FIG. 12C

| Description | Primer name and sequence (5'-3') |
| --- | --- |
| c, Cloning primers for generating pCMV-Tag1-mAIRE-GFP plasmids | |
| Full length AIRE | – |
| AIREΔNLS | D106_R GTCCACATCTTTTGGGAAGCCG<br>D182_F ATTCAGACCATGGCAGCTTCTGTC |
| Full length eGFP | GFP_F ATGGTGAGCAAGGGCGAGGAG<br>GFP_R CTTGTACAGCTCGTCCATGCCG |
| AIRE of AIREΔNLS in pCMV-Tag1 vector | TGA-SalI_F TGATGACAGGTCGACCTCGAGC<br>AIRE_R GGAAGAGAAGGGTGGTGTCTCGG |

FIG. 16A

| Target | Primer name and sequence (5'–3') | |
| --- | --- | --- |
| | Forward | Reverse |
| **a**, Human genes | | |
| *AIRE* primer pair 1 | GATGACCTGGAGTCCCTTCT | CTCATCAGAGCTGCATGTCC |
| *AIRE* primer pair 2 | CCAGAAGAATGAGGACGAG | AGCCGTCACAGCAGATGAG |
| *ACTB* | AGAGCTACGAGCTGCCTGAC | AGCACTGTGTTGGCGTACAG |
| Iμ-Cγ1 | Iμ GTGATTAAGGAGAAACACTTTGAT | Cγ1_R CCAGGGCTGCTGTGCCCCCA |
| Iμ-Cγ3 | | Cγ3_R CCAGGGCCGCTGTGCCCCCA |

FIG. 16B

| **b**, Mouse genes | | |
| --- | --- | --- |
| *Actb* | TGCGTGACATCAAAGAGAAG | CGGATGTCAACGTCACACTT |
| *Aicda* | GAAAGTCACGCTGGAG | TCTCATGCCGTCCCTT |
| Iα-Cμ circle transcript | Iα CCAGGCATGGTTGAGATAGAGATAG | Cμ AATGGTGCTGGGCAGGAAGT |
| Iγ1-Cμ circle transcript | Iγ1 GGCCCTTCCAGATCTTTGAG | |
| Iμ-Cμ germline transcript | Iμ CTCTGGCCCTGCTTATTGTTG | Cμ' GAGACATTTGGGAAGGACTGACT |
| Iα-Cα germline transcript | Iα CCTGGCTGTTCCCCTATGAA | Cα GAGCTGGTGGGAGTGTCAGTG |
| Sμ (after ChIP) | Sμ_F TAGTAAGCGAGGCTCTAAAAAGCAT | Sμ_R AGAACAGTCCAGTGTAGGCAGTAGA |
| Iμ (after ChIP) | Iμ_F GCTCAGCCTGGACTTTCGGTTTGGT | Iμ_R GGAGTCAAGATGGCCGATCAGAACC |
| Sγ1 (after ChIP) | Sγ1_F TATGATGGAAAGAGGGTAGCATTCACC | Sγ1_R CTCCTTCCCAATCTCCCGTG |

FIG. 17A

| Antigen | Conjugation | Isotype | Clone | Manufacturer | Use |
|---|---|---|---|---|---|
| a, Antibodies to human antigens | | | | | |
| AID | – | Rat IgG2a | mAID-2 | eBioscience 14-5959 | WB |
| | – | Rabbit IgG | – | See ref. [17] | IP |
| | AF647 | Rat IgG2b | EK2-5G9 | BD 565785 | FC |
| AIRE | – | Mouse IgG1 | C-2 | Santa Cruz sc-373703 | WB |
| | APC | Recombinant Human IgG | REA352 | Miltenyi Biotec 130-105-401 | IF |
| | eF570 | Rat IgG2a | TM-724 | eBioscience 41-9534 | FC |
| | PE | Recombinant Human IgG | REA352 | Miltenyi Biotec 130-105-359 | FC |
| Bcl10 | – | Mouse IgG1 | 331.3 | Santa Cruz sc-5273 | IP |
| CD19 | Biotin | Mouse IgG1 | HIB19 | Biolegend 302204 | MACS, IF |
| | eF450 | Mouse IgG1 | HIB19 | Tonbo 75-0199-T100 | FC |
| | PE | Mouse IgG1 | 4G7 | BD 349209 | FC, IF |
| | PE | Mouse IgG1 | HIB19 | BD 555413 | FC, IF |
| | PE-CF594 | Mouse IgG1 | HIB19 | BD 562321 | FC |
| | PE-Cy7 | Mouse IgG1 | HIB19 | eBioscience 25-0199 | FC |
| | QDot655 | Mouse IgG1 | SJ25C1 | Thermo Fisher Scientific Q10179 | FC |
| | BV786 | Mouse IgG1 | SJ25C1 | BD 563326 | FC |
| CD24 | APC-eF780 | Mouse IgG1 | eBioSN3 | eBioscience 47-0247 | FC |
| CD27 | AF647 | Mouse IgG1 | O323 | Biolegend 302812 | FC |
| CD38 | APC | Mouse IgG1 | HIT2 | Biolegend 303510 | FC |

FIG. 17A (cont'd)

| Antigen | Conjugation | Isotype | Clone | Manufacturer | Use |
|---|---|---|---|---|---|
| CD45 | PE-Cy7 | Mouse IgG1 | HIT2 | Biolegend 303510 | FC |
| | eF450 | Mouse IgG1 | 2D1 | eBioscience 48-9459 | FC |
| | PE-Cy7 | Mouse IgG1 | HI30 | Tonbo 60-0459 | FC |
| EpCAM | AF488 | Mouse IgG2b | 9C4 | Biolegend 324210 | IF |
| Erk1/2 | – | Mouse IgG1 | L34F12 | Cell Signalling 4696 | WB |
| p-Erk1/2 | – | Rabbit IgG | D13.14.4E | Cell Signalling 4370 | WB |
| Hsp90 | – | Rabbit IgG | C45G5 | Cell Signalling 4877 | WB |
| IgD | Biotin | Goat IgG $F(ab)_2$ | – | Southern Biotech 2032-08 | MACS |
| | FITC | Goat IgG $F(ab)_2$ | – | Southern Biotech 2032-02 | FC, IF |
| | FITC | Mouse IgG2a | IA6-2 | BD 555778 | FC |
| Lamin B1 | – | Rabbit IgG | – | Santa Cruz sc-20682 (H-90) | WB |
| NF-κB p65 | – | Mouse IgG1 | F6 | Santa Cruz sc-8008 | WB |
| NF-κB p65 Ser536 | – | Rabbit IgG | 1091B | R&D MAB72261 | WB |
| β-Actin | – | Mouse IgG1 | AC-15 | Sigma-Aldrich A5441 | WB |

FIG. 17B

| Antigen | Conjugation | Isotype | Clone | Manufacturer | Use |
|---|---|---|---|---|---|
| **b**, Antibodies to mouse antigens | | | | | |
| AID | – | Rat IgG2a | mAID-2 | eBioscience 14-5959 | WB |
| | – | Rabbit IgG | – | See ref. [17] | IP, ChIP |
| AIRE | – | Rabbit IgG | – | Santa Cruz sc-33188 (H-300) | WB |
| | – | Goat IgG | – | Santa Cruz sc-17986 (D-17) | IP |
| | – | Rat IgG2c | 5H12 | eBioscience 14-5934 | WB |
| | eF660 | Rat IgG2c | 5H12 | eBioscience 50-5934 | IF |
| | APC | Recombinant Human IgG | REA352 | Miltenyi Biotec 130-105-401 | IF (can stain mouse AIRE) |
| B220 | APC-Cy7 | Rat IgG2a | RA3-6B2 | Biolegend 103224 | FC |
| BAFF-R | APC | Rat IgG1 | eBio7H22-E16 | eBioscience 17-5943 | FC |
| CD138 | Biotin | Rat IgG2a | 281-2 | Biolegend 142514 | FC |
| | PE-Cy7 | Rat IgG2a | 281-2 | Biolegend 142511 | FC |
| CD16/CD32 | – | Rat IgG2b | 2.4G2 | Tonbo 70-0161, BD 553141 | Fc Block |
| CD19 | Biotin | Rat IgG2a | 1D3 | BD 553784 | FC, IF |
| | BV650 | Rat IgG2a | 6D5 | Biolegend 115541 | FC |
| | FITC | Rat IgG2a | 1D3 | Tonbo 35-0193 | FC |
| | Pacific Blue | Rat IgG2a | 6D5 | Biolegend 115523 | FC |
| | PE-CF594 | Rat IgG2a | 1D3 | BD 562291 | FC |
| CD21 | APC | Rat IgG2b | 7G6 | BD 558658 | FC |
| CD23 | PE | Rat IgG2a | B3B4 | BD 553139 | FC |
| CD25 | APC | Rat IgG1 | PC61.5 | Tonbo 20-0251 | FC |

FIG. 17B (cont'd)

| | | | | | |
|---|---|---|---|---|---|
| CD3 | APC-Cy7 | Rat IgG2b | 17A2 | Tonbo 25-0032 | FC |
| CD38 | PE-Cy7 | Rat IgG2a | 90 | Biolegend 102717 | FC |
| CD4 | – | Rat IgG2b | GK1.5 | Biolegend 100401 | IHC, IF |
| | FITC | Rat IgG2b | GK1.5 | Biolegend 100406, BD 553729 | FC |
| | PE | Rat IgG2b | GK1.5 | Biolegend 100408 | FC |
| | PerCP-Cy5.5 | Rat IgG2b | GK1.5 | Biolegend 100434 | FC |
| CD40 | – | Hamster IgM | HM40-3 | eBioscience 16-0402 | Stim |
| | FITC | Hamster IgM | HM40-3 | BD 553723 | FC |
| CD45 | violetFluor450 | Rat IgG2b | 30-F11 | Tonbo 75-0451 | FC |
| CD62L | PE-Cy7 | Rat IgG2a | MEL-14 | BD 560516 | FC |
| CD80 | PerCP-Cy5.5 | Hamster IgG2 | 16-10A1 | BD 560526 | FC |
| CD83 | BV650 | Rat IgG1 | Michel-19 | Biolegend 121515 | FC |
| CD86 | APC | Rat IgG2a | GL-1 | BD 558703 | FC |
| CD93 | PE | Rat IgG2b | AA4.1 | Biolegend 136503 | FC |
| CXCR4 | Biotin | Rat IgG2b | 2B11 | eBioscience 13-9991 | FC |
| CXCR5 | PE | Rat IgG2b | L138D7 | Biolegend 145504 | FC |
| FAS | PE | Hamster IgG2 | Jo2 | BD 554258 | FC |
| Foxp3 | V450 | Rat IgG2b | MF23 | BD 561293 | FC |
| GAPDH | – | Rabbit IgG | 14C10 | Cell Signalling 2188 | WB |
| GL7 | AP647 | Rat IgM | GL7 | BD 561529 | FC |
| Hsp90 | – | Rabbit IgG | C45G5 | Cell Signalling 4877 | WB |
| I-$A^b$ | PerCP-Cy5.5 | Rat IgG2a | AF6-120.1 | Biolegend 116416 | FC |
| ICOSL | PE | Rat IgG2a | HK5.3 | Biolegend 107405 | FC |

FIG. 17B (cont'd)

| | | | | | |
|---|---|---|---|---|---|
| IgA | FITC | Rat IgG1 | C10-3 | BD 559354 | FC |
| | HRP | Goat IgG | – | Bethyl A90-103P | ELISA |
| IgD | PE-Cy7 | Rat IgG2a | 11-26c | eBioscience 25-5993 | FC |
| IgG | ALP | Horse IgG | – | Vector Laboratories AP-2000 | ELISA |
| IgG1 | HRP | Goat IgG | – | Jackson Immunoresearch 115-035-205 | ELISA |
| | PE-CF594 | Rat IgG1 | A85-1 | BD 562559 | FC |
| IgG2b | HRP | Goat IgG | – | Jackson Immunoresearch 115-035-207 | ELISA |
| IgG3 | HRP | Goat IgG | – | Jackson Immunoresearch 115-035-209 | ELISA |
| IgM | – | Goat IgG F(ab)$_2$ | – | Southern Biotech 1022-01 | Stim |
| | APC | Rat IgG2a | RMM-1 | Biolegend 406509 | FC |
| | HRP | Goat IgG | – | Bethyl A90-101P | ELISA |
| IL-17A | BV650 | Rat IgG1 | TC11-18H10 | Biolegend 506929 | FC |
| IL-22 | AF647 | Goat IgG | – | Biolegend 516406 | FC |
| Ly-6G | AF647 | Rat IgG2a | 1A8 | Biolegend 127610 | IF |
| $NP_{36}^{\Delta}$ | PE | – | – | Biosearch N-5070-1 | FC |
| PD-1 | FITC | Hamster IgG | J43 | eBioscience 11-9985 | FC |
| | PE-Cy7 | Hamster IgG | J43 | eBioscience 25-9985 | FC |
| PD-L1 | PE-Cy7 | Rat IgG2b | 10F.9G2 | Biolegend 124314 | FC |
| PD-L2 | PE | Rat IgG2a | TY25 | BD 557796 | FC |
| Pol II | – | Goat IgG | – | Bethyl A303-835A | WB |
| Pol II Ser5 | – | Rabbit IgG | – | Bethyl A304-408A | WB |
| Spt5 | – | Rabbit IgG | – | Santa Cruz sc-28678 | WB |
| TCRβ | PerCP-Cy5.5 | Hamster IgG | H57-597 | Biolegend 109227 | FC |

FIG. 17B (cont'd)

| | | | | | |
|---|---|---|---|---|---|
| IgA | FITC | Rat IgG1 | C10-3 | BD 559354 | FC |
| | HRP | Goat IgG | – | Bethyl A90-103P | ELISA |
| IgD | PE-Cy7 | Rat IgG2a | 11-26c | eBioscience 25-5993 | FC |
| IgG | ALP | Horse IgG | – | Vector Laboratories AP-2000 | ELISA |
| IgG1 | HRP | Goat IgG | – | Jackson Immunoresearch 115-035-205 | ELISA |
| | PE-CF594 | Rat IgG1 | A85-1 | BD 562559 | FC |
| IgG2b | HRP | Goat IgG | – | Jackson Immunoresearch 115-035-207 | ELISA |
| IgG3 | HRP | Goat IgG | – | Jackson Immunoresearch 115-035-209 | ELISA |
| IgM | – | Goat IgG $F(ab)_2$ | – | Southern Biotech 1022-01 | Stim |
| | APC | Rat IgG2a | RMM-1 | Biolegend 406509 | FC |
| | HRP | Goat IgG | – | Bethyl A90-101P | ELISA |
| IL-17A | BV650 | Rat IgG1 | TC11-18H10 | Biolegend 506929 | FC |
| IL-22 | AF647 | Goat IgG | – | Biolegend 516406 | FC |
| Ly-6G | AF647 | Rat IgG2a | 1A8 | Biolegend 127610 | IF |
| $NP_{36}^{\Delta}$ | PE | – | – | Biosearch N-5070-1 | FC |
| PD-1 | FITC | Hamster IgG | J43 | eBioscience 11-9985 | FC |
| | PE-Cy7 | Hamster IgG | J43 | eBioscience 25-9985 | FC |
| PD-L1 | PE-Cy7 | Rat IgG2b | 10F.9G2 | Biolegend 124314 | FC |
| PD-L2 | PE | Rat IgG2a | TY25 | BD 557796 | FC |
| Pol II | – | Goat IgG | – | Bethyl A303-835A | WB |
| Pol II Ser5 | – | Rabbit IgG | – | Bethyl A304-408A | WB |
| Spt5 | – | Rabbit IgG | – | Santa Cruz sc-28678 | WB |
| TCRβ | PerCP-Cy5.5 | Hamster IgG | H57-597 | Biolegend 109227 | FC |

FIG. 17D

| Isotype | Conjugation | Clone | Manufacturer | Use |
|---|---|---|---|---|
| **d**, Isotype control antibodies | | | | |
| Goat IgG | – | – | Santa Cruz sc-2028 | IF, IP |
| | AF647 | Poly24030 | Biolegend 403006 | FC |
| Goat IgG F(ab')2 | Biotin | – | Southern Biotech 0110-08 | FC |
| | FITC | – | Southern Biotech 0110-02 | FC, IF |
| Hamster IgG2 | PE | B81-3 | BD 550085 | FC |
| | PerCP-Cy5.5 | B81-3 | BD 560562 | FC |
| Hamster IgM | FITC | G235-1 | BD 553960 | FC |
| Mouse IgG1 | AF647 | MOPC-21 | Biolegend 400155 | FC |
| | APC | MOPC-21 | BD 555751, Biolegend 400120 | FC |
| | Biotin | MOPC-21 | Biolegend 400103 | FC |
| | PE | MOPC-21 | BD 555749 | FC |
| | PE-Cy7 | MOPC-21 | BD 555872, Biolegend 400126 | FC |
| Mouse IgG2a | FITC | X39 | BD 349051 | FC |
| Rabbit IgG | – | – | Santa Cruz sc-2027 | IF, IP, ChIP |
| | – | – | R&D AF008 | IF, IP, ChIP |
| Rat IgG1 | BV650 | RTK2071 | Biolegend 400437 | FC |
| Rat IgG2a | – | RTK2758 | Biolegend 400501 | IHC |
| | APC | RTK2758 | Biolegend 400511 | FC |
| | Biotin | Rat IgG2a | eBioscience 13-4321 | FC, IF |
| | eF570 | eBR2a | eBioscience 41-4321 | FC |
| | PE | eBR2a | eBioscience 12-4321 | FC |

FIG. 17D (cont'd)

| | | | | |
|---|---|---|---|---|
| | PerCP-Cy5.5 | RTK2758 | Biolegend 400531 | FC |
| | PE-Cy7 | RTK2758 | Biolegend 400521 | FC |
| Rat IgG2b | – | eB149/10H5 | eBioscience 14-4031 | IF, IHC, WB |
| | AF647 | A95-1 | BD 557691 | FC |
| | Biotin | RTK4530 | Biolegend 400603 | FC |
| | eF660 | eB149/10H5 | eBioscience 50-4031 | FC, IF |
| | PE | A95-1 | BD 553989 | FC |
| | PE-Cy7 | RTK4530 | Biolegend 400617 | FC |
| Recombinant human IgG | APC | REA293 | Miltenyi Biotec 130-104-615 | IF |
| | PE | REA293 | Miltenyi Biotec 130-104-613 | FC |

FIG. 17E

| Secondary antibody/reagent | Conjugation | Manufacturer | Use |
|---|---|---|---|
| e. Secondary antibodies | | | |
| Anti-biotin IgG | Magnetic microbeads | Miltenyi Biotec 130-090-485 | MACS |
| Donkey anti-goat IgG | HRP | Santa Cruz sc-2020 | WB |
| Donkey anti-mouse IgG | AF546 | Thermo Fisher Scientific A10036 | IF |
| | CF647 | Sigma-Aldrich SAB4600176 | IF |
| | HRP | Santa Cruz sc-2318 | WB |
| Donkey F(ab')2 anti-rat IgG | HRP | Jackson Immunoresearch 712-036-153 | WB |
| Goat F(ab')2 anti-mouse IgG | Cy3 | Jackson Immunoresearch 115-166-006 | IF |
| | FITC | Southern Biotech 1032-02 | IF |
| Goat F(ab')2 anti-rabbit IgG | Cy3 | Jackson Immunoresearch 111-166-047 | IF |
| Goat anti-rabbit IgG | HRP | Santa Cruz sc-2004 | WB |
| Streptavidin | AF488 | Thermo Fisher Scientific S11223 | IF |
| | AF546 | Thermo Fisher Scientific S11225 | IF |
| | PerCP-Cy5.5 | BD 551419 | FC |
| | BV605 | Biolegend 405229 | FC |
| | QDot605 | Thermo Fisher Scientific Q10101MP | FC |

METHODS FOR THE PRODUCTION OF THERAPEUTIC, DIAGNOSTIC, OR RESEARCH ANTIBODIES

CROSS REFERENCE TO RELATED APPLICATION(S)

This application claims priority to U.S. Provisional Application No. 62/552,292, filed on Aug. 30, 2017, which is incorporated by reference in its entirety as if fully set forth herein.

FIELD OF THE DISCLOSURE

The current disclosure provides down-regulating autoimmune regulator (AIRE) function in B cells to produce antibodies that can be high affinity and/or neutralizing. The antibodies produced by the methods disclosed herein can be class-switched and have a high degree of somatic hypermutations as compared to antibodies produced in the absence of AIRE downregulation.

BACKGROUND OF THE DISCLOSURE

A healthy immune system harbors a properly diversified and selected repertoire of antibodies that is critical for effective immune defense and prevention of autoimmunity. B cells play a major role in this process by producing antigen-specific antibodies against pathogens and imparting immunological memory. For the successful generation of B cell immunity, naive B cell populations with membrane immunoglobulin receptors (B cell receptors, BCRs) recognizing specific antigens are selectively activated in specialized microenvironments called germinal centers (GCs) in secondary lymphatic organs such as the lymph nodes, tonsils, and spleen.

In the weeks following antigenic stimulation in the GC, the specific antibodies that are produced by B cells increase their affinity for the antigen in a gradual and stepwise manner, termed affinity maturation. Affinity maturation involves two interrelated processes: (1) somatic hypermutation (SHM) and (2) clonal selection.

During SHM, mutations are generated in the variable, antigen-binding coding sequences (known as complementarity-determining regions (CDR)) of immunoglobulin genes. The mutation rate is up to 1,000,000 times higher than in cell lines outside of the lymphoid system. The increased mutation rate results in 1-2 mutations per CDR. These mutations alter the binding specificity and binding affinities of the resultant antibodies that are produced.

During clonal selection, B cells that have undergone SHM must compete for growth limiting resources, including the availability of antigen. Follicular dendritic cells (FDCs) of the GCs present antigen to the B cells, and only the B cells expressing BCRs with the higher affinities for the antigen are selected to survive. Over several rounds of selection, the resultant secreted antibodies produced will have effectively increased affinities for the antigen.

Beyond SHM and clonal selection, GC B cells additionally go through class switch recombination (CSR) which is a process that irreversibly rearranges the immunoglobulin (Ig) heavy chain constant region genes. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgA is similarly subdivided into subclasses including IgA1 and IgA2. Class switch recombination rearranges the immunoglobulin (Ig) heavy chain constant region genes from IgM or IgD to IgG, IgA or IgE. Class switch recombination allows effector function to change while maintaining antigenic specificity. Examples of different effector functions include antibody-dependent cell-mediated cytotoxicity (ADCC); phagocytosis; down regulation of cell surface receptors (e.g. B cell receptors); and B cell activation.

Generation of such long-lived, high affinity class-switched antibodies with neutralization functions protects individuals from re-infection following a first exposure to an antigenic pathogen. This process underlies the success of most vaccines. Antibodies also play large roles in a variety of therapeutic, diagnostic, and research uses.

SUMMARY OF THE DISCLOSURE

The current disclosure provides systems and methods that improve the ability to generate antibodies against specific antigens. The systems and methods improve the ability to generate antibodies by down-regulating the function of the molecule autoimmune regulator (AIRE) in B cells. Down-regulating AIRE function results in the production of antibodies with increased somatic hypermutation (SHM) and class switch recombination (CSR), thereby facilitating the development of antibodies for clinical and biomedical research applications.

In particular embodiments, the produced antibodies are neutralizing antibodies. In particular embodiments, neutralizing antibodies significantly reduce or block the binding of pathogens and/or their virulence molecules to a host's cellular receptors, such that the pathogens are no longer able to cause cellular damage or enter the host's cells. In particular embodiments, neutralizing antibodies are produced following increased SHM in the FR regions of antibodies. In particular embodiments, the produced antibodies are high affinity antibodies.

REFERENCE TO SEQUENCE LISTING

The nucleic acid and amino acid sequences listed below are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "Sequence Listing.txt" created on or about Aug. 29 2018, with a file size of 84 KB, contains the sequence listing for this application and is hereby incorporated by reference in its entirety.

BRIEF DESCRIPTION OF THE DRAWINGS

The patent or application file contains at least one drawing executed in color. Copies of this patent or patent application publication with color drawings will be provided by the Office upon request and payment of the necessary fee.

Many of the drawings submitted herewith are better understood in color, which is not available in patent application publications at the time of filing. Applicants consider the color versions of the drawings as part of the original submission and reserve the right to present color images of the drawings in later proceedings.

FIG. 1A, Immunofluorescence analysis of the tonsillar tissue of a healthy donor for IgD, CD19, AIRE and DAPI-stained DNA, and the thymic tissue of a healthy donor for EpCAM, AIRE and DNA. The dotted line marks the boundary between tonsil follicular mantle zone and the follicle. Bars: 20 μm. The results represent 5 healthy tonsil donors and 2 healthy thymus donors. FIG. 1B, Flow cytometric analysis of AIRE expression in tonsillar $CD19^+$ $IgD^+CD38^-$ naive B cells, $CD19^+IgD^{+CD}38^+$ FGC B cells, $CD19^+IgD^-CD38^+$ GC B cells and $CD19^+IgD^-CD38^-$ memory B cells. The data represent those from 5 donors. FIG. 1C, Immunofluorescence analysis of the splenic tissue of a B6 mouse immunised with 3 doses of sheep red blood cells (SRBCs) for IgD, AIRE, CD19 and DNA, and the thymic tissue of an immunised B6 mouse for UEA-1, AIRE and DNA. Bar: 20 μm. The results represent the splenic tissues of 5 mice and the thymic tissue of 3 mice. FIG. 1D, FIG. 1E, Flow cytometric and statistical analyses of AIRE (GFP) expression in splenic and ILN viable $CD19^+B220^+$ $FAS^+GL7^+$ GC B cells, $CD19^+B220^+FAS^-GL7^-$ non-GC B cells and $CD19^{lo}B220^{lo}CD138^+$ plasma cells (PCs) of B6 mice (shaded histograms, n=4) or B6.$Aire^{Adig}$ mice (histograms, n=4) after immunization with 5 doses of $NP_{32}$-KLH. The results represent or compare 4 B6 and 4 B6.$Aire^{Adig}$ mice. FIG. 1F, Flow cytometric analysis of CD83 and CXCR4 expression on total and $GFP^+$ splenic GC B cells of an immunised B6.$Aire^{Adig}$ mouse, showing the distribution of $GFP^+$ GC B cells in $CXCR4^{hi}CD83^-$ DZ and $CXCR4^{lo}CD83^+$ LZ B cells. The result represents 4 B6.$Aire^{Adig}$ mice. FIG. 1G, Immunofluorescence analysis of the tonsillar tissue of a HIGM3 patient for IgD, AIRE, CD19 and DNA. The dotted line marks the boundary between follicular mantle zone and the follicle. Bars: 20 μm. FIG. 1H, Flow cytometric analysis of AIRE (GFP) expression in splenic B cells of a B6 or B6.$Aire^{Adig}$ mouse treated for 3 d with medium or CD40L with or without I L-4 in the absence (vehicle) or presence of CAPE. The data represent the results from 3 B6 and 3 B6.$Aire^{Adig}$ mice. P<0.01, *P<0.001, by 2-tailed t-test.

FIGS. 2A-2D, Immunofluorescence analysis of tonsillar (2A, 2B) and splenic (2C, 2D) tissues of healthy donors for IgD, AIRE, CD19 and DNA, showing the presence of AIRE in the nuclei of follicular GC B cells. Follicular $IgD^+$ plasmablasts (arrow heads) did not contain AIRE. The areas 1 and 2 outlined in FIG. 2A and FIG. 2C are shown in with a higher magnification of FIG. 2B and FIG. 2D, respectively. Dotted lines mark the boundary between follicular mantle zone and the follicle. Bars: 40 μm (FIG. 2A) and 15 μm (FIG. 2B). FIG. 2E, Flow cytometric gating strategy for identifying human peripheral blood naive ($IgD^+CD27^-$), MZ ($IgD^+CD27^+$), switched memory ($IgD^-$ CD27+), double-negative ($IgD^-CD27^-$) B cells, and transitional ($CD24^{hi}CD38^{hi}$), mature ($CD24^{int}CD38^{int}$), memory ($CD24^{hi}CD38^-$) B cells and plasma cells ($CD24^-CD38^{hi}$). 2F, AIRE expression in human peripheral blood B cell subsets, as determined by flow cytometry. The result is representative of 8 healthy donors. FIG. 2G, Flow cytometric gating strategy for identifying mouse splenic non-GC ($CD19^+B220^+GL7^-FAS^-$), GC ($CD19^+B220^+GL7^+FAS^+$) B cells and plasma cells ($CD19^{lo}B220^{lo}CD138^+$). FIG. 2H, AIRE expression in mouse peripheral blood, splenic, MLN, PP and thymic B cells of B6.$Aire^{Adig}$ mice. The data are representative of 12 B6.$Aire^{Adig}$ and 6 B6 mice that were age- and sex-matched and housed in the same SPF room.

FIGS. 3A-3D. AIRE expression in GC B cells requires CD40 signalling. FIGS. 3A-3D, Immunofluorescence analysis of tonsillar tissues of a healthy donor and a HIGM3 patient for IgD, AIRE, CD19 and DNA, showing the lack of AIRE expression in GC B cells in the HIGM3 patient. The HIGM3 tonsil harbors giant follicles with defective follicular Ig class switch recombination (CSR) and hence showing follicular IgD staining without follicular $IgD^+$ plasmablasts, although extrafollicular and subepithelial $IgD^+$ plasmablasts are present and generated via T cell-independent mechanisms. Chen et al., *Nature Immunology* 10, 889-898 (2009). The areas outlined in FIG. 3A and FIG. 3C are shown with a higher magnification in FIG. 3B and FIG. 3D, respectively. The dotted lines outline the follicles. Bars: 100 μm (FIGS. 3A, 3C) or 25 μm (FIGS. 3B, 3D).

FIG. 4A, FIG. 4B, qRT-PCR and Western Blot analyses of AIRE transcript and protein levels, the protein levels of total and Ser536-phosphorylated NF-κB p65, and total and Thr202/Tyr204-phosphorylated Erk1/2 in human peripheral blood $IgD^+$ B cells treated with medium or CD40L, or CD40L and IL-4, in the presence of vehicle or CAPE for 3 d. FIG. 4C, FIG. 4D, qRT-PCR and Western Blot analyses of AIRE transcript and AIRE protein levels in human 2E2 B cells treated with medium (Control) or CD40L and IL-21 for 3 d. FIG. 4E, FIG. 4F, qRT-PCR and Western Blot analyses of Aire transcript and AIRE protein levels in mouse CH12 cells treated with anti-CD40, TGF-β1 and ng/ml IL-4 for 3 d. *P<0.05, P<0.01, *P<0.001, by 2-tailed t-test. The data represent 3-4 experiments.

FIG. 5A, Purity of $Aire^{+/+}$ and $Aire^{-/-}$ littermate donor B cells before adoptive transfer. FIG. 5B, Cell surface expression of the differentiation and activation markers CD21, CD23, CD38, CD40, CD62L, CD80, CD86, CD93, I-$A^b$, BAFF-R and immunoglobulin IgM and IgD on purified $Aire^{+/+}$ and $Aire^{-/-}$ littermate donor B cells before adoptive transfer, as determined by flow cytometry. FIG. 5C, Percentage of $GL7^+FAS^+$ GC B cells in the spleens of μMT recipients of either $Aire^{+/+}$ or $Aire^{-/-}$ B cells that were immunised i.p. with 5 doses of $NP_{32}$-KLH. Flow cytometry was performed 4 d after the last immunization. FIG. 5D, Cell surface expression of the co-stimulatory or co-inhibitory molecules CD80, CD86, PD-L1, PD-L2 and ICOSL on $GL7^+FAS^+$ GC B cells in the spleens of μMT recipients after immunizations. Shaded histograms indicate the staining using isotype-matched control antibodies. FIGS. 5E, 5F, Percentage of splenic $PD\text{-}1^+CXCR5^+$ $T_{FH}$ cells and $PD\text{-}1^+CXCR5^+$ $Foxp3^+CD25^+$ $T_{FR}$ cells in the spleens of immunised μMT recipients. The results shown represent 4 experiments, each including B cells from 3-5 age- and sex-matched littermate donor mice and 6-8 age- and sex-matched littermate μMT recipient mice. FIG. 5G, CFSE dilution in purified B cells from age- and sex-matched littermate donor $Aire^{+/+}$ and $Aire^{-/-}$ mice treated with medium (Control) or CD40L and IL-4 for 5 or 7 d. Non-viable cells were excluded from the analysis. FIG. 5H, Six-hour EdU incorporation by $Aire^{+/+}$ or $Aire^{-/-}$ B cells stimulated for 5 d with CD40L and IL-4. 5I, Apoptosis of $Aire^{+/+}$ or $Aire^{-/-}$ B cells treated with medium (Control) or CD40L and IL-4 for 3 or 7 d, as determined by Annexin V and 7-AAD staining by flow cytometry. The results shown are representative of 3 experiments, each including cells from 2-3 age- and sex-matched littermate $Aire^{+/+}$ and $Aire^{-/-}$ mice.

FIG. 6A, Flow cytometric analysis of surface IgD and IgM on $NP_{36}$-binding B cells in μMT recipients of $Aire^{+/+}$ or $Aire^{-/-}$ B cells immunised with 5 doses of $NP_{32}$-KLH. The result represents 3 age- and sex-matched μMT recipients each of B cells from 3-5 age- and sex-matched littermate donor $Aire^{+/+}$ or $Aire^{-/-}$ mice. FIG. 6B, The ratios of the titers of circulating $NP_4$-binding to $NP_{29}$-binding IgM, IgG1, IgG2b and IgG3 in immunized μMT recipient mice of $Aire^{+/+}$ or $Aire^{-/-}$ B cells. The results represent 4 experiments, each including B cells from 3-5 age- and sex-matched littermate donor mice and 6-8 age- and sex-matched littermate μMT recipient mice. FIG. 6C, Flow cytometric analysis of surface IgM, IgG1 and IgA by $Aire^{+/+}$ or $Aire^{-/-}$ mouse splenic B cells stimulated ex vivo for 4 d. The results represent 3 experiments. FIG. 6D, ELISA of IgG1 and IgA in supernatants of $Aire^{+/+}$ or $Aire^{-/-}$ mouse splenic B cells stimulated ex vivo for 5 d with anti-CD40 and IL-4 (for IgG1) or anti-CD40, TGF-β and IL-4 (for IgA). The results represent 3 experiments. FIGS. 6E, 6F, Flow cytometric and statistical analyses of IgA CSR in WT and $Aire^{-/-}$ CH12 cells treated with medium (Control) or stimulated with anti-CD40, TGF-β and IL-4 for 3 d. Relative CSR (FIG. 6E) was determined as the ratio of the percentages of $IgA^+IgM^-$ cells in stimulated samples to control samples followed by normalization of such ratios by setting the values of WT CH12 cells to 1. The results represent or compare 3 experiments involving WT, clones 43, 53 and 69, and 11 additional experiments involving WT and clone 69. FIG. 6G, qRT-PCR analysis of the Iα-Cμ circle transcript levels in WT and $Aire^{-/-}$ CH12 cells treated with medium (Control) or stimulated with anti-CD40, TGF-β and IL-4 for 3 d. The results compare 3 experiments. FIG. 6H, Flow cytometric analysis of IgA CSR in $Aire^{-/-}$ CH12 cells (clone 69) transfected with a construct expressing either NLS-deficient AIRE-GFP ($AIRE^{\Delta NLS}$-GFP) or WT AIRE-GFP ($AIRE^{WT}$-GFP) and treated with medium (Control) or stimulated with anti-CD40, TGF-β and IL-4 for 3 d. The results represent 2 experiments. *P<0.05, P<0.01, *P<0.001, by 2-tailed t-test (FIG. 6B, 6D, 6F) or 1-tailed t-test (FIG. 6G).

FIGS. 7A-7F. Validation of $Aire^{-/-}$ CH12 cell clones. FIGS. 7A-7C, DNA sequencing (right panels) of the Aire gene (SEQ ID NO: 4) showing CRISPR-introduced mutations causing frame shift in both alleles. The deleted nucleotides are shaded in dark gray (top panels) with the deletion site indicated by dark gray arrows (bottom panels) in the sequencing results. The axons of Aire are shaded in light gray, with the amino acid translation shown above the nucleotide sequence and the stop codon introduced shaded in gray and marked with an asterisk. FIG. 7D, Verification of Aire mutations in CH12 clones by PCR using primers that only anneal to the WT sequence, giving no amplification in clones 43, 47 and 53. Clone 47 has a 3-bp deletion in both Aire alleles causing a single amino acid deletion, and hence was not used in experiments. FIG. 7E, Verification of Aire mutations in both alleles of CH12 clone 69 by PCR showing no amplification using primer pair #2 which anneals to the WT but not the mutated sequence. Primer pair #1 amplifies a sequence immediately downstream of the mutation site, and primer pair #3 is specific for the single-stranded repair template used in CRISPR. FIG. 7F, Western Blot analysis of AIRE protein expression in WT and $Aire^{-/-}$ CH12 cells.

FIG. 8A, qRT-PCR analysis of the Iγ1-Cμ circle transcript level in $Aire^{+/+}$ CH12 cells and $Aire^{-/-}$ CH12 cell clones 43, 53 and 69 that were either unstimulated or stimulated with anti-CD40, TGF-β1 and IL-4 for 3 days. The result was normalised using the respective Actb transcript level, and expressed as fold of induction relative to unstimulated $Aire^{+/+}$ CH12 cells. The data are representative of three experiments. FIGS. 8B, 8C, Western Blot analysis of AID in WT and $Aire^{-/-}$ CH12 cells that were either unstimulated or stimulated with anti-CD40, TGF-β1 and IL-4 for 3 d. Lamin B1 and GAPDH were used as the control for nuclear and cytoplasmic proteins, respectively. The data are representative of 2 experiments. FIG. 8D, qRT-PCR analysis of Aicda and the Iμ-Cμ and Iα-Cα germline transcript levels in $Aire^{+/+}$ CH12 cells and $Aire^{-/-}$ CH12 cell clones 43, 53 and 69 that were either unstimulated or stimulated with anti-CD40, TGF-β1 and IL-4 for 3 d. FIG. 8E, Flow cytometric analysis of apoptosis by Annexin V and 7-AAD staining of WT and $Aire^{-/-}$ CH12 cells treated with medium (Control) or stimulated with anti-CD40, TGF-β1 and IL-4 for 3 d. FIG. 8F, Percentages of late apoptotic (Annexin $V^+$7-$AAD^+$) and early apoptotic (Annexin $V^{30}$ 7-$AAD^-$) in WT and $Aire^{-/-}$ CH12 cells treated with medium (Control) or stimulated with anti-CD40, TGF-β1 and IL-4 for 3 d. *P<0.05, by 2-tailed t-test. The data represent 4 experiments.

FIG. 9A, Imaging flow cytometric analysis of AIRE and AID in tonsillar $IgD^-CD38^+$ GC B cells of a healthy donor. Bars: 7 μm. The results represent 3 donors. FIG. 9B, FIG. 9C, Co-IP of AIRE and AID in tonsillar $CD19^+$ total, $IgD^+$ naive and FGC and $CD19^+IgD^-$ GC and memory B cells of a healthy donor, and in splenic $CD19^+$ B cells of a B6 mouse after 3 doses of immunization with SRBCs. The results are representative of tonsils of 4 donors and spleens of 3 mice. FIG. 9D, The domain structures of recombinant WT and mutant human AIRE and AID molecules. Dotted lines indicated the deleted regions in the mutant proteins. FIG. 9E, Co-IP of WT AID and WT or mutant AIRE in HKB-11 cells 24 h after transfection of plasmid(s) encoding WT AID and WT or mutant AIRE proteins. FIG. 9F, The domain structures of recombinant WT and mutant human AID molecules. FIG. 9G, Co-IP of WT AIRE and WT or mutant AID in HKB-11 cells 24 h after transfection of plasmid(s) encoding WT AIRE and WT or mutant AID proteins. The results in FIG. 9E and FIG. 9G are representative of 3 experiments. FIG. 9H, A dot blot assay for the genomic uracil content in WT and $Aire^{-/-}$ CH12 cells after 48 or 72 h of treatment without or with anti-CD40, TGF-β and IL-4. The results represent 3 experiments. FIG. 9I, ChIP-qPCR analysis for the interaction of AID with Sμ, Iμ and Sγ1 regions in WT and $Aire^{-/-}$ CH12 cells after 72 h of treatment without or with anti-CD40, TGF-β and IL-4. The results represent 3 experiments. FIG. 9J, Co-IP of AID with pSer5-Pol II, total Pol II, Spt5 and AIRE in WT and $Aire^{-/-}$ CH12 cells after 72 h of treatment without or with anti-CD40, TGF-β and IL-4. The results represent 3 experiments. *P<0.05, P<0.01, *P<0.001, by 2-tailed t-test.

FIG. 10A, The gating strategy to identify tonsillar naive ($IgD^+CD38^-$), founder GC (FGC) ($IgD^+CD38^+$), GC ($IgD^-CD38^+$) and switched memory ($IgD^-CD38^-$) B cells and switched plasma cells (PCs) ($IgD^-CD38^{hi}$) on the imaging flow cytometer. The plot displays MACS-purified $CD19^+$ tonsillar B cells. FIGS. 10B-10F, Imaging flow cytometry of AIRE and AID in tonsillar GC, naive, FGC, switched memory B cells and switched PCs of a healthy donor. DNA was counterstained with DAPI. Samples stained with isotype-matched control antibodies were used to define the fluorescence baseline for AIRE and AID. Four representative cells in each population stained with AIRE and AID or with isotype control antibodies were shown. Bars: 7 μg.

FIG. 11A, Co-IP of AIRE and AID in splenic B cells of immunised WT or $Aicda^{-/-}$ mice. The data represent 2 experiments. FIG. 11B, Western Blot analysis of Bcl10 in cytoplasmic and nuclear extracts of Ramos B cells unstimulated or stimulated with TNF for 24 h. FIG. 11C, Co-IP of AID and AIRE or Bcl10 in Ramos B cells unstimulated or stimulated with TNF for 24 h. The data in FIG. 11B and FIG. 11C represent 3 experiments. FIG. 11D, The principle of the uracil dot blot assay for the quantitation of genomic uracil. In stimulated $Aire^{+/+}$ or $Aire^{-/-}$ B cells, AID deaminates C to U in Ig V and S regions. U is excised by either endogenous Uracil N-glycosylase (UNG) or exogenously added *Escherichia coli* Uracil DNA glycosylase (UDG) during the assay to generate abasic sites (asterisk), which exist in an equilibrium between the closed and open ring forms. The active aldehyde in the open ring form reacts with the biotinylated aldehyde-reactive probe (Biotin-ARP), allowing biotinylation of the abasic site. Quantitation of biotinylated abasic sites with fluorochrome- or HRP-conjugated streptavidin after DNA dot blot by imaging or ELISA gives genomic U content. An increase in genomic U content in $Aire^{-/-}$ B cells indicates increased activity of AID in the absence of AIRE. FIG. 11E, A representative standard calibration curve of the fluorescence intensity vs. uracil number of the assay.

FIGS. 12A-12C. Primers for cloning human AIRE and AID constructs.

FIG. 13A, The sorting and sequencing strategies for $Aire^{+/+}$ and $Aire^{-/-}$ donor B cells in μMT recipients after immunizations with 5 doses of $NP_{32}$-KLH. NP-specific B cells were sorted based on $NP_{36}$ binding. FIG. 13B, The SHM landscape across IgHV, including FR2, CDR2, FR3, CDR3 and FR4, of $NP_{36}$-binding $IgM^-IgD^-$ or $IgM^+IgD^+$ $Aire^{+/+}$ and $Aire^{-/-}$ donor B cells in μMT recipients after immunizations with $NP_{32}$-KLH. The result represents 3 μMT recipients of $Aire^{+/+}$ donor B cells and 3 μMT recipients of $Aire^{-/-}$ donor B cells.

FIG. 14A, Frequencies of C-to-T transitions in SHMs in IgHV of NP-specific $IgG^+$, $IgA^+$ or $IgE^+$ splenic B cells from μMT recipient mice of $Aire^{+/+}$ or $Aire^{-/-}$ B cells after 5 doses of immunizations with $NP_{32}$-KLH. FIG. 14B, qRT-PCR analysis of the fold induction of Iμ-Cγ1 and Iμ-Cγ3 post-switch transcript levels in peripheral blood $IgD^+CD27^-$ naïve B cells from healthy subjects (n=5) or APS-1 patients (n=5) stimulated for 3 d with CD40L and IL-4 or IFN-γ over the respective unstimulated control B cells. FIGS. 14C, 14D, GMS stain of cutaneous *C. albicans* and skin fungal burden (CFU per mg of tissue) in μMT recipient mice of $Aire^{+/+}$ or $Aire^{-/-}$ donor B cells 4 d after infection. Bars: 1 mm (FIG. 14C, upper panels) or 100 μm (FIG. 14C, lower panels). FIG. 14E, Levels of autoantibodies binding to IL-17A, IL-17F and IL-22 in the sera of μMT recipient mice of $Aire^{+/+}$ or $Aire^{-/-}$ donor B cells 4 d after infection. FIG. 14F, Flow cytometric analysis of IL-17A and IL-22 expression in cutaneous $CD4^+$ T cells of μMT recipient mice of $Aire^{+/+}$ or $Aire^{-/-}$ donor B cells 4 d after infection and after ex vivo re-stimulation. FIG. 14G, Immunofluorescence analysis of Ly-6G (red) and DNA (blue) in cutaneous tissues surrounding the *C. albicans* infection site in μMT recipient mice of $Aire^{+/+}$ or $Aire^{-/-}$ donor B cells 4 d after infection. The results in FIGS. 14C-14G represent 1 of 2 experiments, with 4 mice per group in each experiment. FIG. 14H, A simplified schematic of AIRE-mediated GC checkpoint of antibody diversification in B cells. At the T-B cell border of secondary lymphoid organs, B cells present antigens to and receive co-stimulation from DC-activated T cells, which also induce AIRE expression in B cells via CD40. The activated B cells enter the GC DZ and undergo SHM, proliferation and subsequent affinity selection by interacting with antigens on the surface of follicular dendritic cells (FDCs) in LZ. Low-affinity B cells will undergo apoptosis, whereas high-affinity B cells receive help from T follicular helper (TFH) cells to undergo CSR, and subsequently either re-enter the SHM-proliferation cycle in the DZ or exit the GC as plasma cells or memory B cells. AIRE in B cells limits autoantibody generation by restraining excessive AID activity in the GC, *$P<0.05$, $P<0.01$, by 1-tailed t-test (FIGS. 14A, 14B left panel, FIG. 14D, 14**E) or 1-tailed Mann-Whitney U test (b right panel).

FIG. 15A, Flow cytometric gating strategy for identifying mouse skin viable $CD45^+TCR\gamma\delta^+TCR\beta^-\gamma\delta$ T cells, $CD45^+TCR\gamma\delta^-TCR\beta^+CD3^+CD4^+$ $CD4^+$ T cells and $CD45^+TCR\gamma\delta^-TCR\beta^+CD3^+CD4^-$ $CD8^+$ T cells. FIG. 15B, IHC of $CD4^+$ T cells in cutaneous tissues surrounding the infection site in μMT recipient mice of $Aire^{+/+}$ or $Aire^{-/-}$ donor B cells 4 d after infection. Bars: 100 μm. FIG. 15C, Flow cytometric analysis of IL-17A and IL-22 expression in cutaneous $CD8^+$ and γδ T cells of μMT recipient mice of $Aire^{+/+}$ or $Aire^{-/-}$ donor B cells 4 d after infection. Data represent 2 experiments.

FIGS. 16A, 16B. qRT-PCR primers used in Example 1.

FIGS. 17A-17E. Antibodies used in Example 1.

DETAILED DESCRIPTION

Figure 1A:
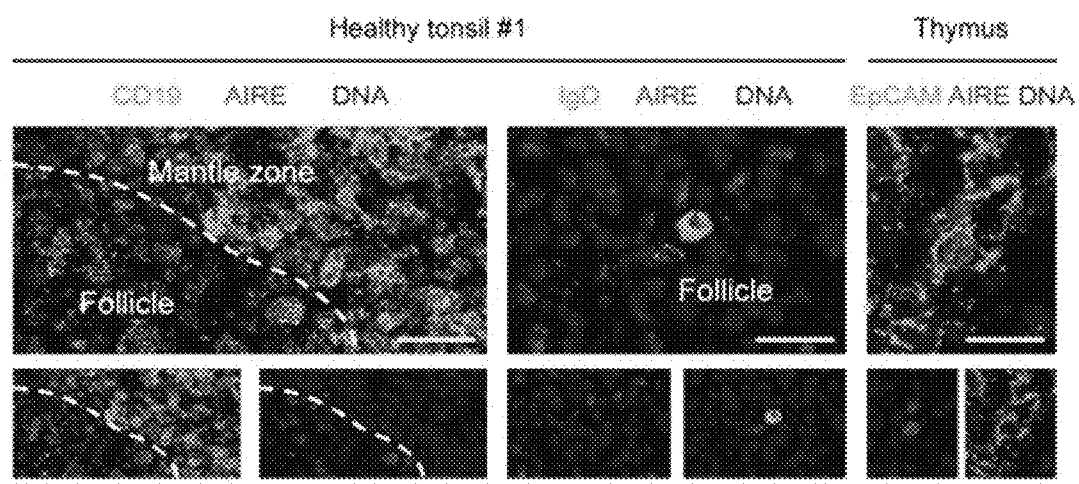
FIGS. 1A-1H. GC B cells express AIRE in a CD40-dependent manner.

A healthy immune system harbors a properly diversified and selected repertoire of antibodies that is critical for effective immune defense and prevention of autoimmunity. Mature B cells undergo antigen-driven antibody diversification via somatic hypermutation (SHM) and class-switch recombination (CSR) mediated by the enzyme activation-induced cytidine deaminase (AID) in germinal centres (GCs) of secondary lymphoid organs. Muramatsu, et al. *Cell* 102, 553-563, (2000); Revy, et al. *Cell* 102, 565-575, (2000).

Uncontrolled AID function can precipitate autoimmunity and cancer. Vinuesa, et al. *Nature reviews. Immunology* 9, 845-857, (2009); Casellas, et al. *Nature reviews. Immunology* 16, 164-176, (2016). Mutations in the autoimmune regulator (AIRE) gene, which normally promotes central and peripheral T cell tolerance (Anderson, et al. *Science* 298, 1395-1401, (2002); Gardner, et al. *Science* 321, 843-847, (2008); Malchow, et al. *Science* 339, 1219-1224, (2013)), cause autoimmune polyglandular syndrome type 1 (APS-1) (Nagamine, et al. *Nature genetics* 17, 393-398, (1997); Finnish-German, *Nature genetics* 17, 399-403, (1997)) associated with aberrant production of autoantibodies by B cells, organ-specific autoimmunity and increased susceptibility to mucocutaneous *Candida albicans* infection. Anderson, et al. *Science* 298, 1395-1401, (2002).

The current disclosure provides that AIRE in GC B cells inhibits immunoglobulin affinity maturation (e.g., SHM) and CSR. When AIRE function is down-regulated, antigen-specific B cells develop into antibody-secreting plasma cells that produce antibodies with increased affinity and/or neutralization function. The down-regulation of AIRE improves antibody production not only in cultured B cells, but also in mouse models with AIRE deficiency. Moreover, in AIRE-deficient mice, there is an increased population of helper T cells (Tfh). Tfh cells are a type of T cell that specializes in promoting GC B cells to produce high affinity class-switched antibodies and evoking a more rapid memory B cell response to previously encountered antigens.

The systems and methods of the disclosure can be used for the generation of antibodies in both the primary immune response and the recall immune response in vivo as well as in B cell cultures in vitro. Uses of generated antibodies include therapeutic uses (e.g., antibody-based therapeutics for cancer, autoimmune, and inflammatory diseases) and diagnostic and/or research uses (e.g., flow cytometry, imaging, immunohistochemistry, western blot).

Particular embodiments include increasing SHM and CSR during antibody production by selecting a first population of B cells with down-regulated AIRE function; and contacting the selected B cell population with an antigen; thereby increasing SHM and CSR during antibody production. In particular embodiments, the increase can be in relation to antibodies produced by selecting a second population of B cells with normal AIRE function; and contacting the second selected B cell population with the same antigen under comparable conditions.

Figure 6A:
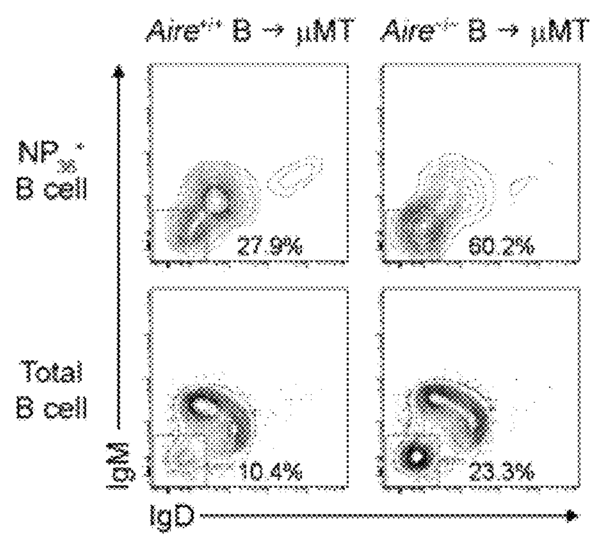
FIGS. 6A-6H. AIRE in B cells inhibits Ig diversification.
Figure 6B:
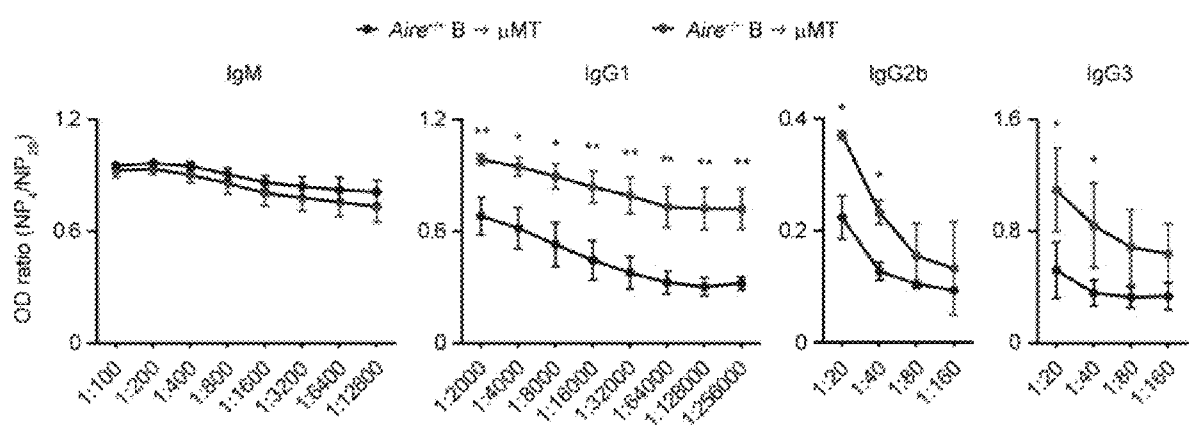
Figure 6C:
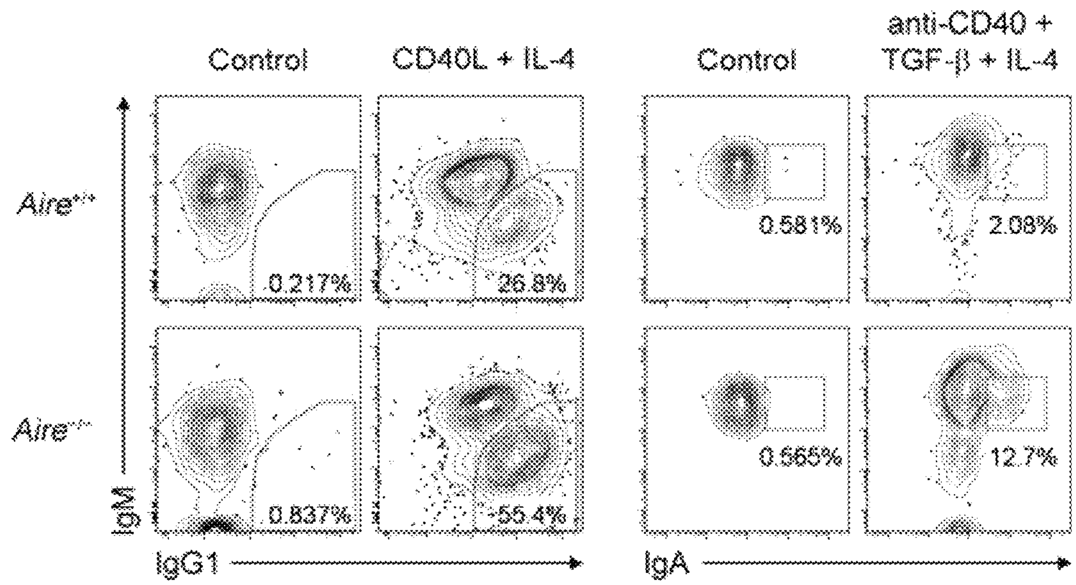

In particular embodiments, increased SHM can be confirmed by the methods used to generate the data presented in FIG. 6B. Briefly, antigens of a lower oligomeric number (in this case $NP_4$) and those of a higher oligomeric number (in this case $NP_{29}$) are coated onto the wells of microtiter plates. Samples containing the antibodies whose affinity is to be determined are applied to the coated microtiter plates. Antibodies of high affinity would be able to bind to the antigens with a lower oligomeric number, and those of both high and low affinity would be able to bind to the antigens with a higher oligomeric number. The ratios of binding to the lower oligomeric antigens to the higher oligomeric antigens would be an indication of the proportion of high-affinity antibodies in a given sample. In particular embodiments, the increase can be a statistically-significant increase.

In particular embodiments, increased CSR can be confirmed by the methods used to generate the data presented in FIGS. 6C, 6D, 6E, 6F and 6G. Briefly, the expression of cell surface immunoglobulin is measured by flow cytometry. A reduction in IgM, the antibody expressed before CSR, and an increase in various subclasses of IgG, IgA or IgE expression on the cell surface indicates CSR. In addition, the secretion of the various classes of IgG, IgA or IgE into the supernatant would also increase after the B cells are class switched. In particular embodiments, the changes can be statistically-significant changes.

In particular embodiments, "under comparable conditions" refers to experimental conditions under which one of ordinary skill the art would expect similar results (i.e., lack of a statistically significant difference between groups), but for an experimental variable.

Particular embodiments include methods of producing neutralizing antibodies against a pathogen by selecting a population of B cells with down-regulated AIRE function; and contacting the selected B cell population with an antigen of the pathogen; thereby producing neutralizing antibodies against the pathogen.

Function as a neutralizing antibody can be shown through the ability to block or reduce cellular function as measured by flow cytometry. In particular embodiments percent neutralization can refer to a percent decrease in infectivity in the presence of an antibody, as compared to pathogen infectivity in the absence of the antibody. For example, if half as many cells in a sample become infected in the presence of an antibody, as compared to in the absence of the antibody, this can be calculated as 50% neutralization. In particular embodiments neutralizing antibodies result in at least 40% neutralization, at least 50% neutralization, at least 60% neutralization, at least 70% neutralization, at least 80% neutralization, or at least 90% neutralization. In particular embodiments, antibodies produced according to the disclosure can block infection by a pathogen (i.e., 100% neutralization).

Particular embodiments include methods of producing antibodies with high affinity for an antigen by selecting a population of B cells with down-regulated AIRE function; and contacting the selected B cell population with the antigen; thereby producing antibodies with high affinity for the antigen.

In particular embodiments, high affinity can be confirmed by an increased ratio of binding to $NP_4$ to $NP_{29}$ of the antibodies made by $Aire^{-/-}$ B cells than those made by $Aire^{+/+}$ B cells under comparable conditions. In particular embodiments, the increased ratio can be statistically-significant.

Particular embodiments include kits for producing antibodies with increased SHM and CSR including: a B cell population with down-regulated AIRE function; and an antigen.

Particular embodiments include kits for producing antibodies with increased SHM and CSR including: a B cell population; gene editing agents to down-regulate AIRE function and/or CD40 function in the B cell population; and an antigen.

Aspects of the current disclosure are now described in more detail.

Embodiments disclosed herein include utilizing B cells with down-regulated AIRE activity. In particular embodiments, B cells may naturally have down-regulated AIRE function, as compared to a reference level. Reference levels can include "normal" or "control" levels or values, defined according to, e.g., discrimination limits or defining thresholds, in order to define down-regulated AIRE function. The reference level can include AIRE function levels typically found in natural B cells not associated with a condition that includes down-regulated AIRE function. Other terms for "reference levels" include "index," "baseline," "standard," "healthy," etc. In particular embodiments, "reference level" can refer to a standardized control value for normal AIRE function which represents levels not associated with any pathological disease or condition.

In particular embodiments, B cells may have experimentally down-regulated AIRE function. In these embodiments, normal AIRE function refers to AIRE function observed in the absence of an experimental procedure to down-regulate AIRE function. Down-regulated AIRE function refers to AIRE function following an experimental procedure to down-regulate AIRE function. The different levels can be compared to confirm down-regulated AIRE function, as is understood by one of ordinary skill in the art.

Any method to down-regulate AIRE function can be used. Particular embodiments can utilize gene-editing agents. As used herein, gene editing agents modify or affect a B cell's endogenous genome. In particular embodiments, the modification includes removal or disruption of an endogenous gene such that the endogenous gene's encoded protein is no longer expressed, expressed to a reduced degree, expressed as an incomplete protein, an unstable protein, an incorrectly folded protein and/or a nonfunctional protein. For example, as disclosed herein, AIRE mutants missing one or more of the N-terminal caspase activation and recruitment domain (CARD) and/or nuclear localization signal (NLS) lose the ability to interact with AID. Thus, these forms of AIRE are down-regulated. The current disclosure also provides that AIRE expression in B cells is dependent on CD40 signaling. Accordingly, AIRE function can be down-regulated by interfering with CD40 expression and/or signaling.

Particular embodiments utilize CRISPR-Cas to down-regulate AIRE. CRISPR-Cas systems include CRISPR repeats and a set of CRISPR-associated genes (Cas).

The CRISPR repeats (clustered regularly interspaced short palindromic repeats) include a cluster of short direct repeats separated by spacers of short variable sequences of similar size as the repeats. The repeats range in size from 24 to 48 base pairs and have some dyad symmetry which implies the formation of a secondary structure, such as a hairpin, although the repeats are not truly palindromic. The spacers, separating the repeats, match exactly the sequences from prokaryotic viruses, plasmids, and transposons. The Cas genes encode nucleases, helicases, RNA-binding proteins, and a polymerase that unwind and cut DNA. Cas1, Cas2, and Cas9 are examples of Cas genes.

The source of CRISPR spacers indicate that CRISPR-Cas systems play a role in adaptive immunity in bacteria. There are at least three types of CRISPR-Cas immune system reactions, and Cas1 and Cas2 genes are involved in spacer acquisition in all three. Spacer acquisition, involving the capture and insertion of invading viral DNA into a CRISPR locus occurs in the first stage of adaptive immunity. More particularly, spacer acquisition begins with Cas1 and Cas2 recognizing invading DNA and cleaving a protospacer, which is ligated to the direct repeat adjacent to a leader sequence. Subsequently, single strand extension repairs take place and the direct repeat is duplicated.

The next stage of CRISPR-related adaptive immunity involves CRISPR RNA (crRNA) biogenesis, which occurs differently in each type of CRISPR-Cas system. In general, during this stage, the CRISPR transcript is cleaved by Cas genes to produce crRNAs. In the type I system, Cas6e/Cas6f cleaves the transcript. The type II system employs a trans-activating (tracr) RNA to form a dsRNA, which is cleaved by Cas9 and RNase III. The type III system uses a Cas6 homolog for cleavage.

In the final stage of CRISPR-related adaptive immunity, processed crRNAs associate with Cas proteins to form interference complexes. In type I and type II systems, the Cas proteins interact with protospacer adjacent motifs (PAMs), which are short 3-5 bp DNA sequences, for degradation of invading DNA, while the type III systems do not require interaction with a PAM for degradation. In the type III-B system, the crRNA basepairs with the mRNA, instead of the targeted DNA, for degradation.

CRISPR-Cas systems thus function as an RNAi-like immune system in prokaryotes. The CRISPR-Cas technology has been exploited to inactivate genes in human cell lines and cells. As an example, the CRISPR-Cas9 system, which is based on the type II system, has been used as an agent for genome editing.

The type II system requires three components: Cas9, crRNA, and tracrRNA. The system can be simplified by combining tracrRNA and crRNA into a single synthetic single guide RNA (sgRNA).

At least three different Cas9 nucleases have been developed for genome editing. The first is the wild type Cas9 which introduces double strand breaks (DSBs) at a specific DNA site, resulting in the activation of DSB repair machinery. DSBs can be repaired by the non-homologous end-joining (NHEJ) pathway or by homology-directed repair (HDR) pathway. The second is a mutant Cas9, known as the Cas9D10A, with only nickase activity, which means that it only cleaves one DNA strand and does not activate NHEJ. Thus, the DNA repairs proceed via the HDR pathway only. The third is a nuclease-deficient Cas9 (dCas9) which does not have cleavage activity but is able to bind DNA. Therefore, dCas9 is able to target specific sequences of a genome without cleavage. By fusing dCas9 with various effector domains, dCas9 can be used either as a gene silencing or activation tool.

Other gene-editing agents may also be used. For example, particular embodiments can utilize transcription activator-like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or by homologous recombination (HR) with an exogenous double-stranded donor DNA fragment.

As indicated, TALENs have been engineered to bind a target sequence and cut DNA at the location of the target sequence. The TALEs of TALENs are DNA binding proteins secreted by Xanthomonas bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. The FokI domain functions as a dimer requiring two constructs with unique DNA binding domains for sites on the target sequence. The FokI cleavage domain cleaves within a five or six base pair spacer sequence separating the two inverted half-sites.

Particular embodiments can utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the MegaTAL only requires the delivery of a single peptide chain for functional activity.

Particular embodiments can utilize zinc finger nucleases (ZFNs) as gene editing agents. ZFNs are a class of site-specific nucleases engineered to bind and cleave DNA at specific positions. ZFNs are used to introduce DSBs at a specific site in a DNA sequence which enables the ZFNs to target unique sequences within a genome in a variety of different cells. Moreover, subsequent to DSB, homologous recombination or non-homologous end joining takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease.

Particular embodiments may also utilize interfering RNA-type mechanisms to down-regulate AIRE.

SEQ ID NOs: 1-4 (see FIG. 18) provide exemplary human and mouse AIRE protein and gene sequences. SEQ ID NO: 4 provides an exemplary AIRE gene sequence reflecting GenBank NC_000076.6. SEQ ID NOs: 5-8 provide exemplary human and mouse CD40 protein and gene sequences. Additional nucleic acid sequences encoding AIRE and CD40 proteins can be identified by those of ordinary skill in the art, and can include one or more of various sequence polymorphisms, mutations, and/or sequence variants (e.g., splice variants or codon optimized variants). Sequence information provided by public databases can be used to identify additional gene and protein sequences that can be used with the systems and methods disclosed.

Available prediction software can be used to generate guide RNA sequences to use in the aforementioned gene-editing methods. The utilized guide RNA sequences will be rare or unique in the genome to minimize or eliminate interaction with potential off-target sites. Particular embodiments can utilize the following two single guide RNA (sgRNA) sequences: AIREsg2 (Exon 1) 5'GCACCGCACCGAGATCGCGG (TGG)3' (SEQ ID NO: 9) and AIRE sg3 (Exon 3) 5'ACCTAAACCAGTCCCG-GAAA (GGG)3' (SEQ ID NO: 10).

Embodiments disclosed herein include producing antibodies by exposing B cells with down-regulated AIRE function to antigens. Any antigen can be used. Particular examples include bacterial antigens, viral antigens, fungal antigens, and cancer antigens.

Exemplary bacterial antigens include anthrax protective antigen, lipopolysaccharides, toxin A (tcdA), toxin B (tcdB), capsular polysaccharides, diptheria toxin, α-crystallin, mycolic acid, heat shock protein 65 (HSP65), hemagglutinin, pertactin, FIM2, FIM3, adenylate cyclase, pneumolysin, pneumococcal capsular polysaccharides, type 3 secretion system (T3SS), PcrV protein, PsI exopolysaccharide, rompA, α toxin, and tetanus toxin.

Exemplary viral antigens include envelope glycoprotein B, CMV pp65, EBV EBNAI, EBV P18, EBV P23, the S, M, and L proteins of hepatitis B virus, the pre-S antigen of hepatitis B virus, HBCAG DELTA, HBV HBE, hepatitis C viral RNA, HCV NS3, HCV NS4, HIV gp32, HIV gp41, HIV gp120, HIV gp160, HIV P17/24, HIV P24, HIV P55 GAG, HIV P66 POL, HIV TAT, HIV GP36, the Nef protein, hemagglutinin, neuraminidase, the measles virus fusion protein, rabies glycoprotein, rabies nucleoprotein, the respiratory syncytial viral fusion protein VP7sc, protein E1, and protein E2.

Exemplary fungal antigens include spherule antigens, capsular polysaccharides, heat shock protein 60 (HSP60), gp63, lipophosphoglycan, merozoite surface antigens, sporozoite surface antigens, circumsporozoite antigens, gametocyte/gamete surface antigens, the blood-stage antigen pf 155/RESA, glutathione-S-transferase, paramyosin, trichophytin, SAG-1, and p30.

Exemplary cancer antigens include CD19, CD20, CD33, CD133, ERBB2, GD2, HER2, mesothelin, PSCA, PSMA, ROR1, and WT1.

Particular embodiments disclosed herein include producing antibodies by exposing B cells with down-regulated AIRE function to antigens and adjuvants. An adjuvant refers to a material that enhances the immune response to an antigen. The precise mode of action is not understood for all adjuvants, but such lack of understanding does not prevent their use.

Any adjuvant can be used within the teachings of the current disclosure. Exemplary adjuvants include Toll-like receptor ligands, squalene-based adjuvants, alum, STING agonists, and cytokines.

Exemplary Toll-like receptor ligands include CpG, Cpg-28, Polyriboinosinic polyribocytidylic add (Poly(I:C)), α-galactoceramide, MPLA, Motolimod, imiquimod, MGN1703, and Hiltonol.

Squalene is a triterpene that can be derived from certain plant sources, such as rice bran, wheat germ, amaranth seeds, and olives, as well as from animal sources, such as shark liver oil. Examples of squalene-based adjuvants include MF59® (Novartis, Basel, Switzerland) and Addavax™ (InvivoGen, San Diego, Calif.).

Alum refers to a family of salts that contain two sulfate groups, a monovalent cation, and a trivalent metal, such as aluminum or chromium. Alum is an FDA approved adjuvant.

"STING" is an abbreviation of "stimulator of interferon genes". Exemplary STING agonists include c-AIMP; (3',2') c-AIMP; (2',2')c-AIMP; (2',3')c-AIMP; c-AIMP(S); c-(dAMP-dITMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)](POM)2; and DMXAA.

Naturally occurring antibody structural units include a tetramer. Each tetramer includes two pairs of polypeptide chains, each pair having one light chain and one heavy chain.

The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific antigen epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989).

As indicated previously, SMH occurs in the CDR regions including the 3 heavy chain CDRs and the 3 light chain CDRs. Systems and methods disclosed herein can result in an increased mutation rate in CDR regions and/or FR regions (see, e.g., FIG. 13B). Thus, as used herein, increased SHM can include increased SHM in CDR regions and/or FR regions. An important feature of many neutralizing antibodies (e.g., HIV-1 neutralizing antibodies) is the increased number of mutations in FR regions (which is usually not mutated or poorly mutated during "regular" SHM (i.e., SHM in the absence of AIRE downregulation). Particular embodiments disclosed herein include producing antibodies with increased FR mutations.

The carboxy-terminal portion of each chain defines a constant region that can be responsible for effector function. Examples of effector functions include: C1q binding and complement dependent cytotoxicity (CDC); antibody-dependent cell-mediated cytotoxicity (ADCC); phagocytosis; down regulation of cell surface receptors (e.g. B cell receptors); and B cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgA is similarly subdivided into subclasses including IgA1 and IgA2. As indicated previously, CSR rearranges the immunoglobulin (Ig) heavy chain constant region genes from IgM or IgD to an IgG, IgA or IgE.

A human antibody is one which includes an amino acid sequence which corresponds to that of an antibody produced by a human or a human cell or derived from a non-human source that utilizes human antibody repertoires or other human antibody-encoding sequences.

Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Human antibodies may be prepared by administering an antigen to a transgenic animal that has been modified to produce intact human antibodies or intact antibodies with human variable regions in response to antigenic challenge. Such animals contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Traditional strategies for hybridoma development using mice, llamas, chicken, rats, hamsters, rabbits, etc. can also be used.

If produced antibodies are not human, such antibodies can be humanized. A "humanized" antibody refers to a chimeric antibody including amino acid residues from non-human CDRs and amino acid residues from human FRs. In particular embodiments, a humanized antibody will include substantially all of at least one, and typically two, variable domains, in which all or substantially all of the CDRs correspond to those of a non-human antibody, and all or substantially all of the FRs correspond to those of a human antibody. A humanized antibody optionally may include at least a portion of an antibody constant region derived from a human antibody. A "humanized form" of an antibody, e.g., a non-human antibody, refers to an antibody that has undergone humanization.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Nati. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

A human consensus framework is a framework which represents the most commonly occurring amino acid residues in a selection of human immunoglobulin variable light ($V_L$) or variable heavy ($V_H$) framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

Once antibodies have been generated, their CDRs can be identified. Definitive delineation of a CDR and identification of residues including the binding site of an antibody can be accomplished by solving the structure of the antibody and/or solving the structure of the antibody-antigen complex. In particular embodiments, this can be accomplished by methods such as X-ray crystallography.

CDRs from antibodies produced according to the methods disclosed herein can be utilized in a variety of binding domain formats. For example, particular embodiments can include binding fragments of an antibody, e.g., Fv, Fab, Fab', $F(ab')_2$, Fc, and single chain Fv fragments (scFvs) or any biologically effective fragments of an immunoglobulin that bind specifically to targeted antigen.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody, but lack the constant regions. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including $V_L$, $V_H$, CL and CH1 domains. A $F(ab')_2$ fragment is a bivalent fragment including two Fab fragments linked by a disulfide bridge at the hinge region. For discussion of Fab and $F(ab')_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011))) can also be formed. Antibody fragments can also include isolated CDRs. For a review of antibody fragments, see Hudson, et al., Nat. Med. 9 (2003) 129-134.

Unless otherwise indicated, the term "antibody" includes antibodies including two full-length heavy chains and two full-length light chains, the fragments as described above, and variants. Furthermore, unless explicitly excluded, antibodies can include monoclonal antibodies, human or humanized antibodies, bispecific antibodies, polyclonal antibodies, linear antibodies, minibodies, domain antibodies, synthetic antibodies, chimeric antibodies, antibody fusions, and fragments thereof, respectively.

A monoclonal antibody refers to an antibody obtained from a population of substantially homogeneous antibodies, i.e., the individual antibodies including the population are identical and/or bind the same antigen epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes of an antigen, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, monoclonal antibodies can be made by a variety of techniques, including the hybridoma method, recombinant DNA methods, and methods utilizing transgenic animals containing all or part of the human immunoglobulin loci.

Variants of antibodies can include those having one or more conservative amino acid substitutions or one or more non-conservative substitutions that do not adversely affect the binding of the antibody.

In particular embodiments, a conservative amino acid substitution may not substantially change the structural characteristics of the reference antibody (e.g., a replacement amino acid should not tend to break a helix that occurs in the reference sequence, or disrupt other types of secondary structure that characterizes the reference sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden & J. Tooze, eds., Garland Publishing, New York, N.Y. (1991)); and Thornton et al., Nature, 354:105 (1991).

In particular embodiments, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

In particular embodiments, a $V_L$ region can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared to an antibody produced and characterized according to methods disclosed herein. An insertion, deletion or substitution may be anywhere in the $V_L$ region, including at the amino- or carboxy-terminus or both ends of this region, provided that each CDR includes zero changes or at most one, two, or three changes and provided an antibody including the modified $V_L$ region can still specifically bind its target antigen with an affinity similar to the reference antibody.

In particular embodiments, a $V_H$ region can be derived from or based on a disclosed $V_H$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with when compared to an antibody produced and characterized according to methods disclosed herein. An insertion, deletion or substitution may be anywhere in the $V_H$ region, including at the amino- or carboxy-terminus or both ends of this region, provided that each CDR includes zero changes or at most one, two, or three changes and provided an antibody including the modified $V_H$ region can still specifically bind its target epitope with an affinity similar to the reference antibody.

In particular embodiments, one or more amino acid modifications may be introduced into the Fc region of an antibody, thereby generating an Fc region variant. The Fc region variant may include a human Fc region sequence (e.g., a human IgG1, IgG2, IgG3 or IgG4 Fc region) including an amino acid modification (e.g. a substitution) at one or more amino acid positions.

In particular embodiments, variants have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live.

Antibodies produced according to the methods disclosed herein have high affinity for their target antigens. In particular embodiments "affinity" refers to the strength of the sum total of noncovalent interactions between a single binding site of an antibody and its target antigen. Unless indicated otherwise, "binding affinity" refers to intrinsic binding affinity which reflects a 1:1 interaction between members of a binding pair (i.e., antibody and target antigen). The affinity of an antibody for its target antigen can generally be represented by the dissociation constant (Kd) or the association constant ($K_A$). Affinity can be measured by common methods known in the art.

In particular embodiments, binding affinities can be assessed in relevant in vitro conditions, such as a buffered salt solution approximating physiological pH (7.4) at room temperature or 37° C.

In particular embodiments, "high affinity" means that the antibody associates with its target antigen with a dissociation constant (1(D) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the antibody does not bind to other biomolecules present, (e.g., it binds to other biomolecules with a dissociation constant (KD) of $10^{-4}$ M or more, in particular embodiments of from $10^{-4}$ M to 1 M).

In particular embodiments, "high affinity" means that the antibody associates with its target antigen with an affinity constant (i.e., association constant, $K_A$) of $10^7$ $M^{-1}$ or more, in particular embodiments of from $10^5$ $M^{-1}$ to $10^{13}$ $M^{-1}$, in particular embodiments of from $10^5 M^{-1}$ to $10^{10}$ $M^{-1}$, in particular embodiments of from $10^5$ $M^{-1}$ to $10^8$ $M^{-1}$, in particular embodiments of from $10^7$ $M^{-1}$ to $10^{13}$ $M^{-1}$, or in particular embodiments of from $10^7$ $M^{-1}$ to $10^8$ $M^{-1}$. The term can be further used to indicate that the antibody does not bind to other biomolecules present, (e.g., it binds to other biomolecules with an association constant ($K_A$) of $10^4$ $M^{-1}$ or less, in particular embodiments of from $10^4$ $M^{-1}$ to 1 $M^{-1}$).

In particular embodiments, "high affinity" is relative to an antibody produced in the absence of AIRE down-regulation.

In particular embodiments, developed antibodies can be produced from a gene using a protein expression system. Protein expression systems can utilize DNA constructs (e.g., chimeric genes, expression cassettes, expression vectors, recombination vectors) including a nucleic acid sequence encoding the protein or proteins of interest operatively linked to appropriate regulatory sequences. In particular embodiments, such DNA constructs are not naturally-occurring DNA molecules and are useful for introducing DNA into host-cells to express selected proteins of interest. In particular embodiments, a DNA construct that encodes an antibody can be inserted into cells (e.g., bacterial, mammalian, insect, etc.), which can produce the antibody encoded by the DNA construct.

Operatively linked refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N.Y., 1989.

Expression control sequences are DNA sequences involved in any way in the control of transcription or translation. Suitable expression control sequences and methods of making and using them are well known in the art. Expression control sequences generally include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979.

The promoter may include, or be modified to include, one or more enhancer elements. In particular embodiments, the promoter will include a plurality of enhancer elements. Promoters including enhancer elements can provide for higher levels of transcription as compared to promoters that do not include them.

For efficient expression, the coding sequences can be operatively linked to a 3' untranslated sequence. In particular embodiments, the 3' untranslated sequence can include a transcription termination sequence and a polyadenylation sequence. The 3' untranslated region can be obtained, for example, from the flanking regions of genes.

In particular embodiments, a 5' untranslated leader sequence can also be employed. The 5' untranslated leader sequence is the portion of an mRNA that extends from the 5' CAP site to the translation initiation codon.

In particular embodiments, a "hisavi" tag can be added to the N-terminus or C-terminus of a gene by the addition of nucleotides coding for the Avitag amino acid sequence, "GLNDIFEAQKIEWHE" (SEQ ID NO: 11), as well as the 6x histidine tag coding sequence "HHHHHH (SEQ ID NO: 12)". The Avitag avidity tag can be biotinylated by a biotin ligase to allow for biotin-avidin or biotin-streptavidin based interactions for protein purification, as well as for immunobiology (such as immunoblotting or immunofluorescence) using anti-biotin antibodies. The 6x histidine tag allows for protein purification using $Ni^{-2+}$ affinity chromatography.

In particular embodiments, the DNA constructs can be introduced by transfection, a technique that involves introduction of foreign DNA into the nucleus of eukaryotic cells. In particular embodiments, the proteins can be synthesized by transient transfection (DNA does not integrate with the genome of the eukaryotic cells, but the genes are expressed for 24-96 hours). Various methods can be used to introduce the foreign DNA into the host-cells, and transfection can be achieved by chemical-based means including by the calcium phosphate, by dendrimers, by liposomes, and by the use of cationic polymers. Non-chemical methods of transfection include electroporation, sono-poration, optical transfection, protoplast fusion, impalefection, and hydrodynamic delivery. In particular embodiments, transfection can be achieved by particle-based methods including gene gun where the DNA construct is coupled to a nanoparticle of an inert solid which is then "shot" directly into the target-cell's nucleus. Other particle-based transfection methods include magnet assisted transfection and impalefection.

EXEMPLARY EMBODIMENTS

Exemplary Embodiments—Set 1

1. A method of increasing somatic hypermutation (SHM) and class switch recombination (CSR) during antibody production including selecting a first population of B cells with down-regulated autoimmune regulator (AIRE) function; and contacting the first selected B cell population with an antigen; thereby increasing SHM and CSR during antibody production wherein the increase is in relation to antibodies produced by selecting a second population of B cells with normal AIRE function; and contacting the second selected B cell population with the same antigen under comparable conditions.

2. A method of embodiment 1 further including contacting the first selected B cell population and the second selected B cell population with an adjuvant.

3. A method of embodiment 1 or 2 further including isolating the produced antibodies with increased SHM and CSR.

4. A method of any of embodiments 1-3 further including determining the CDR sequences of the produced antibodies with increased SHM and CSR.

5. A method of any of embodiments 1-4 further including modifying B cells to down-regulate AIRE function.

6. A method of embodiment 5 wherein the modifying produces the selected population of B cells of embodiment 1.

7. A method of embodiment 5 or 6 wherein the modifying includes AIRE gene editing and/or CD40 gene editing.

8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.

9. A method of any of embodiments 5-8 wherein the AIRE gene editing includes contacting the modified B cells with SEQ ID NO: 9 and SEQ ID NO: 10.

10. A method of any of embodiments 5-8 wherein the modifying results in AIRE protein that does not interact with AID.

11. A method of embodiment 10 wherein the AIRE protein lacks its caspase activation and recruitment domain (CARD) and/or its nuclear localization signal (NLS).

12. A method of embodiment 10 wherein the AIRE protein lacks amino acids 110-114 and 131-133 or lacks amino acids 101-180.

13. A method of any of embodiments 1-12 wherein the selected first and second B cell populations are within different but comparable in vitro culture conditions.

14. A method of embodiment 13 further including stimulating the first and second B cell populations within the in vitro culture conditions.

15. A method of embodiment 14 wherein the stimulating includes adding CD40L, IL-4, IFN-γ or TGF-β

16. A method of any of embodiments 1-12 wherein the selected first and second B cell populations are in vivo in a subject.

17. A method of embodiment 16 wherein the in vivo selected B cell populations are within a mouse, llama, chicken, rat, hamster, or rabbit.

18. A method of embodiment 16 or 17 further including administering the selected first population of B cells to the subject.

19. A method of embodiment 18 wherein the selected first population of B cells are $AIRE^{-/-}$.

20. A method of embodiment 17 wherein the mouse produces human antibodies.

21. A method of any of embodiments 1-20 wherein the produced antibodies are human antibodies.

22. A method of any of embodiments 1-20 wherein the produced antibodies are non-human antibodies.

23. A method of embodiment 22 further including humanizing the produced antibodies.

24. A method of any of embodiments 1-23 wherein the antigen is a viral antigen, a bacterial antigen, a fungal antigen, or a cancer antigen.

25. A method of any of embodiments 2-24 wherein the adjuvant is a Toll-like receptor ligand, a squalene-based adjuvant, alum, a STING agonist, and/or a cytokine.

26. A method of any of embodiments 1-25 wherein the increased SHM is within CDR regions, FR regions, or CDR regions and FR regions.

Exemplary Embodiments—Set 2

1. A method of producing a neutralizing antibody including selecting a population of B cells with down-regulated autoimmune regulator (AIRE) function; and contacting the selected B cell population with an antigen; thereby producing a neutralizing antibody.

2. A method of embodiment 1 further including contacting the selected B cell population with an adjuvant.

3. A method of embodiment 1 or 2 further including isolating the neutralizing antibody.

4. A method of any of embodiments 1-3 further including determining the CDR sequences of the neutralizing antibody.

5. A method of any of embodiments 1-4 further including modifying B cells to down-regulate AIRE function.

6. A method of embodiment 5 wherein the modifying produces the selected population of B cells of embodiment 1.

7. A method of embodiment 5 or 6 wherein the modifying includes AIRE gene editing and/or CD40 gene editing.

8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.

9. A method of any of embodiments 5-8 wherein the AIRE gene editing includes contacting the modified B cells with SEQ ID NO: 9 and SEQ ID NO: 10.

10. A method of any of embodiments 5-8 wherein the modifying results in AIRE protein that does not interact with AID.

11. A method of embodiment 10 wherein the AIRE protein lacks its caspase activation and recruitment domain (CARD) and/or its nuclear localization signal (NLS).

12. A method of embodiment 10 wherein the AIRE protein lacks amino acids 110-114 and 131-133 or lacks amino acids 101-180.

13. A method of any of embodiments 1-12 wherein the selected B cell population is within in vitro culture conditions.

14. A method of embodiment 13 further including stimulating the B cell population within the in vitro culture conditions.

15. A method of embodiment 14 wherein the stimulating includes adding CD40L, IL-4, IFN-γ or TGF-β

16. A method of any of embodiments 1-12 wherein the selected B cell population is in vivo in a subject.

17. A method of embodiment 16 wherein the in vivo selected B cell population is within a mouse, llama, chicken, rat, hamster, or rabbit.

18. A method of embodiment 16 or 17 further including administering the selected B cell population to the subject.

19. A method of embodiment 18 wherein the selected B cell population is $AIRE^{-/-}$.

20. A method of embodiment 17 wherein the mouse produces a human neutralizing antibody.

21. A method of any of embodiments 1-20 wherein the produced neutralizing antibody is a human neutralizing antibody.

22. A method of any of embodiments 1-20 wherein the produced neutralizing antibody is a non-human neutralizing antibody.

23. A method of embodiment 22 further including humanizing the produced neutralizing antibody.

24. A method of any of embodiments 1-23 wherein the antigen is a viral antigen, a bacterial antigen, a fungal antigen, or a cancer antigen.

25. A method of any of embodiments 2-24 wherein the adjuvant is a Toll-like receptor ligand, a squalene-based adjuvant, alum, a STING agonist, and/or a cytokine.

Exemplary Embodiments—Set 3

1. A method of producing antibodies with high affinity for an antigen including selecting a population of B cells with down-regulated autoimmune regulator (AIRE) function; and contacting the selected B cell population with the antigen; thereby producing antibodies with high affinity for the antigen.

2. A method of embodiment 1 further including contacting the selected B cell population with an adjuvant.

3. A method of embodiment 1 or 2 further including isolating the produced antibodies.

4. A method of any of embodiments 1-3 further including determining the CDR sequences of the produced antibodies.

5. A method of any of embodiments 1-4 further including modifying B cells to down-regulate AIRE function.

6. A method of embodiment 5 wherein the modifying produces the selected population of B cells of embodiment 1.

7. A method of embodiment 5 or 6 wherein the modifying includes AIRE gene editing and/or CD40 gene editing.

8. A method of embodiment 7 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.

9. A method of any of embodiments 5-8 wherein the AIRE gene editing includes contacting the modified B cells with SEQ ID NO: 9 and SEQ ID NO: 10.

10. A method of any of embodiments 5-9 wherein the modifying results in AIRE protein that does not interact with AID.

11. A method of embodiment 10 wherein the AIRE protein lacks its caspase activation and recruitment domain (CARD) and/or its nuclear localization signal (NLS).

12. A method of embodiment 11 wherein the AIRE protein lacks amino acids 110-114 and 131-133 or lacks amino acids 101-180.

13. A method of any of embodiments 1-13 wherein the selected B cell population is within an in vitro culture.

14. A method of embodiment 13 further including stimulating the B cell population within the in vitro culture conditions.

15. A method of embodiment 14 wherein the stimulating includes adding CD40L, IL-4, IFN-γ or TGF-β.

16. A method of any of embodiments 1-15 wherein the selected B cell population is in vivo.

17. A method of embodiment 16 wherein the in vivo selected B cell populations are within a mouse, llama, chicken, rat, hamster, or rabbit.

18. A method of embodiment 16 or 17 further including administering the selected first population of B cells to the subject.

19. A method of embodiment 18 wherein the selected first population of B cells are $AIRE^{-/-}$.

20. A method of embodiment 17 wherein the mouse produces human antibodies.

21. A method of any of embodiments 1-20 wherein the produced antibodies are human antibodies.

22. A method of any of embodiments 1-21 wherein the produced antibodies are non-human antibodies.

23. A method of embodiment 22 further including humanizing the produced antibodies.

24. A method of any of embodiments 1-23 wherein the antigen is a viral antigen, a bacterial antigen, a fungal antigen, or a cancer antigen.

25. A method of any of embodiments 2-24 wherein the adjuvant is a Toll-like receptor ligand, a squalene-based adjuvant, alum, a STING agonist, and/or a cytokine.

Exemplary Embodiments—Set 4

1. A kit for antibodies including: a B cell population with down-regulated AIRE function; and an antigen.

2. A kit of embodiment 1 further including an adjuvant.

3. A kit of embodiment 1 or 2 further including CD40L, IL-4, IFN-γ and/or TGF-β.

4. A kit of any of embodiments 1-3 wherein the B cell population is in vitro.

5. A kit of any of embodiments 1-3 wherein the B cell population is in vivo.

6. A kit of any of embodiments 1-3 including an in vitro B cell population with down-regulated AIRE function and an in vivo B cell population with down-regulated AIRE function.

7. A kit of any of embodiments 1-6 wherein the B cell population is $AIRE^{-/-}$.

8. A kit of any of embodiments 1-6 wherein the B cell population expresses an AIRE protein that does not interact with AID.

9. A kit of embodiment 8 wherein the AIRE protein lacks its caspase activation and recruitment domain (CARD) and/or its nuclear localization signal (NLS).

10. A kit of embodiment 9 wherein the AIRE protein lacks amino acids 110-114 and 131-133 or lacks amino acids 101-180.

11. A kit of embodiment 5 or 6 wherein the in vivo B cell population is within a mouse, llama, chicken, rat, hamster, or rabbit.

12. A kit of embodiment 11 wherein the mouse produces human antibodies.

13. A kit of any of embodiments 1-12 wherein the antigen is a viral antigen, a bacterial antigen, a fungal antigen, or a cancer antigen.

14. A kit of any of embodiments 2-13 wherein the adjuvant is a Toll-like receptor ligand, a squalene-based adjuvant, alum, a STING agonist, and/or a cytokine.

Exemplary Embodiments—Set 5

1. A kit for producing antibodies including: a B cell population; gene editing agents to down-regulate AIRE function and/or CD40 function in the B cell population; and an antigen.

2. A kit of embodiment 1 further including an adjuvant.

3. A kit of embodiment 1 or 2 further including CD40L, IL-4, IFN-γ and/or TGF-β.

4. A kit of any of embodiments 1-3 wherein the B cell population is in vitro.

5. A kit of any of embodiments 1-3 wherein the B cell population is in vivo.

6. A kit of any of embodiments 1-3 including an in vitro B cell population with down-regulated AIRE function and an in vivo B cell population with down-regulated AIRE function.

7. A kit of any of embodiments 1-6 wherein the B cell population is $AIRE^{-/-}$.

8. A kit of any of embodiments 1-6 wherein the B cell population expresses an AIRE protein that does not interact with AID.

9. A kit of embodiment 8 wherein the AIRE protein lacks its caspase activation and recruitment domain (CARD) and/or its nuclear localization signal (NLS).

10. A kit of embodiment 9 wherein the AIRE protein lacks amino acids 110-114 and 131-133 or lacks amino acids 101-180.

11. A kit of embodiment 5 or 6 wherein the in vivo B cell population is within a mouse, llama, chicken, rat, hamster, or rabbit.

12. A kit of embodiment 11 wherein the mouse produces human antibodies.

13. A kit of any of embodiments 1-12 wherein the antigen is a viral antigen, a bacterial antigen, a fungal antigen, or a cancer antigen.

14. A kit of any of embodiments 2-13 wherein the adjuvant is a Toll-like receptor ligand, a squalene-based adjuvant, alum, a STING agonist, and/or a cytokine.

15. A kit of any of embodiments 1-14 wherein the AIRE gene editing and/or CD40 gene editing includes CRISPR-Cas gene editing, transcription activator like effector nuclease (TALEN) gene editing, MegaTal gene editing, or zinc finger nuclease (ZFN) gene editing.

16. A kit of any of embodiments 1-15 wherein the gene editing agents include SEQ ID NO: 9 and/or SEQ ID NO: 10.

Also provided is use of a method or kit of any of the preceding embodiments to increase SHM mutations in the FR regions of antibodies.

Example 1. AIRE inhibits AID-mediated antibody diversification in germinal centre B cells and limits autoimmunity. Example 1 shows that AIRE is expressed in GC B cells in a CD40-dependent manner, interacts via its caspase activation and recruitment domain (CARD) and nuclear localization signal (NLS) with AID, and negatively regulates AID-mediated antibody diversification. AIRE-deficient mouse B cells undergo elevated CSR and affinity maturation after antigenic stimulation, which correlates with enhanced generation of genomic uracil, elevated Ig SHM, augmented AID targeting to Ig switch regions and increased interaction of AID with transcriptionally stalled RNA polymerase II (Pol II). Consistently, naive B cells of APS-1 patients undergo increased CSR upon stimulation ex vivo. Mice with AIRE deficiency in B cells have elevated levels of autoantibodies against T helper 17 ($T_H17$) effector cytokines and heightened skin *C. albicans* burden after infection, which recapitulates APS-1 patients. The disclosed results define a previously unknown but crucial B cell-intrinsic AIRE-dependent GC checkpoint of antibody diversification that limits autoimmunity, and illuminate new approaches of generating high-affinity neutralizing antibodies for therapeutic, diagnostic and research applications.

Figure 1B:
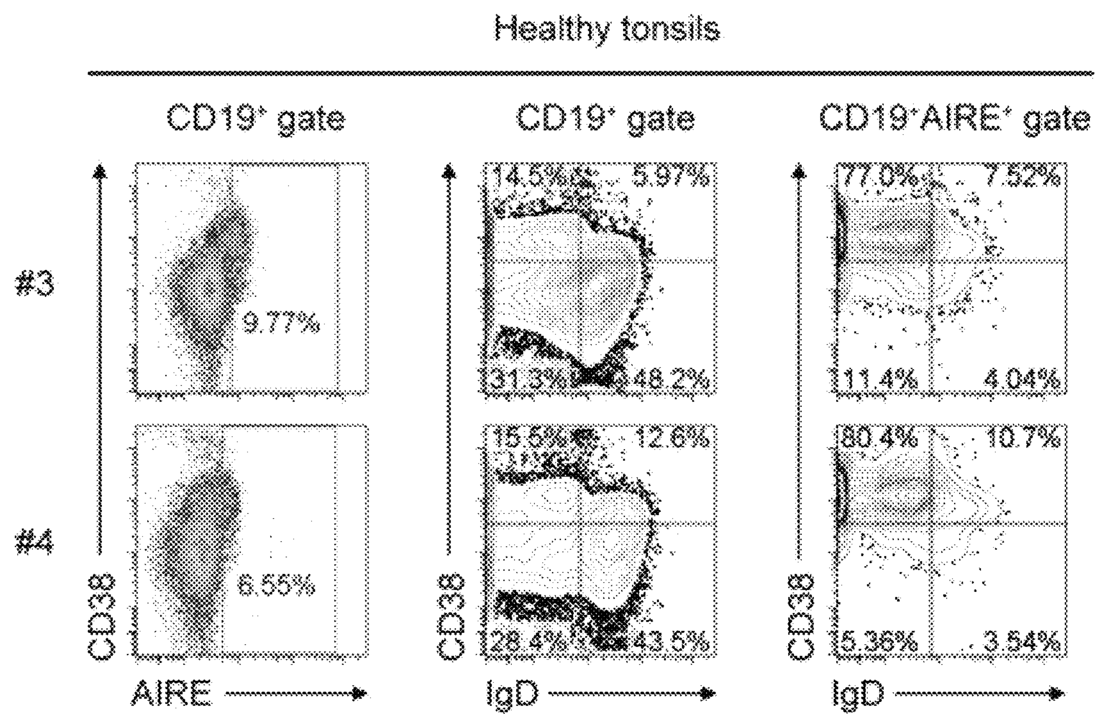
Figure 1C:
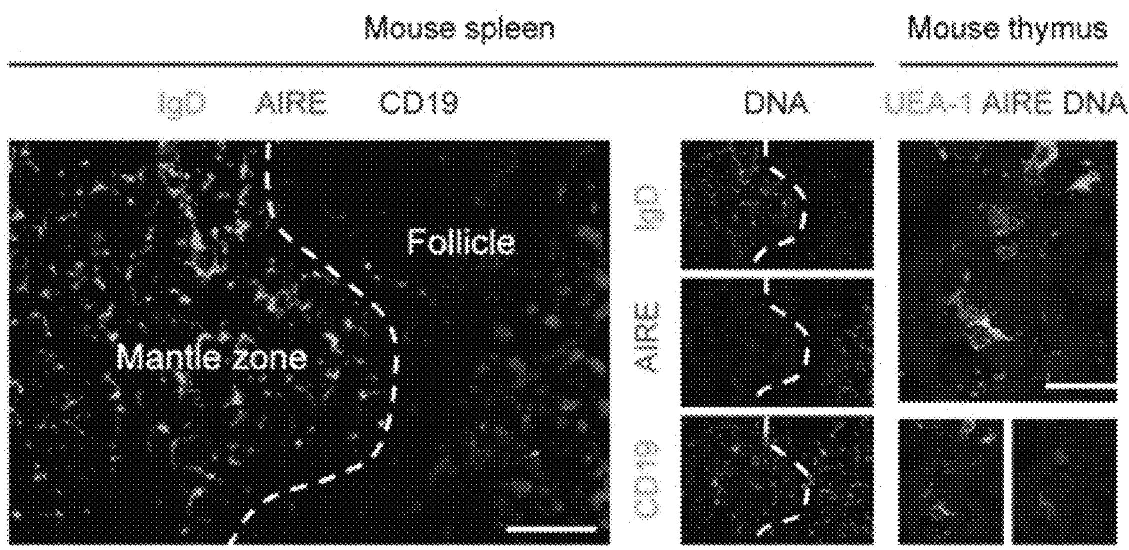
Figure 1D:
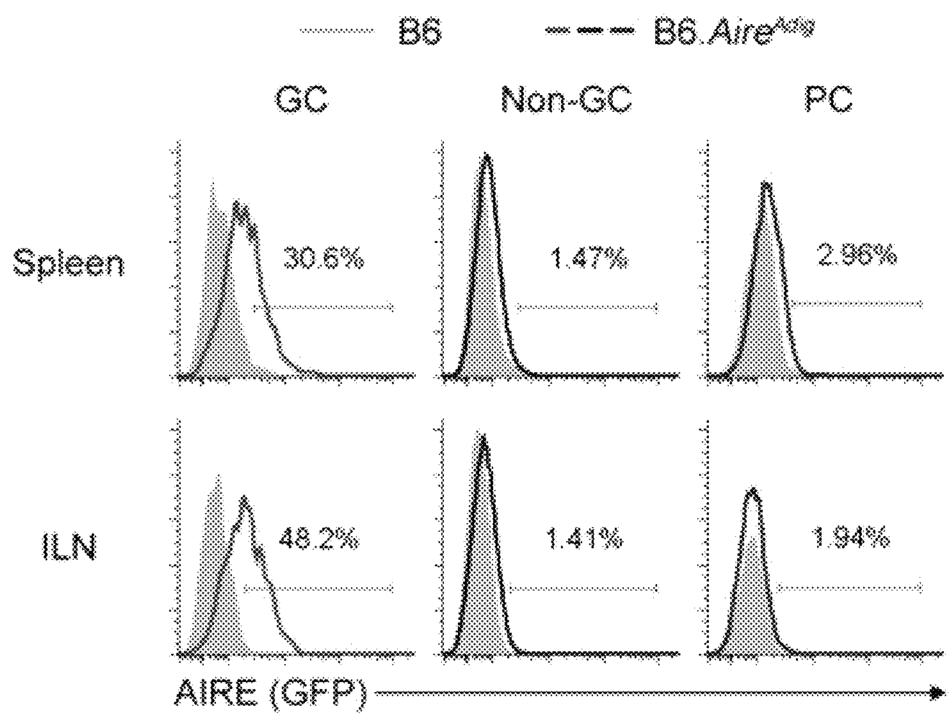
Figure 1E:
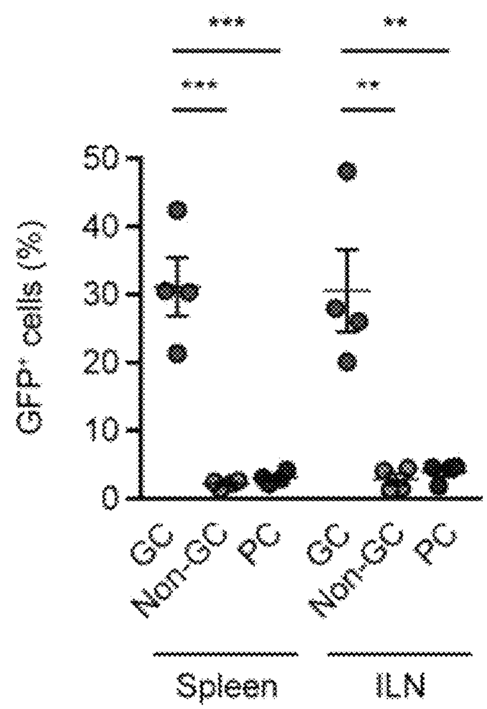
Figure 1F:
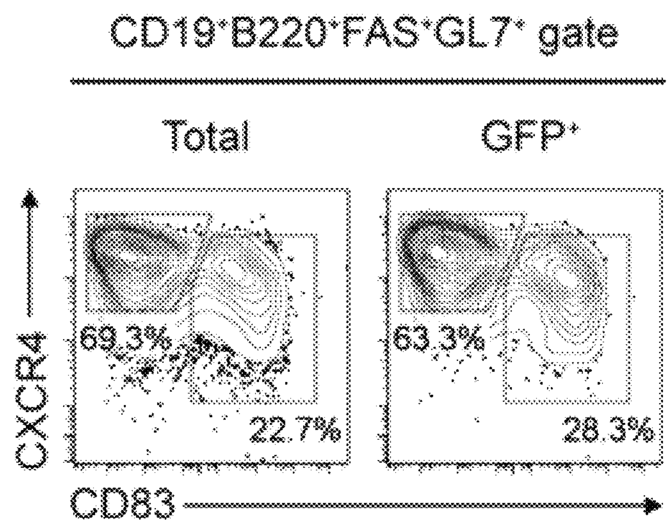
Figure 2A:
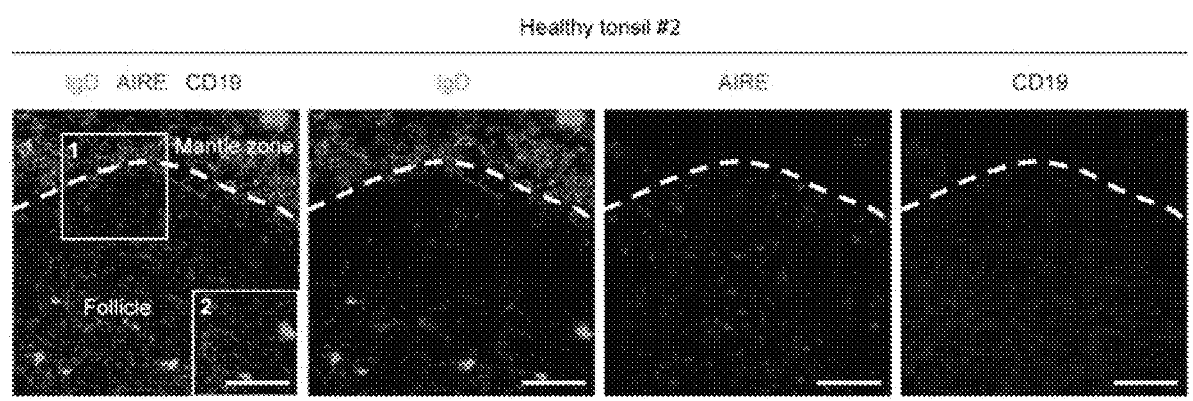
FIGS. 2A-2H. GC B cells in secondary lymphoid tissues express AIRE.
Figure 2B:
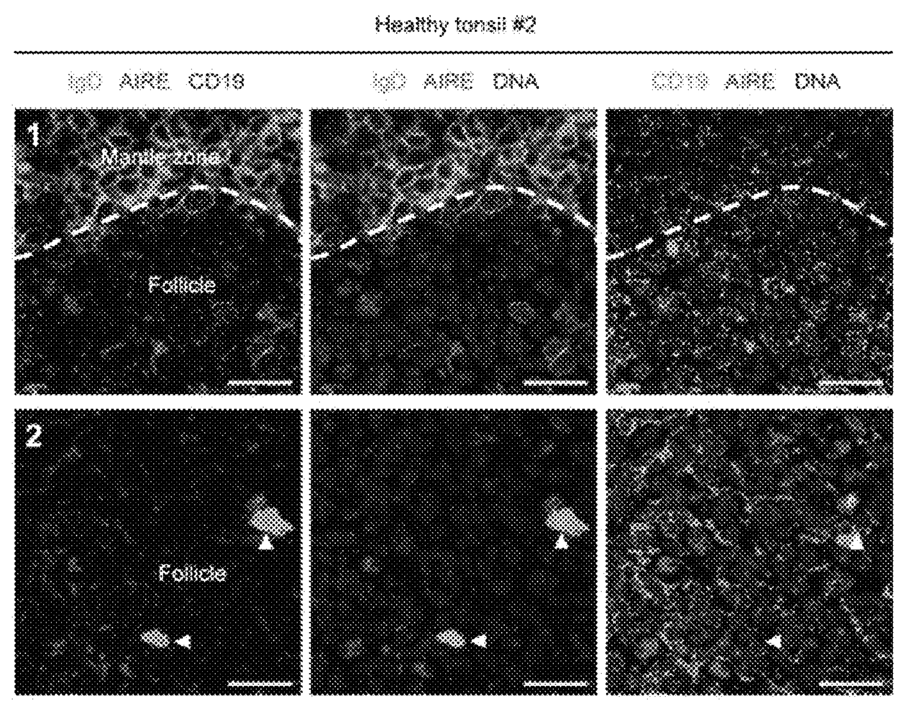
Figure 2C:
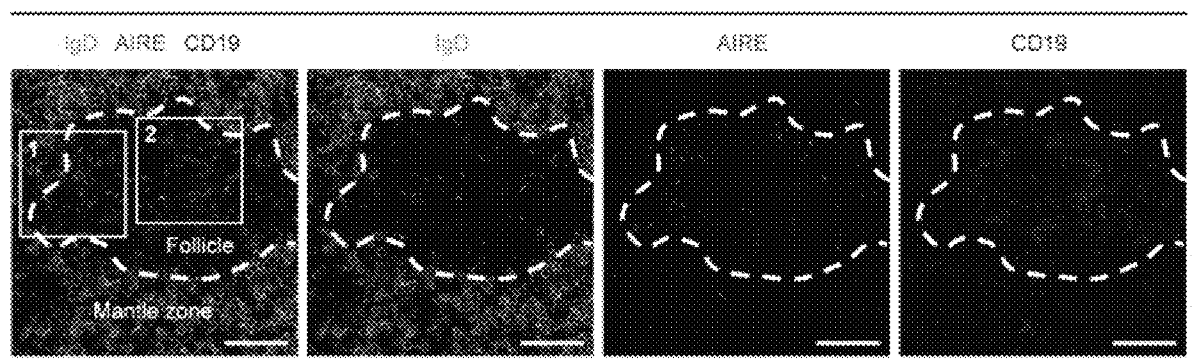
Figure 2D:
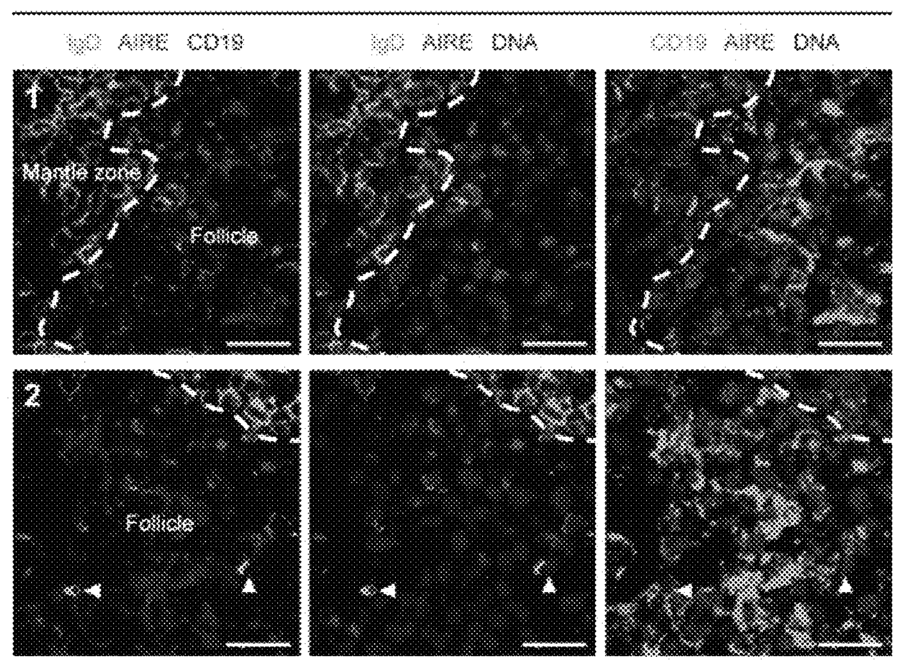
Figure 2E:
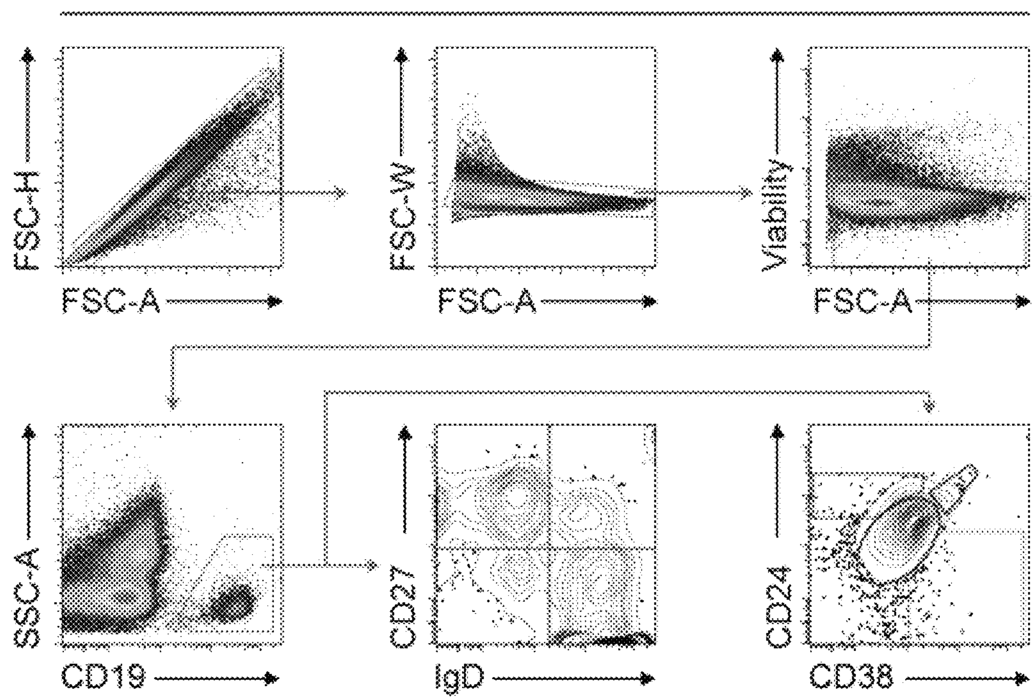
Figure 2F:
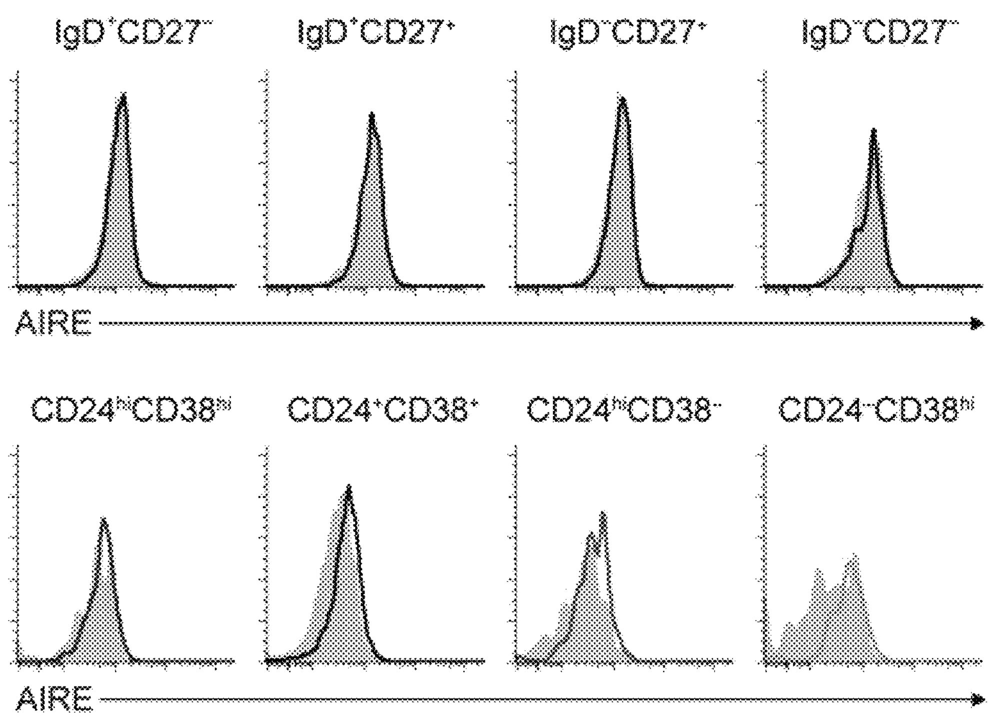
Figure 2G:
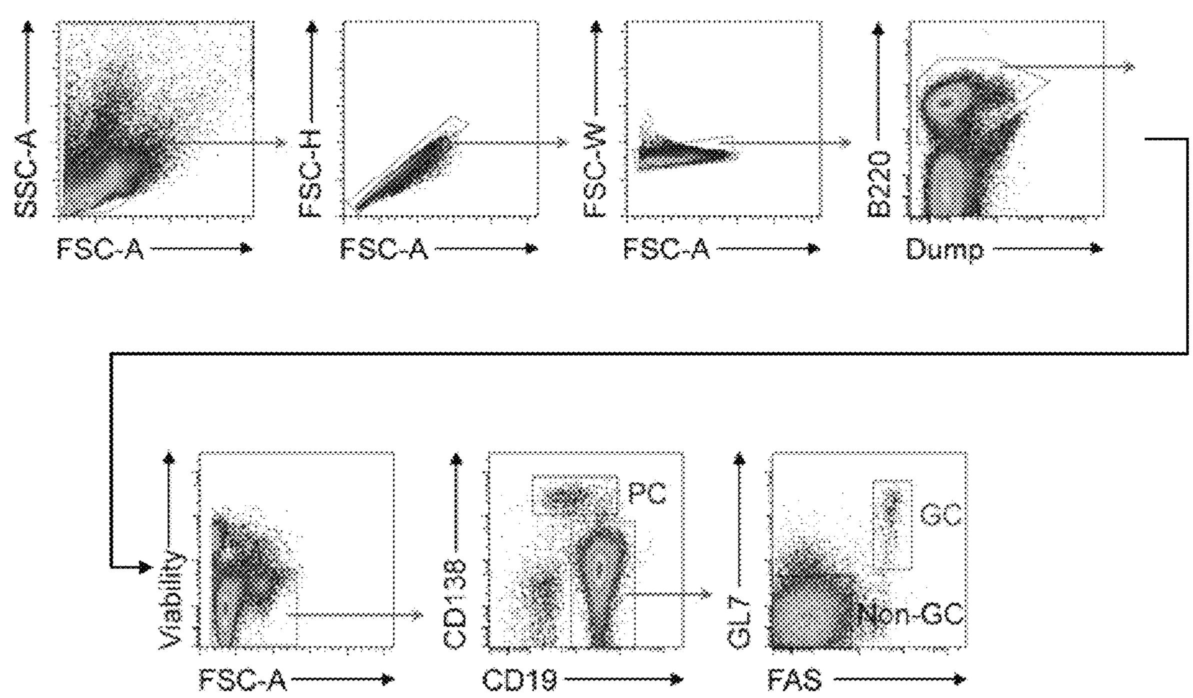
Figure 2H:
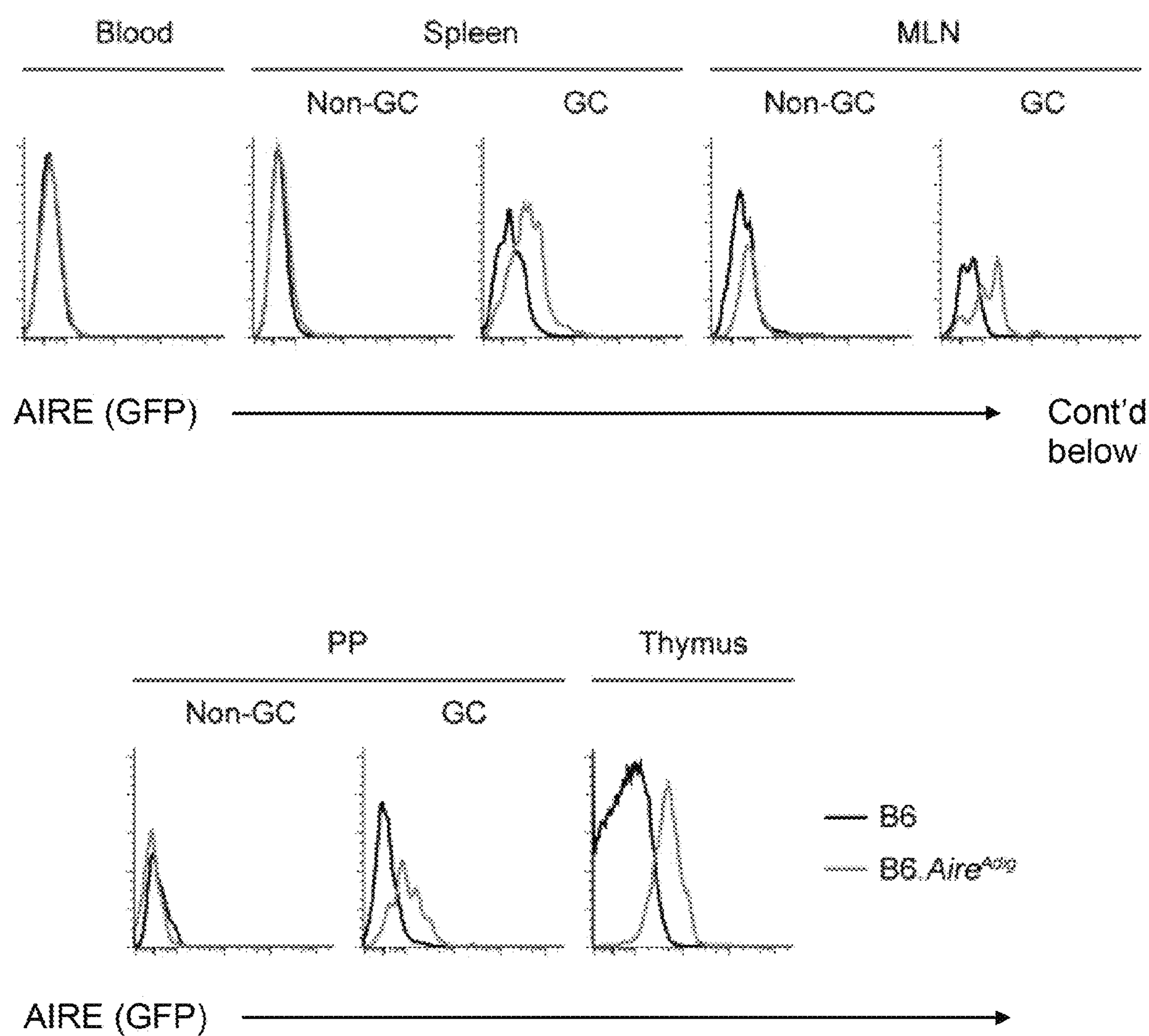

AIRE is essential to central and peripheral T cell tolerance, which consequently regulates humoral immunity. Anderson, et al. *Science* 298, 1395-1401, (2002); Gardner, et al. *Science* 321, 843-847, (2008); Malchow, et al. *Science* 339, 1219-1224, (2013). To determine whether AIRE has a B cell-intrinsic function in humoral immunity, AIRE expression in B cells of human secondary lymphoid tissues was examined by immunofluorescence using an antibody that detects AIRE in the nuclei of thymic medullary epithelial cells (mTECs) (FIG. 1A). $IgD^-$ B cells were identified inside tonsillar and splenic follicles that harbored nuclear AIRE (FIG. 1A, FIGS. 2A-2D). In contrast, tonsillar $IgD^+$ B cells in the mantle zone and $IgD^+$ plasmablasts in GCs and extrafollicular areas (Chen, et al. *Nature immunology* 10, 889-898, (2009)) expressed little or no AIRE (FIG. 1A, FIGS. 2A-2D). Peripheral blood $IgD^+CD27^-$ or $CD24^+CD38^{lo}$ naive, $IgD^+CD27^+$ circulating marginal zone, $IgD^-CD27^+$ or $CD24^{hi}CD38^-$ memory, $IgD^-CD27^-$ atypical memory and $CD24^{hi}CD38^{hi}$ transitional B cells as well as $CD24^-CD38^{hi}$ plasma cells (PCs) did not express AIRE either (FIGS. 2E,2F). Consistent with their follicular localization, tonsillar $AIRE^+$ B cells were mostly $IgD^-CD38^+$ GC B cells (FIG. 1B). AIRE expression was similarly found in B cells in the splenic follicles of immunized mice (FIG. 1C). In the $Aire^{Adig}$ reporter mice (Gardner, et al. *Science* 321, 843-847, (2008)), B cell AIRE expression was detected in $FAS^+GL7^+$ GC B cells in the spleen, inguinal lymph nodes (ILNs), mesenteric lymph nodes (MLNs) and Peyer's patches (PPs) and in thymic B cells, but not in $FAS^-GL7^-$ non-GC B cells or $CD138^+$ PCs in these tissues or in peripheral blood B cells (FIGS. 1D, 1E, FIGS. 2G, 2H), and there was no preferential distribution of AIRE in $CXCR4^+CD83^-$ dark zone (DZ) vs. $CXCR4^{lo}CD83^+$ light zone (LZ) B cells (FIG. 1F). These data indicate that AIRE expression in GC B cells is a conserved characteristic of human and mouse secondary lymphoid tissues.

Figure 1G:
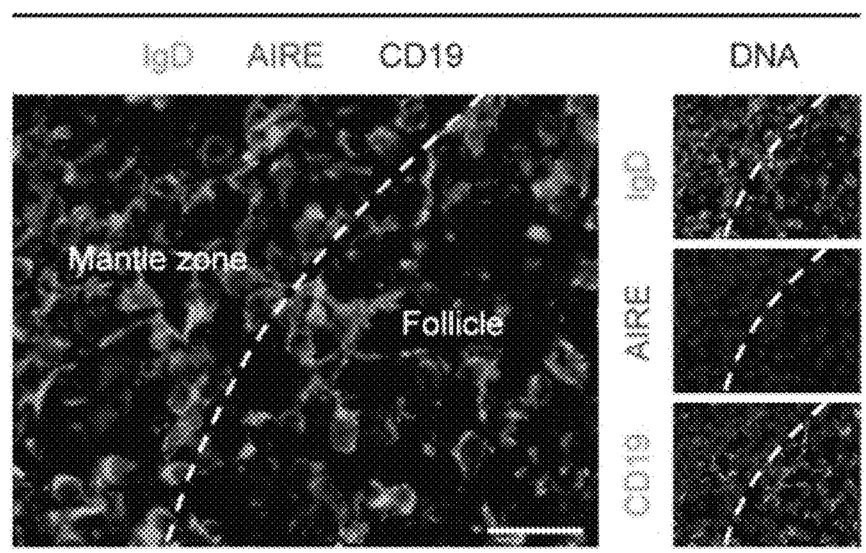
Figure 1H:
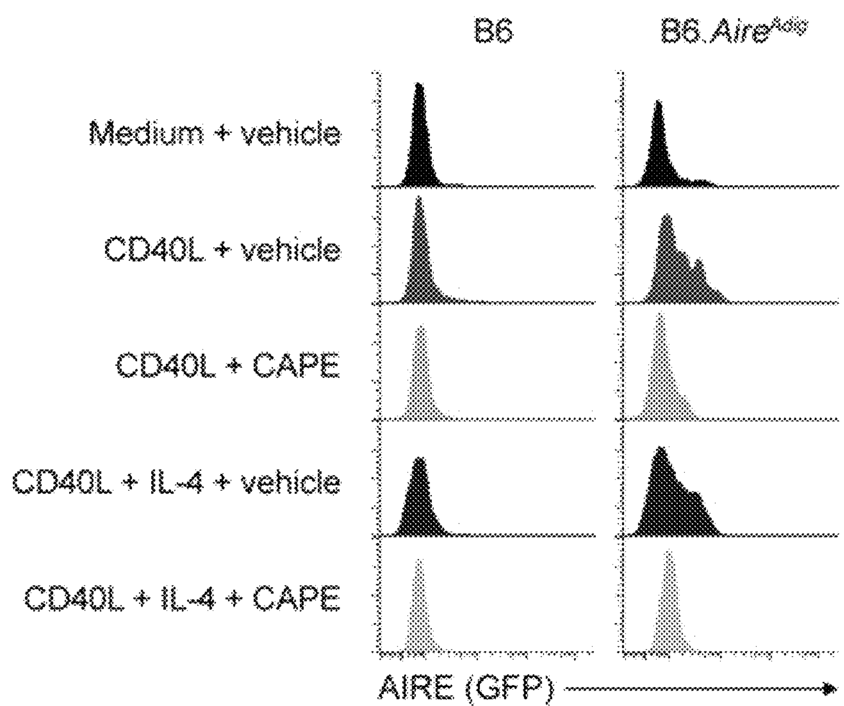
Figure 3A:
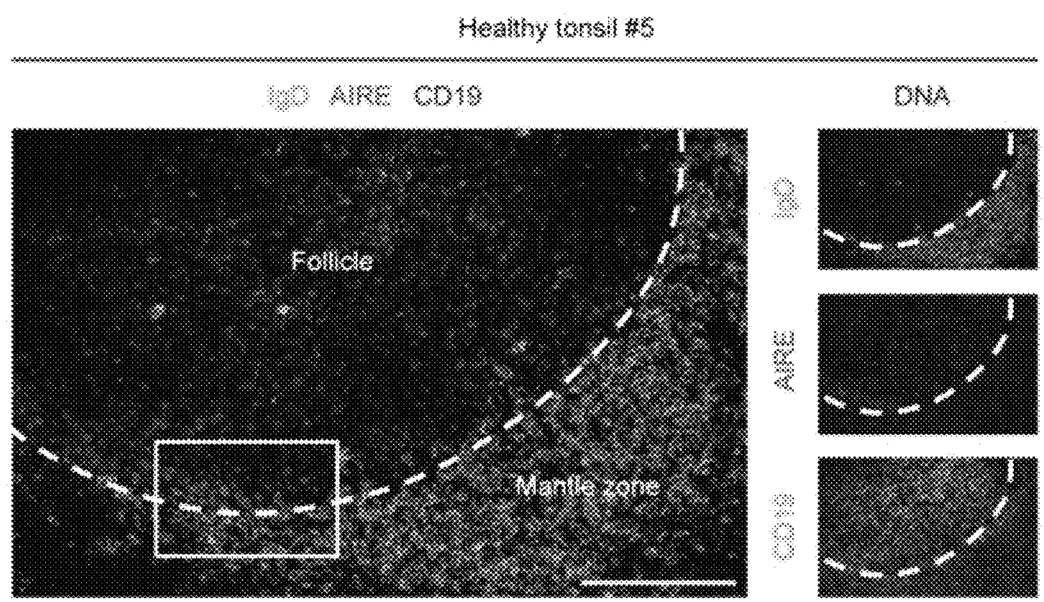
Figure 3B:
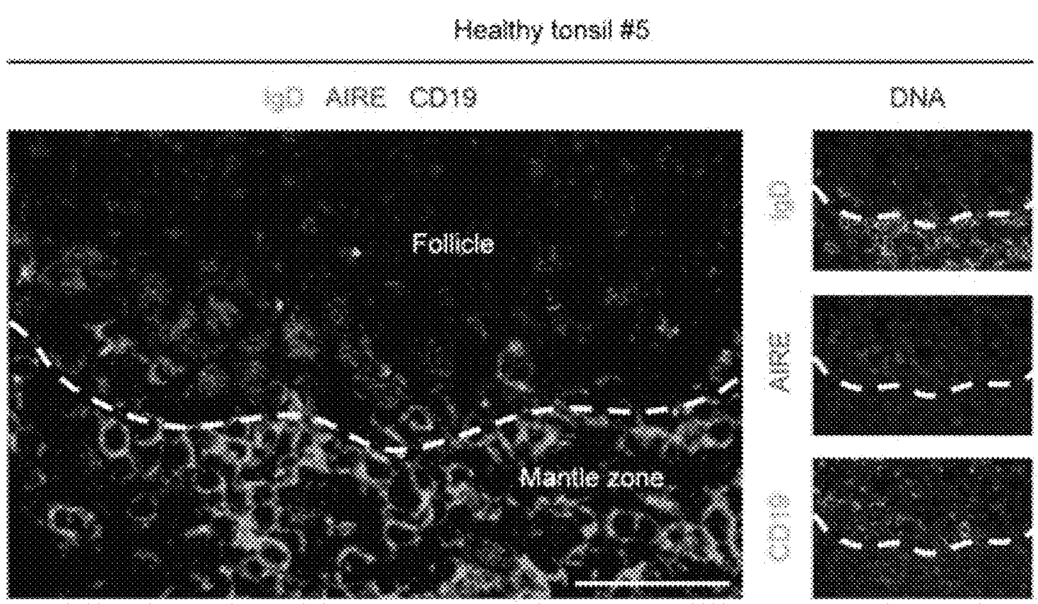
Figure 3D:
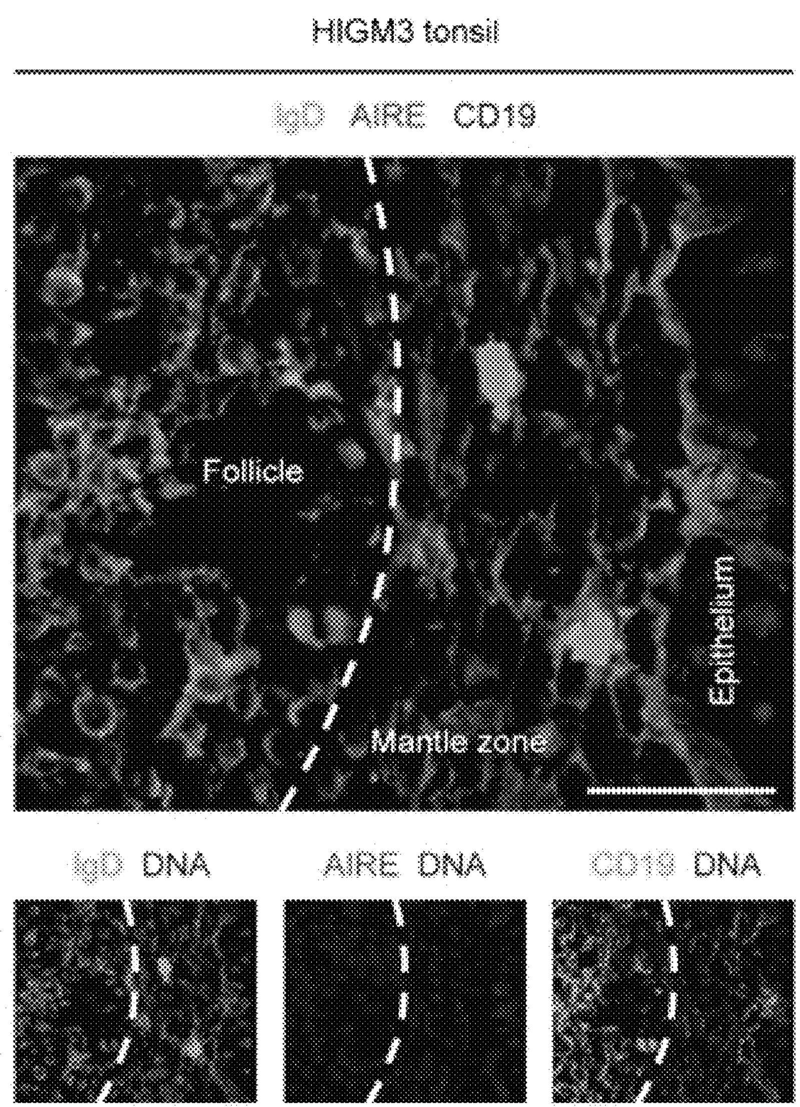
Figure 4A:
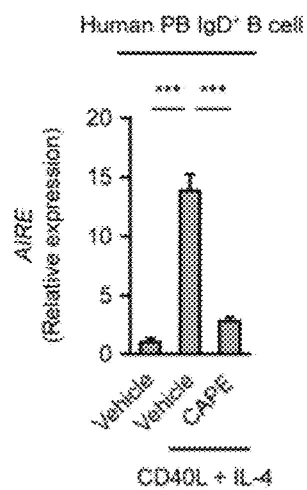
FIGS. 4A-4F. AIRE expression in B cells is induced by CD40 ligation in vitro.
Figure 4B:
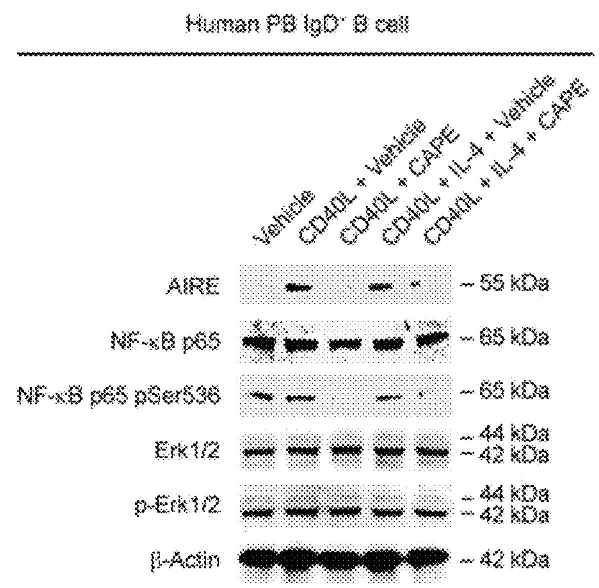
Figure 4C:
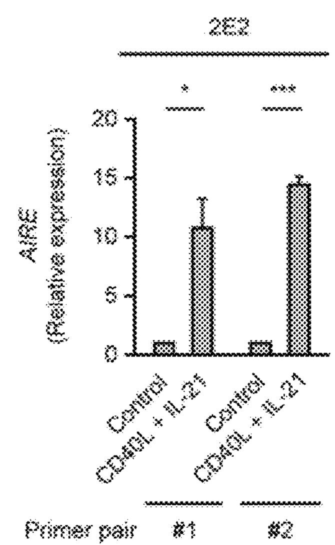
Figure 4D:
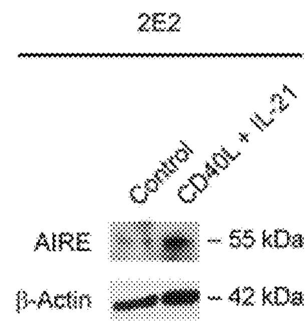
Figure 4E:
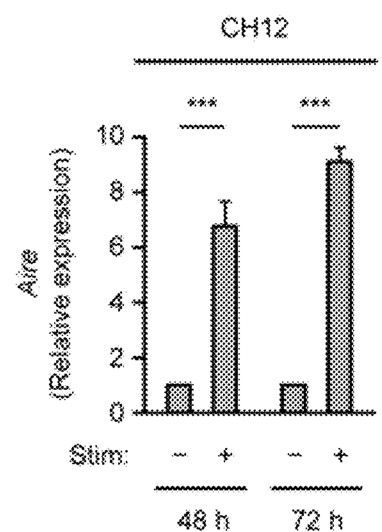
Figure 4F:
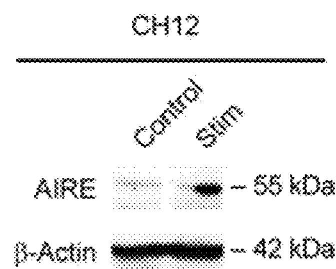

It was further sought to identify the regulation of GC B cell AIRE expression and examined the role of CD40 signalling, which is critical for T cell-dependent GC B cell responses (Liu, et al. *Nature* 342, 929-931, (1989)) and was previously reported to promote AIRE expression by mTECs and thymic B cells. Akiyama, et al. *Immunity* 29, 423-437, (2008); Yamano, et al. *Immunity* 42, 1048-1061, (2015). In contrast to the prominent AIRE expression in tonsillar follicular B cells of healthy subjects (FIG. 1A, FIGS. 2A, 2B, FIGS. 3A, 3B), tonsillar follicular B cells of a patient with the rare primary immunodeficiency hyper-IgM syndrome type 3 (HIGM3), which is caused by loss-of-function mutations in the CD40 gene (Durandy, et al. *Immunological reviews* 203, 67-79, (2005)), did not express AIRE (FIG. 1G, FIGS. 3C, 3D). AIRE mRNA and protein levels were induced in human peripheral blood $IgD^+$ B cells upon stimulation with CD40 ligand (CD40L) alone or with IL-4, which was inhibited by caffeic acid phenethyl ester (CAPE), a selective inhibitor of nuclear factor-kappa B (NF-κB) (Natarajan, et al. *Proceedings of the National Academy of Sciences of the United States of America* 93, 9090-9095, (1996)), the transcription factor activated by CD40 (FIGS. 4A, 4B). Similarly, mouse splenic B cells expressed AIRE upon CD40L stimulation ex vivo, which was abrogated by CAPE (FIG. 1H). In addition, human 2E2 and mouse CH12 cells, two B cell lines that undergo CD40L-induced CSR in vitro, had increased AIRE mRNA and protein expression upon CD40 ligation (FIGS. 4C-4F). Therefore, CD40 signalling is required for AIRE expression in GC B cells in vivo and promotes AIRE expression by B cells in vitro.

Figure 5A:
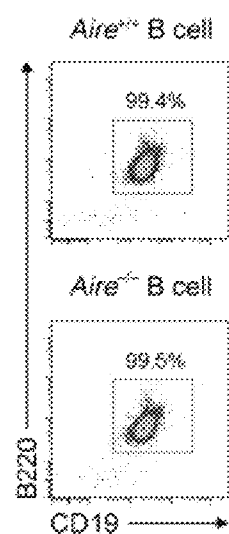
FIGS. 5A-5I. $Aire^{+/+}$ and $Aire^{-/-}$ B cells had a similar phenotype before transfer and entered GC reaction equally in immunised μMT recipients in vivo, and exhibited similar proliferation and apoptosis during ex vivo stimulation.
Figure 5B:
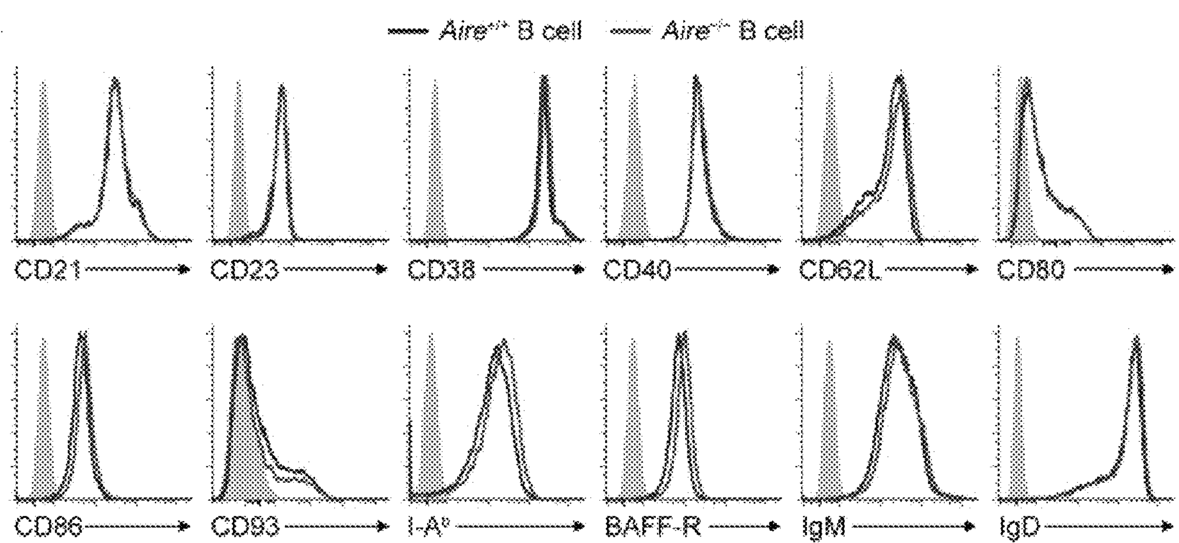
Figure 5C:
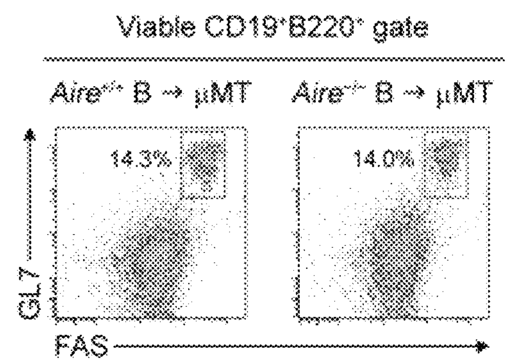
Figure 5D:
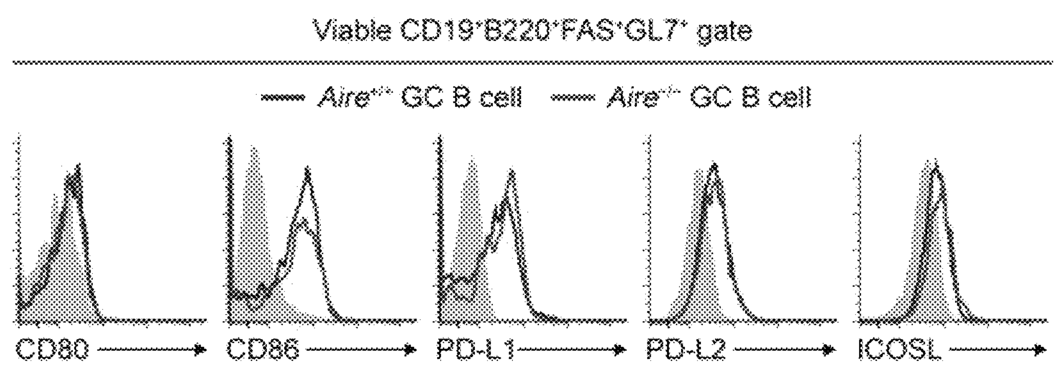
Figure 5E:
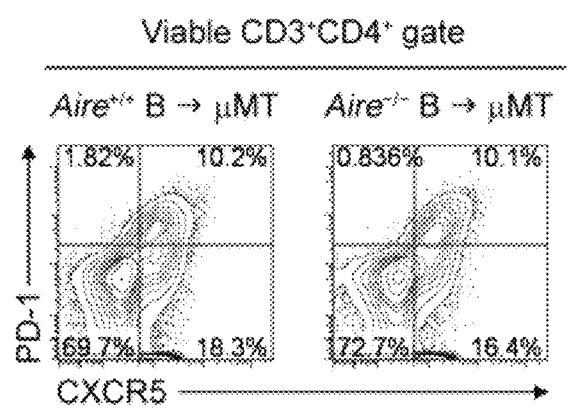
Figure 5F:
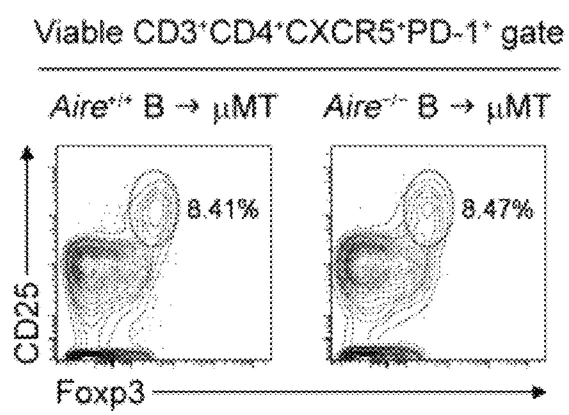

The B cell-deficient μMT recipient mice reconstituted with resting B cells from either $Aire^{+/+}$ or $Aire^{-/-}$ naive donor mice (FIG. 5A) was employed to determine the B cell-intrinsic function of AIRE in antibody response. Before adoptive transfer, $Aire^{+/+}$ and $Aire^{-/-}$ donor B cells exhibited a similar phenotype (FIG. 5B). Following repeated systemic immunization with the T cell-dependent antigen $NP_{32}$-KLH, $Aire^{+/+}$ and $Aire^{-/-}$ donor B cells equally entered the splenic GC compartment (FIG. 5C) and showed similar expression of major co-stimulatory and co-inhibitory molecules (FIG. 5D), but NP-specific $Aire^{-/-}$ donor B cells exhibited elevated CSR by harboring a much higher fraction of $IgM^{-}IgD^{-}$ cells than NP-specific $Aire^{+/+}$ donor B cells (FIG. 6A), and underwent increased affinity maturation by producing IgG1, IgG2b and IgG3, but not IgM, of higher $NP_4$ to $NP_{29}$ binding ratios (FIG. 6B). Of note, μMT recipients of $Aire^{+/+}$ and $Aire^{-/-}$ B cells had a similar proportion of $CXCR5^{+}PD\text{-}1^{+}$ follicular helper T ($T_{FH}$) cells (FIG. 5E) and $Foxp3^{+}$ $CD25^{+}$ follicular regulatory T (TFR) cells in the spleen (FIG. 5F). These results suggest that AIRE inhibits antibody CSR and SHM in a GC B cell-intrinsic manner.

Figure 5G:
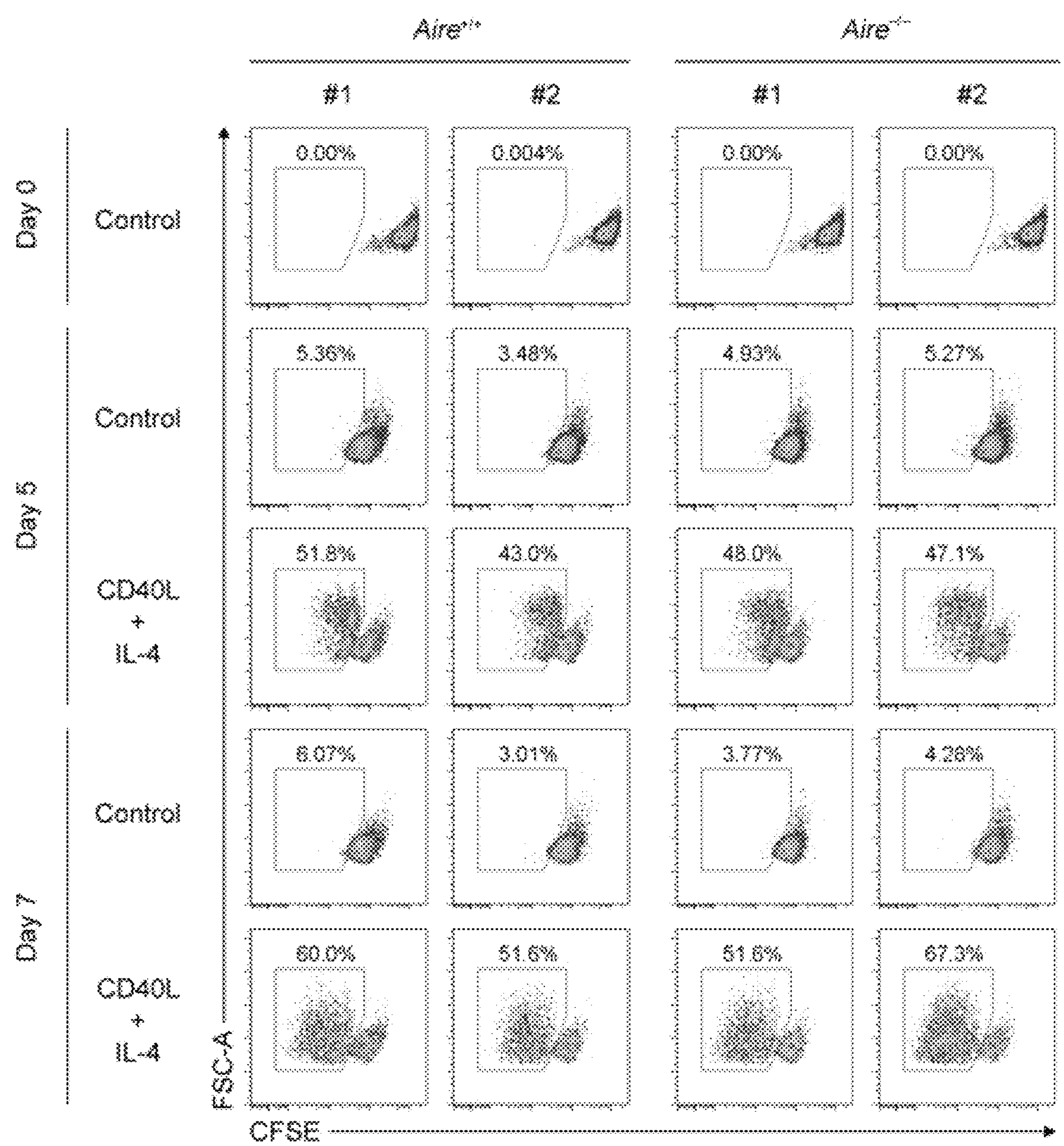
Figure 5H:
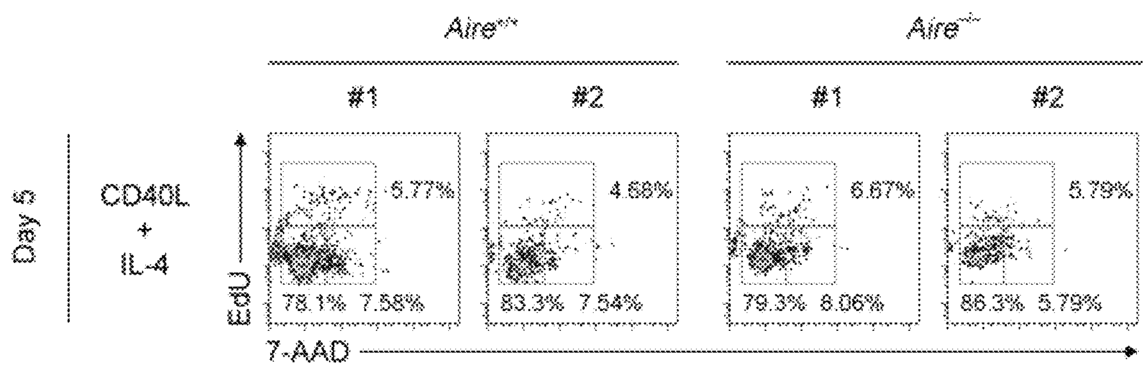
Figure 5I:
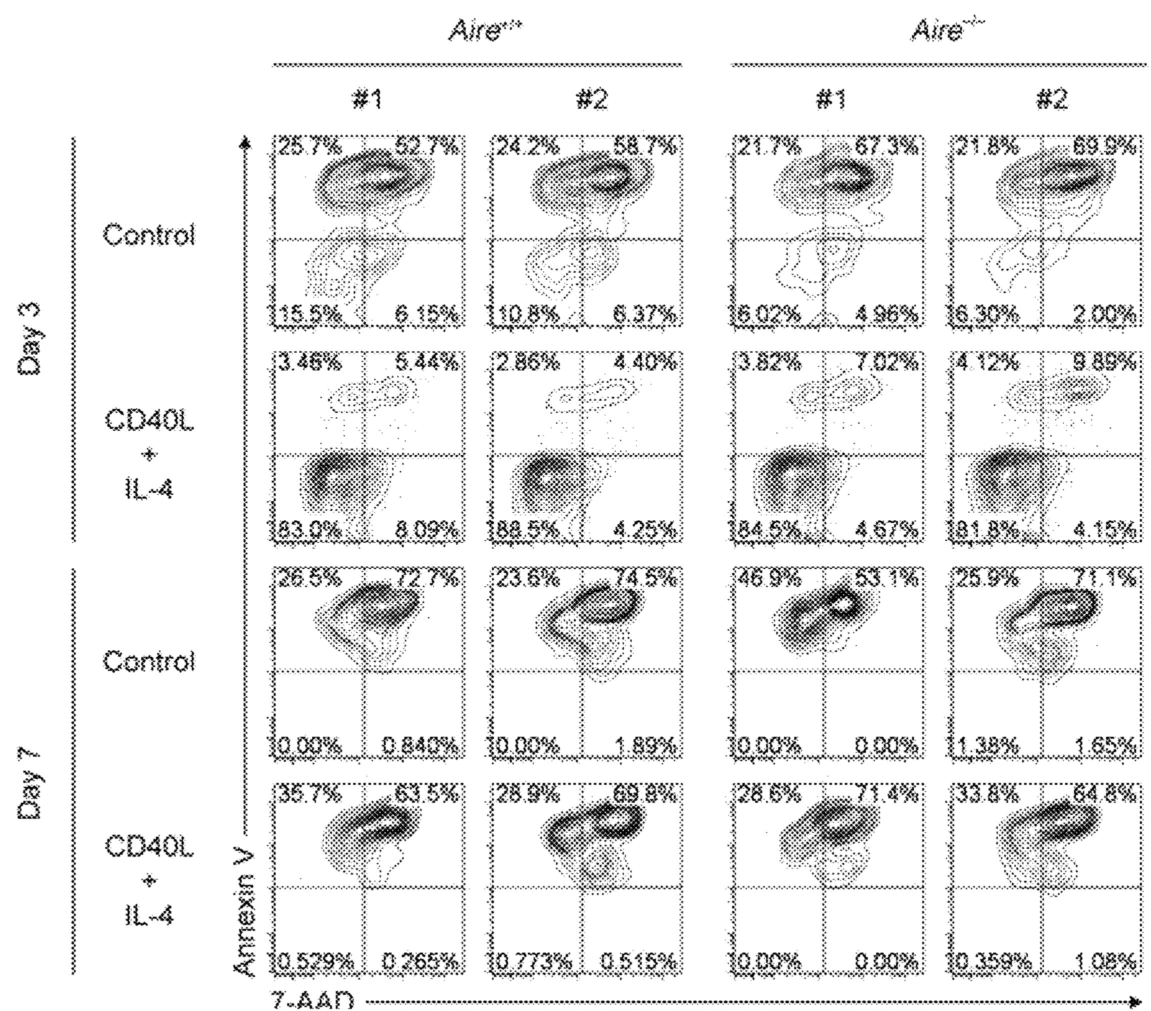
Figure 6D:
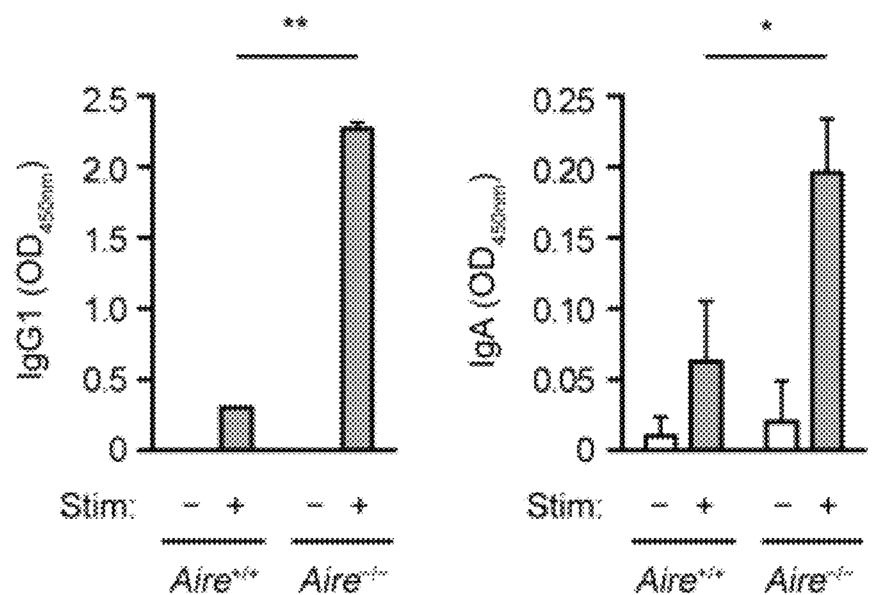
Figure 6E:
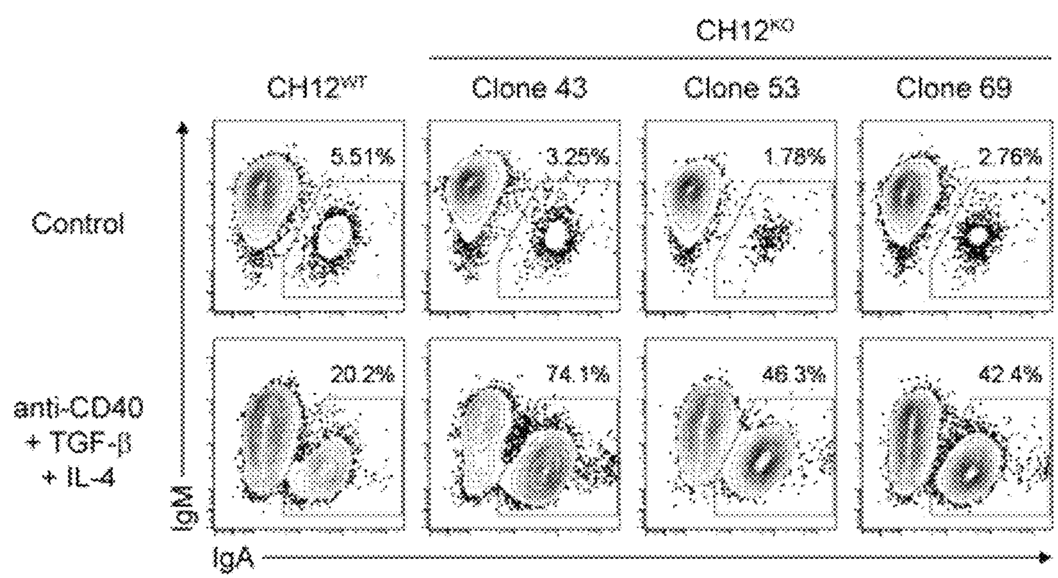
Figure 6F:
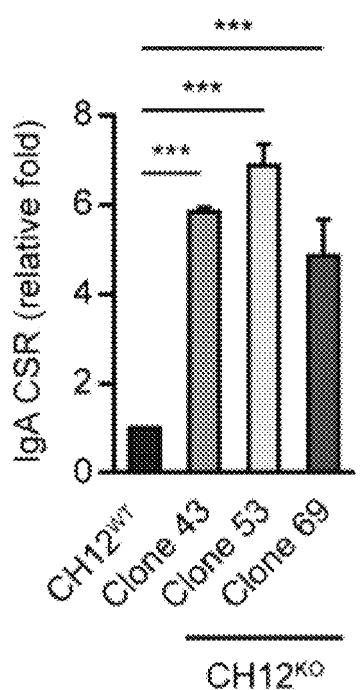
Figure 6G:
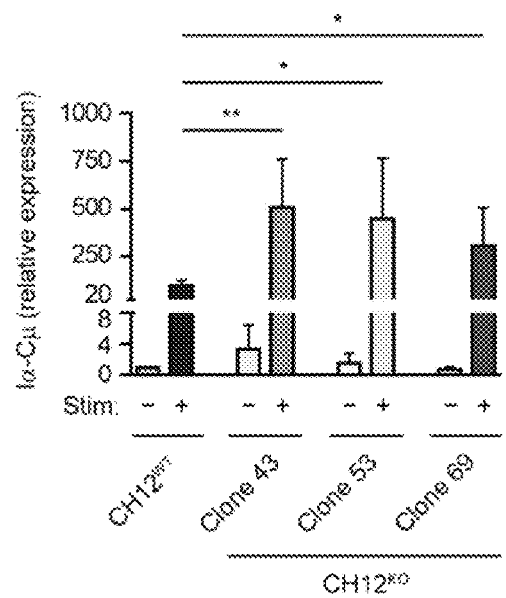
Figure 6H:
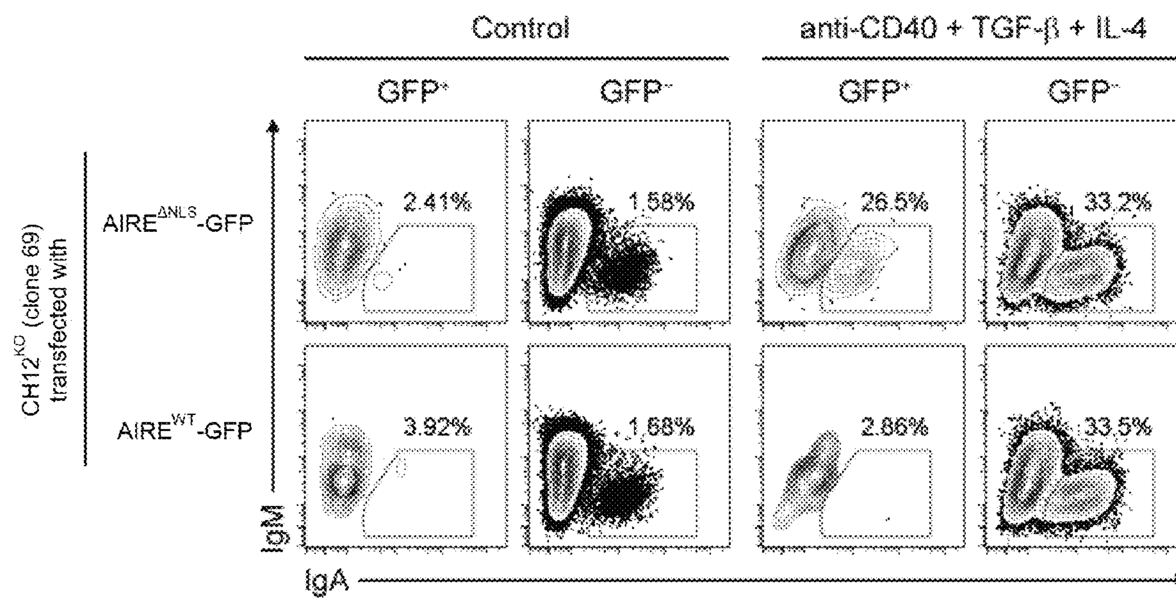
Figure 7A:
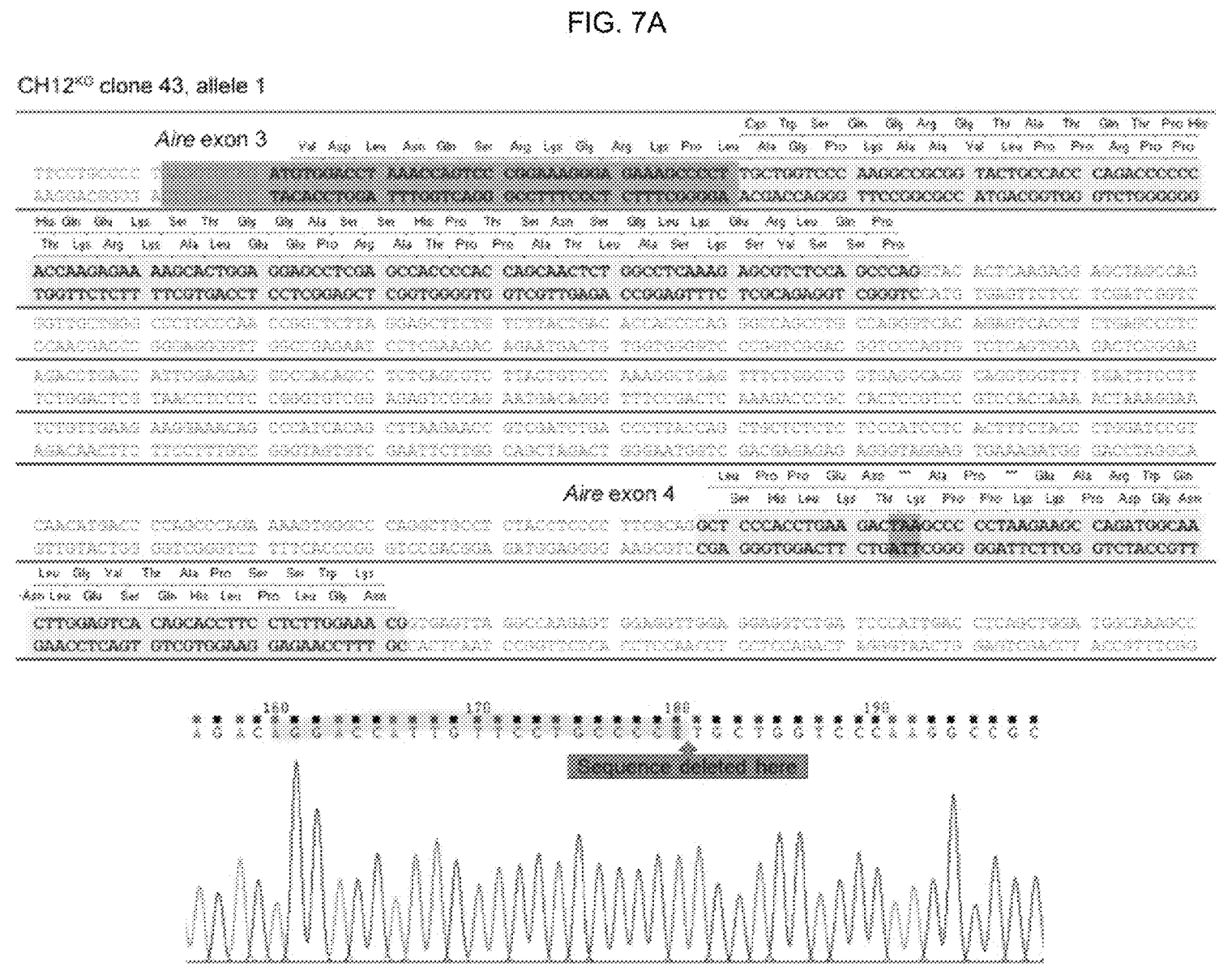
Figure 7A:
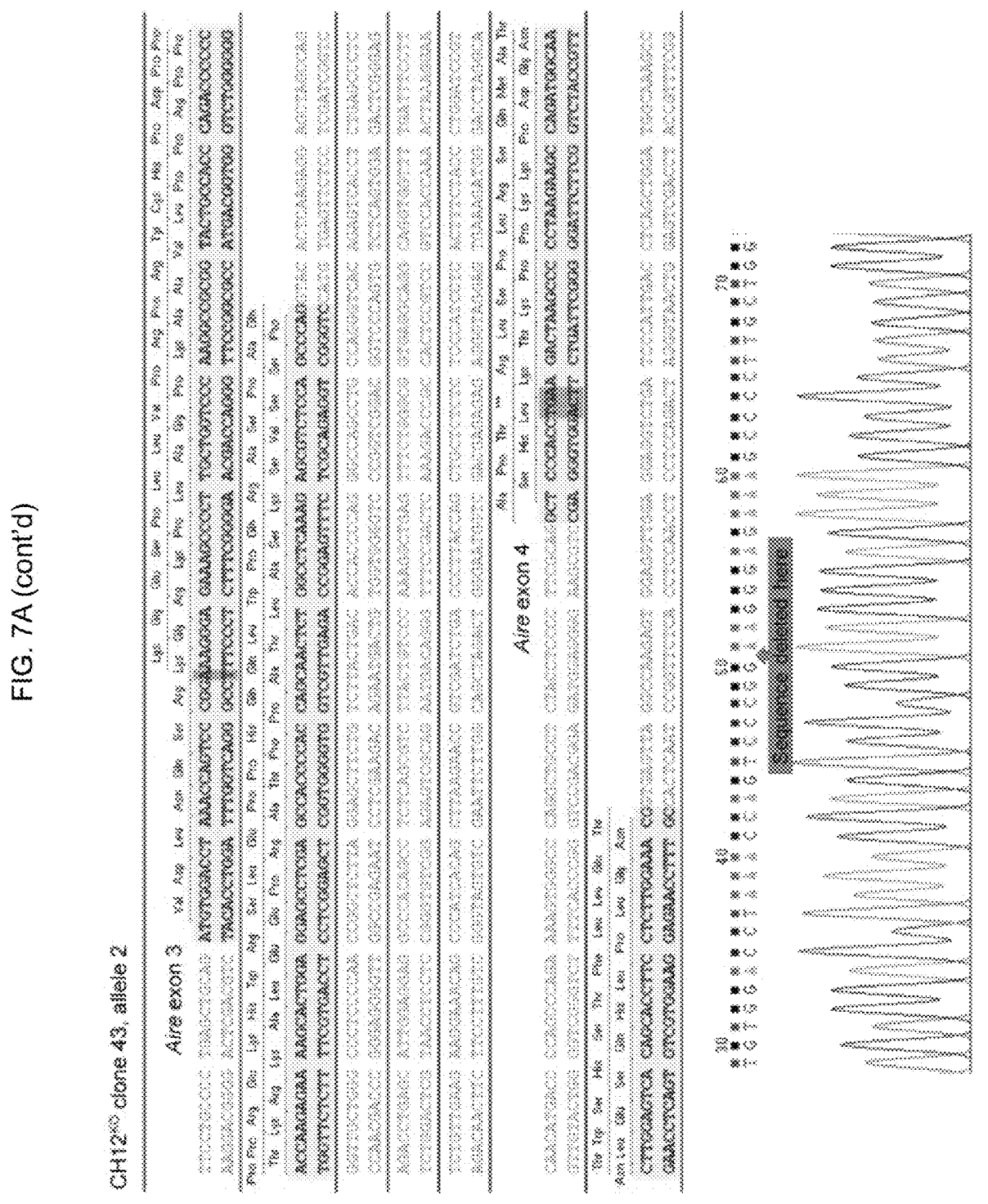
Figure 7B:
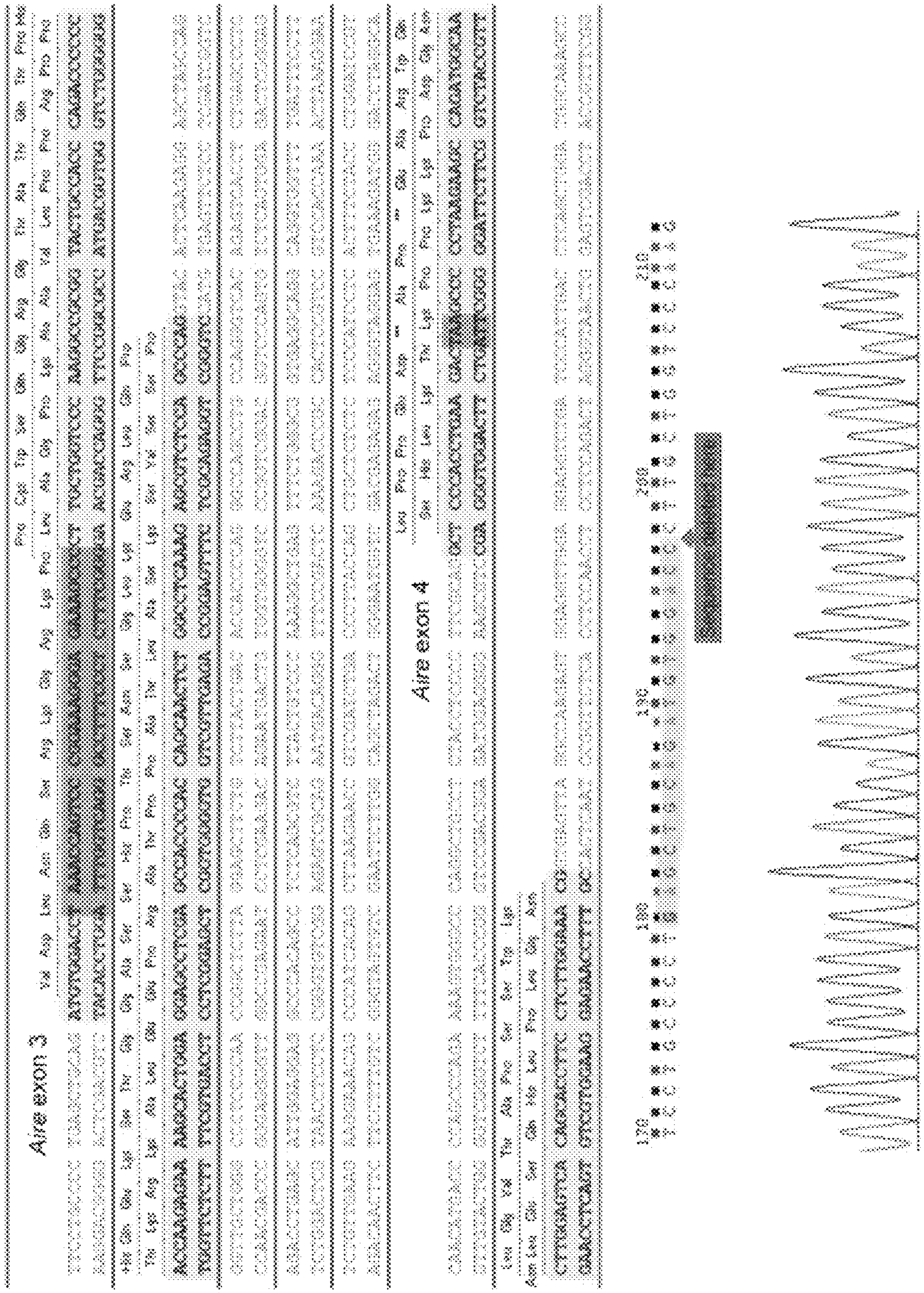
Figure 7C:
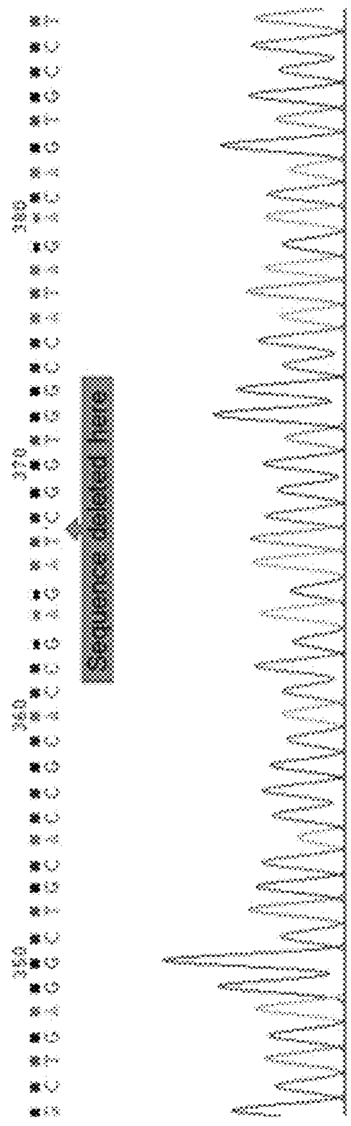
Figure 7D:
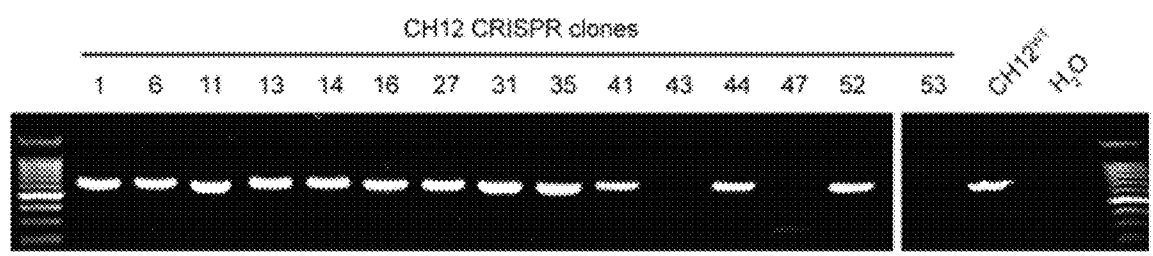
Figure 7E:
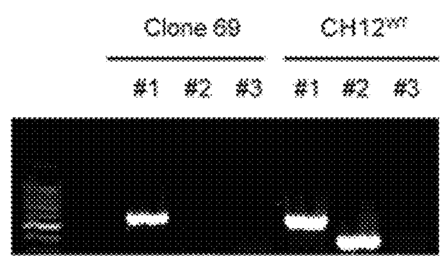
Figure 7F:
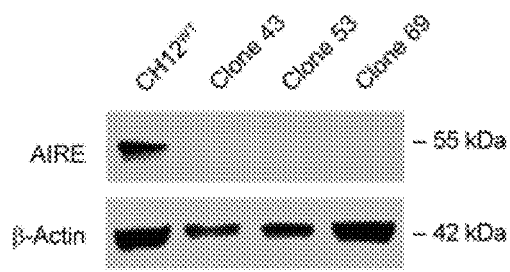
Figure 8A:
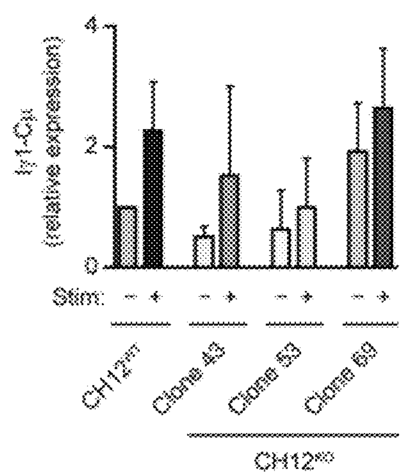
FIGS. 8A-8F. AIRE deficiency does not affect the expression of AID or germline transcripts in CH12 cells.
Figure 8B:
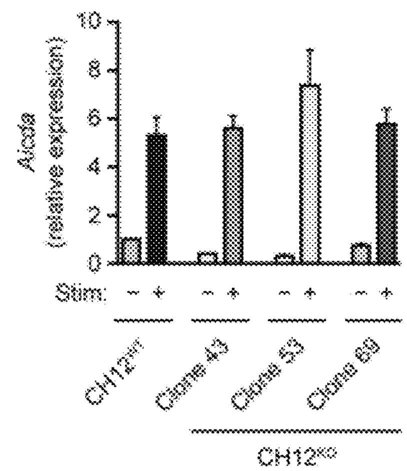
Figure 8C:
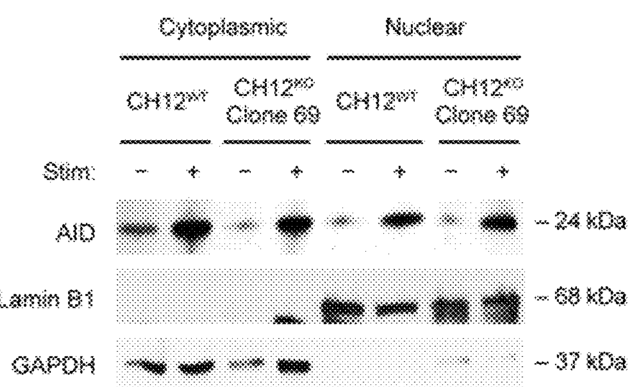
Figure 8D:
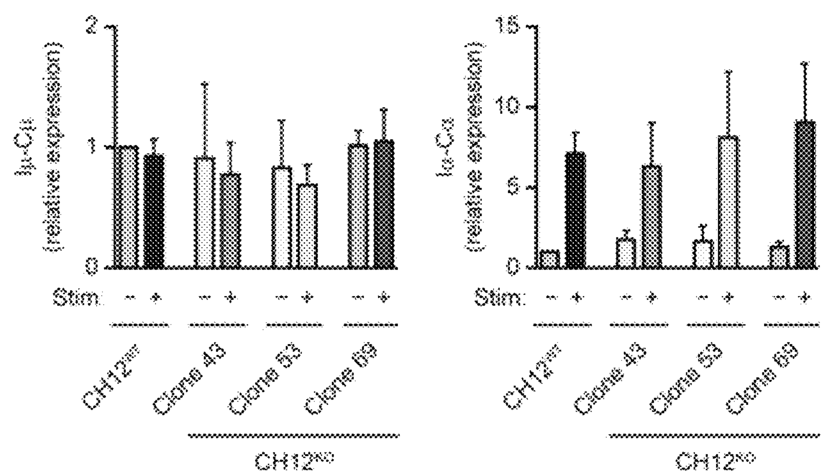
Figure 8E:
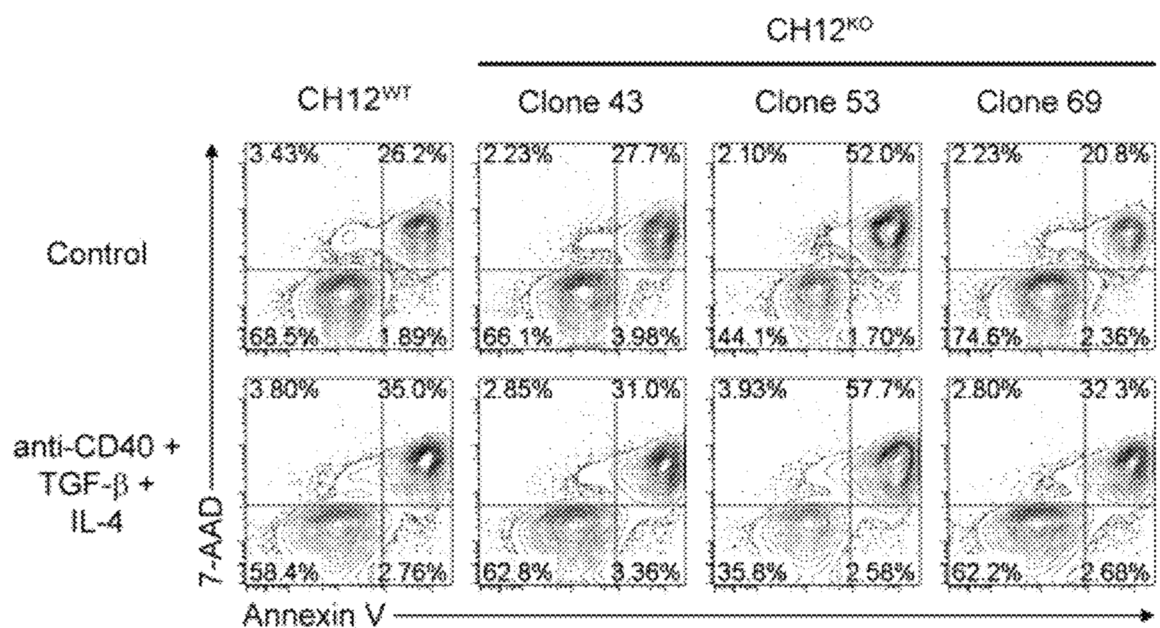
Figure 8F:
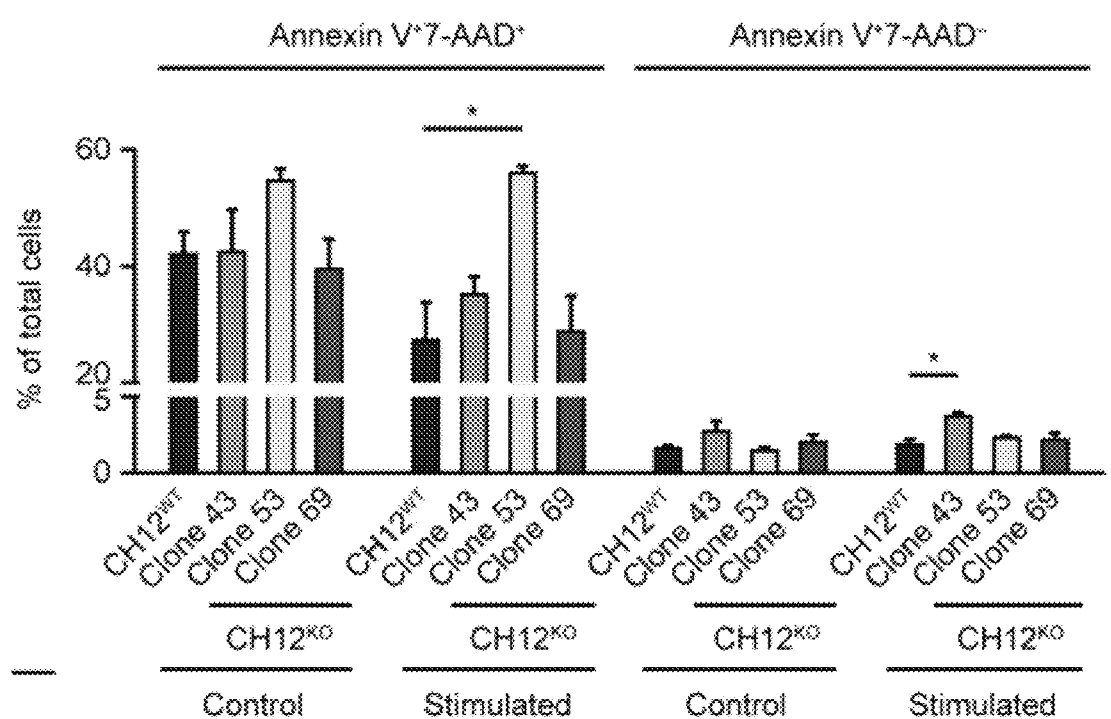

To verify the B cell-intrinsic inhibitory function of AIRE in CSR, splenic B cells of naïve $Aire^{+/+}$ and $Aire^{-/-}$ mice were compared for their ability to undergo CSR ex vivo. $Aire^{-/-}$ B cells underwent increased CSR (FIG. 6C) and secreted more class-switched antibodies upon stimulation in culture (FIG. 6D). The enhanced CSR of and antibody production by $Aire^{-/-}$ B cells were not caused by altered proliferation or apoptosis ex vivo (FIGS. 5G-5I). Using CRISPR-mediated gene editing, the Aire gene was disrupted in CH12 cells, a mouse B cell line that class-switches from IgM to IgA upon stimulation with anti-CD40, TGF-β and IL-4 (Nakamura, et al. *International immunology* 8, 193-201, (1996)), and identified 3 $Aire^{-/-}$ CH12 clones which were frame-shifted in both Aire alleles (FIGS. 7A-7E), devoid of AIRE protein expression (FIG. 7F) and intact at CRISPR off-target sites (not shown). Upon stimulation, these $Aire^{-/-}$ CH12 clones underwent elevated IgA CSR (FIGS. 6E, 6F) with concomitantly increased levels of the Iα-Cμ (FIG. 6G) but not Iγ1-Cμ circle transcript (FIG. 8A) compared to their parental $Aire^{+/+}$ CH12 cells. Exaggerated IgA CSR in $Aire^{-/-}$ CH12 cells was not a result of increased induction of the CSR-mediating enzyme activation-induced cytidine deaminase (AID) (FIGS. 8B, 8C) or germline transcription (FIG. 8D), nor a result of increased survival (FIGS. 8E, 8F). Remarkably, WT AIRE, but nota nuclear localization signal (NLS) deletion mutant AIRE ($AIRE^{\Delta NLS}$), suppressed cytokine-induced CSR when re-introduced into $Aire^{-/-}$ CH12 cells (FIG. 6H). These results reaffirm the B-cell intrinsic function of AIRE in inhibiting CSR.

Figure 9A:
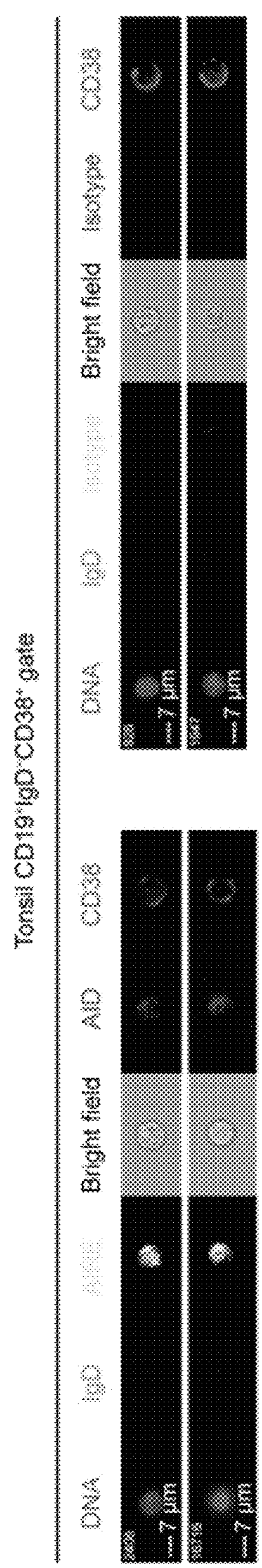
FIGS. 9A-9J. AIRE interacts with AID in GC B cells and inhibits AID activity by reducing AID targeting to Ig S region and stalled Pol II.
Figure 9B:
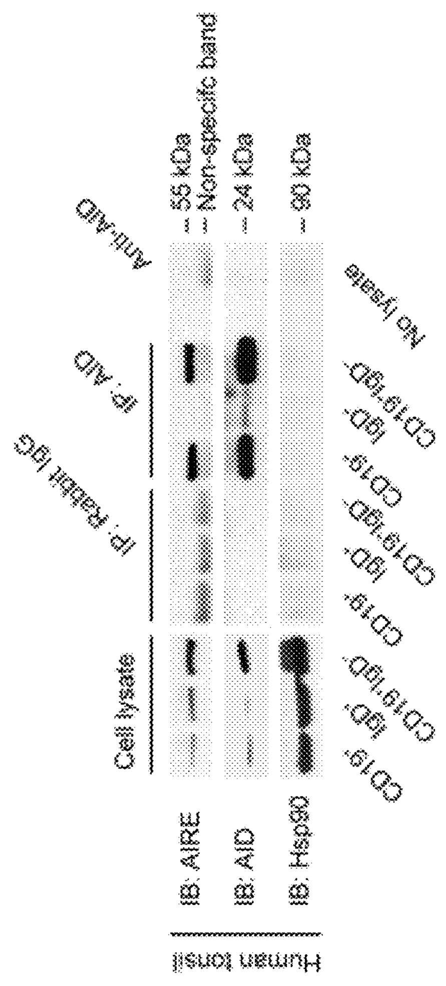
Figure 9C:
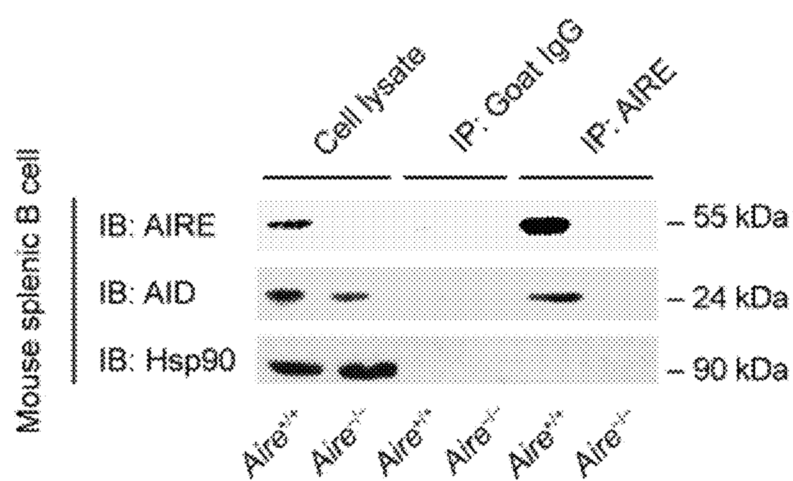
Figure 10A:
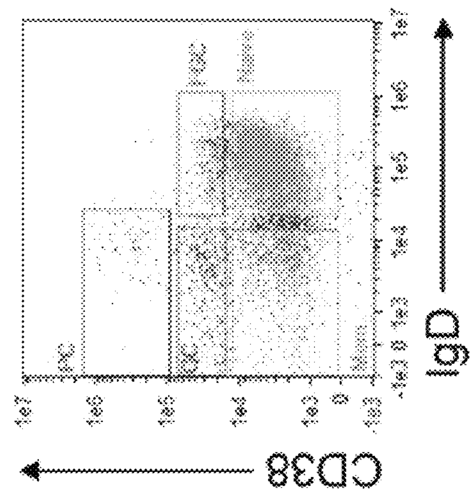
FIGS. 10A-10F. AIRE and AID co-localize in the nuclei of GC B cells.
Figure 10B:
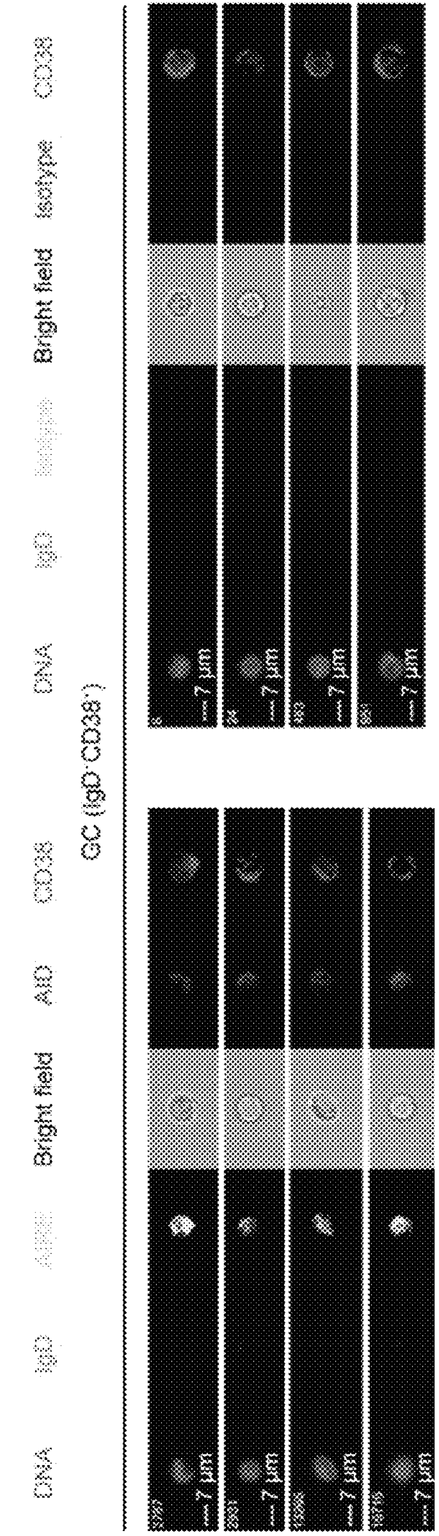
Figure 10C:
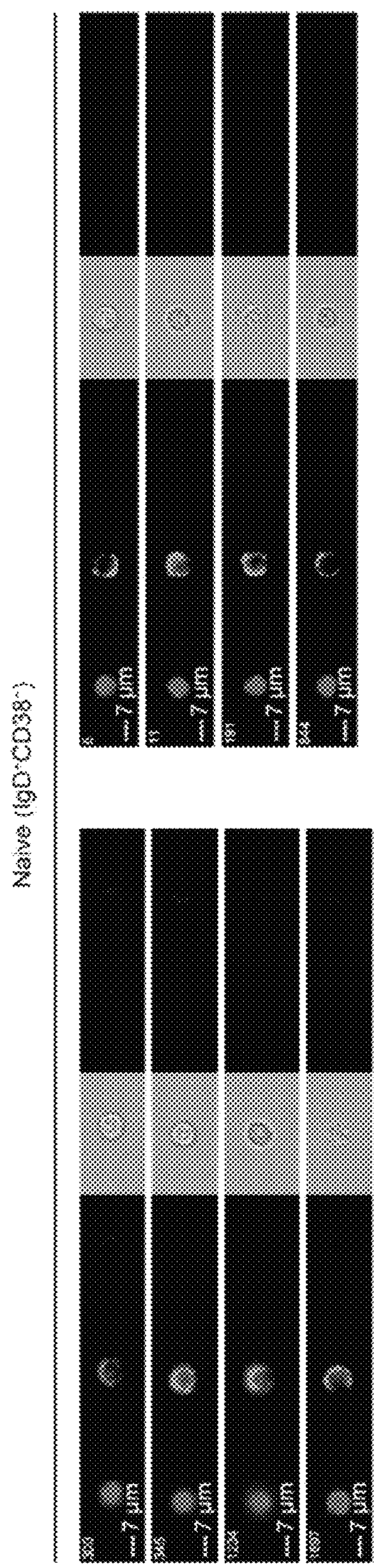
Figure 10D:
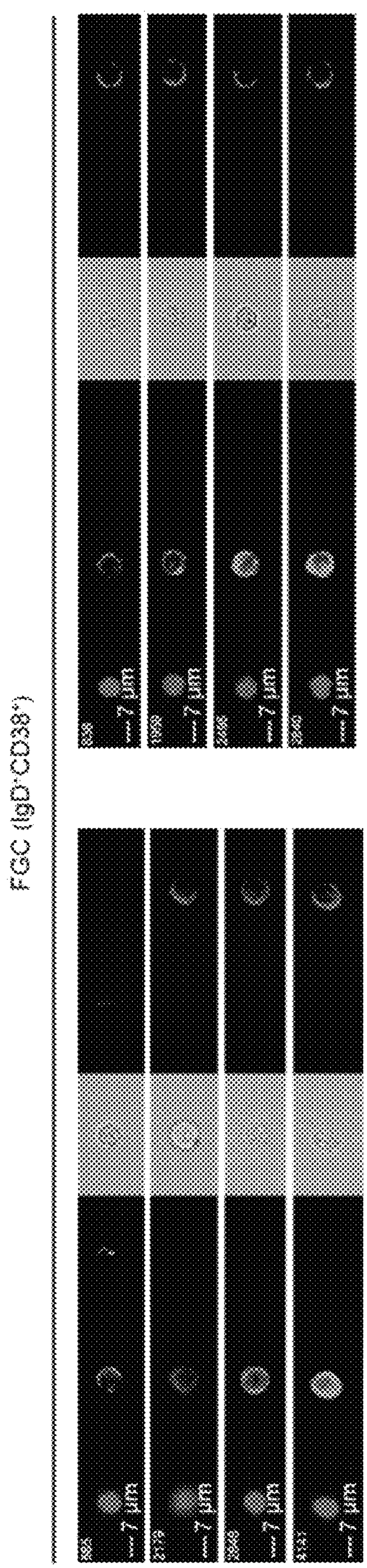
Figure 10E:
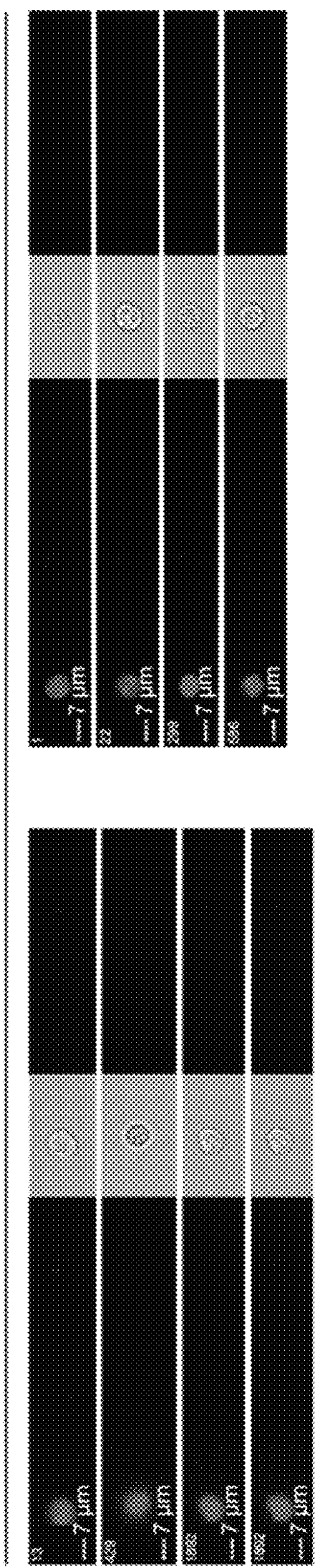
Figure 10F:
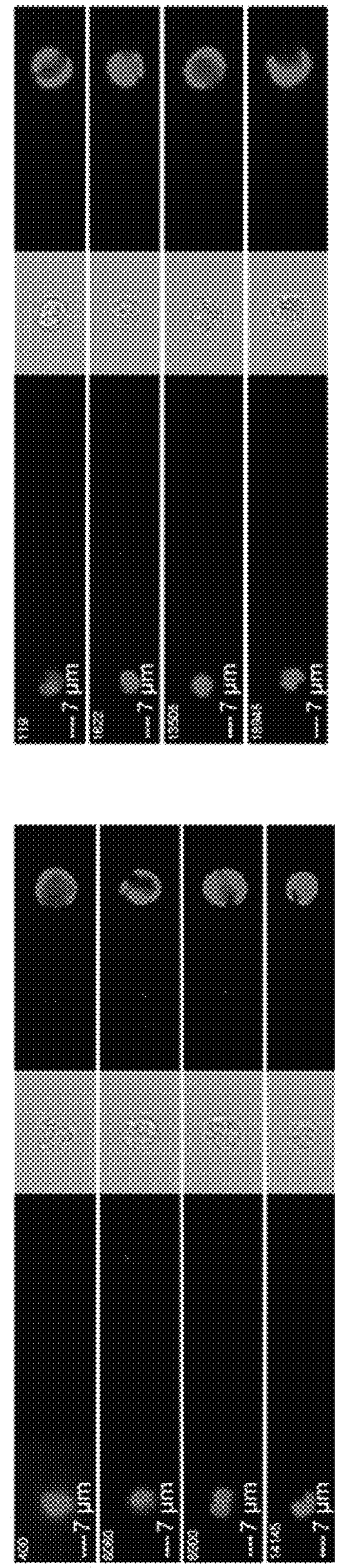
Figure 11A:
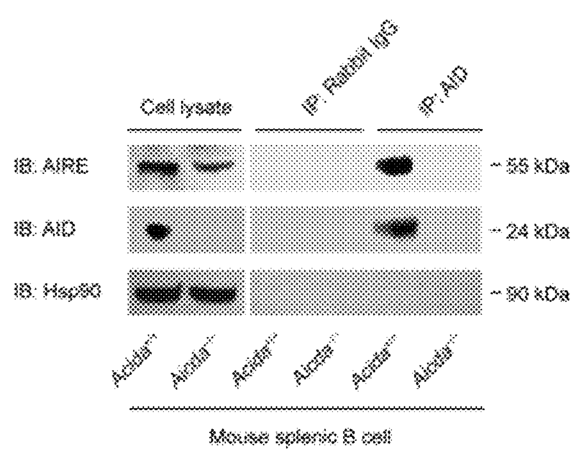
FIGS. 11A-11E. AIRE interacts with AID but not Bcl10 in B cells, and inhibits AID activity.

As AID is the obligatory enzyme that mediates CSR and SHM (Muramatsu, et al. *Cell* 102, 553-563, (2000)), whether AIRE inhibits AID activity in B cells was examined. AIRE and AID co-localized in the nuclei of tonsillar $IgD^{-}$ $CD38^{+}$ GC B cells (FIG. 9A, FIGS. 10A, 10B) but not in $IgD^{+}CD38^{-}$ naive B cells, $IgD^{-}CD38^{-}$ switched memory B cells or $IgD^{-}CD38^{hi}$ switched plasma cells (PCs), albeit a low level of nuclear AIRE and AID were detected in a small fraction of $IgD^{+}CD38^{+}$ founder GC (FGC) B cells (FIGS. 10C-10F). Using an AID antibody validated for immunoprecipitation (IP) and Chromatin IP (ChIP) (Vuong, et al. *Nature immunology* 10, 420-426, (2009)), it was found that AIRE interacted with AID in human tonsillar $CD19^{+}$ and $CD19^{+}IgD^{-}$ cell fractions (FIG. 9B). AIRE also co-immunoprecipitated with AID in splenic B cells of immunized WT but not $Aire^{-/-}$ or $Aicda^{-/-}$ mice (FIG. 9C, FIG. 11A). These data collectively demonstrate that AIRE interacts with AID in GC B cells in vivo and in B cell lines undergoing Ig diversification in vitro.

Figure 9D:
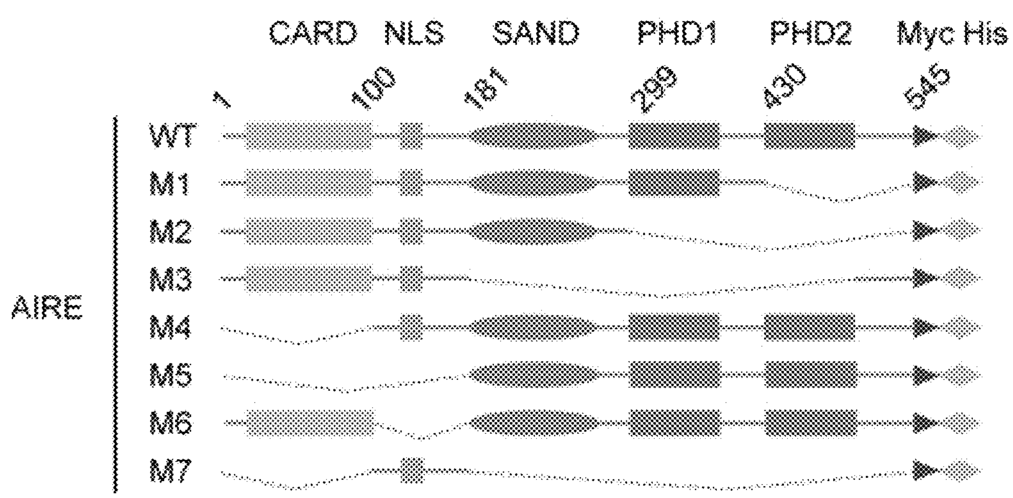
Figure 9E:
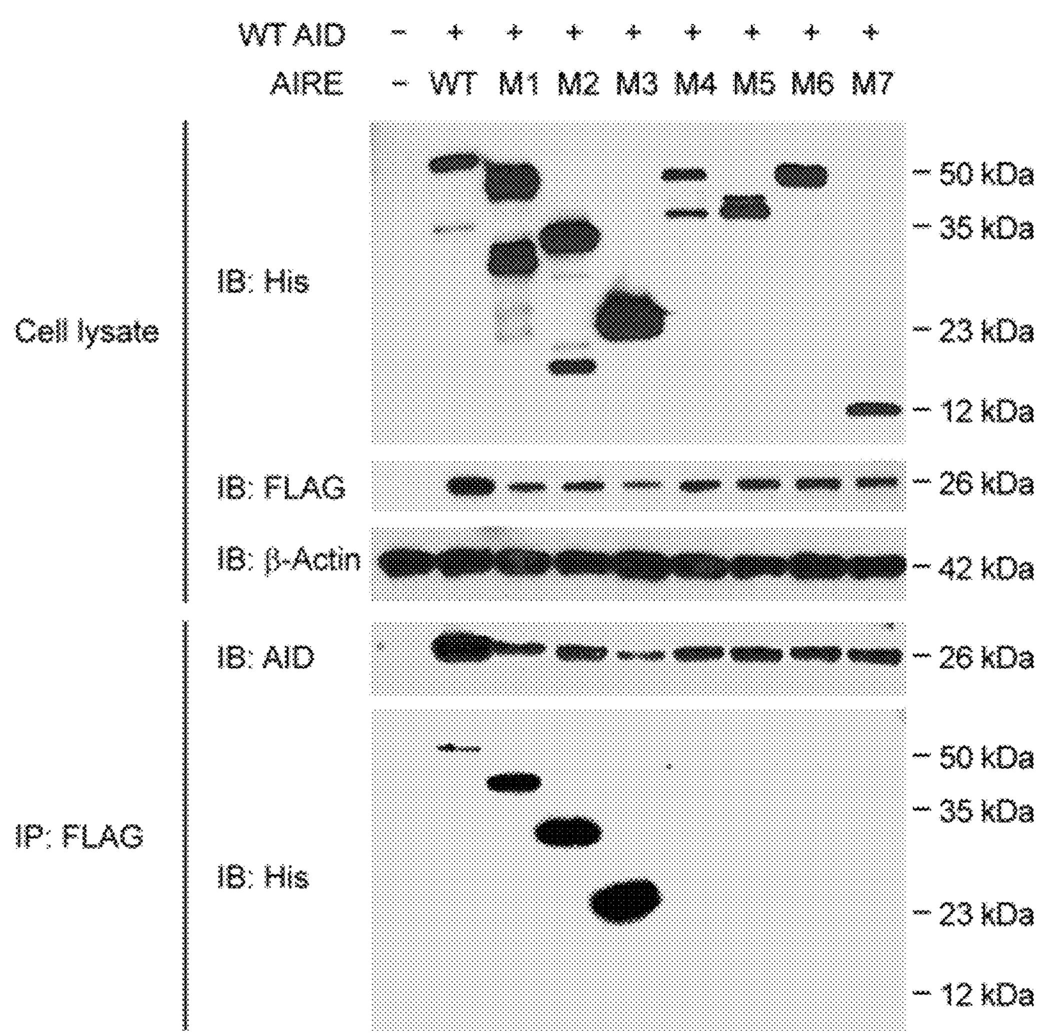
Figure 9F:
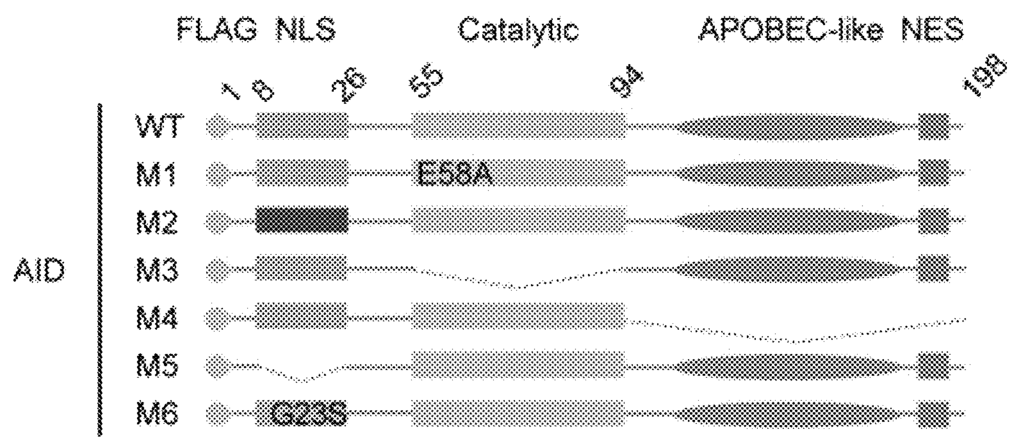
Figure 9G:
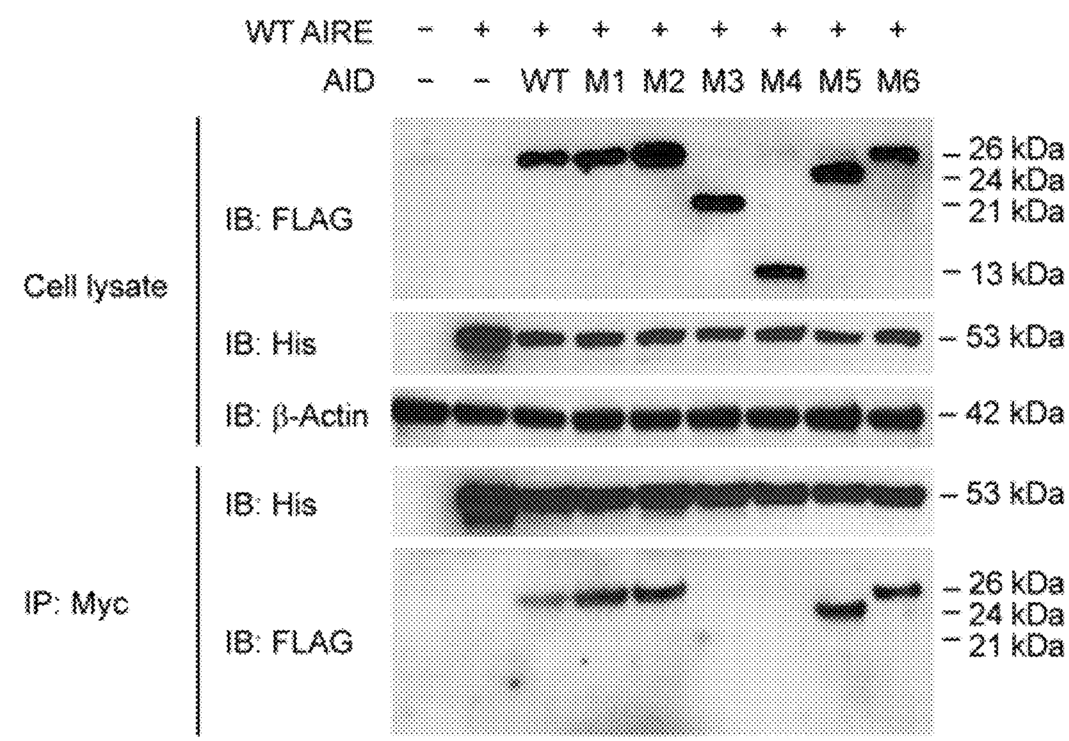
Figure 11B:
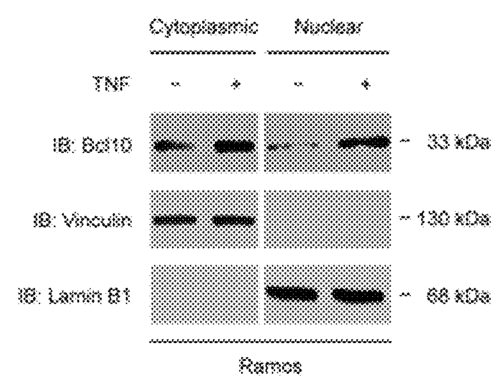
Figure 11C:
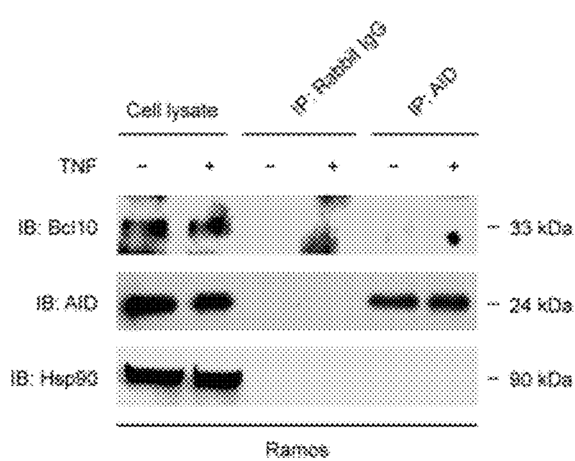

A series of deletion mutants of AIRE with C-terminal Myc and His tags were subsequently generated to characterize its interaction with AID (FIG. 9D, FIG. 12A). AIRE mutants missing the N-terminal caspase activation and recruitment domain (CARD) and/or nuclear localization signal (NLS) lost the ability to interact with AID (FIG. 9E), which demonstrates a requirement for the CARD and NLS of AIRE for interaction with AID and echoes the earlier result showing the dependence for NLS of AIRE in inhibiting CSR in CH12 cells (FIG. 6H). The CARD-dependent interaction with AID was specific to AIRE, as another CARD-containing protein, Bcl10, which undergoes TNF-induced nuclear translocation (Yeh, et al. *J Biol Chem* 281, 167-175, (2006)) (FIG. 11B), did not interact with AID in the human Ramos B cell line which undergoes constitutive Ig diversification in culture (Sale & Neuberger, Immunity, 9, 859-869 (1998)) (FIG. 11C). Furthermore, using a series of deletion, domain replacement or point mutants of AID with an N-terminal FLAG tag (FIG. 9F, FIG. 12B), it was found that the interaction between AID and AIRE required both the catalytic and APOBEC-like domains of AID, although the catalytic activity of AID was not necessary, as the catalytically inactive $AID^{E58A}$ mutant (Patenaude, et al. *Nat Struct Mol Biol* 16, 517-527, (2009)) still interacted with AIRE (FIG. 9G). The AID mutation G23S, which substantially abrogates SHM but not much CSR activity (Wei, et al. *Nature immunology* 12, 264-270, (2011)), did not affect the interaction with AIRE (FIG. 9G).

Figure 9H:
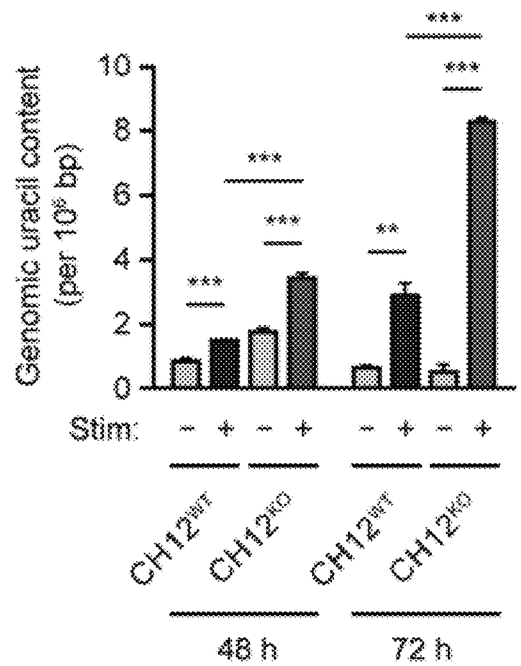
Figure 9I:
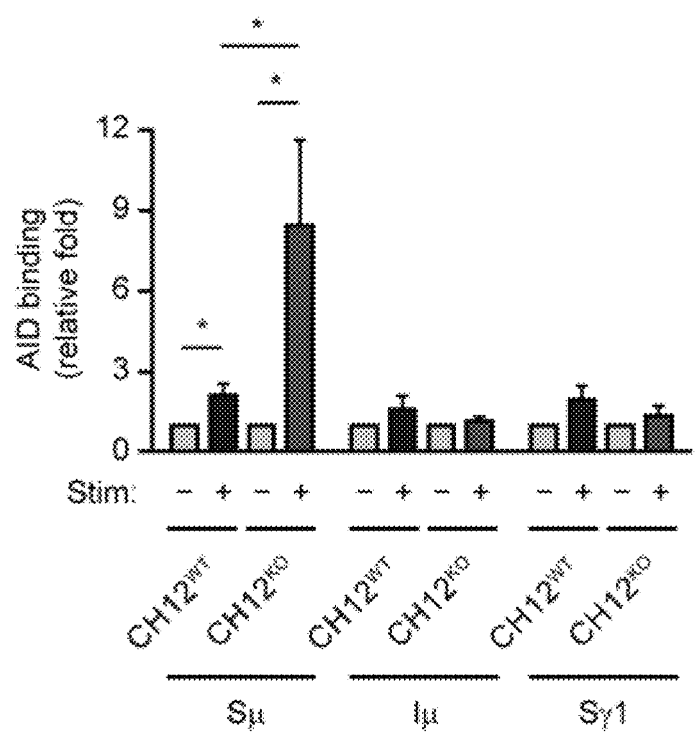
Figure 9J:
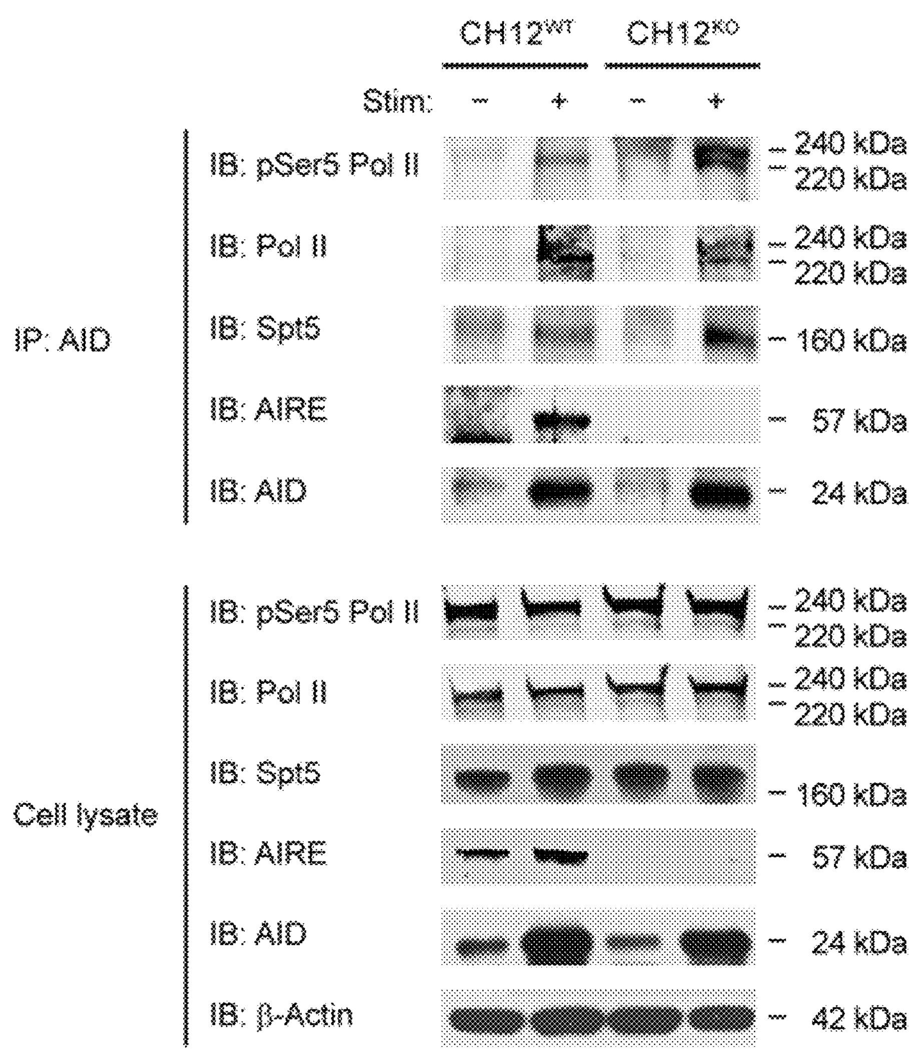
Figure 11D:
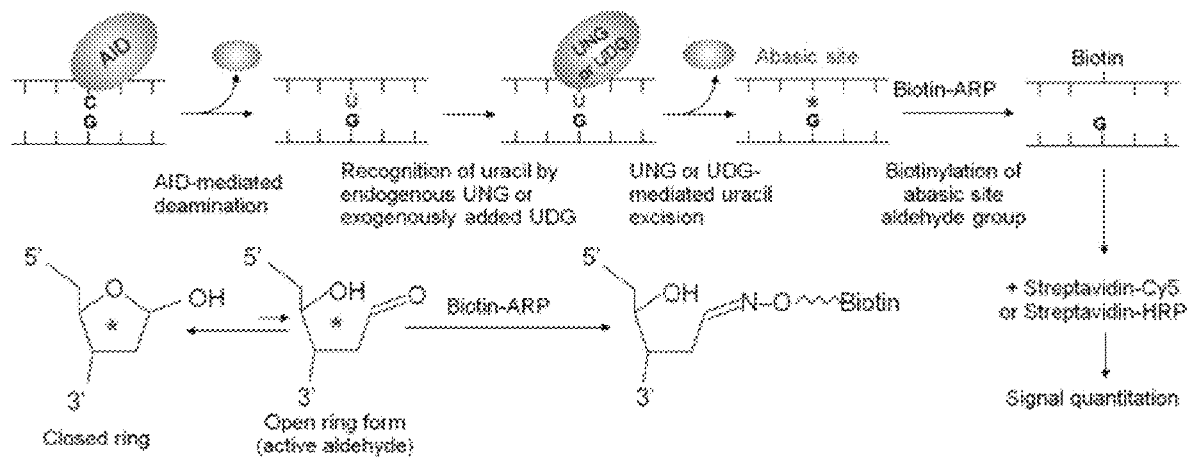
Figure 11E:
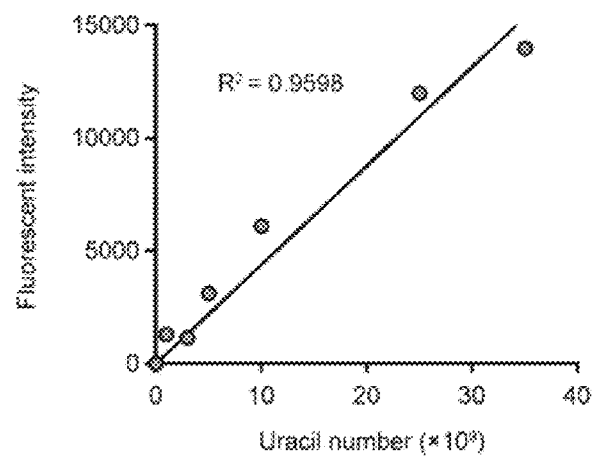

A genomic uracil dot blot assay was then employed to directly test the effect of AIRE on the activity of AID (FIGS. 11D, 11E). Upon stimulation to undergo CSR, $Aire^{-/-}$ CH12 cells harbored higher numbers of genomic uracil than $Aire^{+/+}$ CH12 cells (FIG. 9H), reflecting an inhibitory role of AIRE in AID's deaminase activity. Maul, et al. *Nature immunology* 12, 70-76, (2011). Considering that the function of AID requires its proper targeting to the Ig heavy chain (IgH) switch (S) regions at sites of Pol II stalling (Pavri, et al. *Cell* 143, 122-133, (2010)), increased AID binding to the Sμ but not Iμ or Sγ1 region (FIG. 9I) and increased AID interaction with transcriptionally stalled (Ser5) Pol II and its associated factor Spt5 (Peterlin & Price, *Molecular cell* 23, 297-305, (2006)) in stimulated $Aire^{-/-}$ CH12 cells compared to stimulated $Aire^{+/+}$ CH12 cells (FIG. 9J) were found. These data are consistent with a function of AIRE in unleashing stalled Pol II by recruiting the positive transcription elongation factor b (P-TEFb) complex (Oven, et al. *Mol Cell Biol* 27, 8815-8823, (2007)), and suggest that AIRE inhibits AID function by promoting Pol II escape from stalling and reducing AID targeting to its DNA substrate.

Figure 13A:
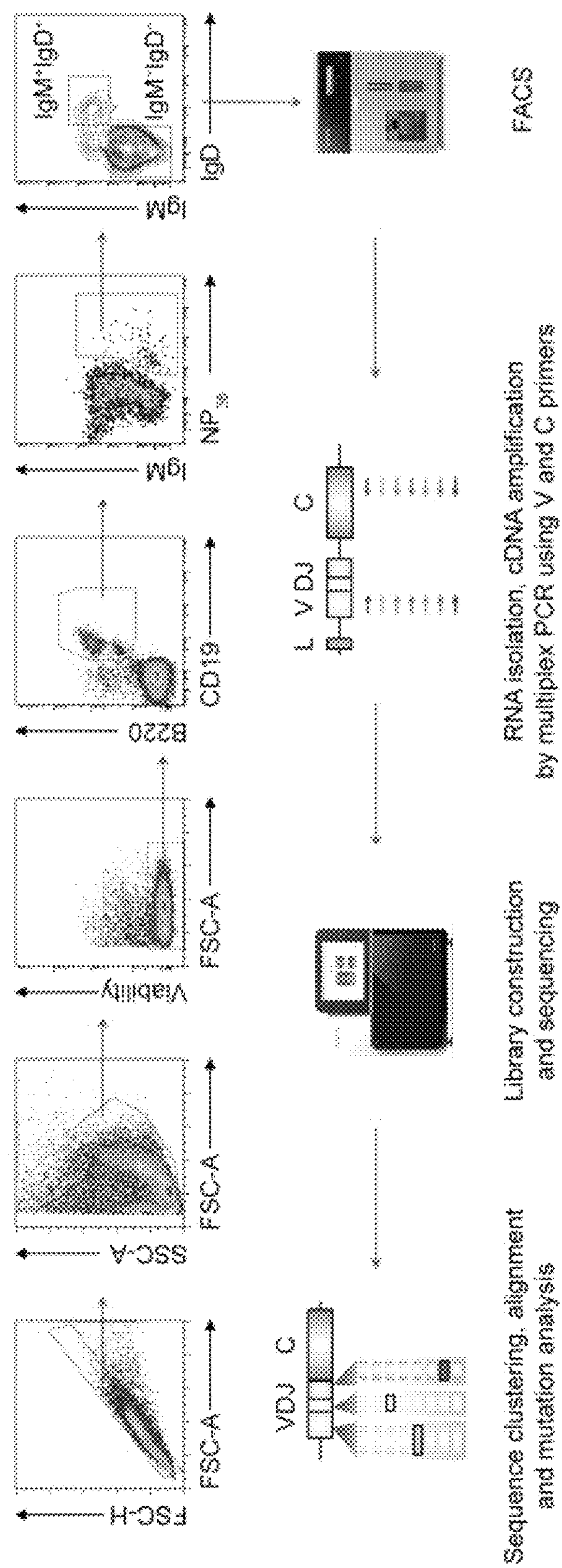
FIGS. 13A, 13B. $Aire^{-/-}$ donor B cells class-switched to IgG or IgE have increased IgH CDR2 SHMs than their $Aire^{+/+}$ counterparts after repeated immunizations.
Figure 13B:
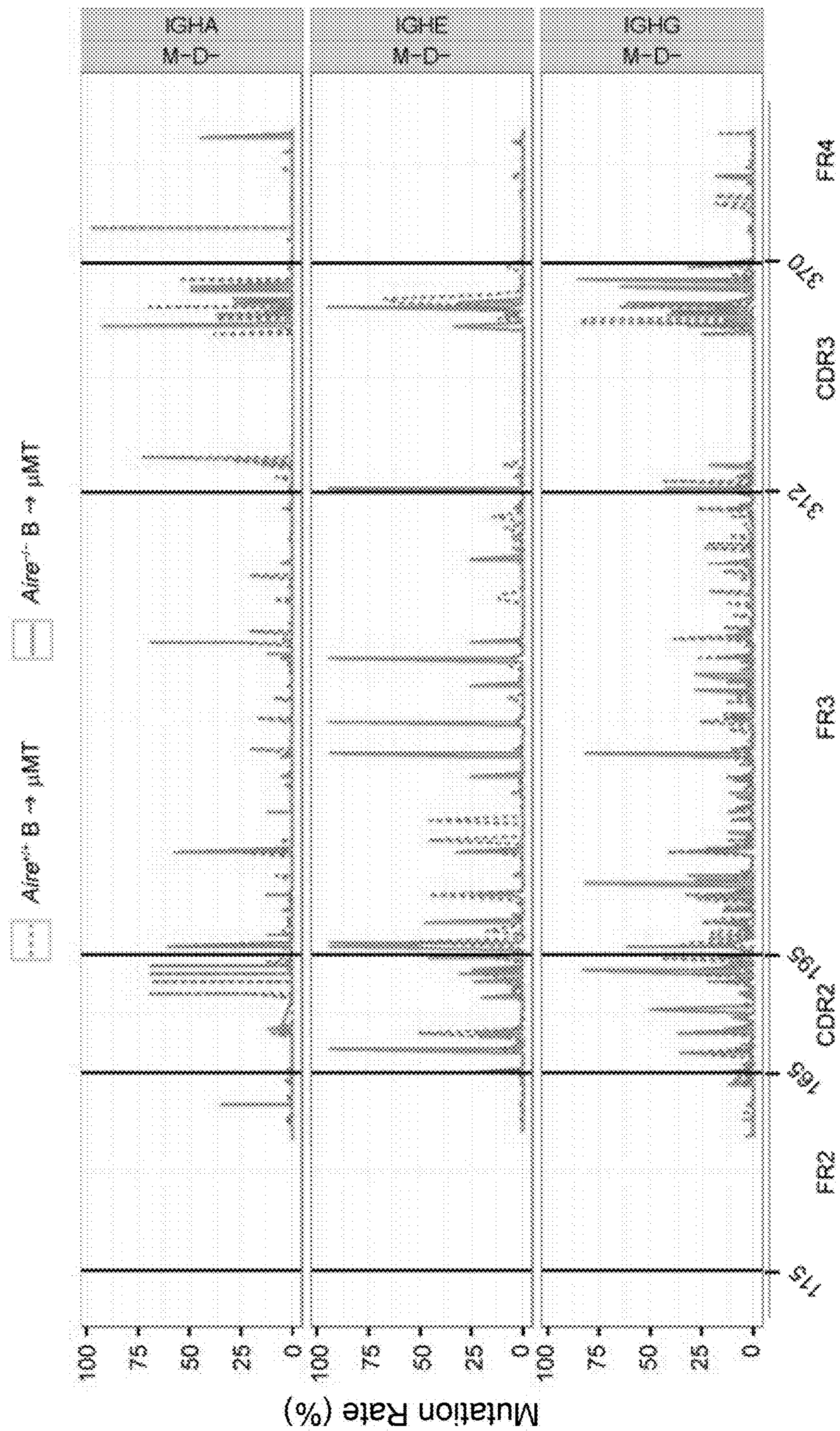
Figure 13B:
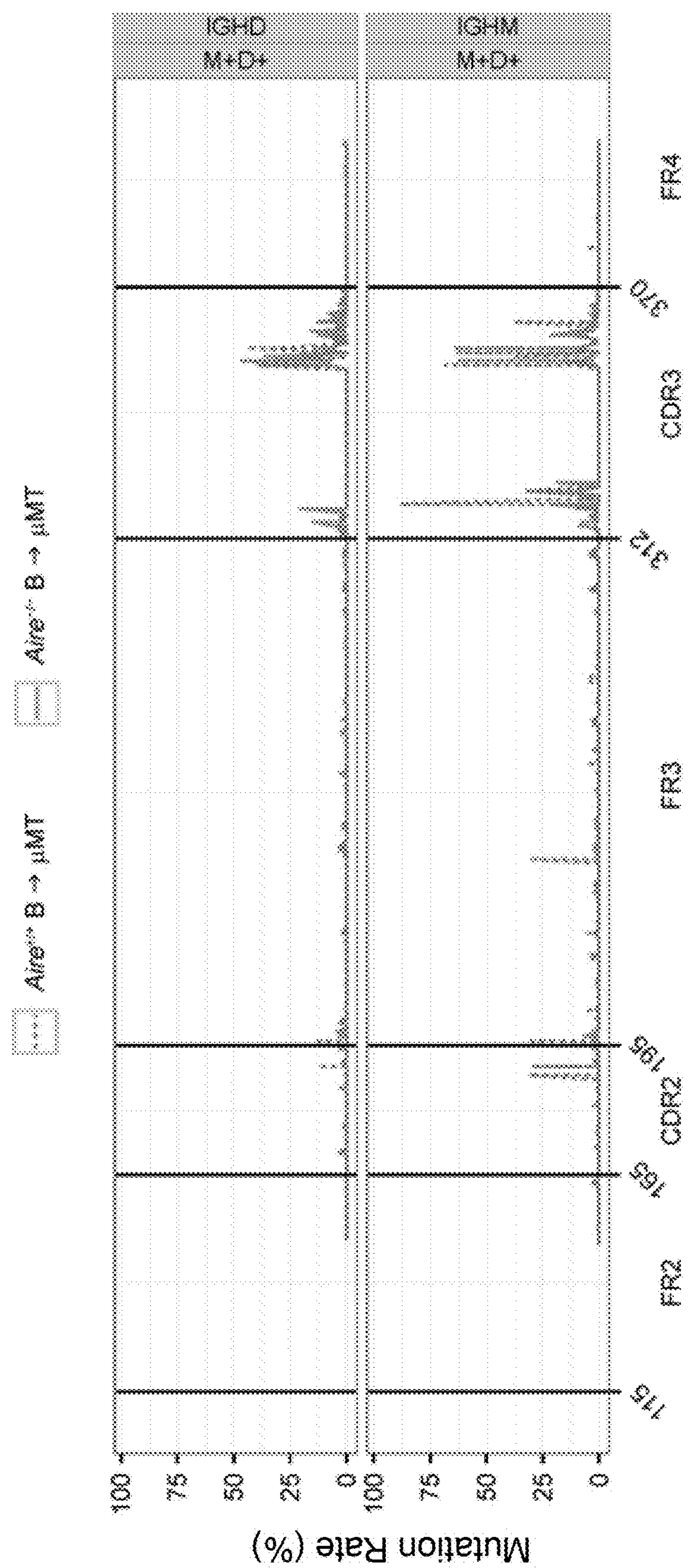
Figure 14A:
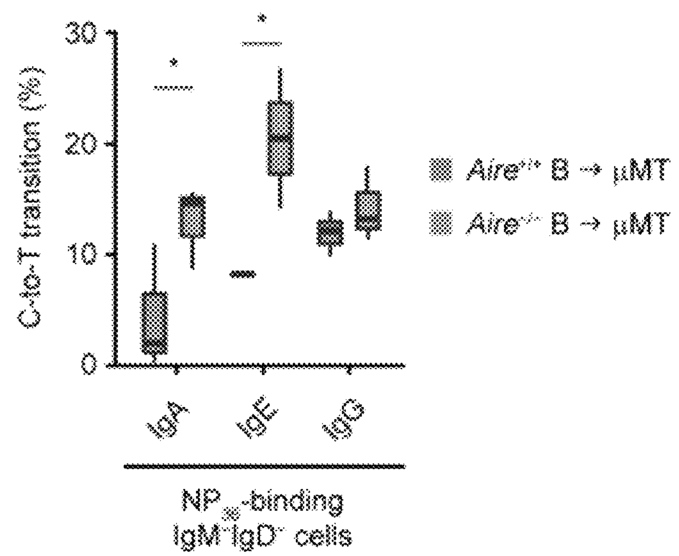
FIGS. 14A-14H. AIRE deficiency in B cells promotes humoral autoimmunity and compromises cutaneous anti-*Candida* defense.

Given that the vast majority of APS-1 patients mysteriously develop chronic mucocutaneous candidiasis (CMC) as an early clinical symptom, which may result from the aberrant production of class-switched neutralizing autoantibodies against $T_H17$ cytokines that can impair anti-*C. albicans* immunity (Puel, et al. *The Journal of experimental medicine* 207, 291-297, (2010); Kisand, et al. *The Journal of experimental medicine* 207, 299-308, (2010); Meyer, et al. *Cell* 166, 582-595, (2016)), the molecular and functional impact of B cell-intrinsic AIRE in humoral immunity and anti-*Candida* defense was sought. The IgH variable region (IgHV) SHM landscape of antigen-specific $Aire^{+/+}$ and $Aire^{-/-}$ donor B cells after repeated immunization of recipient μMT mice with $NP_{32}$-KLH (FIG. 13A) were first compared. NP-specific $Aire^{-/-}$ B cells in the recipients' spleen that class-switched to IgG or IgE exhibited higher rates of IgHV SHMs in complementarity-determining region 2 (CDR2) and framework region 3 (FR3) than $Aire^{+/+}$ donor B cells (FIG. 13B). There was also an increased frequency of C-to-T transitions in the SHMs in the IgHV coding sequences in NP-specific $Aire^{-/-}$ donor B cells compared to $Aire^{+/+}$ donor B cells (FIG. 14A), a signature associated with the action of AID in IgHV. Maul, et al. *Nature immunology* 12, 70-76, (2011).

Figure 14B:
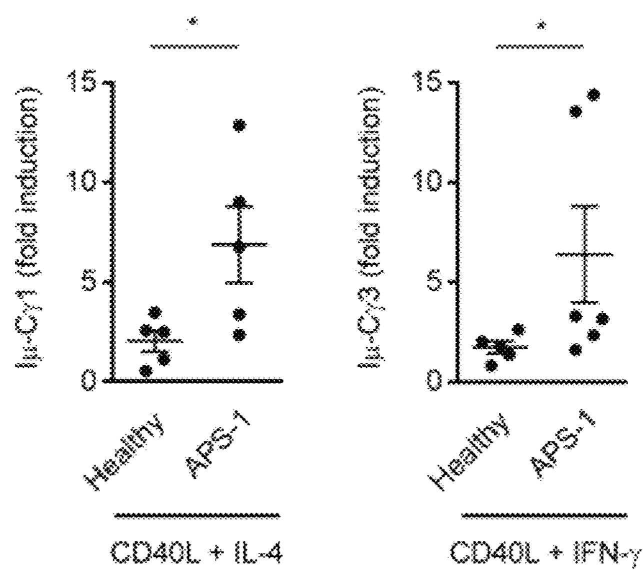
Figure 14C:
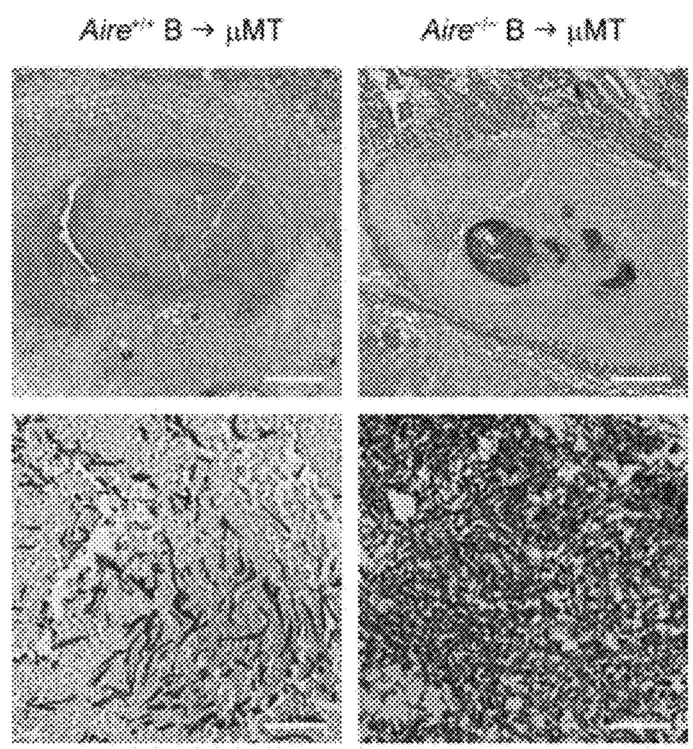
Figure 14D:
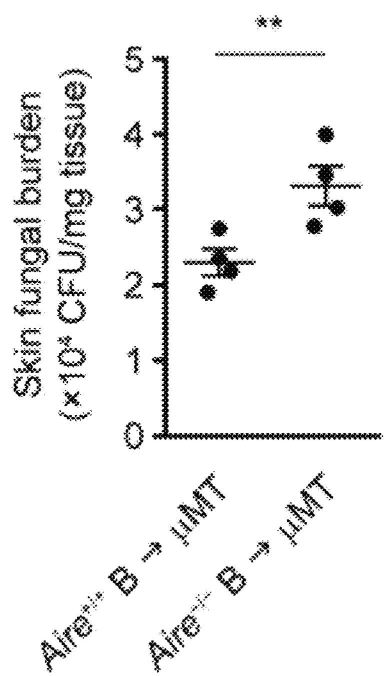
Figure 14E:
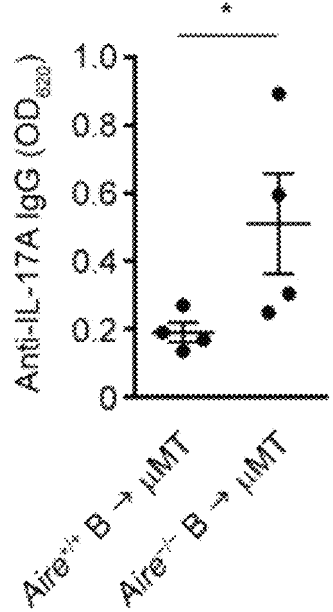
Figure 14F:
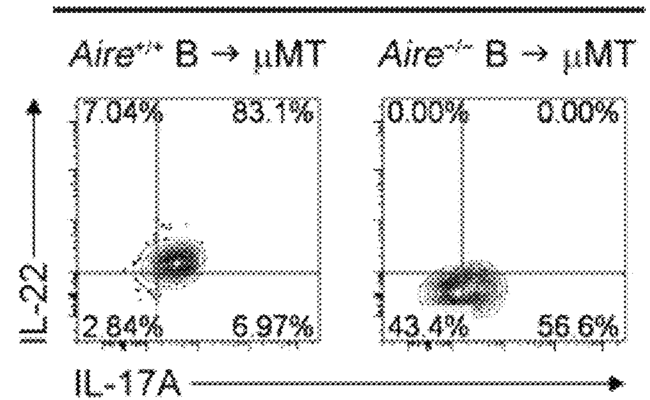
Figure 14G:
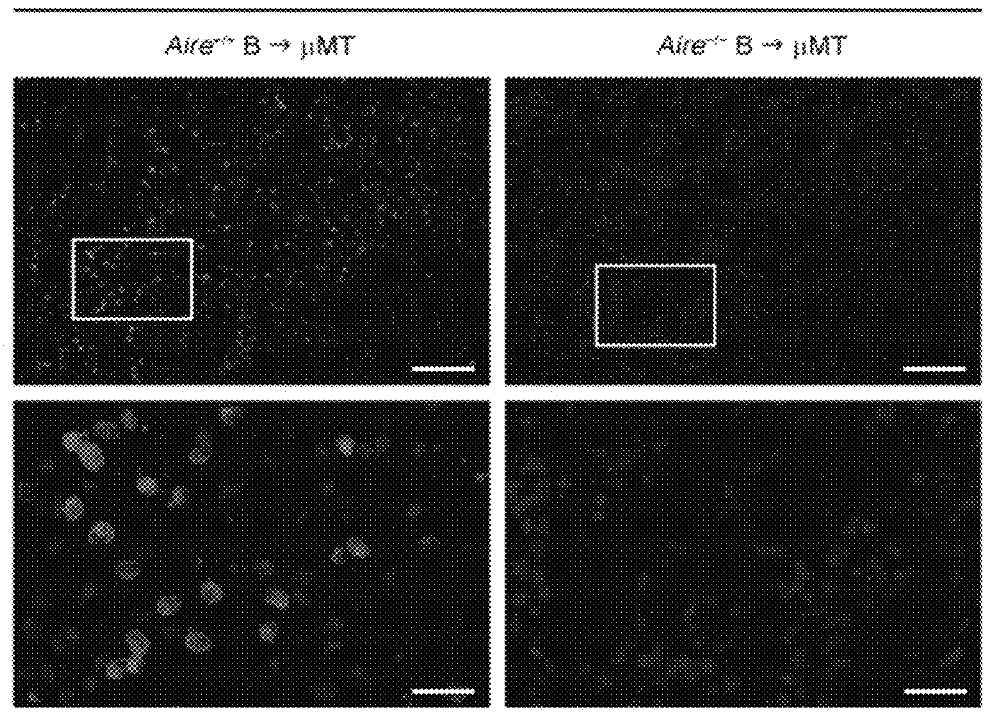
Figure 15A:
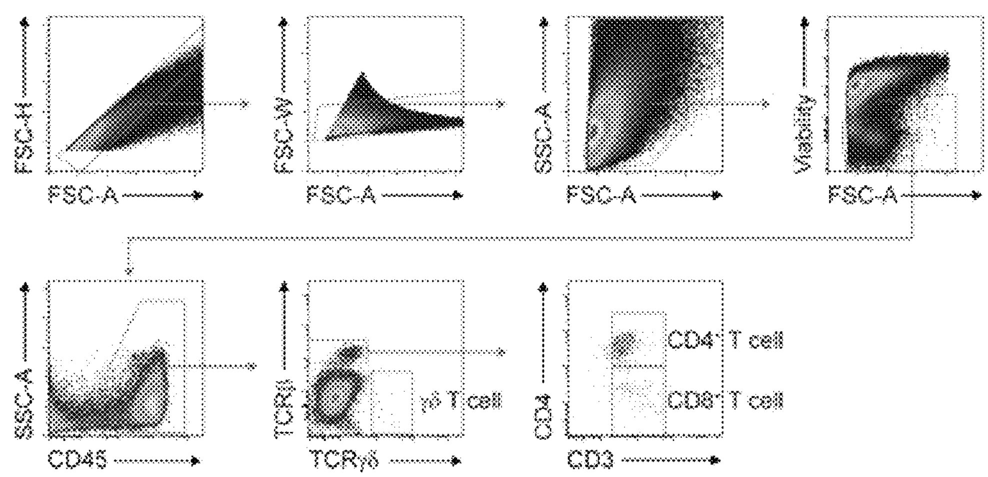
FIGS. 15A-15C. AIRE deficiency in B cells impairs $T_H17$ immunity against cutaneous *C. albicans* infection.
Figure 15B:
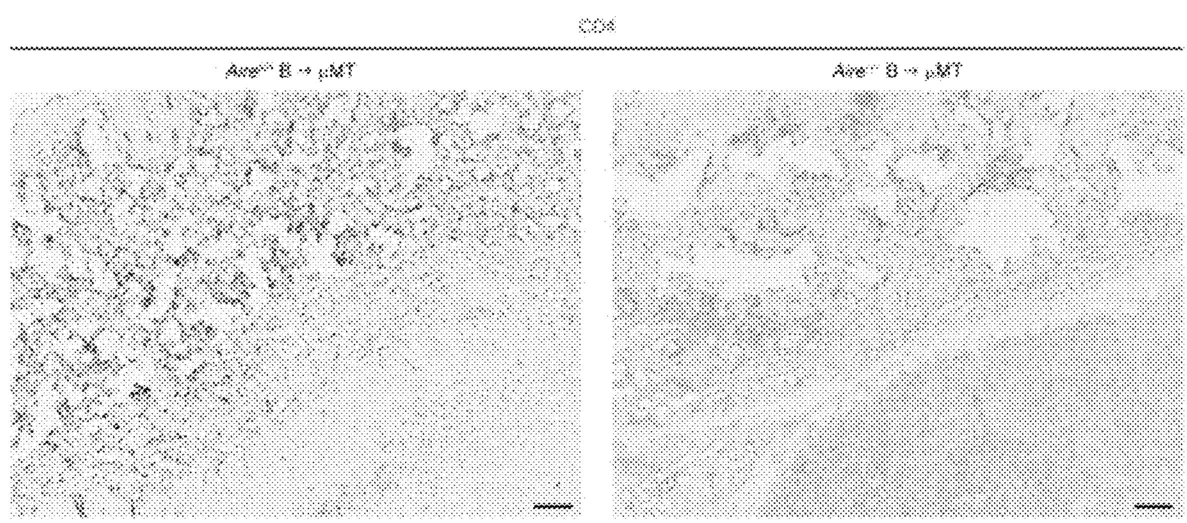
Figure 15C:
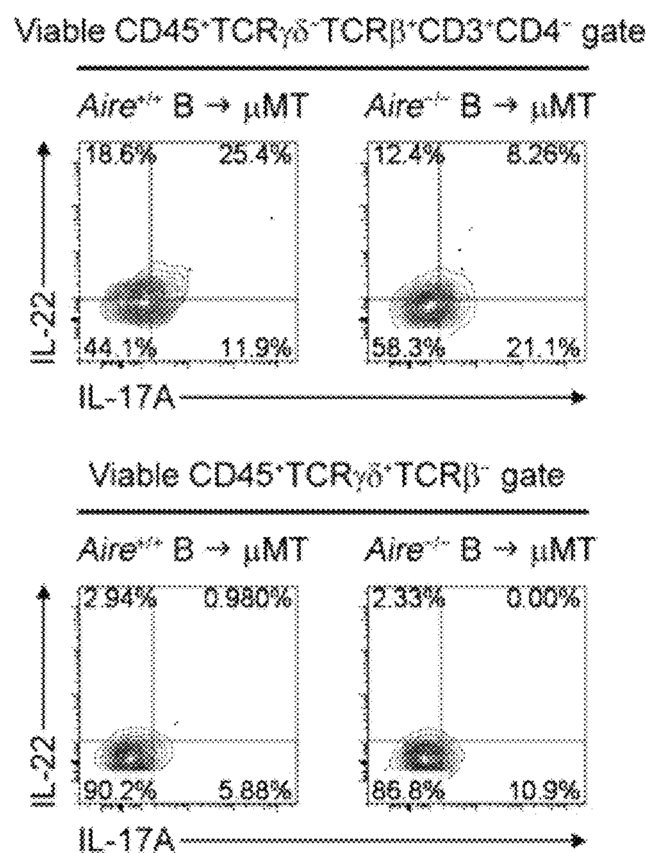

Furthermore, naïve B cells of APS-1 patients underwent elevated CSR than those of healthy donors upon stimulation ex vivo (FIG. 14B). It was then asked whether AIRE deficiency in peripheral B cells could promote APS-1-like CMC. After exposure to heat-killed *C. albicans* and subsequent cutaneous infection with live *C. albicans* pseudohyphae, μMT recipient mice of $Aire^{-/-}$ B cells had heightened fungal burden in the skin 4 d after infection (FIGS. 14C, 14D) and concomitant elevation of autoantibodies to IL-17A, IL-17F and IL-22 in the sera as compared to μMT recipients of $Aire^{+/+}$ B cells (FIG. 14E). μMT recipients of $Aire^{-/-}$ B cells also had reduced IL-17A- and IL-22-producing $CD4^+$ T cells (FIGS. 15A, 15B, FIG. 14F) but not γδ T cells (FIG. 15C), and diminished neutrophils infiltration (FIG. 14G) at the dermal infection site. Therefore, AIRE deficiency in peripheral B cells impairs cutaneous anti-*Candida* defense and promotes APS-1-like CMC by engendering humoral autoimmunity.

Figure 14H:
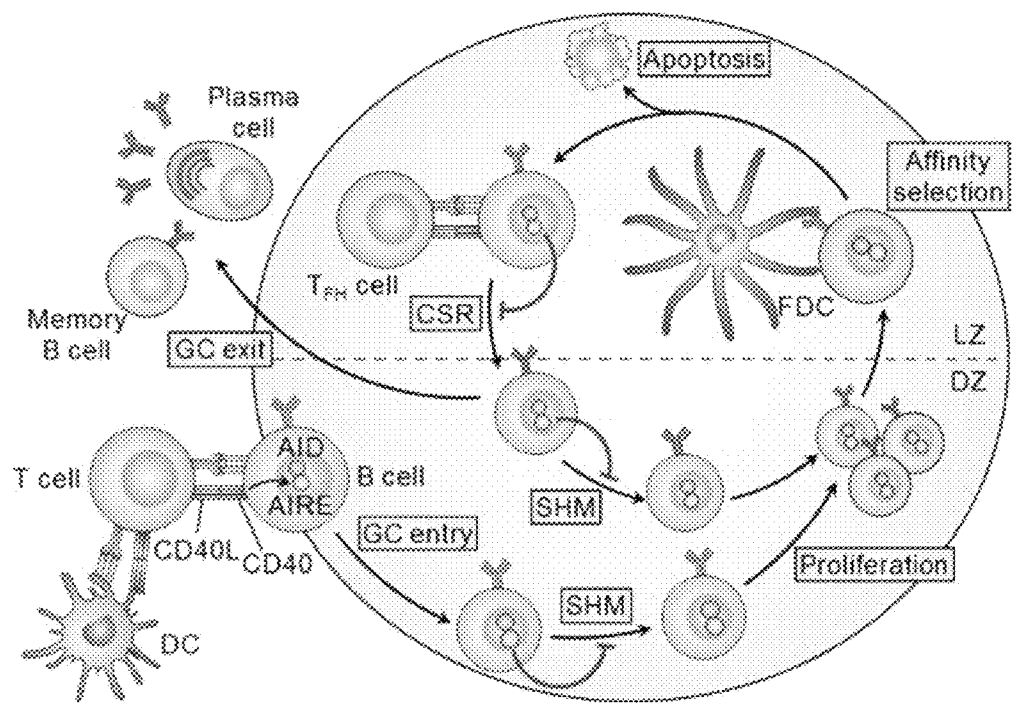

Collectively, this Example defines a crucial B cell-intrinsic AIRE-dependent GC checkpoint of peripheral antibody diversification which suppresses humoral autoimmunity that can arise from the GC reaction (Vinuesa et al., Nature Review. Immunology, 9, 845-857 (2009)) (FIG. 14H), and offers mechanistic insights into the production of high-affinity autoantibodies in many APS-1 patients. Puel, et al. *The Journal of experimental medicine* 207, 291-297, (2010); Kisand, et al. *The Journal of experimental medicine* 207, 299-308, (2010); Meyer, et al. *Cell* 166, 582-595, (2016). These findings also highlight the emerging idea that peripheral tolerance mechanisms can be barriers to the generation of effective immunity, and controlled breaching of peripheral tolerance can permit neutralizing antibody responses that can be therapeutically beneficial. Meyer, et al. *Cell* 166, 582-595, (2016); Schroeder, et al. *The Journal of experimental medicine*, (2017); Rosenspire & Chen, *Frontiers in immunology* 6, 580, (2015). This has broad implications for new approaches of generating high-affinity neutralizing antibodies for therapeutic, diagnostic and research applications against, for example, infectious diseases and cancer.

Detailed Methods. Human subjects. Autoimmune polyglandular syndrome type 1 (APS-1) patients with loss-of-function mutations in the AIRE gene were enrolled in the study with an approved protocol of the Ethics Committee of Medicine of the Hospital District of Helsinki and Uusimaa (HUS), Finland. Hyper-IgM syndrome type 3 (HIGM3) patients with loss-of-function mutations in the CD40 gene were enrolled in the study with an approved Institutional Review Board (IRB) protocol of the Icahn School of Medicine at Mount Sinai. Peripheral blood leukocytes of anonymous healthy donors were obtained from the Southeast Michigan branch of American Red Cross with a protocol approved by the IRB of Wayne State University (WSU) and the Detroit Medical Centre (DMC). Tonsil, thymus and spleen tissues were obtained after pediatric tonsillectomy, cardiac surgery and splenectomy, respectively, from the Children's Hospital of Michigan with an IRB protocol approved by WSU and DMC.

Human blood and tissue sample processing and cell isolation. Peripheral blood mononuclear cells (PBMCs) of APS-1 patients and healthy controls were purified using Ficoll-Paque Plus (GE Healthcare 17-1440-03). Live ($7AAD^-$ or Ghost Violet $510^-$) naive B cells ($CD19^+IgD^+$ $CD27^-$) and class-switched memory B cells ($CD19^+IgD^-$ $CD27^+$) were sorted from the PBMCs to a purity of ≥99% on a FACSAria II sorter (BD). PBMCs of anonymous healthy donors were isolated using a Histopaque-1077 gradient (Sigma-Aldrich 10771) following the manufacturer's instruction. Red blood cells (RBCs) were lysed using an ammonium-chloride-potassium (ACK) lysing buffer (Thermo Fisher Scientific A1049201). $IgD^+$ or $CD19^+$ B cells were purified from PBMCs by magnetic-activated cell sorting (MACS) with a biotinylated goat $F(ab')_2$ anti-human IgD antibody and anti-biotin magnetic microbeads (Miltenyi Biotec 130-090-485) as previously reported. Chen, et al. *Nature immunology* 10, 889-898, (2009).

The purity of the $IgD^+$ B cells ranged from 92% to 99% as determined by flow cytometry with CD19 staining. $CD19^+$ B cells were similarly separated from PBMCs using a biotinylated mouse anti-human CD19 (clone HIB19) antibody, with purity ranging from 94% to 98% as determined by flow cytometry using a different clone (SJ25C1) of CD19 antibody. Human tonsil and spleen tissues were minced into small pieces, meshed through 100 μm cell strainers, and pelleted at 600 g for 5 min at 4° C. Spleen cells were treated with an ACK buffer to remove erythrocytes and filtered through 40 μm cell strainers. Tonsil and spleen cells were then washed with phosphate-buffered saline (PBS). Thymic cell suspensions were obtained by mincing human thymus tissues into small pieces and mechanically removing thymocytes followed by 2 rounds of digestion with 0.2% (w/v) Collagenase II (Worthington Biochemical LS004177) and 0.1 mg/ml DNase I (Roche 11284932001) in Hank's Balanced Salt Solution (HBSS) for 45 min at 37° C. with shaking. The digested samples were filtered through 70 μm cell strainers and washed with PBS.

Mice. C57BL/6J mice (Jackson stock number 000664), $Aire^{+/-}$ (B6.129S2-$Aire^{tm1.1Doi}$/J, Jackson stock number 004743) and μMT (B6.12952-$Ighm^{tm1Cgn}$/J, Jackson stock number 002288) were purchased from the Jackson Laboratory. $Aire^{Adig}$ mice in C57BL/6 background were previously reported. Gardner et al., Science, 321, 843-847 (2008). $Aicda^{-/-}$ mice[1] were generously provided by Dr. Tasuku Honjo (Kyoto University, Japan). These mice were maintained in the same room at the specific pathogen-free (SPF) facility of the Division of Laboratory Animal Resources (DLAR) at Wayne State University. $Aire^{-/-}$ mice were generated by mating $Aire^{+/-}$ mice, and age-and sex-matched $Aire^{+/+}$ littermates were used as controls for ex vivo and in vivo experiments. All breeding and experimental protocols were approved by Wayne State University Institutional Animal Care and Use Committee (IACUC).

Mouse blood and tissue cell isolation. Blood, spleen, inguinal lymph nodes, mesenteric lymph node and Peyer's patches were collected from euthanized mice. Adjacent fat and other tissues were removed before single cells suspensions were prepared, filtered through 100 μm cell strainer. RBCs from blood were removed by centrifugation on Histopaque 1077, and those in spleens were lysed using an ACK buffer. The cells were washed in PBS and counted before cell sorting, flow cytometry or purification by MACS. Resting B cells were isolated from the spleens of age- and sex-matched $Aire^{+/+}$ or $Aire^{-/-}$ littermates by MACS using a B Cell Isolate Kit (Miltenyi Biotec 130-090-862). The purity of the isolated B cells ranged from 97-99.6% as determined by flow cytometry based on CD19 and B220 staining.

Mouse immunization. $2.5\times10^7$ purified $Aire^{+/+}$ or $Aire^{-/-}$ B cells were introduced via the tail vein into each recipient μMT littermate mouse. One day after the adoptive transfer, each recipient was intraperitoneally (i.p.) immunized with 1 dose of 100 μg $NP_{32}$-KLH (Biosearch Technologies N-5060) in Complete Freund's Adjuvant (Thermo Fisher Scientific 77140) and 4 doses of 100 μg $NP_{32}$-KLH in Incomplete Freund's Adjuvant (Thermo Fisher Scientific 77145) once every week. Four days after the last immunization, mice were sacrificed and blood and spleens were collected for ELISA, flow cytometry or cell sorting. In some experiments, mice were immunized with 200 μl of 2% sheep red blood cells in sterile PBS for 3 times, with each dose being 1 week apart.

*Candida albicans* culture. A single colony of *C. albicans* (ATCC MYA-2876) was cultured in YPD broth (BD 242820) at 30° C. for 16 h with shaking at 220 rpm. *C. albicans* existed in blastospore form after the 16 h culture. The concentration of the culture was quantitated using a haemocytometer. The culture was diluted 1:10 with fresh YPD broth containing 10% (v/v) heat-inactivated FBS (Thermo Fischer Scientific 26140079) and grown at 37° C. for 3 h with shaking at 220 rpm. An aliquot of the culture was removed and examined under the microscope to ensure that 95% of blastospores switched to the virulent pseudohyphal form. The culture was pelleted by centrifugation at 4,000 rpm for 10 minutes, washed with PBS twice and resuspended in PBS at the concentration of $5\times10^6$ CFU per 50 μl based on the quantitation of the culture 3 h ago. The pseudohyphae samples were used for either intradermal infection of mice or the preparation of heat-killed samples by treatment at 95° C. for 2 h followed by 3 rounds of sonication on ice at 30% maximum power for 5 seconds per round using a sonifier (Thermo Fisher Scientific Q500).

Cutaneous *C. albicans* infection of mice. $5\times10^7$ purified $Aire^{+/+}$ or $Aire^{-/-}$ B cells were introduced via the tail vein into each recipient μMT mouse littermate. Starting from the day of adoptive transfer, 5 doses each of $10^6$ CFU heat-killed *C. albicans* pseudohyphae were given intraperitoneally to each recipient mouse every 4 d. Four days after the last injection, mice were infected with $5\times10^6$ CFU live *C. albicans* pseudohyphae in 50 μl PBS per spot at the deep dermis of the shaved dorsal region. Conti, et al. *Curr Protoc Immunol* 105, 19 16 11-19 16 17, (2014). The actual dose of infection was determined by immediately plating serial dilutions of the inoculum on YPD agar in triplicate, incubating the plates at 28° C. for 24 h and colony enumeration. The inoculum size per spot ranged between $3.8\text{-}12.3\times10^6$ CFU in various experiments. Four days after the infection, blood was obtained after sacrificing the mice. The entire dermal injection site was excized for histological evaluation of fungal burden by Grocott's methenamine silver (GMS) stain or by plating, or for determination of effector T cell response by flow cytometry. For GMS stain, the tissues were immediately fixed in 10% formalin overnight and embedded in paraffin before sectioning. For plating, each tissue was weighed, minced, grounded thoroughly and resuspended in sterile PBS. Serial dilutions of the suspensions were plated on YPD agar in triplicate and incubated at 28° C. for 24 h before colony enumeration. The fungal load was calculated as CFU per mg of tissue. For flow cytometry, the tissues were washed in FBS-free RPMI-1640 twice, minced and digested in FBS-free RPMI-1640 containing 0.7 mg/ml collagenase II (Worthington LS004177), 2 mM EDTA and 25 mM HEPES at 37° C. for 1 h. The digested samples were passed through a 70 μm cell strainer, washed twice with RPMI-1640 containing 10% FBS, 2 mg/ml glutamine, 100 U/ml penicillin, 100 μg/ml streptomycin and 25 μg/ml amphotericin B. The samples were then cultured in this medium further supplemented with 500 ng/ml PMA, 500 ng/ml ionomycin and 1 μg/ml GolgiPlug (BD 555029) at 37° C. for 5 h before being harvested for flow cytometric analysis.

Culture and stimulation or primary B cells. Peripheral blood $IgD^+$ or $CD19^+$ B cells of healthy donors, $CD19^+IgD^+CD27^-$ B cells of APS-1 patients or mouse splenic B cells were cultured in RPMI-1640 medium (Sigma-Aldrich R8578) supplemented with 2 mM L-glutamine, 2 mg/ml $NaHCO_3$, 100 U/ml penicillin, 100 μg/m1 streptomycin, 0.25 μg/ml amphotericin B and 10% FBS (Thermo Fisher Scientific 26140-079 or Sigma-Aldrich F4135). Peripheral blood $IgD^+$ or $CD19^+$ B cells of healthy donors were stimulated with 500 ng/ml soluble CD40L (sCD40L) (Peprotech 310-02) and 100 ng/ml IL-4 (Peprotech 200-21) or 100 ng/ml IL-21 (Peprotech 200-04). Peripheral blood IgD+ $CD27^-$ naive B cells of healthy subjects or APS-1 patients were stimulated with 500 ng/ml sCD40L and 100 ng/ml IL-4 or 100 ng/ml IFN-γ (Peprotech 300-02). Purified mouse splenic B cells were stimulated with 500 ng/ml sCD40L (Peprotech 315-15) with or without 100 ng/ml IL-4 (Peprotech 214-14), 100 ng/ml IL-21 (Peprotech 210-21) or 25 μM CAPE (Cayman Chemical 70750). In some experiments, sCD40L was replaced with 5 μg/ml anti-CD40. To determine cell proliferation, the cells were labelled with carboxyfluorescein succinimidyl ester (CFSE) (Biolegend 422701) according to the manufacture's protocol prior to culture. Alternatively, 10 μM 5-ethynyl-2'-deoxyuridine (EdU) was added to the culture medium for 6 hours before EdU incorporation was determined by flow cytometry using a Click-iT EdU Flow Cytometry Assay Kit (Thermo Fisher Scientific C10418) according to the manufacturer's protocol.

Culture and stimulation of B cell lines. The human $IgM^+IgD^+$ 2E2 B cell line (He, et al. *Journal of immunology* 173, 4479-4491, (2004)) and Ramos B cell line (ATCC CRL-1596) were cultured in the above RPM1-1640 medium. 2E2 cells were stimulated with 500 ng/ml sCD40L with 100 ng/ml IL-21. WT CH12 cells (from Dr. Tasuku Honjo, Kyoto University, Japan) and $Aire^{-/-}$ CH12 cells were cultured in the above RPM1-1640 medium further supplemented with 5% (v/v) NCTC-109 (Sigma-Aldrich N1140) and 50 μM β-mercaptoethanol (Sigma-Aldrich M3148). To induce IgA switching, the cells were stimulated with 1 μg/ml anti-mouse CD40 (eBioscience 16-0402), 12.5 ng/ml IL-4 (R&D 404-ML) and 1 ng/ml TGF-β1 (R&D 7666-MB/CF) for 3 d. The human embryonic kidney cell/Burkitt's lymphoma fusion cell line HKB-11 (ATCC 12568) was cultured in DMEM/F12 (Sigma-Aldrich D8437)

supplemented with 2 mM L-glutamine, 100 U/ml penicillin, 100 μg/ml streptomycin, 0.25 μg/ml amphotericin B and 10% FBS.

Generation and validation of $Aire^{-/-}$ CH12 cells. Several clones of $Aire^{-/-}$ CH12 cells were generated by targeting the Aire gene using the CRISPR/Cas9 system as described in Ran, et al. *Nat Protoc* 8, 2281-2308, (2013). Single guide RNAs (sgRNA) targeting exon 1 or exon 3 of mouse Aire gene (GenBank NC_000076.6) were designed using the online tool at http://crispr.mit.edu. Sequences with the highest score for the respective region were selected to express sgRNAs, pairs of oligonucleotides were synthesized and cloned into pSpCas9(BB)-2A-Puro plasmid (Addgene 48139) as reported in Ran, et al. *Nat Protoc* 8, 2281-2308, (2013). The sgRNA expression plasmid was then transfected into CH12 cells using electroporation (square wave pulse at 200 V for 30 ms) in serum-free RPMI-1640 with 5 mM glutathione in a 4-mm cuvette. 24 hours after transfection, cells were resuspended in 125 ng/ml puromycin for 48 hours. After a brief expansion in puromycin-free media, single cell clones from transfected cells were screened for loss of the sgRNA targeting site using PCR. Clones with deletions in both alleles were identified by PCR. To determine the exact genomic modifications in each clone, the sgRNA-targeting sites were amplified with primer pairs spanning the targeting sites, and PCR products were sequenced directly using the respective forward primer. In addition, PCR products from clones 43 and 53 were cloned into the pGEM-T Easy vector and sequenced with T7 primer. All three mutant clones used were confirmed to harbor frameshift mutations on both alleles, resulting in termination shortly after the frameshift site. The potential off-target sites in the mouse genome for each guide were identified by the same online tool (http://crispr.mit.edu). Cas9 generally does not tolerate more than 3 mismatches. Hsu, et al. *Nat Biotechnol* 31, 827-832, (2013).

All off-target sites in a potential gene-coding region with non-zero scores (up to 4 mismatches) were verified by sequencing to be intact. The lack of AIRE protein expression in these clones was finally confirmed by Western Blot.

Plasmids. Full-length human AIRE cDNA sequence was cloned into pcDNA3.1(−) with tandem C-terminal Myc and 6-Histidine tag (Thermo Fisher Scientific V38520). Sequences coding various domains of AIRE were deleted using a Phusion Site-Directed Mutagenesis Kit (Thermo Fisher Scientific F541) using appropriate primers (FIG. 12A). Briefly, to delete a specific section of AIRE in the vector, a pair of outward primers was designed to amplify the remaining region together with the plasmid backbone. PCR product was then phosphorylated at 5' end and ligated with Quick T4 ligase (New England Biolabs M2200L) to recircularize it. Human AID was obtained by cloning full-length AICDA into pFLAG-CMV2 vector with an N-terminal FLAG tag (Sigma-Aldrich E7033). Domain-specific deletion mutants and G23S and E58A point mutants of AID were generated using the Phusion Site-Directed Mutagenesis kit using appropriate primers (FIG. 12B). The full-length Egfp sequence from pcDNA3-eGFP (from Dr. Thilo Hagen, National University of Singapore) was then cloned in frame to the C-terminus of AIRE or AIREΔNLS using blunt end ligation of PCR-amplified fragments (FIG. 12C).

Transfection. $10^6$ seeded HKB-11 cells were cultured to 70-90% confluence and transfected with 4 μg plasmid DNA using Lipofectamine 3000 (Thermo Fisher Scientific L3000015) in Opti-MEM (Thermo Fisher Scientific 31985070) by following the manufacturer's instruction. $10^6$ CH12 cells were suspended in a 4-mm electroporation cuvette containing 600 μl sterile PBS. Electroporation was performed using the Bio-Rad Gene Pulser Xcell system (voltage=550 V, capacitance=50 μF, resistance=∞, time constant=1.2 ms). The electroporated cells were transferred to 10 cm culture dishes, subsequently divided equally into 2 dishes containing the CH12 cell culture media supplemented with 250 μg/ml Geneticin, with one dish left unstimulated and the other stimulated with 1 μg/ml anti-CD40, 1 ng/ml TGF-β1 and 12.5 ng/ml IL-4 for 4 d.

Immunoprecipitation. Cultured cells were harvested, washed with cold PBS twice and lysed with a CelLytic M buffer (Sigma-Aldrich C2978) containing 1× protein inhibitor cocktail (Sigma-Aldrich P8340) and 1× Halt phosphatase Inhibitor (Thermo Fisher Scientific 78426) for 60 minutes on ice. The lysates were centrifuged at 12,000 g for 15 minutes at 4° C. Protein concentration in the supernatants was determined by a BCA Protein Assay Kit (Thermo Fisher Scientific 23225). Equal amounts of lysate supernatants were used for immunoprecipitation with specific or isotype control antibodies using protein G magnetic beads (Cell Signaling 8740 or Thermo Fisher Scientific 88847) according to the manufacturers' instructions.

RNA extraction and quantitative real-time polymerase chain reaction. RNA was extracted from cells or tissues other than those from the APS-1 patients using TRIzol (Thermo Fisher Scientific 15596026). cDNA synthesis was performed using the Superscript III first strand synthesis system (Thermo Fisher Scientific 188080051) in a thermocycler (Bio-Rad T100). qRT-PCR was performed with PowerSYBR Green Master Mix (Thermo Fisher Scientific 4367660) on a StepOnePlus instrument (Applied Biosystems) using pairs of sense and anti-sense primers targeting the genes of interest (FIGS. 16A, 16B). For APS-1 patients' peripheral blood $IgD^{+}CD27^{-}$ B cells, following stimulation, the cells were washed and stored in RNAlater (Thermo Fisher Scientific AM7020). Prior to RNA isolation, cells were pelleted and the RNAlater was removed. RNA was isolated using the lysis and stop solutions in a Cells-to-$C_T$ 1-step SYBR Green kit (Thermo Fisher Scientific A25601) and amplified using an iTaq Universal SYBR Green One-Step kit (Bio-Rad 172-5150) on a StepOnePlus instrument using pairs of sense and anti-sense primers targeting the genes of interest (FIG. 16A). The ACTB (Actb) gene was used as an internal control for normalization.

Chromatin immunoprecipitation and quantitative real-time PCR. ChIP was performed using a ChIP assay kit (EMD Millipore 17-295) based on the manufacturer's instructions with slight modifications. Following 3 d of stimulation of $10^6$ CH12 cells as described above, formaldehyde was added to the culture to the final concentration of 1% and incubated for 10 minutes at 37° C. to crosslink chromatin. The cells were pelleted, washed twice in PBS, resuspended in an SDS lysis buffer (1% SDS, 10 mM EDTA, 50 mM Tris, pH 8.1) for 10 minutes on ice. DNA was sheared by 3 rounds of sonication on ice at 30% maximum power for 3 seconds per round using a sonifier (Thermo Fisher Scientific Q500). After centrifugation at 13,000 rpm for 10 minutes, the supernatants were harvested, diluted 10-fold in a ChIP dilution buffer (0.01% SDS, 1.1% Triton X-100, 1.2 mM EDTA, 16.7 mM Tris-HCl, 167 mM NaCl, pH 8.1) containing protease inhibitors, and precleared with 50% protein A agarose/salmon sperm DNA slurry for 30 minutes at 4° C. with rotation. After setting aside an aliquot as input, an AID or control antibody was then added and incubated overnight at 4° C. with rotation, followed by the addition of 50% protein A agarose/salmon sperm DNA slurry for 1 h at 4° C. with rotation. The agarose was then pelleted and sequentially washed once with the low salt wash buffer, once with the high salt wash buffer, once with the LiCI wash buffer and twice with TE buffer, all of which were components of the kit. DNA in the bound chromatin was eluted from the beads using an elution buffer (1% SDS, 0.1 M $NaHCO_3$, pH 8.0), reverse-crosslinked from proteins by incubation at 65° C. for 4 h in the presence of 200 mM NaCl, cleaned by 20 μg/ml RNase A treatment for 30 minutes at 37° C. followed by 40 μg/ml proteinase K treatment for 1 h at 45° C., purified using phenol/chloroform extraction followed by ethanol precipitation with carrier glycogen according to the kit's manual and resuspended in TE buffer for quantitative real-time PCR analysis using PowerSYBR Green Master Mix (Thermo Fisher Scientific 4367660) with the primers in FIG. 16B on a StepOnePlus instrument (Applied Biosystems). The fold enrichment of DNA was calculated using the $\Delta\Delta C_T$ method with control antibody-precipitated samples as an internal reference, and further compared among different CH12 cells and treatments.

Protein extraction and Western Blot. Cells were pelleted and washed twice with ice-cold PBS, lysed with a pH 8.0 protein extraction buffer containing 20 mM Tris-HCl, 150 mM NaCl, 1% IGEPAL CA-630 (NP-40, Sigma-Aldrich 18896), 0.1% sodium dodecyl sulphate (SDS), 1 mM EDTA and protease and phosphatase inhibitor cocktail for 30 minutes on ice. Supernatants were collected after centrifugation, heated at 98° C. in SDS sample buffer with 4% β-mercaptoethanol for 5 minutes to denature proteins. Proteins were resolved in 4-20% Bis-Tris gels (GeneScript M42012) or 10% Tris-Glycine gels (Bio-Rad 4561034) and transferred to 0.2 μm polyvinylidene fluoride (PVDF) membranes (Bio-Rad 1620177). The membranes were blocked with 5% (w/v) non-fat milk in Tris-buffered saline with Tween-20 for 30 minutes to 1 h, incubated with primary antibodies (FIGS. 17A-17D) overnight at 4° C. and subsequently with secondary antibodies conjugated to HRP (FIG. 17E). Signals were visualized with clarity western-blot ECL substrate (Bio-Rad 170-5061) and exposed on autoradiograph films.

Conventional flow cytometry. Cells were incubated with an Fc blocking reagent (Miltenyi Biotec 130-059-901 or Tonbo Biosciences 70-0161) and stained in PBS at 4° C. with antibodies to various cell surface antigens (FIGS. 17A-17D). For staining of intracellular molecules, cells were subsequently fixed and permeabilized using a CytoFix/CytoPerm kit (BD 554722) or a Transcription Factor Buffer set (BD 562725). Isotype-matched control antibodies were used to define the baseline staining for the molecules of interest. Cells or beads stained with each fluorochrome were used to establish fluorescent compensation. 7-aminoactinomycin D (7-AAD, Tonbo Biosciences 13-6993-T500 or BD 559925) or Ghost Dye Violet 510 (Tonbo Biosciences 13-0870-T500) was used to identify and exclude non-viable cells from the analysis. Events were acquired on an LSR II or LSR Fortessa flow cytometer (BD) and analysed using FlowJo 7.6 (Tree Star).

Imaging flow cytometry. $CD19^+$ B cells were purified from tonsillar cell suspensions by MACS with a biotinylated anti-CD19 antibody and anti-biotin microbeads (FIG. 17A). The cells were then incubated with an Fc blocking reagent and stained at 4° C. with antibodies to surface IgD and CD38, fixed and permeabilized, and stained for AID and AIRE or with isotype control antibodies, (FIGS. 17A, 17D). Nuclei were counter stained with 4',6-diamidine-2'-phenylindole dihydrochloride (DAPI, Sigma-Aldrich D9542). Tonsillar cells stained with each fluorochrome were used to establish fluorescent compensation. Cells were imaged on an ImageStream X Mark II imaging flow cytometer (Amnis) and data were analysed using IDEAS 6.1 (Amnis).

Immunofluorescence analysis. Frozen human tissues were stored at −80° C. before 6-7 μm tissue sections were made using a cryostat (Leica CM1950). Sections were fixed with 4% paraformaldehyde, permeabilized in PBS containing 0.2% Triton X-100, blocked with PBS containing 1% BSA, 100 μg/ml human IgG and 10% serum from the source of the fluorochrome-conjugated antibodies, and stained with various combinations of primary antibodies against the molecules of interest (FIGS. 17A, 17B, 17D), followed by appropriate fluorochrome-conjugated secondary antibodies (FIG. 17E). Nuclei were visualized with DAPI. Following washing, slides were mounted using a FluoroSave reagent (EMD Millipore 345789) and imaged on a confocal microscope (Zeiss LSM 780 or Leica TCS SP5). Pseudocolor images were processed using Photoshop CS6 (Adobe).

ELISA. ELISA to determine NP-specific antibody affinity maturation was performed as previously described (Ballon, et al. *The Journal of clinical investigation* 121, 1141-1153, (2011)) with minor modifications in the reagents. Briefly, each serum sample was titrated on both $NP_{29}$-BSA- and $NP_4$-BSA-coated microtiter plates. The ratio of binding to $NP_4$-BSA and $NP_{29}$-BSA is an indicator of relative Ig affinity maturation. Bound antibodies were detected using horseradish peroxidase (HRP)-conjugated goat-anti-mouse IgG1, IgG2b or IgG3 (FIG. 17B). The colorimetric reaction was terminated with the addition of an equal volume of 1 M $H_2SO_4$ and quantitated on a microplate reader (BioTek Epoch) at 450 nm. ELISA to determine IgG1 and IgA secretion by ex vivo stimulated mouse B cells was performed using a mouse IgG1 or IgA quantitation set (Bethyl E90-105 or E90-103). Anti-IL-17A, IL-17F and IL-22 autoantibodies in mouse sera were measured using microtiters plates coated with 1 μg/ml recombinant murine IL-17A (Rockland 010-001-B32), IL-17F (Rockland 010-001-B32) or IL-22 (GoldBio 1310-22). The plates were blocked with 10% BSA in PBS, washed, incubated with mouse serum samples, washed and then incubated with an alkaline phosphatase (ALP)-conjugated horse-anti-mouse IgG antibody (1:500, Vector Laboratories AP-2000). Following washing, the colorimetric reaction was developed using the BluePhos phosphatase substrate system (KPL 50-88-02) and quantitated on a microplate reader (BioTek Epoch) at 620 nm.

IgHV repertoire and mutation analysis. Live ($7\text{-}AAD^-$) unswitched ($IgM^+IgD^+$) or switched ($IgM^-IgD^-$) NP-specific B cells ($CD19^+B220^+NP_{36}{}^+$) in the spleens of immunized μMT recipients were sorted using a SONY SH800 cell sorter (SONY Biotechnology) and resuspended in RNAProtect solution (QIAGEN 76526). High-throughput IgHV repertoire profiling by RNA-Seq was performed iRepertoire, Inc. The raw sequences were processed and analysed using the IMonitor 1.1.0 pipeline. Zhang, et al. *Genetics* 201, 459-472, (2015). With this pipeline tool, each sequence was mapped to the *Mus musculus* germline V-D-J sequences (IMGT, http://www.imgt.org/vquest/refseqh.html) to identify the V, D and J gene segments, and the CDRs, such as CDR3, were also determined for clonal clustering. The sequences observed only once in a sample were filtered off to reduce the sequencing error. Subsequently, the sequences were normalized according to the number of cells in each sample. By comparing the sequence of each clone with the germline sequence, the mismatches of nucleotides were regarded as potential mutations. To eliminate PCR noise and sequencing errors, the first 25 bp of the sequences corresponding to the primer-binding site were excluded from the analysis, and the sequences were filtered if 3 successive mismatches were observed in them. Finally, the mutation rate for each IMGT position in the IgHV was calculated if the sequencing depth for that position was ≥10, and the frequency of each type of nucleotide substitution at these mutated positions were computed for each Ig isotype.

Statistical analysis. Results are expressed as mean±S.E.M. Statistical difference was assessed by t-test or Mann-Whitney U test as stated in the figure legends, unless otherwise indicated.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the production of antibodies with increased SHM and CSR following AIRE downregulation, as described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

SEQUENCES

AIRE [*Homo sapiens*]: Accession: CAA08759.1 (SEQ ID NO: 1)
MATDAALRRLLRLHRTEIAVAVDSAFPLLHALADHDVVPEDKFQETLHLKEKEGCPQAFHALLS
WLLTQDSTAILDFWRVLFKDYNLERYGRLQPILDSFPKDVDLSQPRKGRKPPAVPKALVPPPRL
PTKRKASEEARAAAPAALTPRGTASPGSQLKAKPPKKPESSAEQQRLPLGNGIQTMSASVQRA
VAMSSGDVPGARGAVEGILIQQVFESGGSKKCIQVGGEFYTPSKFEDSGSGKNKARSSSGPK
PLVRAKGAQGAAPGGGEARLGQQGSVPAPLALPSDPQLHQKNEDECAVCRDGGELICCDGC
PRAFHLACLSPPLREIPSGTWRCSSCLQATVQEVQPRAEEPRPQEPPVETPLPPGLRSAGEEV
RGPPGEPLAGMDTTLVYKHLPAPPSAAPLPGLDSSALHPLLCVGPEGQQNLAPGARCGVVVTG
LRCRSCSGDVTPAPVEGVLAPSPARLAPGPAKDDTASHEPALHRDDLESLLSEHTFDGILQWAI
QSMARPAAPFPS AIRE [*Homo sapiens*]: NCO Reference Sequence: NC_000021.9 (SEQ ID NO: 2)
CGCGGGGGTATAACAGCGGCGCGCGTGGCTCGCAGACCGGGGAGACGGGCGGGCGCAC
AGCCGGCGCGGAGGCCCCACAGCCCCGCCGGGACCCGAGGCCAAGCGAGGGGCTGCCA
GTGTCCCGGGACCCACCGCGTCCGCCCCAGCCCCGGGTCCCCGCGCCCACCCCATGGC
GACGGACGCGGCGCTACGCCGGCTTCTGAGGCTGCACCGCACGGAGATCGCGGTGGCC
GTGGACAGCGCCTTCCCACTGCTGCACGCGCTGGCTGACCACGACGTGGTCCCCGAGGA
CAAGTTTCAGGTGGGCTCCCCGCCCGCCCCCCGCTGCCCCCAGGCCCTGTGAGCCAGGG
ATAGTCCCCGGGGAAGTTCCAGGAGGACCCCGCCCCTCCAGATCCCCAAGCCCCTCCAG
CCTTCCCCAACTCCCTCCCCACAAGGAGCCAGGGGCGTCCCTGATGACAAGTTAGAAGTT
GGTCCCCTTCCCCCAGCCGTCCCCACACCTCACCCCCAAGCCAAGGGAATGGCCTCCAG
GTTCCCCCAGCCCCACCCTCAACACCCCTACACCACCACCTGACTCCACCACAAGCCGAG
GAGATGGGCGTGGAGCTGTCCAGGTCGCCAGCGCCTCTGCCTGGGAGCTCCACCCTCTA
GTCATGATGGAGATGGGCAGGCCGCAGGGTGTGGGGGACCATGGCAGGGACCCTCATGC
CACCCCACTGCAGGAGACGCTTCATCTGAAGGAAAAGGAGGGCTGCCCCCAGGCCTTCCA
CGCCCTCCTGTCCTGGCTGCTGACCCAGGACTCCACAGCCATCCTGGACTTCTGGAGGGT
GCTGTTCAAGGACTACAACCTGGAGCGCTATGGCCGGCTGCAGCCCATCCTGGACAGCTT
CCCCAAAGGTGGGTCCTGGTGGACTCAGCCATGCTGGGGGCCTGGGGCAGCTGCTGTCA
CCTGCTCAGCCCAGCTGGACTGGAACCGGAGTGGTGTTTGAGGAGCCCGTGGGTGATGT
TCCAGGACCGTCTTGGATCCTAAGAGGCAAAGGGGCCAGGCCTCACCTGTCTGGCCAAG
GTGTCCAGTTCTGGGGCCCACCCTACCCCTGGAGAAAACCCTGAGGTTGGGACCCTGCTC
CTGCCCCTGAGCTGCAGATGTGGACCTCAGCCAGCCCCGGAAGGGGAGGAAGCCCCCGG
CCGTCCCCAAGGCTTTGGTACCGCCACCCAGACTCCCCACCAAGAGGAAGGCCTCAGAAG
AGGCTCGAGCTGCCGCGCCAGCAGCCCTGACTCCAAGGGGCACCGCCAGCCCAGGTACC
CTCCCTGCAGGGGAAGCCAGCCAGGGTCTCCAGTCTTCCCGGGCTTCCCCGGGAGCCCA
CGCCCCCTCCCCACCCGGGCTCCCACCCACTGGGTGTGGGGCCAGCCTGCCTGGGGCT
GTGGGGGTCTCCTCTGGGTACTAGACCCACACACTGGACCAGCCTCTCAGCTCCCTCCTG
CCTGAAGGCTGAGCTCCCCGGAGCTGGTGAAGTAGGCGGGCGGGTCTCATTTCCCTTTTA
CTGATGAGAAACCAGAGCCCGGCAAAGGGACTACCCAGCACTGGACCGCCCCCTCCACG
CCCTCCCACCGCGGGCCCCTGCCCACCGGCACTCACCCCCACTGAGAGGGGAGGCCAG
GCTGCCCCCAGCTCCCCCATTCAGGCTCTCAACTGAAGGCCAAGCCCCCCAAGAAGCCG
GAGAGCAGCGCAGAGCAGCAGCGCCTTCCACTCGGGAACGGTGAGCGGGGCCCAGTGG
GAGCGCCTCCCTTCTCCCTGGCCAGGGGCAAGGGGTCAGGGGTCAGAGCAGGGCCTGC
CCTCTGAGACCCTGTCCTAGGGGCTGGGGACGTGCTGGCCTGGTGTGTCATTCCAAGGG
CCTAAGCTGCACCACCAGACCCAGGAAGGGGACACCTTGGGTCTAAGCATGATCTTGCCA
GTCGCCCCTGCCCCCACTGCACCCTGGTTCTGGGACCCCCTTCTCAGGCACCTTCTCTGC
CCGTCCACTCCCTATCCTTCAGGACCAGCCTAGACATAGCTTCCTCCAGAAAATCATCCCT
GGCCCCCAGCTGCATGCAGGCTGAACCCTTCCTGTCCCCTTCTCCTTCCTTCCCAGGGCA
CTGGACTCCAGAGACCCCCTATCTCCCTGAGGGCAGAGCCTAGGAACTCTGTGTCCCTCC
CGGCACAATACAGGGCCCATGTCATGGGGGGGTGGGTCTGGTCATTGGTCATGCCTTCCT
ATCCATTGTGCCAGCTCTGCTGACACTGCCACCCCCCAGCACACGCACACTTGGGTGCAC
ACACGAACACACACACATTCTCATGTCTCTGCACTTACCTGTGGGCTGTCTGCACATGGCAGG
GCTGGGTCCCCTCCTTGGCCTGCCCTGGCTGGAAGGAAAGGGCTCTGCAGCCCAGTGCT
GCCTGCTTCTGGCATAGAGTATGTGCTTGGGAACAGTCTTCCCCACGGGTGACCCCAATG
GGTGTTCCCTTTCCCAGGGATTCAGACCATGTCAGCTTCAGTCCAGAGAGCTGTGGCCAT
GTCCTCCGGGGACGTCCCGGGAGCCCGAGGGGCCGTGGAGGGGATCCTCATCCAGCAG
GTGTTTGAGTCAGGTAGACGCTGTGGCGGGGAGATGGGGCTGATGGGGAGACCCAGGCT
CCAAGATGGAAGGAGGACCACGCCCCTTTGCATCCTGGTGGTCCCACAGCAGACCGGACT
GTTGCTCAGGTAGCCAGAGTTTCTGCCTGTGGTTCTGCTGACTTTGGAGGAGGAGGGTGA
GCACTGAAGTCTCCCTGTCGGGGGACCTTCTGCAAGGCCAGCGGTCCAGGCCCACATCC
CCACCCGGGATGTACAGCACTCCCCAGTCACCTCCATCCATGTGCATGGGCCCTCCTGGG
CCATGGGGTTGCATCCTTAGAAAGTTCTGCCTGTGCTGCTGAGACCCTCCAGGGTATCGG
CATTCTTCAACCAGGACAGCCTGTAGCATAGCGTCCTTGCCCCCCATACCCTGGCCAGCC
TGCAGCATCCTCGCCCGCCATTCCCTGGCCAGCCGCTGACCCCATGCAATCACCAGTGCC
ATCTGACCAGGGCACAGCAGGGCCGCTGGTGGCAGACCCACCGTGCCATCGGGGCATTC
CATCTCAAGTCCCTGACACGGTGTCTCCTCGGTGCTGGACATGGGCTGGGAACACCAAGC
ACAGCCAGGGCCCTGGTCTTGCACCTCTGGATGGTCCCAAGGCCCACTGTGTTACTTCCT
AAGGCTGTTGGTTAAATTGGCACAAACTGGGAGGCTTGAAATGACAGAAATGCCAACATCG
AGGTGTCTCGGGGCCACACTCCCTCTGGAGGCTCCAGGGAAGAATCCTTCCTTGTGTCTC -continued

| SEQUENCES |
| --- |
| CCAGCTGCTGGTCATTATGGGGGTACCCCTGTGCTCCTTGTTCCTGGGCTCAGGACCCAC<br>CGCTCCAGCCTCTGCTTCTGTGGTCTCACAGCTGTCTCCCACGTGTCCTCTTTATAAGGAC<br>ACCAGTCATTGAACTTATGGTCCAGTGTGACCTCATCTTAACTAATCACATCTACAAAGACC<br>CTGATTTCAAGTAAGGTCACACTCTGAGGTTCTGGGTGGACGTGAACTTCGGGGGACGCT<br>GTTGAACACCCTGGTGTAGATCCAGGACAATCCCCGGGCCCCAGACTCGACTGGGGTGG<br>GGGCGGGCTGGAGGAATGCAGGCTGTGGGAACTCCACCTGTCTCTGCTAGACCCCACCC<br>TGGGGCCTACACGACTGCCAAGGCAGGTCCTGCTGGGCGGGTGAGCCAGGACCAGCCG<br>GCATCTCCTCCCAGGCGGCTCCAAGAAGTGCATCCAGGTTGGCGGGGAGTTCTACACTCC<br>CAGCAAGTTCGAAGACTCCGGCAGTGGGAAGAACAAGGCCCGCAGCAGCAGTGGCCCGA<br>AGCCTCTGGTTCGAGCCAAGGGAGCCCAGGGCGCTGCCCCCGTAAGCACCTGACCTTCC<br>CTGGGGAGCCTGGCTCTTGATGCCCCCCGCCCCAGGAACAGCGTTGCCTCTGGGGGAGT<br>GGCTCTGCTGGGGGCTGGGGGCTGCTGCCGAGAGACGCCTGGTGCCACAGCCATGTGCA<br>CCCTCGCTGCTGAGGCTGCCCCCATTGCTGACGCCCCTCTTCCTTGCAGGGTGGAGGTGA<br>GGCTAGGCTGGGCCAGCAGGGCAGCGTTCCCGCCCCTCTGGCCCTCCCCAGTGACCCCC<br>AGCTCCACCAGGTAATGCCCTAGACCACAGGAGAGGCCCCTGTCTGCCCTTGCTCCCCTC<br>GGGTGGGTCCTGCTGCCTCTGCCTTTACCTGGGCACTCAGGGATGAGCACCGGGGCCTG<br>AGCCCCTACCCACAGGGTACAGCTCTTTTTCTTTAATAGACAGTATTTTTTTCCTGATAATAC<br>GCAATGGTAATAGTTTAAATGAGTCAGAGAAAGTGAGGTCTTCTCAGGCTCTTAAGAGCAT<br>GGCGTTTGGTCCAGGCTGTACCCGCTGCTCTCAGCTGGGCCCGTGGGTGGGCCGGGCGC<br>CCCTGCTATAGCCAGGAGGTCAAGGATCCACTGGGAATGCCATGCTCATCTTTCGTCCCC<br>AGCATGGTTTCTTAATGGGGTAGAAGCAGTGTGGGGGGTGCCTGCCGTGGTGGGTTACAG<br>ATCTTGACCACTTGGCACCAGGGGCTCTGTGGGGCCCTGGCACTTAGCAGTGACAGGAGC<br>CAGTCCTGCCCTGCAGGAGCACCCGGGCTGGTGGGCGTCTGGGGGATTGTTAGAATGAG<br>TGAGGTCATTGCCGTGCAGGACCAGCCTAGCCTGGCTGTCTGGGGGGATTCTGGAGGAA<br>GTGGTACCTGGGAGACCCCTGAAGGCACAGCAGGCACCATCCAGGCAGGGCACAAGGAC<br>GGTGGGGGCTGCAGGTGGAGGATTCAGCAGGCGCTGAGGTCGGGAGAGACCTCCCTGG<br>GCCTGGCCCCACTGCCCTGTGAGGAAGGGTTCATGTGGTTGGTGTACAGTTCCGGGGCC<br>CCTGGAACGCAGCAGCCTGCAAGAAACCGGGTTTTCTTCCCAATAGGGATGGCCCCGGG<br>GGGTGTCTGTTGGAGACCAGATGGATGGGGAACAGGTGGTCAGGGCAGAATTTCAGGCC<br>CTGGCAGCATGGGAGCAGGGCAGAGACTGGGGAGTTCAGGTACCCAGAGATGCTGCTGG<br>GGGAGCTGTTTTGGGAAGGAGGTGGCTCTCAGGAGGGTGCTGCACCCCAGCCCAGTCTG<br>CATGGGCGTCTCTTGCCTGTGCCAGAAGAATGAGGACGAGTGTGCCGTGTGTCGGGACG<br>GCGGGGAGCTCATCTGCTGTGACGGCTGCCCTCGGGCCTTCCACCTGGCCTGCCTGTCC<br>CCTCCGCTCCGGGAGATCCCCAGGTGAGCCTGCACCTCTGCCAGCGCAACCAGGCCACC<br>CCGGTTCACGGCCGCCTCCACCCACTGACCCTGAAGGGAAGCCACCCCAAGCCTCTCCC<br>ATCCAAGATGGAAAGGGGTTCTGAGTCAGGTCACTGGGCCGTGGGGCCGGGGCCTGGGG<br>TTTTCCCACCCTGCCACCTGCCTCCCGGTCTGGCCACACCTGCTGCCCAGCCTGGACAGC<br>TGGGCCCCTGAGGGCAGCAAAGCAGAACAGAGGCCCAGGGCGAAGATGCCACCCTGTCC<br>AAGCTCATCCCAGGCTGCAGCCCACGCCCCCATGGGTAGCCGGCCCCCACCCCCAAGCC<br>CCACCCCAGAGTCCCACTCCAGACAGGGCTGGGGAGCACAGAGGCCACAGAGCTGTGCC<br>CCCCAGGGCAGGTGGGAGTTTGTCCACCAATGCACAGGACGCCGGGCTTAGTGGGGGCG<br>GGAGGCCTCCTCTGCGTTCACATCCCGGTGCTCCTTCCCCACGGCCCACCGAGCCCTGC<br>CCCCATTCCAACCCCACAGGACGTGGCAGTCTGTGGGAGGAAGAGCTCTGGGTGCAGTG<br>GGGACCCACGTTCAGGCGAGGCTCTGCCCCAGCCCCTGAGTGGCCGTCATCAGGCCCCC<br>TCTCAGCCTTGTGCCTCATCACTAGAATAAGGGGCACAGTGGGGGTCATTGCTCGGCTCC<br>TGAAGCCGTTCCTCCTTGCCGTCTCTTTCTGCCCTTGATCACCTCCCCATTCTGCTGGGTG<br>CCATTCCCCTTAACAGGTGGGTCAGTTTAGGGAGGCCCCCGGCAGGGCCCAGCCCTGAG<br>AGGCAGGCAAAGCCACCAGGGCTCGCAGGTGTTGGGGATTCCTGGGGTTCATCAGAGAG<br>CACGCCAAGGGGACCCTGATCACGCTGGCCAGGGCCACCCCACGAAGGGTAAATGTCCC<br>CCTGCTGGGCTCTCCCTTCCTGTGTCTCTGCCCATCTCTCTGCTGTGCCTCGGTTCCCCCT<br>CTGTGAAAAGACATGGTCGGAGCCCTGGAGCTCCACCCGTGGGTTTGGGGATCTGTCACC<br>CGCTGTCTTGTTCTGCATGTCTCTGACTGGTGGACACACGAGCAGTGGGACCTGGAGGTG<br>CTCCAGCTGCCTGCAGGCAACAGTCCAGGAGGTGCAGCCCCGGGCAGAGGAGCCCCGG<br>CCCCAGGAGCCACCCGTGGAGACCCCGGTATGGCCACGCCCCCTCCTAGCCGGGCCACC<br>CCTCCTGTCCACATGGCCACGCCCCCTCCTAGGCTGGGCCACCCCCTCCTGTCCGTCTGT<br>CCCCTGGAGTCCTGTGGGACAGGACTGCCCCAGCCATAGCACTATGTCCCCCATGCCCAA<br>GCCCGGTCCTTGTGGTCTCCTGCAGTGGAGTCCCCATCATGGTTCCTGTGGGCCTAAACC<br>CAGCTCTCCTGGCTGCGGGTCCACCCCGGGGGGCACTATGAGCATTGATAACGGCCCCG<br>GAAGATGTGTTCCTTGTTCTGCTGCTGTGAGGGTAGTAGGTCTACTGTGCACAGACCCAGT<br>GTTCCCTCTGACAGCCCTGAGGGCCAGGGGGCCCCCCGTGTGTAGACGGGGGAGGAGG<br>GAGGACCACAGAGCCAGGAAGTGCCACAGCCTTTCCCACTCAGTGTGGACGCCTTCCACC<br>ATGCCAGCCCTCCGCCCCCACCATGCCAGGCCTCTGCCCCCACCCTGCTGCCCTGGGTTT<br>CAGGGTCCCAGCAGTCACTGACTCCTGGGTGGTGCCGGGCAGGCGCCCGCTGCCCCTCT<br>GATGCTGACCCTTGGGTTCCAGCTCCCCCCGGGGCTTAGGTCGGCGGGAGAGGAGGTAA<br>GAGGTCCACCTGGGGAACCCCTAGCCGGCATGGACACGACTCTTGTCTACAAGCACCTGC<br>CGGCTCCGCCTTCTGCAGCCCCGCTGCCAGGGCTGGACTCCTCGGCCCTGCACCCCCTA<br>CTGTGTGTGGGTCCTGAGGGTCAGCAGGTGAGCGGGGAGTGGGGGTCAGGGTGGGCTC<br>TTCAAGGAGCCCAGGACCTACGGGGCGGATGAATTCACCTGAAACAGGAGGAGAGGGAG<br>GCCAGGCGAGAAAGGCTCCGGGAGGCACAGGGCCTGGGGCTGTGGGGGGAGCGTGGG<br>GGGCTGCGGGGGGAAGGGGACGCTCCTAGACCTCCACTCCAGCTCCTGGCCCTGGGCAT<br>TACTGCTCCCCCCACAAGGCAGGACAATGAAGGGGGGGATGTCCCAGCACACGTGGGAG<br>CCCTCCCCTCCCTGCCTCAATTCCCTTCCCTGCACCCCTGTGGGCACCGCCTTTCAGGAG<br>ACTCCCGCACTCAGCCCCAAAGGAGGCCAGGCCCGCCAAGCAGGAGAGAGGTGCGGGC<br>GCCAGGCTTGCAGGCAGCAGCCTGAGGGTGCTTGGGTCGCCCCTGCCTCCTGGGGATGG<br>GACTGGTCCCGCTGTCCTGCAGCCTGCGTGGCACCGTGAGGCTCCTCACTTGCGCCTAGA<br>CCCGCCGTCCAGCCCTGGGTGGTCCCAGGGGAGAGCGCACAGGGCTCGGGTTCGGGTT<br>CAGCTACATTTCCCCCGGCCCCCCGCGTCACCCCGCGCTGTTGCCTCCCACAGAACCTGG |

-continued

| SEQUENCES |
| --- |
| CTCCTGGTGCGCGTTGCGGGGTGTGCGGAGATGGTACGGACGTGCTGCGGTGTACTCAC TGCGCCGCTGCCTTCCACTGGCGCTGCCACTTCCCAGCCGGCACCTCCCGGCCCGGGTG AGTGAGCGTGGTCGGCGGGGAGGCCTGAACCCACACCCACACCCTACACCCCACCCCAC ACTCCCCACCCACATCATACAGCCCACAACCACACCCCACCCACACCCCACACTCCCACC CACACCTTGCACCCCACCCCACACCCATGCCCTGCACCCACACCCTACACTCCACAGCCA CACTCCACCACACCCCCACCCACACCCTACTCCCCACCTCATACCCTGCACCTCACCACAC TCCACAGCCACACCCCACCCCACACCCCACACTCCCACCCACACCCTACACCCACCCCAC ACCCTACACCCAACCCAAACCCACCCAAACCCACCACTCCCACTCTCCACCCACACCCACA CCCCTTCCTCACACCCCACACCCCCATCCCCCACTCACCACCCACGCCCACACCCCACAC CCCATACCCCGGAGGTGGCACTCCTGCTCCCCCCCAGGGCTGGCAGCCCCTCATCCTCT GCTGCAGGACGGGCCTGCGCTGCAGATCCTGCTCAGGAGACGTGACCCCAGCCCCTGTG GAGGGGGTGCTGGCCCCAGCCCCGCCCGCCTGGCCCCTGGGCCTGCCAAGGTCAGTG CCGCAGGGGCCCTCCATGCATGCCGGTGCTGGGGGTGGGGAACCCCTTGGGTTGGTGTT GGGGGAGCACATCTCAGGGCAGACCCTGGGTGCCAGCTTCGAGGGCTTGCACCAGACGC ACTGACCATGTGCTCATTATCTGTAGAAAATATTTCCCCTTTAAACCAATTCTTTTTGGCAAC TTAAATATAGTTAAAAAGGAAGCTCCCCCCGAGGGTTGGTGGCTGACGTCACGGTTGGCT GTGTGGCCGCCTCACAGCATGAGCCTGAGAGTCCTGCCAGGGCTCCCTGGTGGGGTGAA GGGAGAGCGGGAGCGCCCGGCCTGCAGGAGCAAACCCCCACCCTGTCTGACCCCTCCAG GTTGTCTCACCCCCAGCCCTCCCTGGGGCCAGGATCCACCCCACTGTGTGGCCAGAGCC CTCTCAGAGAGGCAAAGTGACCCCGGGTCCAGCCAGTAGCTCTTCCTGTCCTCCTGCTCC GGGGTCAGAGAGGACCTGGGTGGCGCGGAGACCCCTGACTGCTGGGGCGGCTGGGCTT GCCCTGGAGCTGGGTGTGGGGGAGGCCCGAGTCGCTGCTGCAGGAGCCTCCGGGGGGG TGGCCTCTTGCCCTGACCGTCCCCAGCAGAGGCCTCCTGAGCACATCCTGGCCACCGAG GAGCCTTTAGGGATCCTGGGGTGATGACACGTCCCACCTGCTCCACTGGCCCATGCTCTT TCCCAGCTGTGCCTCCGCCCCGTATACACCGTGTGGGTGACAGGCCACCCCGGCGTGGT ACTCCCCAGGAGGGTGACAGCCTACCCCAGCGTGGTACTCCCCGGGCAGGTGACAGGCT TCCCCGGCATGCAGGCTCTGGCCTGGCATGGCACAAGCCTCAGACCCAGCCCTGCCCTT GGGGCTTTTGTGGAACAGTGGCGTGGCCCACAGCTGTCACTGTCCCCTTCCTTCTAGAAG CCTCCCTCCTCACACCACCCATCTGGAGTCAGGAGCCCAGCCGGGCATATACGCAGATGC CCCTCCCTAACCCCAGGCAGCTTTCCTGCAACTGCTCCCGCAGCGGGTACCTCGTCATTA ACCTCCTGGGTTCTGTCTCTGAACAGCAGAGACCTCTTTCTTGTCATCGTGATGTGAAATG TAACGCCATGTCAGAGGAAAAGTTCTGGCTGGCCTTGGCCTCCCCCCTCAGCCTGCCCCC TTCCTCCAGGGTGGTTGGACGTGGCCCCAGACCCCATCCTGAGCAGCTCTCCCACCCCCT GGGAGCATCCTTAGGACCGGGGAGCATCCAGGGGCTTTCCCCTCCAGACCGGGCAGCCC CTCCCTCAGCCATGCAGGGCTGCCGGGCCTCGCAGCGCCAGTGTTCACCCGAGTGGAGG AGCTGGGATGTGGCTGTTTGGGGCCACAAATGGGGAATTCCACAGGGTTCAATGTAATAT GGTCTCCTCTCTGCTGGGGGTGCCTGCCTGGGGACCTTCTCCCACTCTGGTCGCTCACCT ATAGTGTGGGCTGGCCCTGGTGGTGCTTGTCGGGGGCGGGGGTGGCATGGACCAGGCA CTTTCCTCTCTGGGCCTCAGACTTCCCCTCTCAGAGTGGGACTCCTTGCTGGTTCCCTGAG CTCCCTCGTTTTCCCCAGGAGGCCACACAGTGTGGAGGCTGTCTGGGGGCCGTGGGCAG CTGGCCGTGGGCAGGACCTGGGGAGGCAGCCCCAGCCCCATCATGCCCACGCAGCCCT GTGCCCCCACCCCCAGTGGAGCTGGGTGTAAGAATTCCCATCTCAGTGTGGGGGAAACAC CCCCGCGGCCCCTAGGCCCTGCGGCCTCTGTACCCCCACCAGGGCTGTGGGAGTTGGGC TGACCTCTTCTCTTTACTGGGTTCCAGGATGACACTGCCAGTCACGAGCCCGCTCTGCACA GGGATGACCTGGAGTCCCTTCTGAGCGAGGTAACGCCTCCCCTGGCCTCCTGGTGCTCCT CCACTCCCCCTCCCCTGCCTCAGCCGGCACCCAGGCTCCCCACTCTGGGGGAGGACTGC CGGCCCCCACTGCTCTTGAGCCGTGGAAACTCAGGCTGTCCCTGCTCCACCCACCAGGAG CCCCAGTGCTGCTGAGCACCTGGCACCCCCCACAGGAGCCCCCCTAGCCCCCTTGCAGG AGCCCCCCCCGGCCCCTCCCCCTGCGGGAGCCCAGTGCTGCTGAGCGCCCCCAGCCCCT CCCCAACAAGAGCCCCCACACGGCCCCTCCCCTGAGGGCCTGCACCCTGGCAGGCAGAG GCTCGAGCACCAGGCTCAAGATCCACTTTCCCAGGGAGGGTGGGGCGTGGGAGTGGGGG GGGGGTCCCAGACCCCGTCCCTCTAAGATTTGCTTGCCCCTCCCAACTCAGGCCTCTCTA CGCTAAGATGGGCAGGTAGAATCTGTGGGGAAAATGTGACTTTTAAGGGCTCTGTCTGTTT TTGCCAAGAGGATAAGCTCCTTCAGCCTCCACGGGTTCTCCTCAGTGTCTGATGTGGCACC CGGGGGTCCCAGCTGACCATGGGGCAGGGGTTCTGCCCTGTGCAGTGGCCGTGCCCCAC ACACCCTGACCGTGCAGGTGTCTGCAGAGCCCCAGGGCCTGAGAGTGGGCCAGGGGGC CCAGCGCTGGGTAATGGAGCTGCCCCTCTGGATGGGGTCCCCGGGTATAGCTGGAGAAA TGAGCGACGGGCTCACAGCCTCTCCCGGGTGGCGGTCTTATTCTGCTGGCATCGTGGGG CCCGTGGCCCCATCCTGTGGGAGCATCAGGCTCCTGAGCAGAATAAGTAGCTGGCCCCG ACCCCCCCACCCTGAAGGAGCCACCCGAGGAGGCAGAACTGCCATGAACTGCCATGGGG ATGTGCCCTGGGCTTATAGGATGTGGTGAAGTACACAGGACAGGGTCCTCGGTCTGGCCT GTGCCATGGGGACCTTGGGCCTCAGTTTCCCCACCTTTGATGGAATACGGTGAAGTGCAC AGGACAGGGTCCTCCCCAGACTGGCCTGTGCCATGGGGCCTCGGGCCTCAGTTTCCCCA CCTTTGACTTAGAGGGAAGGTTGGATGGTGACTTCTTGTAACGATGGCCATGATTCTGTGG CTGCGGCGGGGGCGCACCTGGAGGTTCTCACCGTCACTCTGTCCCGCAGCACACCTTCG ATGGCATCCTGCAGTGGGCCATCCAGAGCATGGCCCGTCCGGCGGCCCCCTTCCCCTCC TGACCCCAGATGGCCGGGACATGCAGCTCTGATGAGAGAGTGCTGAGAAGGACACCTCCT TCCTCAGTCCTGGAAGCCGGCCGGCTGGGATCAAGAAGGGGACAGCGCCACCTCTTGTC AGTGCTCGGCTGTAAACAGCTCTGTGTTTCTGGGGACACCAGCCATCATGTGCCTGGAAAT TAAACCCTGCCCCACTTCTCTACTCTGGAAGTCCCCGGGAGCCTCTCCTTGCCTGGTGAC CTACTAAAAATATAAAAATTAGCTGGGTGTGGTGGTGGGTGCCTGTAATCCCAGCTACATG GGAGCCTGAGGCATGAGAATCACTTGAACTCGGGAGGTGGAGGTTGCAGTGAGCTGAGAT TGCGCCACTGCACTCCAGTCTGGTCGGCAAGAGTGAGACTCCGTCTCAAAAACAAAACAA AACAAAAAAACCACATAACATAAATTTATCATCTCGACCACTTTTCAGTTCAGTGGCATTCAC ATCTCATGTAA |

-continued

| SEQUENCES |
| --- |

AIRE [*Mus musculus*]: Accession: ADZ48462.1 (SEQ ID NO: 3)
MAGGDGMLRRLLRLHRTEIAVAIDSAFPLLHALADHDVVPEDKFQETLRLKEKEGCPQAFHALL
SWLLTRDSGAILDFWRILFKDYNLERYSRLHSILDGFPKDVDLNQSRKGRKPLAGPKAAVLPPR
PPTKRKALEEPRATPPATLASKSVSSPGSHLKTKPPKKPDGNLESQHLPLGNGIQTMAASVQR
AVTVASGDVPGTRGAVEGILIQQVFESGRSKKCIQVGGEFYTPNKFEDPSGNLKNKARSGSSL
KPVVRAKGAQVTIPGRDEQKVGQQCGVPPLPSLPSEPQVNQKNEDECAVCHDGGELICCDGC
PRAFHLACLSPPLQEIPSGLWRCSCCLQGRVQQNLSQPEVSRPPELPAETPILVGLRSASEKT
RGPSRELKASSDAAVTYVNLLAPHPAAPLLEPSALCPLLSAGNEGRPGPAPSARCSVCGDGTE
VLRCAHCAAAFHWRCHFPTAAARPGTNLRCKSCSADSTPTPGTPGEAVPTSGPRPAPGLAKV
GDDSASHDPVLHRDDLESLLNEHSFDGILQWAIQSMSRPLAETPPFSS AIRE [*Mus musculus*]: NCBI Reference Sequence: NC_000076.6 (SEQ ID NO: 4)
AGCACCACGACACCCAAGGAAGGGAGAAGGGAACGCAAGCGCGCGTGGGCCAGCAGGG
GGCGCCGAGGCGCAGCCCCTGTGAGGAAGATGGCAGGTGGGGATGGAATGCTACGCCG
TCTGCTGAGGCTGCACCGCACCGAGATCGCGGTGGCCATAGACAGTGCCTTTCCGCTGCT
GCATGCTCTAGCCGACCACGACGTGGTCCCTGAGGACAAGTTCCAGGTGGGCTCCAGTCC
CGCCCCCGGTGCCTCTCATTCTCCCCACTCCTCCACCCGCAGACTAGGTGTTCCCTCCCA
ACCTCAGCCAAAACCCATACTATACCCATACCCTCCCCCTACCAGCCAAGGAGTGGTCCCA
AGCCCTCCTCAGGAGACCTCTCCAGATCAAGTCCCAGGTGAGTTCCCTAACCTCACACCCT
ATGCCCCCTAACTGCTCCAGGGCCCAGGGATAGACAGGAATAGGCAAGTCTCCCTTATCC
CAAAGAGGCAGGAGTTGGAGAATGATATGCCCAGGTGCCCAATGCTGTCACTGCAGGAGA
CGCTCCGTCTGAAGGAGAAGGAAGGCTGCCCCCAGGCCTTCCACGCCCTGCTGTCCTGG
CTCCTGACCCGGGACAGTGGGGCCATCCTGGATTTCTGGAGGATTCTCTTTAAGGACTAC
AATCTGGAGCGGTACAGCCGCCTGCATAGCATCCTGGACGGCTTCCCAAAAGGTGGGCGT
GTGCTGATTGATGCTGGAGCTGATGCTCAGCCAATGGGTAGCATCGGGGATATGGATACA
AGTCGGCCCATGTTTTCAGGGAGCCACTAGAACTTGGGCAGATCCTAAGAAGCAAAGGGC
AGAGGTCTGCTCTTTCTCGTCCTCAAGAGTGCCCCATTCTAGAGCTCACCCTGAAGATAAG
GCTTTAAGACAGGACCATTGTTCCTGCCCCTGAGCTGCAGATGTGGACCTAAACCAGTCCC
GGAAAGGGAGAAAGCCCCTTGCTGGTCCCAAGGCCGCGGTACTGCCACCCAGACCCCCC
ACCAAGAGAAAAGCACTGGAGGAGCCTCGAGCCACCCCACCAGCAACTCTGGCCTCAAAG
AGCGTCTCCAGCCCAGGTACACTCAAGAGGAGCTAGCCAGGGTTGCTGGGCCCTCCCCA
ACCGGCTCTTAGGAGCTTCTGTCTTACTGACACCACCCCAGGGCCAGCCTGCCAGGGTCA
CAGAGTCACCTCTGAGCCCTCAGACCTGAGCATTGGAGGAGGCCCACAGCCTCTCAGCGT
CTTACTGTCCCAAAGGCTGAGTTTCTGGGCGGTGAGGCAGGCAGGTGGTTTTGATTTCCTT
TCTGTTGAAGAAGGAAACAGCCCATCACAGCTTAAGAACCGTCGATCTGACCCTTACCAGC
TGCTCTCTCTCCCATCCTCACTTTCTACCCTGGATCCGTCAACATGACCCCAGCCCAGAAA
AGTGGGCCCAGGCTGCCTCTACCTCCCCTTCGCAGGCTCCCACCTGAAGACTAAGCCCCC
TAAGAAGCCAGATGGCAACTTGGAGTCACAGCACCTTCCTCTTGGAAACGGTGAGTTAGG
CCAAGAGTGGAGGTTGGAGGAGGTCTGATCCCATTGACCTCAGCTGGATGGCAAAGCCAG
AGAAAGATAGGGACTCCTTAGATCCAACTGTCTTGCCATTCTCCTACCCACAATGCCCTGG
GTGTCTCCTCCCAGACCTCTGCCCATTTTAATGCTCCCAATCTTCTAGCCAGCCCAGAAAA
AGAACCACAAGGAAACTATCCCTGTTCCTCAGCTGCGCCCAACCTTGACCACACCCACCCA
CCATCCACCATCCACCTGTGCTTCCTGGTCCTCACCCCCTGATGGCCTAGGAACTCTGTGC
CCCAGAATAACGCAGGTCCCACGTCACCATGAGATTCTTGTCAATCTGCCATTGGGCTCAA
CATGACCAACACTGCTGTCCCCACGGCCGTGTGCTCATGCACATACGTCTACTTGTGTCAA
ACCCTCTCCAGGAATTCAGACCATGGCAGCTTCTGTCCAGAGAGCTGTGACCGTGGCCTC
TGGGGATGTTCCAGGAACCCGAGGGGCCGTGGAAGGGATCCTTATCCAGCAGGTGTTTGA
GTCAGGTAAATGCATGGAAGCAGGCTGCCAGGGAGACCCAGATTTCAAAATGGAAGGGAG
TGCTTCTAGAGCATCCATGGCCGTGGCTGAGGGCAAGGCAGCCAGTGTGCTTCATTCAGG
TCTGCTGGCTTTGGAGCCCAGTGCTGATGTGGAAGACTCCCTACATGGGTGGATCTTTTGT
CAGGCCAGTGGTTCATAGTCACATTCAGCCATGGAATGCCACCTCTTCCACGTCAAGGGG
TGCTGCTAGTCACAGGGGACATCCTAAGTTTCCCTGTGTGCTCTAGTTCTGTCAAGAGACC
ATAGTGCCCACTAAGACAGCCCACCACATCCTACTGCCCTGTGTCAGGTATCTATGTCCTG
TCCAGTCCCCTCACTCTTTGTCCAGGTTCCTCCCACAATTGCCTACCTACAAGGCTGGCTA
GTGGGGTCACCTTATACAGCCACCCAGATCATCTGAACAAGTCAGAGCTGGGGCCAGACA
CACTCACCATTGCAGAATCTGCTCCACAGCACCTCCTCTGTCCGGGACACTGGACTTGGAT
GCCATGGACAGCCAGAATGGCCTGGGAGCTCATGCCAGCCCTAGTCAGAGCAGCCCCAA
GAATCTTGTCTGACTCTTCTGGGGTTATTAGAACAAAAAGCCCCAGGCTTGTAACAACAGG
TTCCAAAGTCAAGGTGTGGGAAGGGACACGTCCCTTCGTGGGCTTTGGAGGGTCCCTCTG
TTGCCTCTAGCATGAAGTGCTGTTGGAATGCTTACTTCTGAGAATAGCCCCTCTCCAATCT
GACTATTCCTCTCTGACTTCACCTTTCTTTGTAAGAACATTGGATTTAAGGGCTAGTATGAC
ATTTTTAAAAAAAGATTTATTTAATTTATATGAGTACACTGTAGTTGTCTTCAGACACACCAG
AAGAGGGCATCAGATCCCCATTACAGATGGTTGTGAGCCACCATGTGGTTGCTGGGATTT
GAACTCGGGACCTCTGGAATAGCAGTCAGTGCTCTTAACCACTGAACCATTTCTCCAGCCC
GTATGACATCTTTTTTTGTTGTTGGTTTTTCTGTTTGGTTGGTTGCTTCTTTTGTTCGTTTTTG
TTTGTTTGTATTTGAGACAGTTCCTCTGTGTAGCTTTGGCTGTCCTGGAACTCACTCACTCT
GTAGTAGAGCAGGCTGGATTCGAACTCGAGTAGATCTGCCTGCCTCTGCCTCCCAAGGAT
TCAAGATGTGTACCACCATGCCCTGCTATGACATCATCTTAACTAACTCTCTCGCCAAAGAC
CCTGTTTCCAGTAAGGTCCCGTTCTGAGCTTGTGAGGAAGGGCACTGTTTAAGGGTACAGT
CACCAGCAAAGAATCCCTAGCTGTACCCAGCCCCGGTTCTGCCAGACCCCCAGGGTGAGC
TCATTCAGTCTATCTCTCTCCCAGGAAGATCCAAGAAGTGCATTCAGGTTGGGGGAGAGTT
TTATACACCCAACAAGTTCGAAGACCCCAGTGGCAATTTGAAGAACAAGGCCCGGAGTGG
TAGCAGCCTAAAGCCAGTGGTCCGAGCCAAGGGAGCCCAGGTCACTATACCTGTAAGCCT
TATCCAGCATGTCCATTTAGGGGGAGCTGGGCCTTCCTTCCATAGCCTCCCCTCCCCTCCC
CTCCCAAAGAAAGCCTGGAGTTCTTCCCGAGGGTGGGAGTTGCTTCCCAGTGGTACTTGG
TGGCCACATAGATCTTCCCTGACCCTGGCTACTTCGTTAAGACCCTGTGTCTCTCATAGGG -continued

SEQUENCES

TAGAGATGAGCAGAAAGTGGGCCAGCAGTGTGGGGTTCCTCCCCTTCCATCCCTCCCCAG
TGAGCCCCAGGTTAACCAGGTAAGTCCCAAGAAGGGGGTGGGGGTGGGGGAACCAGGAT
ATGGAGGGCAGCTCCCTTCCTCTTCTCTCCCTTCTCTTTCCTCCACCTCCTCCCACTCAGC
TCTTTCTTGGAAGTTTTCAAGGATGCATATTAGGAGATTTCCAATTAGTCACAGCAGGTGAG
CTGCTTTTAAAAAAATCACACGTTCAGCTGGTTGGTATATGCCTTTAATCCCAGCCCTTGGG
AGACAGGGGCAGGCAGATCTCTGTGAATTGGAGGCTAGCCTGGTCTACAGAGTTCCGGGA
CATCCAGGGCTACACCAAGAAACCCTGTCTTGACAACAAACAAACAAAACAAAACAAAACA
AAACAAAACAAAATCACACATTCTGTCCAGATGACAAAAAGCACATTAGCTTCGGGTCGGG
TAGGGCTGCAGATAAAGCCTGAGTATGGGGATTCTCTGAGGGTATCAAGTTATCCTCTCCT
CCCCAGCACCACTGATGTGGTTGTGCCTGCAATCATTGATTATTGAGTCCAACACCTCAGA
GCTAGGTACTCTGCTGGCCCCGGACACCAAAGGTTGAAGGTCCAGTTCTGCCCTGCTCCA
TAAAAGTGCCCTGGTTATTGGGGGCCTATGGACGTTTCCCATGTGCTCACTGTGTGGGCC
CCCACAACCTGGCATCTGGGAGCTTCTTGAGGAGGTTCAGACTCAGAACTCCTTCCATCCT
GATAAGGTAGGGGATGGGGAATGACAGGAGGTACCTAGGGCTAACGGGAAACCCCGTGG
GCCCACCCACCTGCTGTCCTATTAGGTGAGTGGTAGTCAATCCAGGGAACTGTGGGCCTC
CCCACTCTGTGGGTTGTCAGCCTGGGCTACACCGGGACTAGCTATCAGGAGGCAGATCAA
CTTTACTTAGGGTGATTCAAGGCTTTTAAAAAAACAAAAGATTAATTTATTATTTATTATAAGT
ACACTGTAGCTGTCTTCAGTCGCACGGATGGTAGTAAGCCACCATATGGTTGCTGGGATTT
GAACTCAGGACCTTCAGAAGAGCAGTCAGTGCTCTTACCTGCTGAGCCCAATTCAAGGCTT
ATAACGTTTTGGGGGGGGGGGTCTGAGGGTAGGAATATCTAGGATGGGCAAAGGTCATTG
GCTGGGGGCTTGGGGTACCTAAAATGTCTCCTTAGCAAGGGAAAGCATTTCGGAAATCTCA
GGTGCTGAATGAATGGGCGCTTTGTCAGGAGAAAGGAAGTTGGTCCTGTAATTTAACTGAG
GCTACGTGACATTCTTCATGCATCTCTGAGGGCATTCCTAAGCCTGGGGGGGGGGGGG
CGGGGGCGGGGCTTAGAATTCCCCAGACAAGGTCAAAGAAGGAGAAATCCTGTTAATGAA
GGGAGTCCCCCATATTGCGCTGAGCTCAGAAGCTATCCAGTCATGGTGGGATTTTGATCTT
AATTAGCAGAGTTTTCCCACTAGGAACTGCCTGGCACCCAGCACTCCTTCCAGAGAGGGA
CACCCCCCTAGGTCTGTGTGGAACCTAGTACTTCAGAGACCTTGCAGAGCTCAGGCAGGG
GCCAACGAGAGAACCCAGGGGGAACCTGGGAGTCAGTCCTTAGTGGTGAGCATTGTCCCA
AGTGGGTCTCTCAGGTGGATGCTGTGTTCCATTCTGGGTCCCTCTTGCCTGGTCAGAAGAA
CGAGGATGAGTGTGCCGTGTGCCACGACGGAGGTGAGCTCATCTGTTGTGACGGCTGTC
CCCGGGCCTTCCACCTGGCTTGCCTGTCCCCACCTCTGCAGGAGATCCCCAGGTAAGCAG
ACCTCTCCATCTCTGATCCATCACCGTCCTTATCCGCTGACATTGAGGAAGCCTAGAAGCC
TTCACAGAAGACAGTAAGGGCCCTTCAGTAAGATCTGTGGAATGAATAGGGTACTAGCTAT
GGAAATGGTAGGATTCTCTGGCCATACCGAAACCTATCTGTGTTCCCTGCCTCATGGCCCA
CTCAGGGCCAACAGGCCAAAAGGCAGCCATAACATGATGTCCCCAGGCAAAGGTGGCCAT
ATTTGGGCACAGGCCTTTTCCTAAGCACACTGTACCCCCACCCCCTCAAATCTCACTCACA
CAATGATGTACTGTTACCCCTATCACTGACTGCACAACCCTCTGTTCTGAGGAGAGGTAAG
CAGCAGTCTGTGCGGGCTAGCCTGGGCTCTGACCCAGGTCTCTCTGATCCTCTTCCACCA
GGGTCCTTTCCCTCATCTCCCCTTTCCCACTGGTCCATCCCTACAGGACTGTGGGTGTGCC
AAGGATGGAAACAGTGTAGCTGAGAGTCATGCTTATCTCCCCTCCCCCACTGGCCCATCC
CTATAGGACGGTTTGTGCACCTAGGATGGAAACATTGTAGCTGAGAGAGCCCACAGTAATG
CCAGGCCTATGACAAGCAAGCACAGGTGCTGAAGGGTACTGGGCATAGAGTATTCTTAAG
AATTAGCAGAGACCCGCAGGGCATGGTAGTGCACACCTTTAATCCCAGAACTCGGGAGGC
AGAAGCAGGTGGATTTCTGAGTTCGAGGCCAGTCTGGTCTACAGAGTGAGTTCCAGGACA
GCCAGGGCTACATAGAAAAACACTGTCTCCAAAAACCAAAAACCAAAAAAAAAAGGATTC
TAGGGACCCTGACTCTGTCCAGAGCCATGCTCCCGAGGTAAATAGCCCACATTCTATTGAA
CTGCCCTTATGGTACCTAACTCTTTAGTCCCGGGTTTGGCTTCCCACCTATGAATGAGCAT
GGTGACACAGAGGGTCCTCAAGCCATCCTTGCCATACATTTGGGGAAGGGGGGGTGTCTA
TGGTCTCTACTTTGTCTGGCAAGCCTGTGACTAGTGACCTCCTACACAGTGGCCTCTGGAG
ATGCTCCTGCTGCCTCCAGGGCAGAGTCCAACAGAACCTGTCCCAGCCTGAGGTGTCCAG
GCCCCCGGAGCTACCTGCAGAGACCCCGGTATGCCCATATTGGGTCACCCCCTTTCTTCT
CTCTGACTCTCTACAGTCCTATCTTCTGGCTTCACCTGTGAGTCCTGCATGCCCGCCATGC
TCTGTTCTGGTGAATTCCCTGTGGGGTTGAGGGGCCAAGGGATTAAAAACAGCTTCCCAA
GCTGGCTCTGTCCCTCCAGACTCACCACTGCCAATATTCTCCAAAAGCCTTGGTAGCTCTC
CTGTTAGAAACCTAGTTTGCTCTGGCTTGGCCCTGGCTTTTGCTGAGAACCATGGAACCAG
CCACACACTCAGCCTTTCCTTCTCCTCCTCCTCCTCCTCCTCCTCCTCCTCCTCCTCCTCCT
CCTCCTCCTCTTCTTCTCCTAGTTTTATTTTTTAAAGATTTATTTATTTATTATATATGTAAGTAC
ACTGTCACTGTCTTCAGAAACTCCAGAAGAGAGCTTCAGACCTCCTTACAGATGGTTGTGA
GCCACCATGTGGTTGCTGGGATTTGAACTCAGAACCTTTGGAAGAGCAGTCAGTGCTCTTA
ACCACTGAGCCAGTTCTCCATCCCTTTTTTTTTTTTTTTAATTTTGTTTTGTTTTATGTGTATTG
ATGTTTTGCCTGCATGTATGTCTGTGTGAGGGTGTCAAGATCCCTTAGAACTGGAGTTGCA
GACAGTTGTGAGCTGTCATGTAGGTGCTGGGACTTGAACCCGAGTCCTTTAGAAGAGCAG
CCAGTGCTCTTAACTACTGAGCCATCTCTTAAGCTTGTACCAAGCCTTCCCAACCTCAGAC
CCACCACAGCAGCCCAGTCCTGACTCCTAGGTGTTGCTGAGCAGTACCCTGTGGCCCCTG
AATGCTAACCCTTGAATTCCAGATCCTCGTGGGACTGAGGTCAGCTTCAGAGAAAACCAGG
GGCCCATCCAGGGAGCTCAAAGCCAGCTCTGATGCTGCTGTCACATATGTGAACCTGCTG
GCCCCGCACCCTGCAGCTCCTCTGCTGGAGCCTTCAGCACTGTGCCCTCTACTGAGTGCT
GGGAATGAGGGGCGGCCAGTGAGTGAGGAGACCCCTAGGGCCTGGGTGCTATCTTTGGG
GAAGAGGGGCTCTGGACCTACGGGATAGTTGTATGTCCAAAACGGGACCTCTGGTGGACT
CCCGGGGCTAGGAATTAGACGGACATTCCTGGGGTCAGGGGAGGGCTCTGCCAAGAGAC
ACTTGTTCATATAATAGTAACACAGGGACTGTAGGGGAGAGCACCAAGGGAACTCTCCAGC
TGGGCCTTTGAGATGGCTCAGTGGGTAAAAGGGTTTGCAGCCAAGATGGAAGACCTGAGT
TGGATTCCCAAAACTCACATGGTGGAAAGAGTGACTCGGTCTGCAAGTGGTCCTCTGATCT
CCATGTGCATGACCACCAATAAATAGTGAATTAGCTAGAAAGAAGGGAAGGAGGGAAGTAA
GACAGGCAAGCAGGCAGGCAGGCAGGCAGGCAGGCAGGCAGGCAGACAGACAGACAGA
CAGACAGACAGACAGGCTTAGCTTGGTTATCCAGATGATACACCCTCCCCCATCATGAAGC
AGGACAACAAACATCTCGAATCCACAGACCCTGTCCACTTCTGTTGGTTACCTTTCTTTTTT

-continued

| SEQUENCES |
| --- |
| TCTTTTTCAGAGTCCCCACTTTTAAATTTAATTAATTAATTTATTTATTTTACTTATTCACTTTA<br>CATCCCGCTCACTGCCCCTTCCCCATCATCCTCTCGCAGTCTTTCCCCACCCTCTCCCTCC<br>TCCAAAGCTCTTCTGGAGTCCCACATTTGGTAGGATCAGAGCTGGACTCCCAGGATGGACT<br>GGTCCGTGGAAAGCAGCTTGGAAAGGCCGCTTTCTGACCCCTGCTCCCCTCGGGACATCC<br>AGAACTCAGAATTTACAGTCCCACTCACGCGACTTGAAACCCTGAGGTTTCCCAGTTAACC<br>CGGGCTGGTGGGGTGAGCAGGACACGGGCTGGGTTGCCGCCCATGTTGCCCCTGCAGG<br>GTCCAGCACCAAGCGCGCGATGCAGTGTGTGTGGCGATGGCACCGAGGTGTTGCGGTGT<br>GCACACTGTGCCGCTGCCTTCCACTGGCGCTGCCACTTCCCGACGGCCGCCGCCCGGCC<br>GGGGTGAGTAAGGGGGCACCGGGTGGCAGAGTAGCCAGCGATCTCACCCACCCCGAAG<br>GTTCTCCGAGCCAGTGAGCTTTTCCCACTTCTCTCGGACAGGACCAATCTCCGCTGCAAAT<br>CCTGCTCTGCAGACTCGACTCCCACGCCAGGCACACCGGGCGAAGCTGTACCCACCTCTG<br>GGCCCCGTCCAGCACCTGGGCTTGCCAAGGTCAGTGTCTGCTCAGTCCAGGTGAGACCCT<br>GTGGGAGTGGAGGAGAATTTAAACCCATATCCAATAACCGTGTGTCCCATTACTTTTTGTTT<br>GGTTGGGTTTGGGGGATTTGTTTTTTGTTTGTTGTTTTGGATTTTTGTTGGTTTGTTTTGTTT<br>TGTTGAGGTACTACAGATCTCTGGCTGTCTGGAACTTACTCGTAGACCAAGCTGACCTTAA<br>ACTCAGAGATCCACCTACCTCTGCCTCCCAACTGCTGGAATTAAAAGCACATGACCCTTAT<br>TCCTGGACTAACTTTTTTGTTTGTTTTTAAAAATTAATCATTTTTAATCTTTTTTTTAAAGATTT<br>ATTTATTATTATATGTAAGTACACTGTAGCTGTCTTCAGACACTTCAGAAAAGGGAGTCAGA<br>TCTTGTTACAGATGGTTGTGAGCCACCATGTGGTTGCTGGGATTTGAACTCTGGACCTTCG<br>GAAGAGCAGTCGGGTGCTCTTACCCACTGAGCCATCTCACCAGCCCCCCTTTTTTATCTTT<br>TAAGATTTCTTTTTTATTTATATGAGTACATCGTAGCTGCCTTCAGACACACCAGAAGAGGG<br>CATTGGATCCCCATTATAGATGGTTGTGAGCGAGCCACTAAGTAGTTGCTGGGAATTGGAC<br>TCTGGAAGATCTCTCCAGTCCTTGTTTGTTTGTTTGGTTGGTTGGTTGGTTTTTCAAGACAG<br>GGTTTCTCTGTGTTCCCCTGGCTGTCCTGGAACTCACTCTGTAGACTAGGCTGGCCTTGAA<br>CTAAGAAATCAGCCTGCCTCTGCCTCCCAAGTGCTGGGATTAAAGGTGTGTGCCACCACTT<br>CCCAGCCCTTGTTTGTTTTTTTGTTTGTTTGCTTTAAGACTATTGCTGGGATCAAAGGTGTAT<br>GTCACTAATTCTGGCTCCTCAATTACTTTTATAAAGTGTTTTTCAATAAACAGACAACTTATT<br>TTGATAAGTTGAATCTATTTAAAAGGGAAAGGCTGGAAGTGGTAGGGCAGGACATTAACCC<br>TAGCCCCCAGCAGTAAAGATAGGTTGGTCTCTGTAAGTTAGAATCCAGTCTGGTCTGTATC<br>GTGACTTCCAGTTTAGTTAGGGCTACGCAGTCGAACCCTTTCTAGACATAACCAAGTATTTT<br>AAAGGGAAACCTTCCAAATAGCTATGAACTCACTGTTGGTACTGGGTTCCTGGGAGTCCGT<br>GGGCCTCAGAGCTCAGAGCTCTGATCAGGGAGCTCTGGACCTAAGAGCAGTTGGCTTAAT<br>TTGAAATGAGACGACTGGGAGGCACCCAGGGGCCAGATCGTCTGCAGAACAGGTATCAGA<br>ATGGCTGGGACCTCCAGGGCGGCCAACTATTGGCCTGGAGAGAGAGAGAGAGAGAGAGA<br>AAGAGAGAGAGAGAGAGAGAGAGAGAGAGAGAGTTGGGGAGCAGAGCCAAACAAAGCTGCT<br>GGCTTTTGATGACCCCGAGAGCCACCTACCCAAGTCCTCTACCCAGGTGGATCTCTATGTC<br>ACCTCCATTTTTACTAACCAGGCAGGGACCGAGCTTTGTCTGGAGGCCCAAGGAGGAAAG<br>GGCAGTATCCACCTCTATCCACTTGCCATTGCATAATACTGCTAAGACAGACATGGACCCC<br>AGGCTTGGGCCCCTAGCTGTCTCTCAGGTTCATGGGTAAAATGGAGTGATCTTGTAAAGAT<br>GTGTTATGCAAGGTGGCAGAGTGTATGCGCAGCTCACTGCTAGATTCCAGCTTTCCCTGAT<br>AAATTGCCCCCCTAGTTGCAGGTTGACCTTATCTGATTGAGAACATCTGGGAGGCTGCATC<br>AGAATCTATTGCTCCTAGGATTCTACTGGAGGACCCAGTAAAGCATGGGGCAAGGTTTGCT<br>GAGCCTTTAAAACAGTGGTCCTCAGTGATCCTTTGGTGCCAAATGATCTTTTCACAGGATG<br>GCCCAAGACTGTTGGAAATATCTGAGAGTTGGGATTCGTAACAGTAGCACAATTACAGTTA<br>CAAAGTAGCAACAAAAATAATGTTATGGTGGGGGGGGTGTCATCACATCATGAGGAACTG<br>TATTAAAGGGTTGAAGCATTGGGAAGATTGAGAACCACTGTCCTAGAGTCTAGCCACAAAC<br>AGTGAAAGTCACTTCTAGAATGAAGACGAGGATTGAGCAATGGGGCCTCCACTGGCTTCA<br>CTGTGAACTCCTGACAGAGCCTGCCACTCCCTGACTGGAGCTCTGTCACTATGGCCAGGG<br>CAGGTCCAACTAAGTTCAGCTCATGTGACTAGTGAAAGCAGAGAGACACTGGCTGGGTGC<br>TAGCCACCGGGTCTCTTTAGGGGCTACAGGGAATATATAGGACAGATTGTTGCCCTCAGC<br>CTGCCTGTGTCCCCAGCCTGAGGTACTAGGTGTGAGTCTGCTCTGTGGTGGAGTACAGTC<br>TACTGCCCCAAGTCCTGCGTCTGGTCCCTAGCCTGCTGCTAGGTTGGGTTGACTATTGATT<br>CTCTGCTTTGGTTCCAGGTAGGGGACGACTCTGCTAGTCACGACCCTGTTCTACATAGGGA<br>CGACCTGGAGTCCCTCCTCAATGAGGTAATCTGTCACCTAGTCTGGGCTGTGCTCACAGAT<br>TCTTTGCTGCCCCTAGTAGGCAGCACCAGCAGACCAGTGTTACCCTGCCCCCATAGCTGC<br>TCTTCCTAGAAGAGCTTGTTTCCATGTAGGGTGCTGGCCTCCTCCAGGAACCTCACATCTG<br>GGATCCTCACATCAAGACCTCAGAGCCAGGGGGTTTAAGCCCTTGACTTTTCAGGGAAAG<br>CTGGGAGGGTCTTCCAGGGGCCTCTCTCTTACCCCTCCCAACTCAGTTTTCTGTTTCTTGA<br>GGTGGATAGGTGGCCCAGGTCTTTGATTCCCAGTGCTTGAGGTAGATGTAGGAGGACTGT<br>GAGGTGGATACTAATCTGGACTACATTATAAAACCCTATCTCAAAAACCTGAGGGGCTACA<br>GAAATGCAAGAGCATTGTTCTTTCAGAGGACCCAAGTTTGGGGGGGGGGGGTCCCAGCAG<br>CCATGTCAGGTGACTTTTAACTGTTTATCATTCCACTCCAGGGGATCTGAAACCTCTGGCCT<br>CCTCGGGCATCTGTACACACATCACGCACACACACATACTTATACACACAGACACACATAT<br>ACACATAGGTGCATACACACATGTACATACCCACTTTTTTTTTTTTTTTTTTTTGGTTTTTCG<br>AGACAGGGTTTCTCTGTGTAGCCCTGGCTGTCCTAGAACTCACTCTGTAGACCAGGCTGG<br>CCTCAAACTCAGAAATCCACCTGCCTCTGCCTCCCAAGTACTGGGATTAAAGGTGTGTGCC<br>ACCACTGCCCAGCATACATACATACTTAAAAGTAGTAAATTCCCAGAAACCACATGGTGGC<br>TCACAATCATCTGTAATAGAATCTGATGCCCTCTTCTGGTGTGTCTGAAGACAGCTACAGTG<br>TGTGTGTGTGTGTGTGTGTGTGTGTGTGTGTGTGTGTGTGTGAATATTATGTGTATATGCAT<br>ATATATAAATTAAAAAATAGTAAGAATGAATTTCTTCTAGAAAATGAAATAGGGCCCCATCTA<br>TTGCAAGGGCACAAACTCCTTTGGTCATTCCCATACCCCAGGGAGCCCACATGCCTTCTTC<br>AGTGTCCACTGACATTTAGGGAGACTCAACTGGCTGAGGGACAGAGACCTGCCCTGGGCA<br>GAGGGCCATGCACAGGCAGATCTGCAGAAGCACGAGAGAGAGAGAGAGAGAGAGAGAGA<br>GAGAGAGAGAGAGAGAGAGGATCCAGCATGGGTGGACACTGGAAAAACTGAGGACCTTCT<br>CCAGGACTTCCCAGTCCTGTTGGCAGAGAAGAAGGACCCAGCAGAGGAAGCCACACCCA<br>GGGCCCACAGGCTGCTCTAGAGGAGGACTGGATCAAGAGACCTCCCTTCACTGGCATGTC<br>CCATGGGCCCTAGCTCTCAGTCCCCCTCCTTGAACTAGCGGGTCAGGTTGGGTGATACCT |

SEQUENCES

TCATGTCAAGATGGCTCTATGGAGGTGCGACTGCTCTAACCTCCCGTGTCACTCTCTCTCA
GCACTCATTTGACGGCATCCTGCAGTGGGCCATCCAGAGCATGTCACGCCCGCTGGCCGA
GACACCACCCTTCTCTTCCTGATGACAGGTGGCCCAGGAAGGGGTGGGCAGCACAGCATT
GGCTCCCTCCCCACCCAGCCCCATCGGATGAGGCACTCTGTTCTGAGAGGCCTGGGCTG
ATTAGGACCAAGAGCTGGCAGGTTCTGGCCTGCTGGACTCAGCTTGCAGATGGCCCTGAT
CTTTGTAGAGATGCAAGGCCACCCCATATCCTGGAATTAAAGTCACTTCTATGTACTTTGAG
GTA

CD40 type II isoform [*Homo sapiens*]: Accession: CAC29424.1 (SEQ ID NO: 5)
MVRLPLQCVLWGCLLTAVPEPPTACREKQYLINSQCCSLCQPGQKLVSDCTEFTETECLPCG
ESEFLDTWNRETHCHQHKYCDPNLGLRVQQKGTSETDTCTCEEGWHCTSEACESCVLHRSC
SPGFGVKQIATGVSDTICEPCPVGFFSNVSSAFEKCHPWTRSPGSAESPGGDPHHLRDPVCH
PLGAGLYQKGGQEANQ CD40 molecule [*Homo sapiens*]: NCBI Reference Sequence: NC_000020.11
(SEQ ID NO: 6)
AGACCCCGCCCCTTTCCTGGGCGGGGCCAAGGCTGGGGCAGGGGAGTCAGCAGAGGCC
TCGCTCGGGCGCCCAGTGGTCCTGCCGCCTGGTCTCACCTCGCTATGGTTCGTCTGCCTC
TGCAGTGCGTCCTCTGGGGCTGCTTGCTGACCGCTGTGAGTTGTTTTTGCCCCGACCAGA
CGGGAGTTGGGAGTGGGGAATGAGAAGGAAAGGGAAGGAAGACTTCGGGGAAGAGGCCT
TCCTGGCTGATTTTTGTGGGGGCAGGAGGGTGGGTGGGAGCTGGGCAAGGTGCCCCCGC
TCCTGGCTGAATGGGGTGGGCTGCCTCTCTCTTCTCCCGGGCTGGGGTCCCGGGAGCGG
CCTACAGGGGCCGCTCAGGGAAGGCACTGGCTGCCCAAGCGTGCCTAGACGGCCTGGAC
GGGTTTAGGGAGCCTCAGAGGCTGGCCACACAGAGACTGGTAGGGGGTTCAGAGGGCGG
GAAGTGAGGCGGACCAAGGGAAGGGGCGGGTCTGGCCCGTTTCCTGTCCCCTTCTTATTG
TGGACAGATGCCAGCCTCTGTAAGTAGTTATCATCTCCTTGCCAGCTGGGGCTGCCTTCTT
CCAGGGCATCTTGTGGGAACAAGAGATGGGTGCAGAGGCCCAGGTACTTTTGTGAGAAGG
CAAGGAGCTTTTAACATCGCCTTCCACCCCGAACCGTATCTTGGGTGTTCCAACCTAGGAG
GAATCCCCAGGGCTTTGCCTTTTTCTCCTGAATTTAAGATGACATAGGAGACCCCTGGGGA
GATGAACAGTTTATGGGACACAATAAAGGGTTAGGAGACCAGAGTTCTGGTTGGCTCTGAC
AGGGCTGGTGATCAGAGGGCTGGAGAAACCAGGGGTTTCTCCAGGCACCAGAGGGGCTC
AGAGCCAACCAAGCATATCTCCGGGATTTTCAGAAGCCTACACTTGACTCACTTTTTGTTTA
AATGTATTTTTGTAGTTCCTCATTCTGGAGGCTGGGAATCCCCCAAGTACCTGGCTCCTTCA
TCCCAGCCCCTCTGGCCTCCCCCTACTTTAGAGGGCTGTAGATTCCTGCCTGAAGCCTGG
GCAGGAATGACCCATGGTATCAAGGAAAGCAAGGGAAGCAGCAAGGGAAGAGAGGGAGT
GGGGAGGCTGCTTTGGTCCCACAGCTTTCACTTTCACCTGAAGCAATGGCTCTTAGGGAA
CAGGGAGGCAGGGGGAGGGCGGAGCTGGAAAGAGGTAAAGGGGGGCCCTTGTGGTAGG
AGTGGAGAAAGAGCCAGAGGAGGTGGGGTGAAGGGTGTGATCCAGGCTTCTCAAGAGCA
GAGTTTGCCCTCATAACTCCCAACTTTGGCTCCAGGTAGAGGCTGGGCTGTGACAACAATG
TCAGAAGCTATCTATTGAGGGCTTCTTGTGTGTCAGGCTCTGAGCCAAACACTGCCTGTTT
TCTTTGTCTGATTTCTCACAACTCCCCCATTATACAGATGGGCAAATTGAGGCTCAGAAAGG
GGGATTGTCTTGCCAAAGGTCTCATAGCTAGCTAATGGAAGAACCTGGTTGTGAATCTACA
TCTGCATGATTCCCGAGCCTGCCTCTCAGATAGTGAGAGTCTCCAAGCTCTGGTCCTGAGC
TGTTTTGTGGCAGAAGGACCAGAACTATGGGGAGTGAGAACTGGAGATTGACAGACTTTTA
GGGGAGCGTTTTATTTCTCATGTGTTTGAAGATGGTATCAAGGACTTTCCTATCTTTGGGAG
TGTGGGAGCTCCACGTTCACAGGATGGTGTCTTGCAATGAGCTGGTGGGGGGCAGTAGC
CTTTTCTACTTCCTTTCCCATTTTGGGTAAGACACATTTCTGTAAGTAATTTGCTGAGATACC
CAGGTTGAATGAGAGCCACCAGTTAGGTAGGATTCTGGACAGCCAGCCAGGTAGCCGGG
CTGCTTGCCATATATCATGCAAGCAGAAACAAATGAATGATGATTAAAATTGCCATTTAATG
AGCACCTACTATGTTCCTGACACTGTGCTAGGCCATATACATGTATTCTTTCTTATCTTCGT
AATCCAACCTGCAGGGCAGGCATTATTACTCCCATTTTAGAGATAGAGAAACTGAGGCTAA
GAGAAGCAAAATAACTAGTAAGTGTTACAAAGTCAGGACTGGAGTCTAAAGCTGTCTGACT
CTCAAACTTGTGTTCTTTTCACTGGCTGTTCCCAAACTGTGGGACAGTTTTAAGGAGCACAT
GGACATAGAATTAAACATACACTTACTTTACAGTTCTTTTAAAAATCCTTCTCATTTTTTCAAA
GAGGAAGTCTCTGGAGCTAGAATAGAGTTAATGCCTCTCAAAGGCTTGCTAATCCTTCTTTT
AAAACAAAAATCAAGAGCAGGCCTGGGAGGGCCTTCAACAAGCAAACAACCAGCTGGGTT
TTAATAACCTTGTTTTGTTTCCCCAGAATTTATTTTTAGGGTTACCTTTTATTTATGAGAAGTG
ATACTGGTTCTTGTCTCTTGGCAATGATGTGAGGTTTACATTTAAAGTAAATGTACCGGCCA
GGCACGGTGGCTTGTGCCTGTAATCCCAGCACTTTGGGAGGCCAAGGCAGTCAGATCACT
TGAGGTCAGGAGTTTTAGATCAGCCTGGCCAACATGGTGAAACCCTGTCTCTACTAAAAAT
ACATAAATTAGCCGGGCATAGTGGTACACACCTGTAATCCCAGCTACTCAGGAGGCTGAG
GCTGGAGAATTGCTTGAACCCAGGAGATAGAGGTTGCAGTGGGCTGAGATGATGCCACTG
CACTCCAGCCTGGGCGATGGAGCGAGACTCTGTCTCAAAAAATAAAATAAAAGTATTGAAA
TTAACAATAAGTAATTAATAGCATGGGTGGTACCTGGATGTAGTAAAATGGTGAAGATGAAA
CACAAGTTGATGGAGAGAGGAGCATTGAGACCTGAGTTCTCATTTGGACTCTGTCACTGTG
AGACTCTGGGCAAGTGACCCTCCCTCTTTGGTGCTCAGTCTCAACTATCTGTAAAATGAAAG
TGTGAGTTTACCCTTCCAGCTTTACATTCTAGCATTTTATGAGGGAAGGGCTGGATGAACA
GATGATGAGGAGTTGGAGGAAGAAAACATGATGGGCTTTGGAAAGGAGCAGGAAGGGAA
GCAGAAGAATAGGAGGAAGAGGCCAAGTGCTAAACATAGCCCCAAACAGCACTGGGACCA
GCTGAAGTCAGCCAGCTTCAGGACTCCAGGGGAGCTGCTGGAGTCCCCATATCCTATGGG
ATCTTTGGGAAGAGGAATGACTCAGGCATCAAGCCCCAAGGAATTCTGTTCTGTTCAGAGA
ATATTGTGAGTTTACAGTACCATTGCTTTGTAAAAATACCAGAATGATTCTCTGGGTGCGAT
TATAATCAGCTCAGTTGACAATTTACTTGAAAACAAACATGCCAAATATCATGCAGGTTCCA
CTTTCTGTTTTGACTTGCACTTCAGTTTGCAGCCTCTGTCCTGGATGACTTTTACCTTTCTG
CTGAAGAAGTTGCAACGGAGATTTCAAGATCCCTTCAAATTGCACAATTCTGTTTTTAGGTC
CATCCAGAACCACCCACTGCATGCAGAGAAAAACAGTACCTAATAAACAGTCAGTGCTGTT
CTTTGTGCCAGCCAGGTGAGATGCCAACCCTCTAGCCCCATCATGGAGTCCCCCTTTGCTT -continued

SEQUENCES

TGGTGGCAGACGCAGACCCCATATGTTAACTGTAAACTCAAATCTGAAACGACCCATTTCC
CAGCCCTGCTTCACTGTCAGAATGTTCTGGTTCCCTCTCTACCAGGTAAAACTCTGTCTAC
CCTGAACTAGGGATCCCAGCTTCTCCATCTTCCTCGCCTGATTATGAAGGATCCAAGACTT
TCATCTTTGAATCCCCTACCCTAAAGCCTGGCCTGATCATTGTGTGGTTAGTGTCTGACTCA
TGGAGTTGGCCAGAGCCCTCCCTCATTTCCTGATGTTTTCCAGGACAGAAACTGGTGAGTG
ACTGCACAGAGTTCACTGAAACGGAATGCCTTCCTTGCGGTGAAAGCGAATTCCTAGACAC
CTGGAACAGAGAGACACACTGCCACCAGCACAAATACTGCGACCCCAGTGCGTGCGCTGT
TGGGAAAGGGACGCTTGGGAACCGGGCTGATATTCCCGACAATGCAGCCATTCTAATTTTA
TGTAGCCAGGGTCTGCTCTGATTGGTTGGAGTCCGGGCTGTACTGATCATTAAATGATTTG
ATTGCCATCTCTACTTGGAAGAGGGTCTGAGGAAGAAAGAGCAGGCAATGTGGGGAGTGA
GGCTCAGAGCATGGCCCAGCAGGGGGTTCCCATCCTTCCTGCCCTTCTCTTCTCAGACCT
AGGGCTTCGGGTCCAGCAGAAGGGCACCTCAGAAACAGACACCATCTGCACCTGTGAAGA
AGGCTGGCACTGTACGAGTGAGGCCTGTGAGAGCTGTGTCCTGCACCGCTCATGCTCGCC
CGGCTTTGGGGTCAAGCAGATTGGTAAGTGGCTCATCTGGGAATCAGTTTTGGAGGGGGA
CAGAGGAGCTTAGGGCCCAAGGTGAGGGGCTGGGCAGTGGGCACTTAGCCCCAGAGGCA
GAGGAAGCAGAGGCTCCAACCTATGTCGGTATCCCCACTGGAGTGAGCTGCAGACGGGA
CCTTGTTCATTCTGCCTTCTGCCATGGGGATCTGCCTTTGAAGGGCAATGGGAGAAGTCCT
CCTGGGGACTGCAGCTGTCGGGGGCAGTACCACATCGGGGGAAGAGTGCTCAAGGCAGG
AGCTCTTCCCGTCCTGCCTGGCCACTGGCTGCCTTGTGAGCCGGACAGGTGGTCCACTGT
GATGGTTAATGTCCCCCTCCCCACCCACTCCCAGCTACAGGGGTTTCTGATACCATCTGCG
AGCCCTGCCCAGTCGGCTTCTTCTCCAATGTGTCATCTGCTTTCGAAAAATGTCACCCTTG
GACAAGGTATAAGCACTCATCCCTTGTGTTTCCTGCTCTAAGAGTGGCATGGAGCTGCCTC
CATTCTCTCCAGCCACCTGTCCTGTCCCTGCTCCCAGAGGTCCACACACACTCATGTACTT
GTGAAGCATCTGCAGAGTGGCCTCATGGCCAACCAGACAGGCACATTTCCACATTTTTTTT
GCCTGCTGTCTCTTTGAGGTAATAGACACTGTTGATCTCTCGCTTCATGAGAGCCTCCTAT
CTTGGGGGTATTGGGACACTTATTTTAGCTTTCCTTCTGCCCCTCCTGCTTCTCCTCAGTTT
TCCTCGTCTTGCTTTCACCTTACCTGGCTTTCTAGGGCTTTCTGGGCTCTGGGTGCTCACC
CTGAGGGCCTCCCTCTCTTACCTCCAACTCCAAACCCACACCAGGTCCTGCCACTGGCTG
TCTACGTGTTTTGGGAACTTACTGTCTCCACTGTTGTCACTTTAGTTTGGGCCTCATCACTG
TGGTCTGGGTGATGCCTTTTCTGCCTCCTGGCCTCCCTGCCTCTGTCTCTCCCCTCCTGCT
GGTTCTGTCTCCATCCTCTTGCCAACATGAGCGTTCGACAGTTTCTTTCAAATCATGACACT
CTCCTATTTGAGATGCTTCCTGTCTCTCTGTTGGAACTAAGACTCCTTAGCATGGCACCCAA
CCTTCCTGTTGCATTTCCTGCTCTCTTTCCTGCATCGCATAGCTTCATGCTACTTGCAATCC
TCTGAACACACTGTTCATTCTCTTCCATCAAACTCATCTGCCTGGAATACCTTAAACATGGG
CCCCAGGCCAGGCGCGGTGGCTCTTGCCTGTAATCTCAGCACTTTGGATGCCAAGGCGG
GTGGATCACTTGAGGTCAGGAGTTCAAGACCAGCCAGCACAACATGGTAAAAACCCATCTC
TACTAAAAATACCAAAAAATTAGCTGGGTGTGGTGGTGGGCGCCTGTAATCCCAGCTCCTC
GGGAGGCTGAGGCAGGAGAATCACTTGAACCCGGAAGGTGGAGTTTGCAGTGAGCCAAG
ATAGCGCCACTGCACTCCAGCCTGGGCAACAGAGCGACATTCTGTCTCAAAAAACAAACAC
CTGCCCCATTAACTTTTTGCATTTGATTTTTAAAAATGGGCAAGATAGGCACATGGGACAGA
AGGCACAAAAGAGCCAAAGTGATGTCTTTCTCCCATCCCTGCCCCTTAGGCTCCCAGTTCT
TTCTGGAGGGAGCCATTGTTCCTTGCATATCCTTCCAGAGATTCTACATATAAACAAACCAA
CACACACACACACACACACAAACACACACACAAAATTTCCCTCCTTTTACTTTTGCACAAATAG
GAGTATACATTTTATTTGTTAACTGTCTGCCTTTCCCTAATAGATTGAAAATTCCTTAAATGT
AGAAACTTGGCCTTTTTTTTTTCTTCCATTGATACATCCCCTATACCTGGAACAGTACCTGA
CGCATGGTAGGTGCTTAAATTTTTACTGATAAATGTTGACTGATAACTGGAGGCACCACTG
GTATAGTTTTTTTTTTTTTTTTTTTTTTTTTTTTTTTTTGAGACAGAGTCTCACTCTGTCGCCCA
GGCTGGAGTGCAGTGGCGCAATCTCGGCTCACTGCAAGCTCTGCCTCCCAGGTTCACGCC
ATTCTCCTGCCTCAGCCTCCTGAGTAGCTGGGACTATAGGCGCCCGCCACCACACCCGGC
TAATTTTTTTGTATTTTTAGTAGAGACGGCGTTTCACCGTGTTAGCCAGGATGGTCTTGATC
TCCTGACCTCGTGATCCGTCTGCCTTGGCCTCCCAAAGTGCTGGGATTACAGGCGTGAGC
CACCGTGCCCGGCCACCAGTGGTATAGTATTAATGGAATCAGTGCATTGGCTTACGTATCT
GATTACAGCTCAGTAAGTGTGTGACCCTCACTGAGCCTCAGTCTCCTCATCTGAAAAATGG
GAATGACCTTCATTTCACAAGGCTTGAGCTAAAACATGTAAAGTGTATTGTAAATTCCTGA
ATGCTCTACTCATGTAAGACTAAAGTAGGCCGGGCGTGGTGGCTCACACCTGTAATTGCAG
CACTTTGGGAGGCCGAGGAGGGCAGATCATGAGGTCAAGAGATCGAGACCATCCTGGCTA
ATATGGTAAAACCCTGTCTCTACTAAAAATACAAAAATTAGCTGGGCGTGGTGGCGCACAT
CTGTAGTCCCAGCTACTCAGGAGGCGGAGGCAGGAGAATTGCTTGAACCTGGGAGGTGG
AGGTTGCAGTGAGCTGAGATCGCGCCACTGCATTCCAGCCAGTCTGGCGAAAGAGCAAGA
CTCTGTCTCAAAAAAAAAAAAAAAAAAAAAAAAAAGACTAAAGTACATGGTTTCTTCAAAGCTT
CTCTCTCTTTCTCCCACCTTAGATGATTTTTCCTTTGCAATGTCCTGTGTCCATTCCGCCCC
ACTCCTCCTGGGGCCACCTGGACCAGGTCTTCATCATCTCATATCTATATGTTTGCTGTGT
CTCCTGGCTGGCCACTCTTCTGTAATTTCTCCTCCTCTGAGCTCTCTGGGCAGCTGAATCT
TCTCACTAGTGAAGTCGCCTGGTTGGATGCTGATGAGACTGACCAGCTGAATCCAGTTGAA
AACTTCACACTTGGCAGTGATCTGGTTCTAAAGACACAATTTTCCATAGTTTCCTAACACCA
TCCTGCATGCCACCTGCCTTATTTCCCCACATCACATCGTCCCACTTAGCGGGACTGCACT
GCTGATCCAAATTTTACATCCTTTAGGGCCCACTCAGGTCATATGTCCTCAGGGAAGTCTTT
CTGGAAGAACCTTAAACCAGAGGTTCTCAACAGGGGGCAGTTTTGCTCCCTGTGGAACGTT
TGCCAATGTCTGGACACATTTCATTCGTCACAAACGGAGAGGGGGGATGCTACAGGGATCT
GGCGGATAGAGGCCAGGGATGCTGCTGAACATCTGCAATGCATAGGACAGCCCACCCCC
ACCCCCACACCCCCAGTAAATAATGATCCAGCCCAAGTGTCACTGGTGCTGACGTTGAGTA
ACCCTATCTTAAGCTGAACTCATCATCTCTCCATTCCAGCCTTGGTGGATTCTGTCTCCTCT
GAACCATTCCCATCTCACTTTAGCCTACCTAGATCACAAAGCTTGGCACTCATTATAGACTC
CCCTATTTATTACTCCTTCAAGATGTGCAAGAATCTTTTCTCTGCACTTTTAAGTTCTGTAAG
AAGAGTCTGTGTCGTTCCTATAATAACCAGCATAGGACGTTGCACGTGTTGTGTGCTCAGT
GAACCTGGATTTGTTGATTGTTGACTGACTCACTCTAGAGTTGGAAATCTTATGCTTGGGGA
AACTTAATATCTCTTTCTTTCTCTGTGTGTGTGCATTTGTGCACGTGTCTGTGCATAGCTGT

-continued

| SEQUENCES |
| --- |

GAGACCAAAGACCTGGTTGTGCAACAGGCAGGCACAAACAAGACTGATGTTGTCTGTGGT
GAGTCCTGGACAATGGGCCCTGGAGAAAGCCTAGGAAGGTGGGAACTGAAGGGGGAGAT
GAGGCACACAGGAACACTGGATGGGAAAAAGGGGAGGGGAGGCAGTTTGGGGGTGTGGT
ATCACAGCTCTGCCACTTATCTTGGGAGTCTGGGCAAATCACTTCCCCTCTCTTAGCCTCA
GTTTCTTCATCTGTAAAATGGGATGATAACAGCACTTCCTTAGTAGGTTTTGATTTTAGAGT
GAGAAGGTTGGCCTACAGTAAAGATCAGATAATGTAAATCAGTGAAAAAGGTCAGGGGTAA
GAAAATTACATTCTCTTTACCTAACGCTAAATGACCAGTTAATGGGTGCAGCACACCAACAT
GGTACATGTATACATATGTAACAAACCTGCACATTATGCACATGTACCCTAAAGCTTAAAGT
ATAATAATAATAAAATTTAAAAAAACGAAAAATACATTCTCTTTGCTTTTTCTCAAAATGTACT
TTCCTCTTTGTAGGGCTGGGACTAGAATGAGGTGAGCAAGGCACTTGCCCTCGGGCGCAA
TATTTAAGAAGGTGCCATAAAAGTGTAGTAATCAAGGTAAATTCATTTTGATGCAATATTTTT
AAAAATAAAAATTAATGCAAAGAAATCCATGATGAGCAAGATAGCAACATTTTAAATAAAGAA
CAGGATCCGACCCTGTGTTTGCATGACCCTGCCTCACTCACCTCACCCTAATCCTGGCCCT
GGTTCCAGTAAAAGGAATAGGCAGCCAGCCTGCAGGCCGTAGTTTGCTGACTTGGTGTCC
GCCTGATGATTTTCAAAATATGGCATTAAAAGAATGTTTACCTTGATGACTGAGTGTTTTGG
ACATCCTTTTCAATTTTGTCCTGAAACAATTTCATCCCTTGCCTCACGCTAGTCTCCGCCCT
GCCTTTTGGTCTTTCTTTTATTTTCCCACTTTGAAAAAAAAATTCGGCATGAGAAATACTTTA
CCTTTCCCCTCCACTCTTCTATACCAAAAGCAACATGCAGACATGAATCATGCTAGACCTCG
GCATTGGGCAGAGAGCAGGGAGTGGCGGGGAGCATGGTGAGCAGGTGGTGACAGCCAC
TGCCACCACTCGCTTCTAGATGGTTCCCAGGTGGGGAGGCTGCCAACTGGAACCCAGTCT
TCCCAGTTTGTAAGAGAAATCAGATGTCTAGGTTTGAATATGTGATCTCCCAGTTTAAAAAT
GTCGGCAAATATTTCCAAACGTTAAGAAAATGTTCTGGCTCCTTTAAAGACATCTGCCAGCC
ACATTTCCCCAAGGACCGCGGTTTGAACCTTCTGATGTAGATGAGCTCTGACATTGGAAGA
TTCTGGAGTCTGACAAGTCACAGCAGGTTGAGGGTAGGGAGAAACTGCAGGTGAGGGGT
GCATGCTGAAGTCCTGATTTCTCCAGGTCCCCAGGATCGGCTGAGAGCCCTGGTGGTGAT
CCCCATCATCTTCGGGATCCTGTTTGCCATCCTCTTGGTGCTGGTCTTTATCAGTGAGTCC
TCAGGTGGGGAGGTGTTGGGGGAGGGAGGGGGAGACCACCTGTTTCTTATCTGGCCTCTC
CAACTCCCCATCCTTTTTTTTTTTTTTTTTTTTTTTTTAGAAAAGGTGGCCAAGAAGCCAACCAA
TAAGGTAGGTCACCCCTGAGAACCCGGGACAGAGTTTTGACAAACTGGGAAGATGGCCTC
ACGGTTGCCTATGGGGCAGTAAAACTGATTCAGAGTCTGTCTCTGCAGCCAGTGGGGTGG
CAGCAGAATTGGGGACTGTCATCCCCACCCACCATGCTCCTTCCATCCAGAGCTCAATCCC
CCACAGAACTGCCCCTGGCACCACTGGCAGAGCCTAACACTGGCTGTTCTTCACTCCTTTC
CTGGCATTCAACGCGTGGGGAGCTGCATCTTTGGGCCTTGGGGCTGGGTCAAATGGGTG
GGAGCAAATGTGGCAGCCCCTTAAGCCCACTGGCTCCCACTCTGGAAGCTCTTCGTCGCC
CTTGGTGTGGCCAGCAGGGGGCAGGAGGCACCCGAGGAATCAGCACTGACCCGCCGTCT
GGGAAAGGGGGGAGGGCTTGGGGAAGGGATCCGCTTCCCAGGGAGGGGCTCCTCAGAG
GCACAGCTGCCCCTGCTGCTGGGGGTGACCTCACACCTTGCCTCTCCAGGCCCCCCACC
CCAAGCAGGAACCCCAGGAGATCAATTTTCCCGACGATCTTCCTGGCTCCAACACTGCTG
CTCCAGTGCAGGAGACTTTACATGGATGCCAACCGGTCACCCAGGAGGATGGCAAAGAGA
GTCGCATCTCAGTGCAGGAGAGACAGTGAGGCTGCACCCACCCAGGAGTGTGGCCACGT
GGGCAAACAGGCAGTTGGCCAGAGAGCCTGGTGCTGCTGCTGCTGTGGCGTGAGGGTGA
GGGGCTGGCACTGACTGGGCATAGCTCCCCGCTTCTGCCTGCACCCCTGCAGTTTGAGAC
AGGAGACCTGGCACTGGATGCAGAAACAGTTCACCTTGAAGAACCTCTCACTTCACCCTG
GAGCCCATCCAGTCTCCCAACTTGTATTAAAGACAGAGGCAGAAGTTTGGTGGTGGTGGT
GTTGGGGTATGGTTTAGTAATATCCACCAGACCTTCCGATCCAGCAGTTTGGTGCCCAGAG
AGGCATCATGGTGGCTTCCCTGCGCCCAGGAAGCCATATACACAGATGCCCATTGCAGCA
TTGTTTGTGATAGTGAACAACTGGAAGCTGCTTAACTGTCCATCAGCAGGAGACTGGCTAA
ATAAAATTAGAATATATTTATACAACAGAATCTCAAAAACACTGTTGAGTAAGGAAAAAAAGG
CATGCTGCTGAATGATGGGTATGGAACTTTTTAAAAAAGTACATGCTTTTATGTATGTATATT
GCCTATGGATATATGTATAAATACAATATGCATCATATATTGATATAACAAGGGTTCTGGAA
GGGTACACAGAAAACCCACAGCTCGAAGAGTGGTGACGTCTGGGGTGGGGAAGAAGGGT
CTGGGGG

CD40 [*Mus musculus*]: Accession: AAB08705.1 (SEQ ID NO: 7)
MVSLPRLCALWGCLLTAVHLGQCVTCSDKQYLHDGQCCDLCQPGSRLTSHCTALEKTQCHPC
DSGEFSAQWNREIRCHQHRHCEPNQGLRVKKEGTAESDTVCTCKEGQHCTSKDCEACAQHT
PCIPGFGVMEMATETTDTVCHPCPVGFFSNQSSLFEKCYPWTSCEDKNLEVLQKGTSQTNVIC
GLKSRMRALLVIPVVMGILITIFGVFLYIKKVVKKPKDNEMLPPAARRQDPQEMEDYPGHNTAAP
VQETLHGCQPVTQEDGKESRISVQERQVTDSIALRPLV CD40 antigen [*Mus musculus*]: NCBI Reference Sequence: NC_000068.7 (SEQ ID NO: 8)
CCCCGCCCTCTTCCTGGGCGGGACTCCTAGCAGGGACTTTGGAGTGACTTGTGGCTTCAG
CAGGAGCCCTGTGATTTGGCTCTTCTGATCTCGCCCTGCGATGGTGTCTTTGCCTCGGCT
GTGCGCGCTATGGGGCTGCTTGTTGACAGCGGTGAGTGGCTTGTGTTCTAACCTCCAAGG
GAGTTAGGGCTTAGAGAGTGAGAGATGGAAAGAGGAAAGAGGAGACAAGACTTTGGAGAT
GAGAGATCTTCCTACTGGAAGCGGCGGTTAGTAGGATGGGCAAGATCTCTCGCGTCTTGA
CACACACACACACACACAAATGAGGTGGGCTGCTCCTCTTTCCTTCCAGAAGGTCGGG
GTTCTGTTCCACGAAGCCCACAGGGGAACCTTAGGGAGGGCATTCCTCCACAGCGGTGCC
TGGACAGCTTTGTCTGACCCAAGCCTTGGCTCCGGAGCTGACTGCAGAGACTGGAAAGGG
TTAGCAGACAGGAAAGCCTGGCTAGGGGGAAGGGCGGGTCTGGCCTGTTTCCTGTCACTT
TCCCATTGTGGACAGATGTCTGCCACCTGTGGTTATCTTCTCCTTGCCAGTTGGGGCCACT
TTGTCTAGGGAATCTTGTGCGAACAAGACCCCAGGTACTTTTTAGGGAAGAGGTAATTTAC
TAACCACCATACCCGTATCATAGCTGAGCCAATCTAGAGAAATCCCCAAGTTTGTGCCTCT
GCCTCATGAGCTTAAGGTGGTACAGGAGACACCCAGAGGATGAGGAGGAAGAAGAGGAG
GAGGGGGAGGAAGAGGAGGAGGGATAGCTTTAGAACCCAAGAAAGGATAAGAGACCAGA
CTAGGTTTCTCCAGGCACCAGCAGGGCTCAGACCCAATCAAGCGCATCTTGGGGATTTCT
AGAAGCCGGCACTTGATTCGCTTTTGGTTTAAATGTATTTCTGCAGTTCCTCATTCTGGAAC -continued

| SEQUENCES |
| --- |

CTGGGAATCCCCTGACTACCTGAGTCTCAGCCCCTCTCCTCTGGCGAGGCTCCCCTAGCT
TTCAGGCAGGGTAGATTCTTTCCGGTTGGTGACAGGGACTTCGGTAACTTCATGGGTTCTG
AATTGTCCACCCAGGAAGGTGTCGTGGTTCAGGACTGGCTTTCTGCAGCTGGGACAGTCA
GTGCCCTAAGCACATCCCTGTCCATCAGCCAATGTCACCTGTCCATCAGCCAATGTCACCT
ATCCCAGGTTGGTCTAGTTGAGAATGACCTTTCACATTCTTCTTTTTCTTCTGTTCACGCAT
GGTTTGTGTATATGCGTACATCTGTGTGGGAACACACGTGTGCTTGCATGCGGTAGCCTGA
AGTTCATCTCATGAGTCATCCTTGGACACGGTCCCTTCTTAGTCATCCACACAGGGTCTCA
AGCAAACCCAGAGCTCCCCATAGGGCGAGTCTCACACGTCAGCTGGCTCTGGGGACCCTC
TGCTTCTGCCCTCTGAAGCTGGAGTTACAGGGAGGCCACTACAAAGACCTGGTGTTTGCA
CGTGTTTCTGGAGATCAGAATTCTGGCCCACCCATTTATATGGCAAACACCTTGAGAGCTC
AGTCATCTCTCTTGTCCTTGAATCTCTGATCCTCCTGCCTTCACCTCCCTAGTGCATACACC
ACCATGCCCAGTTTTATGTGGCACTTAGAATAGAATCTAGGGCTTCATGCATGCTAGGCAA
GACACTATACTTACTGAGACACACCCCCAGCCAAAGGACATAGACTCTGACATGTGGCCTG
CCAAGAATCACCATGGAGGTTAGCCGCAGGAAAGGAGCAGAAGCGAGACAGTTGCTTTAC
TAGTTTTCATTTTTTACCCCAGGCCAGTGGTTCCTTTCGCAGAGGTGGTCTAAGACCATCA
GAAAACACAGATATTTACATTAGGATTCAGAACAGTAACAAAATTACAATTATGAGGTAGCA
ACAAAAATAATGTTTTGGTTGGGGGGGGGGTCAGCACCACATGAGGAACTGTAATGGGCC
CCAGCGTTAGGACAGTTGAGAACCACTGCTCTAAATAAGACTTTTAGGGAGACTGGATGCA
GGAAGACGGTGAGGTGAGAGAGAAGTGGATGAGGGCCTTTGGGAGGGATGGAGGAAGAA
ACAGAGGTGTGATGAAGGCTAGTCTGGACCACTCAAGAACAAAGTCTGCCCTTGTAAGCC
CCAATCTGGGCTCCAGGGAGGGGCTGGGCCCTGAGAGAAATAGCAGGTGTTCTTTACTGA
CCTCTTCCTGTGCAGGGGGCTGTGAGGGAGACTGCATGTCACCTTCCTGTGTGAGGGAGA
CTGCATGTCACCTTCATTTGATGTCTCCCAACGTCTCTGTTACACGGATGACCAAGATGAG
GCTCAGAAAGGGGAGGGGTTTACCCAAAGCCTCTTGACATGGATATGAAGCTATGTCTGC
CTGACTTCTGAGCCTGCCACTCACGCGGCAAGGGGTCTTCAAGCTGTGGCCCTGAGACCT
ATTGTGGAGGAAGGAACAATGCTCTGGGGGCTGGAAACTGGGGCTGACTGGCCATCAGA
GGGAAAGTGTCTTTTCCAAAGGTGCCATTGAGGATGTCTACTGTTCTAGAAGGAAGGAAGG
AAGGAAGGAAGGAAGGAAGGAAGGAAGGAAGGAAGGAAGGAAAGGAGGGAGGGAGGGAGGGA
GGTGGGAAGTCTCAGGGAAGATAAAACTCAGGGATGATGCCCTGCTGGGGGCAGGTGCT
TTCAGGTACATTTCATTAAGTGATTTGCTCAGATACCCAGTTTGAGTGAGAGTTCTCAATTT
CCTGGATTCTGGACAGTCAGACAGCTACTAGGGTGCAGGACACCAGGGCAGACCCCCATC
ATCTATGTGTGCTGATTAAAGCTGCCATTTTCTGAATACTACCTTGCTATACTGCCAGGCCA
TGGGCAAGTGTTACAATCTCATTTTAAAGGTGAGAACACAGGGCTAGAGAGATGGCTTAGT
GGGTAAGAGCGCACGCTGGCTGCCATAGCCACATTGGGCTGGTACATAAATTCAACAAGA
ATAATAAAAACAAAGGAAACACAGTCTTAGAGAAGCAAAATAATTAGGATGGTGTACTGGCT
AGTTTTGTGTGTCAACTTGACACAGGCTGGAGTTATCACAAAGAAAGGGGCTTCAGTTGGG
GAAATGCCTCCATGAGATCCAGCTGTAAGGCATTTTCTCAAATAGTGATCAAGTGGGGAGG
TCCCCTTGTGGGTGGTGCCATCTCTGGGCTGGTAGTCTTGGTTCTATAAGAGAGCAGGCT
GAGCAAGCCAGGGGAGGCAAGCCAGTAAAGAACATCCCTCCATGGCCTCTGCATCAGCTC
CTGATTCCTGACCTGCTTGAATTCCAGTCCTGGCTTCCTTAGTGATGAACAGCAGCATGAA
AGTGTAAGCTGAATAAACTCTTTCCTCCCCAAGTGCTTCTTGATCGTGATGTTTGTGCAGGA
ATAGAAGCCCTGACTACACAGATGGGATACAGAGTGGTTTGTCCCGTTCTCAAATGTGGGC
TCCACGCAATCGGTAGCTGTGGTTGTTTCTAAAATGTAACCTGGCTTCAAGGAGCACACGA
GCAAGCCGGAGGGCTTAGCTCTGCAGTTAAGAGCATGTGCTGCCCTTGCAGAGAGCTGGA
ATCCGATTCCCAGCTCCCACATTCCACAGCCCCCAGATATCTGATCCCCTCTTCCGAGGGT
ACTTACACCCACACATGTTCATATTCATATATCTACCTATAATCAAACATGAAATAAATCTTG
TGGCTAGAGAGATGCTCAGAATATTGTTGCTCTGGGAGAGGACCCAGGTTCAGTTTTCTAG
CACCCACGTGTGGCCCACAATCATCCTCAACACCAGTTCCAGGGAACCCAGTGCCCTCTT
CTGACCTCCAAGGGCACCAGGCACGCATGTGGAGCATATTCAGGCTACACTTGTACACAT
AAAATAAATAAATCTAATTATTTTTAAAGTCTTAAAAAACAAACAAACAAACCCCCAAACACC
GTCGCCTAAAACCTCAAGGATAGGGTTGTGACTGAAGGCACTTGTCATATAAGCCTGAGGC
CCTGGGTTCATTTCCTGGAACCCATGTAAGGTAGTGTGTGGTGGCAGAAGTCCAAGTCTGA
CATCCTAAGGCTCCTACTGTGAGACAGGAGGTGGGAACAGGAGAACCCCGGAAACTTTCA
GCACATGCAACCAAGAACAACAAAATGATGGTGGCTTAAGCACAGTAGGAGATAGCACTGA
GAGCAGTGTTGGCCACTGACCTCCGTACACTTCCAGTTATGGCAAGAGCACGCTCCAAGC
TGCAGACAGGGCAGTGGGCGTTGCGTGTGCACACACACCAAAACACGGGCCCACTTTATG
GTTCTTAAAAAAAGTTTCTACACTTAAAAAAATGTAGTTTTCGTTATACTTATTTATTTATATA
TTATTTGTATGCATGCATGCATGCATGCGTGCTTGAGTACCAAAGCGTGTGTGTGGTCAGA
GGACAAGTTAGGGAAGCTGGCTCTTCCTACCATGTGATTCTAAGGAACTGAACTCAGGCTG
TCAGGCTTGGCAGCAAGAGCCTTCACCAGCTGAGCCATCTCTCCGGCACCTCTCTCTCTCT
CTCTCTCTCTCTCTCTCTCTCTCTCTCTCTCTCTCTCCCTGTTTGTATTTTTCTTTTTTAA
AAATATTTTTTCAAGTTTTTTTTTTTTTTTAAAGATGTATTTATTTTATGTGAGTACACTGTCACT
GTCTTCAGACACACCAGAAGAGGGCATCAGATTCCATTACAGATGGTTGTGAGCTACCCTG
TGCTTGCTGGGATTTGAACTCAGGACCTTTGGTCAGTGTTCTTAACTGCTGACCCATCTCT
CCAGCCCTGTTTGTATTTTTCAACACAAGGTTTCTCTGTGTAGCCCTGGCCGTTCTAGACCA
GGTTGGCCTCGAACTCAGAGATCCACCTGCCTCTGCCGCCTGAGCGCTGGGATTAAAGGT
GTGCGCCACCACTGCTCAGCTGACTGTTTCTGGAAGTGTTACAGCTCCGCTCTGAGGGAA
ACTTTTCTCTGAGTGTTGTAGATGTGAGGAGAAATCCCGAAAGGCTTCCCTGTGGAGGTGT
TGCATCTCTGAAAGGAAAAGCGGAGTATCACAAAGTCCCACTGCTGGACAAACCTCAGAGA
GTGGCTGCCTCCGCCCAGGGGCGAAGCAGCAGAGAGCTGAGCTGCAGGCAGCTTAGGCA
GTTCTCCAGGGTGGAGTCCTTCTGGGCAGGGATTGGTGAGACTTCATGCTCAAGGATTGG
TGGGTTCGCATAGTTCTTTTATTTTTTCCCAACTAGGAAGTGGGCTCAGGCCTTTCCCCCA
GCTAGAGTTTCACTGTTCTTTAAAAAACATCATTTTGTTTTTATTTCATGTGAATTGGTGTTTT
GCCCTGCATGTTTCTCTGTGTGAGGGTGTCAGATTCCCTGGATCTGGAGTTACAACTGGTG
GTTGTGAGTTGCCATGTGGATGCTGGGAACTGAACTTGGGTCCTCTGAAAGAGTAACCAGT
GCTCTTAGCCATTGAGCCATCTCTCCAGCTCCTCCAAATCCTTTTCTTATTCATTTAAAAAAT
TACATGTATGTATGTATGTATGTATGTATGTATGCATGTTTGTACGCACACACACACACACA

-continued

| SEQUENCES |
| --- |

CACACACACACGGAGATTAGATGCTAACTTTTGAGAGTTGGTTCTCTCCTTCCATTTCTGGG
CCTTGAAATTCTGGTTATCAGTCTTGGCAGCAAGCGCCTTGATTGGCTGAGCCATCTCGCT
CCTTGGTTCTTCAAGGAGTAAGTCTCTGGCGCTAGCTAGATCATAGTTAATGCCTTTTTTT
TTCTTTTTTCTTTTTTTGAGACAGGGTTTCTCTGTGTAGCTTTGGCTGTCTTGGAACTCACTC
TGTAGACCAGGCTGGACTCACAGAGATCTGCCTGCCTCTGCCTCTGGAGTGCTGGGATTA
GAGGCTTATGCCACCACAGTTGGCCAGTTAACACCTCTGAAAGACTTGCTACCAACCCACC
CCAGGCTTAAAAGTAAAATCAAGAGCAGACAGAGCGAAGGATCTCAGCAAAGAAAGCTAC
GCATCGAGGCTTAATAACCCTGTTATGAATCTGTTGAGTGTATTTTTAGGGTTTCTTTTAATT
TATAGGAAGTGATACTTGCTGACCTCTTGATGCAGCAGTAGAAGATTTACAGTTAAAAGAAG
TGTGCTTAAATTAGCAAGAAGCAGCTCATAGCATGGGTGGTCCCCGGATGTTGTAGAAACA
CATGTTGAGAGTCCCGCCCCTGTGGACTCTGTTCAGTGTTGCCCTCTGTGGGGTGATTCTT
ATCTCTTTGGTGGCAGGGAGCTGGGGACAGAAACCGGGAGAAGGGCTGAGGCCAGCTTG
AGCCAGCAGTCTCGGGACTCTGGAGGAAGAACTGGAGTTCTCCCTACCTGCTGCGTCTTT
GGGAGCACTGAAGAGTCCTGTGCATCTGTTCGGATTAGAGGGTTCTGCGTTCTTGCTTTGG
TAGATGGCAGTAAGACGATGTGACAACAGAGTAAAAAAAAAAATAGACCTCACACTCTGGG
GGCTCACTTTTCTGCTTTGGATTTCCACATCAGCTACAGCCTGCGTCTTGGCTAACTTTCAA
CATGCCGGTGGAAGATCCCTTCCAGCTGTCCACTTCTGTTTTAGGTCCATCTAGGGCAGT
GTGTTACGTGCAGTGACAAACAGTACCTCCACGATGGCCAGTGCTGTGATTTGTGCCAGC
CAGGTGAGATGCTAGCCCTCCTGCCCCGTACCAAGACCCTTTCCCTCTTGGATTGCTGGT
GGATGCAGACCCCATATATAGACTGTGAACTCAAGTCTAAAATGACCCATTTCTCCCTCTTC
CTTGATGCCAGAATACCCCAAGCTGTCCCGTCTCTTCCATCTTCCTTACTCGTGTAGGGTC
TGAGATATCCATTCCCAAACTCCAACCCTCTCACCTCCAGTCCTGGCTCCCTGGGTTGTGA
CACAGTCTGTGTCACAGGATTGGCCCAACCTGCCTCATATCCTCCTGTTTTTCAGGAAGCC
GACTGACAAGCCACTGCACAGCTCTTGAGAAGACCCAATGCCACCCATGTGACTCAGGCG
AATTCTCAGCCCAGTGGAACAGGGAGATTCGCTGTCACCAGCACAGACACTGTGAACCCA
GTGCGTGGGGCTGCCTGGGAAGGGGTACTTGAGAACCGGGTTGATGTTCCTAATGCTGAA
ATCCCTCTGTTGTCAGTGGCCAGGGTCTTTCCTGTGAGCTAGAGTCTGGGTTGAAGGGGC
TAGTTGACTGACATCTGTACTGGGAAGAGCGAGAAAACCAGCAGATGACGTGAGGAGTGG
GGTCCTGGCTGCGGCCCAGCGGGTTTTCCCATTCTTCCTTCTCATCTCCGCTCAGATCAAG
GGCTTCGGGTTAAGAAGGAGGGCACCGCAGAATCAGACACTGTCTGTACCTGTAAGGAAG
GACAACACTGCACCAGCAAGGATTGCGAGGCATGTGCTCAGCACACGCCCTGTATCCCTG
GCTTTGGAGTTATGGAGATGGGTGAGTGGCCTGCCTGGGGAAACAGCTCTGTGGGTGGG
AGAGCTGGGGTGAGCTTTGGGTCTCTGGCCTCCAGAAGCTGAGGGCAGAGAAAGTCCCA
CCTGGGCTGGGATCTTTCATTTGGATTTGGACCTGGGCTCTGGGCAGCTTCCTGCGGGGT
TGTGGCCTTCAGGGGCTGTGTTGCCTTGGGGTAAGAAGCTGAGGGCAGGTGTTCTGTCCT
GCCCTGCTTGTCTGCTGGCTCCCTTGGGAGTCAGACACTGTGGCCCAGGTGTCTGCTCAT
GCATCTTTCCGCATCCTTCCAGCCACTGAGACCACTGATACCGTCTGTCATCCCTGCCCAG
TCGGCTTCTTCTCCAATCAGTCATCACTTTTCGAAAAGTGTTATCCCTGGACAAGGTATAAG
GGTCACCTCTCCCTAACCAATGACAGGGTGGGTCTTGTCTCAGTCTCTTTAGCCACCTGCT
GTTCAGTCCCTGACTTTCCCCACCCCCATGGTGGGTCACTTACTGGTGAATGTGACCTTGT
GGCTGGCTTAAGGGACACTTTGTGCAGTTCTTTTAGCTTGCTTCTGCTTAGTTAATAGAAGC
CTGTTGGTCTCCATATCCTCTTGAAGTCTCTTCTTAAAGCATCATGACACTCGTACTCCCCT
TTTCAGTTCACTTTCTTGGTGGGTATGTGTATGTGTGCATGTGTATGCATGTGCATGCATGC
ATGTGTGTGTGCATGCATGTATGAGCATATATATGCATGTGCATGCATGGATGCATGTGCA
CACATGCATGTATGTGCATGTATGTGCATGTGCATTCATGCATGTGTGCATGCATGTGTAT
GCATGCATGTGCATTCATGCATGTGCATTCATGCATGTGTGTGCATGTGTCAGCTATCAGT
TTGGTGTGTTCCTCCTCAGGTACTGTCCACTGTTTTTTGTTTTGTTTGTTTGTTTGTTTTGT
TTTGTTTTGTTTTGAGAGTCCCAACACTGGGACTATAACCACTTGCTACCAAGCATGGATTT
TTTTTTTTTTTTTATCGTGGGTTCCAGGGCTTGAACTCGGGCCCTTGGGTTCACAGTGCTTT
CCTGAGTGAGTTATCAATGCCCCCAGCCCTTCTGGACTCTTACTTGTGTTTGTTGGGCTTT
GTCTGGGTTCTCTGACCACTTCTTTCCACCTCTCCTTGGCTGTCTTATCTACATCTATGGCT
CCATCTCCCCCTGGATCTGTCCTTCAGCCCCCAGATGGTCAAGTCCCACTGCTGAGTGTTA
TGGATCACCAGCACCTCAGACTCTGTGCATCCAAAATGGGCCCCTAGCCAATCCCTGAGC
CCCAGCTGACAGGCAGGTTCTGGCTCCAGGCAGTCACACAGTGAGCTGCCCACCCTTGCC
TTCAACTCCCTGTCAGTCAGGCCCATATGACTGTCTTGGGAATCCACCTCCTCACTCTCTA
GAGTGGTCACGTGAGTTCGCACCTCCTCACTGTGGTGTGGTGATGGCTCTGTCTCCTCATA
GGCTCCCTGCCTCTGGTGTCTCCCTTGGCAGCTTTGCACCATGCTGCTGTTGGGAGCTTC
CGTAGCCCCTTTTGGATCATGTCGCTTCATGATTTAAAGCACTCCACGTCTCCCTGCTGCC
TTTGGGAGGAAGCCCAGACTCCCGGGACTGGGGCTGGGCCTTCCAGCTACAGTTCCTGTC
TCTCCCCCCACACCTCGCACCCTGCACTTGCACCCCGGGCACACTGTTTATTCTTTTGCTT
CAAAGTCTCCTGTTTGGGAGAAAACAATATATATGCCCTATTCTGTTTTTTATAGTTCACATT
TAATGTTTTTTAAATGGGCAAACCTGTCACCTCAGGCTGTTTCCTCACTACTCCTTCAGAGA
GAGAGAGACAGAGAGAGACAGAGACAGAGAGAGACAGAGACAGAGAGAGACAGAGAGAG
ACAGAGACAGAGACTCAGAGACAGTCAGAGAGACAAAGATAGAGACAGAGAAAGAGACAA
TCAGTGAGAGACAGAGGGATAGAGAGAGACAGAGAGTCAGAGAGACAGAGACAGATAGA
GAGACAGAAAGACAGAGACAGAGAGGTGGGGGGAGGAGATAGGGGGAGACAGAGGGAC
AGAGAGACAGAAGGACAGAGAAACTGCTAATAAACAAACACATTGACATACCACTCCCCTC
TGCCATGATACACATATGCACACACACACATACACACACACACACACACACACACACACAC
ACACACACACACACACACACACACACACCACAGTGGTTTCTCTTGTGGTTATAGTGCTTGC
TTGCAGGTCACACTCACCGTCCTCACTGGTGGGTTTAGTTGTTCATAGAAGTTCCCGTCCC
GGAGTCAAATGTGCAACTGCCGCACTGCCCCACTTAGCTGGTTCATGCTGCTGTTTCAACT
TTTATCCCCTTTGGAGACCCTTCGGATCTTCTCTGGGGACCCCCAAATCTGCCTCAGTTTG
TGTGAGACCCTCAGGGATGCCCCTAATCTCGGGAGGCTTCAGCCAACTTGTAAAGGTGCT
GAGGGCCTTTCTCACACAAGGCTAGAGCACGCACGCATTTTCTCTGAAGCCTCTCTTCCAC
CACATCCCGGTTTTCCTTCGCCATGTCCCTTGCCATGTCCCCTCTGTCCCCTCCTCCCAGG
ACCTTCCATCCACACCACACATCTCCACTCCTGTCCTGCCTCTGGCTGCCCACTCTGCTGC
AACGGTCCTCTCACCAGTCAGGTCACTCCCTAGCTGCCTGCCTGCAGCTGCCCTGCCTGC

SEQUENCES

AGCTGCTCATCACCGCACTTGTCACCATGTGACTCCCCTCCTGTCACACTGTTCCTACTTA
GCTGGGTCCCACTTTCCCATCCTTCAATGCCTTCTGATGCCCCCCTTCATGGGGAAGTCTT
CCCAGAAGACCCTGAAAGCAGAGCTTCTTAACGGGGACCAGTTTGGCTCTCTGTGGGGGC
GTTGGCCACATCTGATCATCTTTTGGATGCTGTACTTGGCGGGGAGGCTGTTTCTGGCATT
TGGTTAGTGGAGGCAAAGGTGCTGCTAAATAGTCTGTGAAACAAAGGCCATTTCCCAGCAC
AAAATACCTGCAGATTGGCCATTTCCATTTCAATATGACCGTAACCTTTCCTTTCTGTGGTTT
CTGTTCTTCACTTAATGATCATCTTGGGATGCTGCACTCTAAGTCACGTGCTCAGTGAACAA
GGACTTGCTGCTTGCTGGGGGACTCCCCTGGGCTTGGAAGTCTTATGGCGGGGAGCCCT
GTTTCTGTCTGTCTGTCTGCATGTGTGTGTGTACATGCACATACATGTGTACACATGTGTCT
TTGTGCAGCTGTGAGGATAAGAACTTGGAGGTCCTACAGAAAGGAACGAGTCAGACTAAT
GTCATCTGTGGTGAGTCCAGGGGAGAATGGCCTTGCCAAGTCTTTGGGAAGCAGGGAACT
GGGGAGAGACTGAGGCACGCAGGAACACTGACTGGGATAGGAGTGAGACCAAGAGGCAG
TTTGGGGTACAGTACCTTAGCTCCCGTCTTGGGAGCTGGGTAAGTCACATCCCTTGTCTGA
GCCTCAGTTTCTTCAATTGTGAAATAGGCCCACAGCAGCTCCTTCCTCCCTTACCTGGGTC
GTGTAAGTGGCATTGGAATTTTGCAGTTTGGAAGCTGCTGCCCCTTGCTTGAGGTTCAGGT
TCACTGTGACAGTGTCACCTGGTAACCCCAGTTTGGATGCTAGGATGTAAAACTTGACCAT
CCCCTAATGGATCACAATCTCAGATAACAATAGAGACCAGGCCACTTTTGAATGAGTGAAG
ACAGAGAAGGGTAAGAGAGCTAGGTCTGATGAGCGGGCCTGTCAGCGCAGCTAATTAGAG
GCAAGAGCTTTGTAAGTTCAAGGCTAGCCTGGGCAGCTTAGAAAGATACTGGTTCAACATA
GAAAAGGGCTGCTGAGATGGGTCAGTAAGTTAAGCTCTTGCCTGATGGCCCAGCTTCCAT
CCCCAGCATCCATGGAAAGGTAGAAGGAGAGGATCAGCTCCTAAAAGTTGTCCTCTGACC
GCTGCATGTACAGCACAACACAGCACAGCACATGTGAGTGTGCATACATCATGCACACACA
TCATACATACATCATGTGCACATATCATGCACACACATCATGTGCACACATCATACACACAT
CATGCACACACATCATGTGCACACATCATGCACACACATCATACATACATCATGTGCACATA
TTATGCACACACATCATGTGCACACATCATGCATACACATCATACACACACATCATGCACAC
ACATCATGTGCACATATCATACACACATCACGTACACACATCATGCACACACATCATACACA
CATATCATGTGCACCCATCATGTGCACACATCATACACACATCATGTACATGCACACCCACA
ATAGTGATAAATAAAAGTTTAAATATGTTTCTAGGGCTGGGGAGGTGGCACTTGCTGTTCTG
ACAGAGGACCTGGGTTCAGTTTCCTGAGCCCATGTCATTGCAGTATAAAACTGTCCATGAC
TCCAGCTCCTGGTGATCTGATATCTCTGCTGGCGCTAGGCACATACATGATGCACGTACAT
ACCTCTAGCACTTTCTGATATACATAAATAAAAATAGATACAAATTAAAAGACATTAAAAAAA
AAAGTAAGAAGATAGCTGGGGGTGGGGCTCAGTGGTGGAGCAGTTGTCCAGCATGCTGA
GGTCCTGGGTTAGACCCCCACACTTGCCTAGCATATGTGAGGTCCTGGGTTAGACCCCCA
CACTTGCCTAGCATATGTAAGGTCCTGGGTTAGACCCCCACACTTGTCCAGGATATATGAG
GTCCTGGGTTAGACCCCCACACTTGCCTAGTATATGTGAGGTCCTGGGTTAGACCCCCAC
ACTTGTCCAGGATATGTGAGGTCCTGGGTTAGACCAGTGCCACAAAGTAAAAAGAAAATA
AAAGTGCAGTCTCTTTGCTTTTTCTCAAGATTGCCTTTTTGTCTTGGAAAGGCGTGAGTGGA
TGGAGTGTGAAAAGCACTTGAGTTCATGTGTAACATTTAAGAAGACATCGAGAAGGGACAG
TAAGCAAGAGAAAACATTTTGAGATGATGCTAGAAAAACCAAAAACACTTTTAATAAATCTG
AAACCAAAAAACATGTTGATGCACAACATAGCAAAATTTTAAATTAAGTAAGAGCTGGGCTG
GCGAGATGGCTCAGCGGGTAAGAGCACTGACTGCTCTTCCAGAGGTCCTGAGTTCAAATC
CCAGCAACCACATGGTGGCTCACAACCACCCATAATGAGATCTGATGCCCTCTTCTGGTGT
GTCTGAAGTCAGCTACAGTGTACTTACATATAATAATAAATAAATCTTTAAAAAGTAAGAGCT
GACCTTGCCAGACTCGAGACCCTGCCTACCTTCTTCATCCTAACCTTGGCCCTGGTTCCAA
TACAAGTTTATCTAAAAGCCAGGTAGCCACCTATGGACCTGTGTTTGTTTCACTGGTGTCTG
CCTCCCGACCCATGAGCTGGGTGTGGTGGTACAGGCATGAGAGCCCCAAGTTTAAGGCCA
GCCTGAACCACTTAGTGAGACCCTGTCTCAAAGAAGACTTACCTTCATGACAGTGTGTGTG
TGTGTGTGTGTGTGTGTGTGTATACACACCCCTTGCCTCTAAGAGTACCTGCCTTTTGGTC
TTTTCATTTGTCACTTAGAATAGCAGTGCAGACACAGAGATACTTTGTTTCTCTCCGCCATA
CTTCCATAGCAGATGTAACAATTTGGGGGCTAGTGTAGGGAGGGGTAAAGCAGGCAGGCA
GGCTGTCCCTTCAAGACACAGCTGACGAACACACCAGATGGGAAGTTGGCTCACTGGGGG
CTTCTCATTCCAACTGCAATCTCCCAGAGCTAGAGACTGCTCAAAGGGTAGGAGTATTTAC
TATGCAAGCATGAGCTAGGTGTGGCCACACCACATGTGACTGTGACCTTAATACCATGTGT
AGGGGGGTGGCACTAGAAGGAGAATTGTAGGGTGTTGCCTCCCAGACTAGCTCCAGGCTC
AAGAGACTCTGTCTCAGCAGAAGGTGCAATATGGTGGATCAGGACACCAGCACCCTCCTTT
GGCCTCTGCATGTGTGCACAGATGCACACATCTAAACACATACCAGGCCCACATACACCGT
ACCCCACCACCACACAAAGATGGACTCTCTCAATTTATAAACACTGGCAAATACCATAAAGC
GTTTTAAAAGTTCCCCTAGTGACCACATTACCCACAATGCTACTGCTTAAAAGCTCTGACCT
GGATTCTGGGAGTGTACAGATGCTTTGGGCAAGGAGTGGGAGCACCTGCCAGTGAGAGC
ACCTGCCAGTGGGAGCACACTCCATTGGGAGCACCCGCCAGTGGGAGCATCTGCCAGTG
GGGTCCACTCAAGTCTGTTTCTCCAGGTTTAAAGTCCCGGATGCGAGCCCTGCTGGTCATT
CCTGTCGTGATGGGCATCCTCATCACCATTTTCGGGGTGTTTCTCTATATCAGTGAGTGCT
CAGGAGAGGAAAGGGAGGGAGGGTTCAGCCCTGTCGAACCAGCCTCCTGACTCACCCTC
GCAATGTCCCACACCCCTTCTTCTTCTCACTAGAAAGGTGGTCAAGAAACCAAAGGATAA
TGAGGTAAGCCATCCCTGAGGGAGAGATGCTGGAAAGAGTGACTGGTGGGCAGGGAGGG
AGGCTCACGGCGTAGGGAGACAGACTCAGTAAGCAGAGAGCTTGTATTGGATCCTTGAGT
GTGGACCCATGGAAAAGGCCCATTACACCCACGCTGGTGGGGGCGGGGAGAGGGGGGG
AGGATGGACACAGGGATCTTAGGAGCTTGCTAGCCAACCATGGGCTACTCCAGGTTCCAA
GAGAAACCCTGACTCGGAAAATAAGGGTTAAGAGTGCAAGAAGACACAAGATGTTGACCTC
TAGCCTCTAATAATGTGTACATGGGTGTGTGGACCCTCTACGCCATGAGCATACACCCAAT
ACCACGCCACACTCCGCGCGCGCACATGCGCGCACACACATGCCCAAACAGGTTTAGGGT
CCGTTCCCTGGAACATATAGGTGGGCTACTCGCACCCCCACCCAGCCCTGCTCTCAGTCT
CCATCGCTTCCTCCTACTCAACTACTTCCCCTTAGGGCAGAGCTGGGCACCACTGGCAGA
GAAACTCTGGCTGTGCTTTCCTCCAGCCTTGAATGCTGGGGATGGGAGTCGGCGGCGGG
GGGTGGGGGTGGGGGGTGGGGGTGGGTGGATCCCGCCTTCAGGGGCCAGTAGGTGGAA
CCAAAGGGGCAGTTTCTCCTGCTGGTCTGCAGTGGCTCTGGAAATTTCCTGCCAAATTTCA
TGTGTCCAGCAGGGGGCAGAAGGCATCCAAGAAATCAGTTTTGGTACACCCCCATCCTCC

-continued

| SEQUENCES |
|---|
| CACCCCATTGGAAAGGACTTGAAGGAGGGATTCTATTCCTCAGAGGCAGGGTGGCTCTGT<br>GGCTAGAGGTGACATTGGACCTTATACCTTGACTCCCCAGATCTTACCCCCTGCGGCTCGA<br>CGGCAAGATCCCCAGGAGATGGAAGATTATCCCGGTCATAACACCGCTGCTCCAGTGCAG<br>GAGACGCTGCACGGGTGTCAGCCTGTCACACAGGAGGATGGTAAAGAGAGTCGCATCTCA<br>GTGCAGGAGCGGCAGGTGACAGACAGCATAGCCTTGAGGCCCCTGGTCTGAACCCTGGA<br>ACTGCTTTGGAGGCGATGGCTCGGCTCGGGAGCAGGGGCCTGGCTCTGAGGACTGCTTG<br>CTGACCTTTGAAGTTTGAGATGAGCCAAGACAGAGCCCAGTGCAGCTAACTCTCATGCCTG<br>CCCCCTATCATTTCTCAACTTGCTTTTTAAGGATGGAGGGAGAGCTCGGGCATCGGGGGT<br>CCACAGTGATACCTACCAAGTGCAGCAGTGCAGGACCCAGAGTCGTCTTGCTGCGGCGTT<br>CACTGTAAGGAGTCATGGACACAGGAGTCCGTGGCCCACAGCTTGTGCTGCTAGAGGGCA<br>CCTGGTTGCCCATCAGCAGGGTACTGGCTAAATAAATCTGTAATTATTTATACAATGACATC<br>TCAGAAACTCTAGCAGGTGGGGCAGAAAACAGGTAGTAGAATGATGGGTAGAGAAATAGC<br>TTTTAAAACACATTCCAAGGCAGGTAAGATGGCTTTTGTGAGTAAAGGAGCTTGCTGCCCA<br>AACCCGGTTACCTGATTTTGATCCCTGGGACTTCATGGTAAAAGGGAGAGAACCAAATCCA<br>GAGGGTTGTCATTTGACCTCCATGTGTGCTCTGTGGTAATGTACCCCGTGTGTGCACATGT<br>GCACATATCCTAAAATGGATGTGGTGGTGTATTGTAGAAATTATTTAATCCCGCCCTGGGG<br>TTTCTACCTGTGTGTTACCATTTAGTTCTTGAATAAAAGACACACTCAACCTTTATATTTACA<br>ATAA |
| AID [*Homo sapiens*]: Accession: AAM95438.1 (SEQ ID NO: 13)<br>MDSLLMNRRKFLYQFKNVRWAKGRRETYLCYVVKRRDSATSFSLDFGYLRNKNGCHVELLFL<br>RYISDWDLDPGRCYRVTWFTSWSPCYDCARHVADFLRGNPNLSLRIFTARLYFCEDRKAEPE<br>GLRRLHRAGVQIAIMTFKDYFYCWNTFVENHERTFKAWEGLHENSVRLPRQLRRILLPLYEVDD<br>LRDAFRTWGR |

The invention claimed is:

1. A kit for producing antibodies, comprising:

a B cell population and gene editing agents to down-regulate AIRE function and/or CD40 function in the B cell population; and an antigen, wherein the AIRE gene editing and/or CD40 gene editing comprises CRISPR-Cas gene editing, transcription activator like effector nuclease (TALEN) gene editing, MegaTal gene editing, or zinc finger nuclease (ZFN) gene editing.

2. The kit of claim 1, further comprising one or more of:

an adjuvant;

CD40L, IL-4, IFN-γ and/or TGF-β; or an in vitro B cell population with down-regulated AIRE function and an in vivo B cell population with down-regulated AIRE function.

3. The kit of claim 1, wherein one or more of:

the B cell population is AIRE-/-;

the B cell population expresses an AIRE protein that does not interact with AID;

the B cell population expresses an AIRE protein that does not interact with AID and:

the AIRE protein lacks its caspase activation and recruitment domain (CARD) and/or its nuclear localization signal (NLS); and/or the AIRE protein lacks amino acids 110-114 and 131-133 or lacks amino acids 101-180;

the B cell population is in vivo within a mouse, llama, chicken, rat, hamster, or rabbit;

the antigen is a viral antigen, a bacterial antigen, a fungal antigen, or a cancer antigen; and/or the kit further comprises an adjuvant and the adjuvant comprises a Toll-like receptor ligand, a squalene-based adjuvant, alum, a STING agonist, and/or a cytokine.

4. A kit for producing antibodies, comprising:

a B cell population and gene editing agents to down-regulate AIRE function and/or CD40 function in the B cell population; and an antigen, wherein the gene editing agents comprise SEQ ID NO: 9 and/or SEQ ID NO: 10.

5. The kit of claim 4, further comprising one or more of:

an adjuvant;

CD40L, IL-4, IFN-γ and/or TGF-β; or an in vitro B cell population with down-regulated AIRE function and an in vivo B cell population with down-regulated AIRE function.

6. The kit of claim 4, wherein one or more of:

the B cell population is AIRE-/-;

the B cell population expresses an AIRE protein that does not interact with AID;

the B cell population expresses an AIRE protein that does not interact with AID and:

the AIRE protein lacks its caspase activation and recruitment domain (CARD) and/or its nuclear localization signal (NLS); and/or the AIRE protein lacks amino acids 110-114 and 131-133 or lacks amino acids 101-180;

the B cell population is in vivo within a mouse, llama, chicken, rat, hamster, or rabbit;

the antigen is a viral antigen, a bacterial antigen, a fungal antigen, or a cancer antigen; and/or the kit further comprises an adjuvant and the adjuvant comprises a Toll-like receptor ligand, a squalene-based adjuvant, alum, a STING agonist, and/or a cytokine.

* * * * *

SEQUENCE LISTING

<160> NUMBER OF SEQ ID NOS: 13

<210> SEQ ID NO 1
<211> LENGTH: 515
<212> TYPE: PRT
<213> ORGANISM: Homo sapiens

<400> SEQUENCE: 1

```
Met Ala Thr Asp Ala Ala Leu Arg Arg Leu Leu Arg Leu His Arg Thr
1               5                   10                  15

Glu Ile Ala Val Ala Val Asp Ser Ala Phe Pro Leu Leu His Ala Leu
            20                  25                  30

Ala Asp His Asp Val Val Pro Glu Asp Lys Phe Gln Glu Thr Leu His
        35                  40                  45

Leu Lys Glu Lys Glu Gly Cys Pro Gln Ala Phe His Ala Leu Leu Ser
    50                  55                  60

Trp Leu Leu Thr Gln Asp Ser Thr Ala Ile Leu Asp Phe Trp Arg Val
65                  70                  75                  80

Leu Phe Lys Asp Tyr Asn Leu Glu Arg Tyr Gly Arg Leu Gln Pro Ile
                85                  90                  95

Leu Asp Ser Phe Pro Lys Asp Val Asp Leu Ser Gln Pro Arg Lys Gly
            100                 105                 110

Arg Lys Pro Pro Ala Val Pro Lys Ala Leu Val Pro Pro Pro Arg Leu
        115                 120                 125

Pro Thr Lys Arg Lys Ala Ser Glu Glu Ala Arg Ala Ala Ala Pro Ala
    130                 135                 140

Ala Leu Thr Pro Arg Gly Thr Ala Ser Pro Gly Ser Gln Leu Lys Ala
145                 150                 155                 160

Lys Pro Pro Lys Lys Pro Glu Ser Ser Ala Glu Gln Gln Arg Leu Pro
                165                 170                 175

Leu Gly Asn Gly Ile Gln Thr Met Ser Ala Ser Val Gln Arg Ala Val
            180                 185                 190

Ala Met Ser Ser Gly Asp Val Pro Gly Ala Arg Gly Ala Val Glu Gly
```

```
        195                 200                 205

Ile Leu Ile Gln Gln Val Phe Glu Ser Gly Gly Ser Lys Lys Cys Ile
    210                 215                 220

Gln Val Gly Gly Glu Phe Tyr Thr Pro Ser Lys Phe Glu Asp Ser Gly
225                 230                 235                 240

Ser Gly Lys Asn Lys Ala Arg Ser Ser Ser Gly Pro Lys Pro Leu Val
                245                 250                 255

Arg Ala Lys Gly Ala Gln Gly Ala Ala Pro Gly Gly Gly Glu Ala Arg
            260                 265                 270

Leu Gly Gln Gln Gly Ser Val Pro Ala Pro Leu Ala Leu Pro Ser Asp
        275                 280                 285

Pro Gln Leu His Gln Lys Asn Glu Asp Glu Cys Ala Val Cys Arg Asp
    290                 295                 300

Gly Gly Glu Leu Ile Cys Cys Asp Gly Cys Pro Arg Ala Phe His Leu
305                 310                 315                 320

Ala Cys Leu Ser Pro Pro Leu Arg Glu Ile Pro Ser Gly Thr Trp Arg
                325                 330                 335

Cys Ser Ser Cys Leu Gln Ala Thr Val Gln Glu Val Gln Pro Arg Ala
            340                 345                 350

Glu Glu Pro Arg Pro Gln Glu Pro Pro Val Glu Thr Pro Leu Pro Pro
        355                 360                 365

Gly Leu Arg Ser Ala Gly Glu Glu Val Arg Gly Pro Pro Gly Glu Pro
    370                 375                 380

Leu Ala Gly Met Asp Thr Thr Leu Val Tyr Lys His Leu Pro Ala Pro
385                 390                 395                 400

Pro Ser Ala Ala Pro Leu Pro Gly Leu Asp Ser Ser Ala Leu His Pro
                405                 410                 415

Leu Leu Cys Val Gly Pro Glu Gly Gln Gln Asn Leu Ala Pro Gly Ala
            420                 425                 430

Arg Cys Gly Val Trp Thr Gly Leu Arg Cys Arg Ser Cys Ser Gly Asp
        435                 440                 445

Val Thr Pro Ala Pro Val Glu Gly Val Leu Ala Pro Ser Pro Ala Arg
    450                 455                 460

Leu Ala Pro Gly Pro Ala Lys Asp Asp Thr Ala Ser His Glu Pro Ala
465                 470                 475                 480

Leu His Arg Asp Asp Leu Glu Ser Leu Leu Ser Glu His Thr Phe Asp
                485                 490                 495

Gly Ile Leu Gln Trp Ala Ile Gln Ser Met Ala Arg Pro Ala Ala Pro
            500                 505                 510

Phe Pro Ser
        515


<210> SEQ ID NO 2
<211> LENGTH: 12382
<212> TYPE: DNA
<213> ORGANISM: Homo sapiens

<400> SEQUENCE: 2

cgcgggggta taacagcggc gcgcgtggct cgcagaccgg ggagacgggc gggcgcacag      60

ccggcgcgga ggccccacag ccccgccggg acccgaggcc aagcgagggg ctgccagtgt     120

cccgggaccc accgcgtccg ccccagcccc gggtccccgc gcccacccca tggcgacgga     180

cgcggcgcta cgccggcttc tgaggctgca ccgcacggag atcgcggtgg ccgtggacag     240

cgccttccca ctgctgcacg cgctggctga ccacgacgtg gtccccgagg acaagtttca     300
```

```
ggtgggctcc ccgcccgccc cccgctgccc ccaggccctg tgagccaggg atagtccccg    360
gggaagttcc aggaggaccc cgcccctcca gatccccaag cccctccagc cttccccaac    420
tccctcccca caaggagcca ggggcgtccc tgatgacaag ttagaagttg gtccccttcc    480
cccagccgtc cccacacctc acccccaagc caagggaatg gcctccaggt tcccccagcc    540
ccaccctcaa caccccctaca ccaccacctg actccaccac aagccgagga gatgggcgtg   600
gagctgtcca ggtcgccagc gcctctgcct gggagctcca ccctctagtc atgatggaga    660
tgggcaggcc gcagggtgtg gggaccatg gcagggaccc tcatgccacc ccactgcagg     720
agacgcttca tctgaaggaa aaggagggct gcccccaggc cttccacgcc ctcctgtcct    780
ggctgctgac ccaggactcc acagccatcc tggacttctg gagggtgctg ttcaaggact    840
acaacctgga gcgctatggc cggctgcagc ccatcctgga cagcttcccc aaaggtgggt    900
cctggtggac tcagccatgc tgggggcctg gggcagctgc tgtcacctgc tcagcccagc    960
tggactggaa ccggagtggt gtttgaggag cccgtgggtg atgttccagg accgtcttgg   1020
atcctaagag gcaaaggggc caggcctcac ctgtctggcc aaggtgtcca gttctggggc   1080
ccaccctacc cctggagaaa accctgaggt tgggaccctg ctcctgcccc tgagctgcag   1140
atgtggacct cagccagccc cggaagggga ggaagccccc ggccgtcccc aaggctttgg   1200
taccgccacc cagactcccc accaagagga aggcctcaga agaggctcga gctgccgcgc   1260
cagcagccct gactccaagg ggcaccgcca gcccaggtac cctccctgca ggggaagcca   1320
gccagggtct ccagtcttcc cgggcttccc cgggagccca cgccccctcc ccacccgggc   1380
tcccacccac tgggtgtggg gccagcctgc ctggggctgt gggggtctcc tctgggtact   1440
agacccacac actggaccag cctctcagct ccctcctgcc tgaaggctga gctccccgga   1500
gctggtgaag taggcgggcg ggtctcattt cccttttact gatgagaaac cagagcccgg   1560
caaagggact acccagcact ggaccgcccc ctccacgccc tcccaccgcg ggcccctgcc   1620
caccggcact cacccccact gagaggggag gccaggctgc ccccagctcc cccattcagg   1680
ctctcaactg aaggccaagc cccccaagaa gccggagagc agcgcagagc agcagcgcct   1740
tccactcggg aacggtgagc ggggcccagt gggagcgcct cccttctccc tggccagggg   1800
caaggggtca ggggtcagag cagggcctgc cctctgagac cctgtcctag gggctgggga   1860
cgtgctggcc tggtgtgtca ttccaagggc ctaagctgca ccaccagacc caggaagggg   1920
acaccttggg tctaagcatg atcttgccag tcgcccctgc cccactgca ccctggttct     1980
gggacccccct tctcaggcac cttctctgcc cgtccactcc ctatccttca ggaccagcct  2040
agacatagct tcctccagaa aatcatccct ggcccccagc tgcatgcagg ctgaaccctt   2100
cctgtcccct tctccttcct tcccagggca ctggactcca gagacccccct atctccctga  2160
gggcagagcc taggaactct gtgtccctcc cggcacaata cagggcccat gtcatggggg   2220
ggtgggtctg gtcattggtc atgccttcct atccattgtg ccagctctgc tgacactgcc   2280
accccccagc acacgcacac ttgggtgcac acacgaacac acacattctc atgtctctgc   2340
acttacctgt gggctgtctg cacatggcag ggctgggtcc cctccttggc ctgccctggc   2400
tggaaggaaa gggctctgca gcccagtgct gcctgcttct ggcatagagt atgtgcttgg   2460
gaacagtctt ccccacgggt gaccccaatg ggtgttccct ttcccaggga ttcagaccat   2520
gtcagcttca gtccagagag ctgtggccat gtcctccggg gacgtcccgg gagcccgagg   2580
ggccgtggag gggatcctca tccagcaggt gtttgagtca ggtagacgct gtggcgggga   2640
```

```
gatggggctg atggggagac ccaggctcca agatggaagg aggaccacgc ccctttgcat   2700
cctggtggtc ccacagcaga ccggactgtt gctcaggtag ccagagtttc tgcctgtggt   2760
tctgctgact ttggaggagg agggtgagca ctgaagtctc cctgtcgggg gaccttctgc   2820
aaggccagcg gtccaggccc acatccccac ccgggatgta cagcactccc cagtcacctc   2880
catccatgtg catgggccct cctgggccat ggggttgcat ccttagaaag ttctgcctgt   2940
gctgctgaga ccctccaggg tatcggcatt cttcaaccag gacagcctgt agcatagcgt   3000
ccttgccccc catacccctgg ccagcctgca gcatcctcgc ccgccattcc ctggccagcc   3060
gctgacccca tgcaatcacc agtgccatct gaccagggca cagcagggcc gctggtggca   3120
gacccaccgt gccatcgggg cattccatct caagtccctg acacggtgtc tcctcggtgc   3180
tggacatggg ctgggaacac caagcacagc cagggccctg gtcttgcacc tctggatggt   3240
cccaaggccc actgtgttac ttcctaaggc tgttggttaa attggcacaa actgggaggc   3300
ttgaaatgac agaaatgcca acatcgaggt gtctcggggc cacactccct ctggaggctc   3360
cagggaagaa tccttccttg tgtctcccag ctgctggtca ttatgggggt acccctgtgc   3420
tccttgttcc tgggctcagg acccaccgct ccagcctctg cttctgtggt ctcacagctg   3480
tctcccacgt gtcctcttta taaggacacc agtcattgaa cttatggtcc agtgtgacct   3540
catcttaact aatcacatct acaaagaccc tgatttcaag taaggtcaca ctctgaggtt   3600
ctgggtggac gtgaacttcg gggacgctg ttgaacaccc tggtgtagat ccaggacaat   3660
ccccgggccc cagactcgac tggggtgggg gcgggctgga ggaatgcagg ctgtgggaac   3720
tccacctgtc tctgctagac cccaccctgg ggcctacacg actgccaagg caggtcctgc   3780
tgggcgggtg agccaggacc agccggcatc tcctcccagg cggctccaag aagtgcatcc   3840
aggttggcgg ggagttctac actcccagca agttcgaaga ctccggcagt gggaagaaca   3900
aggcccgcag cagcagtggc ccgaagcctc tggttcgagc caagggagcc cagggcgctg   3960
cccccgtaag cacctgacct tccctgggga gcctggctct tgatgccccc cgccccagga   4020
acagcgttgc ctctgggggga gtggctctgc tgggggctgg gggctgctgc cgagagacgc   4080
ctggtgccac agccatgtgc accctcgctg ctgaggctgc ccccattgct gacgcccctc   4140
ttccttgcag ggtggaggtg aggctaggct gggccagcag ggcagcgttc ccgcccctct   4200
ggccctcccc agtgaccccc agctccacca ggtaatgccc tagaccacag gagaggcccc   4260
tgtctgccct tgctcccctc gggtgggtcc tgctgcctct gcctttacct gggcactcag   4320
ggatgagcac cggggcctga gcccctaccc acagggtaca gctctttttc tttaatagac   4380
agtatttttt tcctgataat acgcaatggt aatagtttaa atgagtcaga gaaagtgagg   4440
tcttctcagg ctcttaagag catggcgttt ggtccaggct gtacccgctg ctctcagctg   4500
ggcccgtggg tgggccgggc gcccctgcta tagccaggag gtcaaggatc cactgggaat   4560
gccatgctca tctttcgtcc ccagcatggt ttcttaatgg ggtagaagca gtgtgggggg   4620
tgcctgccgt ggtgggttac agatcttgac cacttggcac caggggctct gtggggccct   4680
ggcacttagc agtgacagga gccagtcctg ccctgcagga gcacccgggc tggtgggcgt   4740
ctgggggatt gttagaatga gtgaggtcat tgccgtgcag gaccagccta gcctggctgt   4800
ctggggggat tctggaggaa gtggtacctg ggagacccct gaaggcacag caggcaccat   4860
ccaggcaggg cacaaggacg gtgggggctg caggtggagg attcagcagg cgctgaggtc   4920
gggagagacc tccctgggcc tggccccact gccctgtgag gaagggttca tgtggttggt   4980
gtacagttcc ggggccccctg gaacgcagca gcctgcaaga aaccgggttt tcttcccaat   5040
```

```
agggatggcc ccggggggtg tctgttggag accagatgga tggggaacag gtggtcaggg   5100
cagaatttca ggccctggca gcatgggagc agggcagaga ctggggagtt caggtaccca   5160
gagatgctgc tgggggagct gttttgggaa ggaggtggct ctcaggaggg tgctgcaccc   5220
cagcccagtc tgcatgggcg tctcttgcct gtgccagaag aatgaggacg agtgtgccgt   5280
gtgtcgggac ggcggggagc tcatctgctg tgacggctgc cctcgggcct tccacctggc   5340
ctgcctgtcc cctccgctcc gggagatccc caggtgagcc tgcacctctg ccagcgcaac   5400
caggccaccc cggttcacgg ccgcctccac ccactgaccc tgaagggaag ccaccccaag   5460
cctctcccat ccaagatgga aaggggttct gagtcaggtc actgggccgt ggggccgggg   5520
cctggggttt tcccaccctg ccacctgcct cccggtctgg ccacacctgc tgcccagcct   5580
ggacagctgg gcccctgagg gcagcaaagc agaacagagg cccagggcga agatgccacc   5640
ctgtccaagc tcatcccagg ctgcagccca cgcccccatg ggtagccggc ccccaccccc   5700
aagccccacc ccagagtccc actccagaca gggctgggga gcacagaggc cacagagctg   5760
tgccccccag ggcaggtggg agtttgtcca ccaatgcaca ggacgccggg cttagtgggg   5820
gcgggaggcc tcctctgcgt tcacatcccg gtgctccttc cccacggccc accgagccct   5880
gcccccattc caaccccaca ggacgtggca gtctgtggga ggaagagctc tgggtgcagt   5940
ggggacccac gttcaggcga ggctctgccc cagcccctga gtggccgtca tcaggccccc   6000
tctcagcctt gtgcctcatc actagaataa ggggcacagt gggggtcatt gctcggctcc   6060
tgaagccgtt cctccttgcc gtctctttct gcccttgatc acctccccat tctgctgggt   6120
gccattcccc ttaacaggtg ggtcagttta gggaggcccc cggcagggcc cagccctgag   6180
aggcaggcaa agccaccagg gctcgcaggt gttggggatt cctggggttc atcagagagc   6240
acgccaaggg gaccctgatc acgctggcca gggccacccc acgaagggta aatgtccccc   6300
tgctgggctc tcccttcctg tgtctctgcc catctctctg ctgtgcctcg gttcccccctc   6360
tgtgaaaaga catggtcgga gccctggagc tccacccgtg ggtttgggga tctgtcaccc   6420
gctgtcttgt tctgcatgtc tctgactggt ggacacacga gcagtgggac ctggaggtgc   6480
tccagctgcc tgcaggcaac agtccaggag gtgcagcccc gggcagagga gccccggccc   6540
caggagccac ccgtggagac cccggtatgg ccacgccccc tcctagccgg gccacccctc   6600
ctgtccacat ggccacgccc cctcctaggc tgggccaccc cctcctgtcc gtctgtcccc   6660
tggagtcctg tgggacagga ctgccccagc catagcacta tgtcccccat gcccaagccc   6720
ggtccttgtg gtctcctgca gtggagtccc catcatggtt cctgtgggcc taaacccagc   6780
tctcctggct gcgggtccac cccggggggc actatgagca ttgataacgg ccccggaaga   6840
tgtgttcctt gttctgctgc tgtgagggta gtaggtctac tgtgcacaga cccagtgttc   6900
cctctgacag ccctgagggc caggggggccc cccgtgtgta gacgggggag gagggaggac   6960
cacagagcca ggaagtgcca cagcctttcc cactcagtgt ggacgccttc caccatgcca   7020
gccctccgcc cccaccatgc caggcctctg cccccaccct gctgccctgg gtttcagggt   7080
cccagcagtc actgactcct gggtggtgcc gggcaggcgc ccgctgcccc tctgatgctg   7140
acccttgggt tccagctccc cccggggctt aggtcggcgg gagaggaggt aagaggtcca   7200
cctggggaac ccctagccgg catggacacg actcttgtct acaagcacct gccggctccg   7260
ccttctgcag ccccgctgcc agggctggac tcctcggccc tgcacccccct actgtgtgtg   7320
ggtcctgagg gtcagcaggt gagcggggag tgggggtcag ggtgggctct tcaaggagcc   7380
```

-continued

```
caggacctac ggggcggatg aattcacctg aaacaggagg agagggaggc caggcgagaa   7440
aggctccggg aggcacaggg cctggggctg tggggggagc gtggggggct gcggggggaa   7500
ggggacgctc ctagacctcc actccagctc ctggccctgg gcattactgc tccccccaca   7560
aggcaggaca atgaaggggg ggatgtccca gcacacgtgg gagccctccc ctccctgcct   7620
caattccctt ccctgcaccc ctgtgggcac cgcctttcag gagactcccg cactcagccc   7680
caaaggaggc caggcccgcc aagcaggaga gaggtgcggg cgccaggctt gcaggcagca   7740
gcctgagggt gcttgggtcg cccctgcctc ctggggatgg gactggtccc gctgtcctgc   7800
agcctgcgtg gcaccgtgag gctcctcact tgcgcctaga cccgccgtcc agccctgggt   7860
ggtcccaggg gagagcgcac agggctcggg ttcgggttca gctacatttc ccccggcccc   7920
ccgcgtcacc ccgcgctgtt gcctcccaca gaacctggct cctggtgcgc gttgcggggt   7980
gtgcggagat ggtacggacg tgctgcggtg tactcactgc gccgctgcct tccactggcg   8040
ctgccacttc ccagccggca cctcccggcc cgggtgagtg agcgtggtcg gcggggaggc   8100
ctgaacccac acccacaccc tacaccccac cccacactcc ccacccacat catacagccc   8160
acaaccacac cccacccaca ccccacactc ccacccacac cttgcacccc accccacacc   8220
catgccctgc acccacaccc tacactccac agccacactc caccacaccc ccacccacac   8280
cctactcccc acctcatacc ctgcacctca ccacactcca cagccacacc ccaccccaca   8340
ccccacactc ccacccacac cctacaccca ccccacaccc tacacccaac ccaaacccac   8400
ccaaacccac cactcccact ctccacccac acccacaccc cttcctcaca ccccacaccc   8460
ccatccccca ctcaccaccc acgcccacac cccacacccc ataccccgga ggtggcactc   8520
ctgctccccc ccagggctgg cagcccctca tcctctgctg caggacgggc ctgcgctgca   8580
gatcctgctc aggagacgtg accccagccc ctgtggaggg ggtgctggcc cccagccccg   8640
cccgcctggc ccctgggcct gccaaggtca gtgccgcagg ggccctccat gcatgccggt   8700
gctgggggtg gggaacccct tgggttggtg ttgggggagc acatctcagg gcagaccctg   8760
ggtgccagct tcgagggctt gcaccagacg cactgaccat gtgctcatta tctgtagaaa   8820
atatttcccc tttaaaccaa ttctttttgg caacttaaat atagttaaaa aggaagctcc   8880
ccccgagggt tggtggctga cgtcacggtt ggctgtgtgg ccgcctcaca gcatgagcct   8940
gagagtcctg ccagggctcc ctggtggggt gaagggagag cgggagcgcc cggcctgcag   9000
gagcaaaccc ccaccctgtc tgacccctcc aggttgtctc acccccagcc ctccctgggg   9060
ccaggatcca ccccactgtg tggccagagc cctctcagag aggcaaagtg accccgggtc   9120
cagccagtag ctcttcctgt cctcctgctc cggggtcaga gaggacctgg gtggcgcgga   9180
gacccctgac tgctggggcg gctgggcttg ccctggagct gggtgtgggg gaggcccgag   9240
tcgctgctgc aggagcctcc ggggggggtgg cctcttgccc tgaccgtccc cagcagaggc   9300
ctcctgagca catcctggcc accgaggagc ctttagggat cctggggtga tgacacgtcc   9360
cacctgctcc actggcccat gctctttccc agctgtgcct ccgccccgta tacaccgtgt   9420
gggtgacagg ccaccccggc gtggtactcc ccaggagggt gacagcctac cccagcgtgg   9480
tactccccgg gcaggtgaca ggcttccccg gcatgcaggc tctggcctgg catggcacaa   9540
gcctcagacc cagccctgcc cttggggctt ttgtggaaca gtggcgtggc ccacagctgt   9600
cactgtcccc ttccttctag aagcctccct cctcacacca cccatctgga gtcaggagcc   9660
cagccgggca tatacgcaga tgcccctccc taaccccagg cagctttcct gcaactgctc   9720
ccgcagcggg tacctcgtca ttaacctcct gggttctgtc tctgaacagc agagacctct   9780
```

```
ttcttgtcat cgtgatgtga aatgtaacgc catgtcagag gaaaagttct ggctggcctt   9840
ggcctccccc ctcagcctgc ccccttcctc cagggtggtt ggacgtggcc ccagacccca   9900
tcctgagcag ctctcccacc ccctgggagc atccttagga ccggggagca tccaggggct   9960
ttcccctcca gaccgggcag cccctccctc agccatgcag ggctgccggg cctcgcagcg  10020
ccagtgttca cccgagtgga ggagctggga tgtggctgtt tggggccaca aatggggaat  10080
tccacagggt tcaatgtaat atggtctcct ctctgctggg ggtgcctgcc tggggacctt  10140
ctcccactct ggtcgctcac ctatagtgtg ggctggccct ggtggtgctt gtcgggggcg  10200
ggggtggcat ggaccaggca ctttcctctc tgggcctcag acttcccctc tcagagtggg  10260
actccttgct ggttccctga gctccctcgt tttccccagg aggccacaca gtgtggaggc  10320
tgtctggggg ccgtgggcag ctggccgtgg gcaggaccct ggggaggcag ccccagcccc  10380
atcatgccca cgcagccctg tgccccccacc cccagtggag ctgggtgtaa gaattcccat  10440
ctcagtgtgg gggaaacacc cccgcggccc ctaggccctg cggcctctgt acccccacca  10500
gggctgtggg agttgggctg acctcttctc tttactgggt tccaggatga cactgccagt  10560
cacgagcccg ctctgcacag ggatgacctg gagtcccttc tgagcgaggt aacgcctccc  10620
ctggcctcct ggtgctcctc cactccccct cccctgcctc agccggcacc caggctcccc  10680
actctggggg aggactgccg gcccccactg ctcttgagcc gtggaaactc aggctgtccc  10740
tgctccaccc accaggagcc ccagtgctgc tgagcacctg gcacccccca caggagcccc  10800
cctagccccc ttgcaggagc cccccccggc ccctccccct gcgggagccc agtgctgctg  10860
agcgccccca gcccctcccc aacaagagcc cccacacggc ccctcccctg agggcctgca  10920
ccctggcagg cagaggctcg agcaccaggc tcaagatcca ctttcccagg gagggtgggg  10980
cgtgggagtg ggggggggt cccagacccc gtccctctaa gatttgcttg cccctcccaa  11040
ctcaggcctc tctacgctaa gatgggcagg tagaatctgt ggggaaaatg tgacttttaa  11100
gggctctgtc tgtttttgcc aagaggataa gctccttcag cctccacggg ttctcctcag  11160
tgtctgatgt ggcacccggg ggtcccagct gaccatgggg caggggttct gccctgtgca  11220
gtggccgtgc cccacacacc ctgaccgtgc aggtgtctgc agagccccag ggcctgagag  11280
tgggccaggg ggcccagcgc tgggtaatgg agctgcccct ctggatgggg tccccgggta  11340
tagctggaga aatgagcgac gggctcacag cctctcccgg gtggcggtct tattctgctg  11400
gcatcgtggg gcccgtggcc ccatcctgtg ggagcatcag gctcctgagc agaataagta  11460
gctggccccg acccccccac cctgaaggag ccacccgagg aggcagaact gccatgaact  11520
gccatgggga tgtgccctgg gcttatagga tgtggtgaag tacacaggac agggtcctcg  11580
gtctggcctg tgccatgggg accttgggcc tcagtttccc cacctttgat ggaatacggt  11640
gaagtgcaca ggacagggtc ctccccagac tggcctgtgc catggggcct cgggcctcag  11700
tttccccacc tttgacttag agggaaggtt ggatggtgac ttcttgtaac gatggccatg  11760
attctgtggc tgcggcgggg gcgcacctgg aggttctcac cgtcactctg tcccgcagca  11820
caccttcgat ggcatcctgc agtgggccat ccagagcatg gcccgtccgg cggccccctt  11880
cccctcctga ccccagatgg ccgggacatg cagctctgat gagagagtgc tgagaaggac  11940
acctccttcc tcagtcctgg aagccggccg gctgggatca agaaggggac agcgccacct  12000
cttgtcagtg ctcggctgta aacagctctg tgtttctggg gacaccagcc atcatgtgcc  12060
tggaaattaa accctgcccc acttctctac tctggaagtc cccgggagcc tctccttgcc  12120
```

```
tggtgaccta ctaaaaatat aaaaattagc tgggtgtggt ggtgggtgcc tgtaatccca  12180

gctacatggg agcctgaggc atgagaatca cttgaactcg ggaggtggag gttgcagtga  12240

gctgagattg cgccactgca ctccagtctg gtcggcaaga gtgagactcc gtctcaaaaa  12300

caaaacaaaa caaaaaaacc acataacata aatttatcat ctcgaccact tttcagttca  12360

gtggcattca catctcatgt aa                                            12382
```

```
<210> SEQ ID NO 3
<211> LENGTH: 552
<212> TYPE: PRT
<213> ORGANISM: Mus musculus

<400> SEQUENCE: 3

Met Ala Gly Gly Asp Gly Met Leu Arg Arg Leu Leu Arg Leu His Arg
1               5                   10                  15

Thr Glu Ile Ala Val Ala Ile Asp Ser Ala Phe Pro Leu Leu His Ala
            20                  25                  30

Leu Ala Asp His Asp Val Val Pro Glu Asp Lys Phe Gln Glu Thr Leu
        35                  40                  45

Arg Leu Lys Glu Lys Glu Gly Cys Pro Gln Ala Phe His Ala Leu Leu
    50                  55                  60

Ser Trp Leu Leu Thr Arg Asp Ser Gly Ala Ile Leu Asp Phe Trp Arg
65                  70                  75                  80

Ile Leu Phe Lys Asp Tyr Asn Leu Glu Arg Tyr Ser Arg Leu His Ser
                85                  90                  95

Ile Leu Asp Gly Phe Pro Lys Asp Val Asp Leu Asn Gln Ser Arg Lys
            100                 105                 110

Gly Arg Lys Pro Leu Ala Gly Pro Lys Ala Ala Val Leu Pro Pro Arg
        115                 120                 125

Pro Pro Thr Lys Arg Lys Ala Leu Glu Glu Pro Arg Ala Thr Pro Pro
    130                 135                 140

Ala Thr Leu Ala Ser Lys Ser Val Ser Ser Pro Gly Ser His Leu Lys
145                 150                 155                 160

Thr Lys Pro Pro Lys Lys Pro Asp Gly Asn Leu Glu Ser Gln His Leu
                165                 170                 175

Pro Leu Gly Asn Gly Ile Gln Thr Met Ala Ala Ser Val Gln Arg Ala
            180                 185                 190

Val Thr Val Ala Ser Gly Asp Val Pro Gly Thr Arg Gly Ala Val Glu
        195                 200                 205

Gly Ile Leu Ile Gln Gln Val Phe Glu Ser Gly Arg Ser Lys Lys Cys
    210                 215                 220

Ile Gln Val Gly Gly Glu Phe Tyr Thr Pro Asn Lys Phe Glu Asp Pro
225                 230                 235                 240

Ser Gly Asn Leu Lys Asn Lys Ala Arg Ser Gly Ser Ser Leu Lys Pro
                245                 250                 255

Val Val Arg Ala Lys Gly Ala Gln Val Thr Ile Pro Gly Arg Asp Glu
            260                 265                 270

Gln Lys Val Gly Gln Gln Cys Gly Val Pro Pro Leu Pro Ser Leu Pro
        275                 280                 285

Ser Glu Pro Gln Val Asn Gln Lys Asn Glu Asp Glu Cys Ala Val Cys
    290                 295                 300

His Asp Gly Gly Glu Leu Ile Cys Cys Asp Gly Cys Pro Arg Ala Phe
305                 310                 315                 320

His Leu Ala Cys Leu Ser Pro Pro Leu Gln Glu Ile Pro Ser Gly Leu
```

```
                325                 330                 335

Trp Arg Cys Ser Cys Cys Leu Gln Gly Arg Val Gln Gln Asn Leu Ser
            340                 345                 350

Gln Pro Glu Val Ser Arg Pro Pro Glu Leu Pro Ala Glu Thr Pro Ile
        355                 360                 365

Leu Val Gly Leu Arg Ser Ala Ser Glu Lys Thr Arg Gly Pro Ser Arg
    370                 375                 380

Glu Leu Lys Ala Ser Ser Asp Ala Ala Val Thr Tyr Val Asn Leu Leu
385                 390                 395                 400

Ala Pro His Pro Ala Ala Pro Leu Leu Glu Pro Ser Ala Leu Cys Pro
                405                 410                 415

Leu Leu Ser Ala Gly Asn Glu Gly Arg Pro Gly Pro Ala Pro Ser Ala
            420                 425                 430

Arg Cys Ser Val Cys Gly Asp Gly Thr Glu Val Leu Arg Cys Ala His
        435                 440                 445

Cys Ala Ala Ala Phe His Trp Arg Cys His Phe Pro Thr Ala Ala Ala
    450                 455                 460

Arg Pro Gly Thr Asn Leu Arg Cys Lys Ser Cys Ser Ala Asp Ser Thr
465                 470                 475                 480

Pro Thr Pro Gly Thr Pro Gly Glu Ala Val Pro Thr Ser Gly Pro Arg
                485                 490                 495

Pro Ala Pro Gly Leu Ala Lys Val Gly Asp Asp Ser Ala Ser His Asp
            500                 505                 510

Pro Val Leu His Arg Asp Asp Leu Glu Ser Leu Leu Asn Glu His Ser
        515                 520                 525

Phe Asp Gly Ile Leu Gln Trp Ala Ile Gln Ser Met Ser Arg Pro Leu
    530                 535                 540

Ala Glu Thr Pro Pro Phe Ser Ser
545                 550
```

<210> SEQ ID NO 4
<211> LENGTH: 13589
<212> TYPE: DNA
<213> ORGANISM: Mus musculus

<400> SEQUENCE: 4

```
agcaccacga cacccaagga agggagaagg gaacgcaagc gcgcgtgggc cagcaggggg      60

cgccgaggcg cagcccctgt gaggaagatg gcaggtgggg atggaatgct acgccgtctg     120

ctgaggctgc accgcaccga gatcgcggtg gccatagaca gtgcctttcc gctgctgcat     180

gctctagccg accacgacgt ggtccctgag gacaagttcc aggtgggctc cagtcccgcc     240

cccggtgcct ctcattctcc ccactcctcc acccgcagac taggtgttcc ctcccaacct     300

cagccaaaac ccatactata cccatacct ccccctacca gccaaggagt ggtcccaagc     360

cctcctcagg agacctctcc agatcaagtc ccaggtgagt tccctaacct cacaccctat     420

gcccccctaac tgctccaggg cccagggata gacaggaata ggcaagtctc ccttatccca    480

aagaggcagg agttggagaa tgatatgccc aggtgcccaa tgctgtcact gcaggagacg     540

ctccgtctga aggagaagga aggctgcccc caggccttcc acgccctgct gtcctggctc     600

ctgacccggg acagtggggc catcctggat ttctggagga ttctctttaa ggactacaat     660

ctggagcggt acagccgcct gcatagcatc ctggacggct tcccaaaagg tgggcgtgtg     720

ctgattgatg ctggagctga tgctcagcca atgggtagca tcggggatat ggatacaagt     780

cggcccatgt tttcagggag ccactagaac ttgggcagat cctaagaagc aaagggcaga     840
```

```
ggtctgctct ttctcgtcct caagagtgcc ccattctaga gctcaccctg aagataaggc    900
tttaagacag gaccattgtt cctgcccctg agctgcagat gtggacctaa accagtcccg    960
gaaagggaga aagccccttg ctggtcccaa ggccgcggta ctgccaccca gacccccccac  1020
caagagaaaa gcactggagg agcctcgagc caccccacca gcaactctgg cctcaaagag   1080
cgtctccagc ccaggtacac tcaagaggag ctagccaggg ttgctgggcc ctccccaacc   1140
ggctcttagg agcttctgtc ttactgacac caccccaggg ccagcctgcc agggtcacag   1200
agtcacctct gagccctcag acctgagcat tggaggaggc ccacagcctc tcagcgtctt   1260
actgtcccaa aggctgagtt tctgggcggt gaggcaggca ggtggttttg atttcctttc   1320
tgttgaagaa ggaaacagcc catcacagct taagaaccgt cgatctgacc cttaccagct   1380
gctctctctc ccatcctcac tttctaccct ggatccgtca acatgacccc agcccagaaa   1440
agtgggccca ggctgcctct acctcccctt cgcaggctcc cacctgaaga ctaagccccc   1500
taagaagcca gatggcaact tggagtcaca gcaccttcct cttggaaacg gtgagttagg   1560
ccaagagtgg aggttggagg aggtctgatc ccattgacct cagctggatg gcaaagccag   1620
agaaagatag ggactcctta gatccaactg tcttgccatt ctcctaccca caatgccctg   1680
ggtgtctcct cccagacctc tgcccatttt aatgctccca atcttctagc cagcccagaa   1740
aaagaaccac aaggaaacta tccctgttcc tcagctgcgc ccaaccttga ccacacccac   1800
ccaccatcca ccatccacct gtgcttcctg gtcctcaccc cctgatggcc taggaactct   1860
gtgccccaga ataacgcagg tcccacgtca ccatgagatt cttgtcaatc tgccattggg   1920
ctcaacatga ccaacactgc tgtccccacg gccgtgtgct catgcacata cgtctacttg   1980
tgtcaaaccc tctccaggaa ttcagaccat ggcagcttct gtccagagag ctgtgaccgt   2040
ggcctctggg gatgttccag gaacccgagg ggccgtggaa gggatcctta tccagcaggt   2100
gtttgagtca ggtaaatgca tggaagcagg ctgccaggga gacccagatt tcaaaatgga   2160
agggagtgct tctagagcat ccatggccgt ggctgagggc aaggcagcca gtgtgcttca   2220
ttcaggtctg ctggctttgg agcccagtgc tgatgtggaa gactccctac atgggtggat   2280
cttttgtcag gccagtggtt catagtcaca ttcagccatg gaatgccacc tcttccacgt   2340
caaggggtgc tgctagtcac aggggacatc ctaagtttcc ctgtgtgctc tagttctgtc   2400
aagagaccat agtgcccact aagacagccc accacatcct actgccctgt gtcaggtatc   2460
tatgtcctgt ccagtcccct cactctttgt ccaggttcct cccacaattg cctacctaca   2520
aggctggcta gtggggtcac cttatacagc cacccagatc atctgaacaa gtcagagctg   2580
gggccagaca cactcaccat tgcagaatct gctccacagc acctcctctg tccgggacac   2640
tggacttgga tgccatggac agccagaatg gcctgggagc tcatgccagc cctagtcaga   2700
gcagccccaa gaatcttgtc tgactcttct ggggttatta gaacaaaaag ccccaggctt   2760
gtaacaacag gttccaaagt caaggtgtgg gaagggacac gtcccttcgt gggctttgga   2820
gggtccctct gttgcctcta gcatgaagtg ctgttggaat gcttacttct gagaatagcc   2880
cctctccaat ctgactattc ctctctgact tcacctttct ttgtaagaac attggattta   2940
agggctagta tgacattttt aaaaaaagat ttatttaatt tatatgagta cactgtagtt   3000
gtcttcagac acaccagaag agggcatcag atccccatta cagatggttg tgagccacca   3060
tgtggttgct gggatttgaa ctcgggacct ctggaatagc agtcagtgct cttaaccact   3120
gaaccatttc tccagcccgt atgacatctt tttttgttgt tggtttttct gtttggttgg   3180
```

```
ttgcttcttt tgttcgtttt tgtttgtttg tatttgagac agttcctctg tgtagctttg   3240
gctgtcctgg aactcactca ctctgtagta gagcaggctg gattcgaact cgagtagatc   3300
tgcctgcctc tgcctcccaa ggattcaaga tgtgtaccac catgccctgc tatgacatca   3360
tcttaactaa ctctctcgcc aaagaccctg tttccagtaa ggtcccgttc tgagcttgtg   3420
aggaagggca ctgtttaagg gtacagtcac cagcaaagaa tccctagctg tacccagccc   3480
cggttctgcc agacccccag ggtgagctca ttcagtctat ctctctccca ggaagatcca   3540
agaagtgcat tcaggttggg ggagagtttt atacacccaa caagttcgaa gaccccagtg   3600
gcaatttgaa gaacaaggcc cggagtggta gcagcctaaa gccagtggtc cgagccaagg   3660
gagcccaggt cactatacct gtaagcctta tccagcatgt ccatttaggg ggagctgggc   3720
cttccttcca tagcctcccc tcccctcccc tcccaaagaa agcctggagt tcttcccgag   3780
ggtgggagtt gcttcccagt ggtacttggt ggccacatag atcttccctg accctggcta   3840
cttcgttaag accctgtgtc tctcataggg tagagatgag cagaaagtgg gccagcagtg   3900
tggggttcct ccccttccat ccctccccag tgagccccag gttaaccagg taagtcccaa   3960
gaaggggtg ggggtggggg aaccaggata tggagggcag ctcccttcct cttctctccc   4020
ttctctttcc tccacctcct cccactcagc tctttcttgg aagttttcaa ggatgcatat   4080
taggagattt ccaattagtc acagcaggtg agctgctttt aaaaaaatca cacgttcagc   4140
tggttggtat atgcctttaa tcccagccct tgggagacag gggcaggcag atctctgtga   4200
attggaggct agcctggtct acagagttcc gggacatcca gggctacacc aagaaaccct   4260
gtcttgacaa caaacaaaca aaacaaaaca aaacaaaaca aaacaaaatc acacattctg   4320
tccagatgac aaaaagcaca ttagcttcgg gtcgggtagg gctgcagata aagcctgagt   4380
atggggattc tctgagggta tcaagttatc ctctcctccc cagcaccact gatgtggttg   4440
tgcctgcaat cattgattat tgagtccaac acctcagagc taggtactct gctggccccg   4500
gacaccaaag gttgaaggtc cagttctgcc ctgctccata aaagtgccct ggttattggg   4560
ggcctatgga cgtttcccat gtgctcactg tgtgggcccc cacaacctgg catctgggag   4620
cttcttgagg aggttcagac tcagaactcc ttccatcctg ataaggtagg ggatggggaa   4680
tgacaggagg tacctagggc taacgggaaa ccccgtgggc ccacccacct gctgtcctat   4740
taggtgagtg gtagtcaatc cagggaactg tgggcctccc cactctgtgg gttgtcagcc   4800
tgggctacac cgggactagc tatcaggagg cagatcaact ttacttaggg tgattcaagg   4860
cttttaaaaa aacaaaagat taatttatta tttattataa gtacactgta gctgtcttca   4920
gtcgcacgga tggtagtaag ccaccatatg gttgctggga tttgaactca ggaccttcag   4980
aagagcagtc agtgctctta cctgctgagc ccaattcaag gcttataacg ttttgggggg   5040
gggggtctga gggtaggaat atctaggatg ggcaaaggtc attggctggg ggcttggggt   5100
acctaaaatg tctccttagc aagggaaagc atttcggaaa tctcaggtgc tgaatgaatg   5160
ggcgctttgt caggagaaag gaagttggtc ctgtaattta actgaggcta cgtgacattc   5220
ttcatgcatc tctgagggca ttcctaagcc tggggggggg gggggcgggg gcggggctta   5280
gaattcccca gacaaggtca aagaaggaga aatcctgtta atgaagggag tcccccatat   5340
tgcgctgagc tcagaagcta tccagtcatg gtgggatttt gatcttaatt agcagagttt   5400
tcccactagg aactgcctgg cacccagcac tccttccaga gagggacacc cccctaggtc   5460
tgtgtggaac ctagtacttc agagaccttg cagagctcag gcaggggcca acgagagaac   5520
ccagggggaa cctgggagtc agtccttagt ggtgagcatt gtcccaagtg ggtctctcag   5580
```

-continued

```
gtggatgctg tgttccattc tgggtccctc ttgcctggtc agaagaacga ggatgagtgt   5640

gccgtgtgcc acgacggagg tgagctcatc tgttgtgacg gctgtccccg ggccttccac   5700

ctggcttgcc tgtccccacc tctgcaggag atccccaggt aagcagacct ctccatctct   5760

gatccatcac cgtccttatc cgctgacatt gaggaagcct agaagccttc acagaagaca   5820

gtaagggccc ttcagtaaga tctgtggaat gaatagggta ctagctatgg aaatggtagg   5880

attctctggc cataccgaaa cctatctgtg ttccctgcct catggcccac tcagggccaa   5940

caggccaaaa ggcagccata acatgatgtc cccaggcaaa ggtggccata tttgggcaca   6000

ggccttttcc taagcacact gtacccccac cccctcaaat ctcactcaca caatgatgta   6060

ctgttacccc tatcactgac tgcacaaccc tctgttctga ggagaggtaa gcagcagtct   6120

gtgcgggcta gcctgggctc tgacccaggt ctctctgatc ctcttccacc agggtccttt   6180

ccctcatctc ccctttccca ctggtccatc cctacaggac tgtgggtgtg ccaaggatgg   6240

aaacagtgta gctgagagtc atgcttatct cccctccccc actggcccat ccctatagga   6300

cggtttgtgc acctaggatg gaaacattgt agctgagaga gcccacagta atgccaggcc   6360

tatgacaagc aagcacaggt gctgaagggt actgggcata gagtattctt aagaattagc   6420

agagacccgc agggcatggt agtgcacacc tttaatccca gaactcggga ggcagaagca   6480

ggtggatttc tgagttcgag gccagtctgg tctacagagt gagttccagg acagccaggg   6540

ctacatagaa aaacactgtc tccaaaaacc aaaaaccaaa aaaaaaaagg attctaggga   6600

ccctgactct gtccagagcc atgctcccga ggtaaatagc ccacattcta ttgaactgcc   6660

cttatggtac ctaactcttt tagtcccggg tttggcttcc cacctatgaa tgagcatggt   6720

gacacagagg gtcctcaagc catccttgcc atacatttgg ggaagggggg gtgtctatgg   6780

tctctacttt gtctggcaag cctgtgacta gtgacctcct acacagtggc ctctggagat   6840

gctcctgctg cctccagggc agagtccaac agaacctgtc ccagcctgag gtgtccaggc   6900

ccccggagct acctgcagag accccggtat gcccatattg ggtcaccccc tttcttctct   6960

ctgactctct acagtcctat cttctggctt cacctgtgag tcctgcatgc ccgccatgct   7020

ctgttctggt gaattccctg tggggttgag gggccaaggg attaaaaaca gcttcccaag   7080

ctggctctgt ccctccagac tcaccactgc caatattctc caaaagcctt ggtagctctc   7140

ctgttagaaa cctagtttgc tctggcttgg ccctggcttt tgctgagaac catggaacca   7200

gccacacact cagcctttcc ttctcctcct cctcctcctc ctcctcctcc tcctcctcct   7260

cctcctcctc ctcttcttct cctagtttta ttttttaaag atttatttat ttattatatg   7320

taagtacact gtcactgtct tcagaaactc cagaagagag cttcagacct ccttacagat   7380

ggttgtgagc caccatgtgg ttgctgggat ttgaactcag aacctttgga agagcagtca   7440

gtgctcttaa ccactgagcc agttctccat cccttttttt ttttttaat tttgttttgt   7500

tttatgtgta ttgatgtttt gcctgcatgt atgtctgtgt gagggtgtca agatccctta   7560

gaactggagt tgcagacagt tgtgagctgt catgtaggtg ctgggacttg aacccgagtc   7620

ctttagaaga gcagccagtg ctcttaacta ctgagccatc tcttaagctt gtaccaagcc   7680

ttcccaacct cagacccacc acagcagccc agtcctgact cctaggtgtt gctgagcagt   7740

accctgtggc ccctgaatgc taacccttga attccagatc ctcgtgggac tgaggtcagc   7800

ttcagagaaa accaggggcc catccaggga gctcaaagcc agctctgatg ctgctgtcac   7860

atatgtgaac ctgctggccc cgcaccctgc agctcctctg ctggagcctt cagcactgtg   7920
```

-continued

```
ccctctactg agtgctggga atgaggggcg gccagtgagt gaggagaccc ctagggcctg   7980
ggtgctatct ttggggaaga ggggctctgg acctacggga tagttgtatg tccaaaacgg   8040
gacctctggt ggactcccgg ggctaggaat tagacggaca ttcctggggt caggggaggg   8100
ctctgccaag agacacttgt tcatataata gtaacacagg gactgtaggg gagagcacca   8160
agggaactct ccagctgggc ctttgagatg gctcagtggg taaaagggtt tgcagccaag   8220
atggaagacc tgagttggat tcccaaaact cacatggtgg aaagagtgac tcggtctgca   8280
agtggtcctc tgatctccat gtgcatgacc accaataaat agtgaattag ctagaaagaa   8340
gggaaggagg gaagtaagac aggcaagcag gcaggcaggc aggcaggcag gcaggcaggc   8400
agacagacag acagacagac agacagacag gcttagcttg gttatccaga tgatacaccc   8460
tcccccatca tgaagcagga caacaaacat ctcgaatcca cagaccctgt ccacttctgt   8520
tggttacctt tctttttttc tttttcagag tccccacttt taaatttaat taattaattt   8580
atttatttta cttattcact ttacatcccg ctcactgccc cttccccatc atcctctcgc   8640
agtctttccc caccctctcc ctcctccaaa gctcttctgg agtcccacat ttggtaggat   8700
cagagctgga ctcccaggat ggactggtcc gtggaaagca gcttggaaag gccgctttct   8760
gacccctgct cccctcggga catccagaac tcagaattta cagtcccact cacgcgactt   8820
gaaaccctga ggtttcccag ttaacccggg ctggtggggt gagcaggaca cgggctgggt   8880
tgccgcccat gttgcccctg cagggtccag caccaagcgc gcgatgcagt gtgtgtggcg   8940
atggcaccga ggtgttgcgg tgtgcacact gtgccgctgc cttccactgg cgctgccact   9000
tcccgacggc cgccgcccgg ccggggtgag taagggggca ccgggtggca gagtagccag   9060
cgatctcacc caccccgaag gttctccgag ccagtgagct tttcccactt ctctcggaca   9120
ggaccaatct ccgctgcaaa tcctgctctg cagactcgac tcccacgcca ggcacaccgg   9180
gcgaagctgt acccacctct gggccccgtc cagcacctgg gcttgccaag gtcagtgtct   9240
gctcagtcca ggtgagaccc tgtgggagtg gaggagaatt taaacccata tccaataacc   9300
gtgtgtccca ttactttttg tttggttggg tttgggggat ttgtttttttg tttgttgttt   9360
tggatttttg ttggtttgtt ttgttttgtt gaggtactac agatctctgg ctgtctggaa   9420
cttactcgta gaccaagctg accttaaact cagagatcca cctacctctg cctcccaact   9480
gctggaatta aaagcacatg acccttattc ctggactaac ttttttgttt gtttttaaaa   9540
attaatcatt tttaatcttt tttttaaaga tttatttatt attatatgta agtacactgt   9600
agctgtcttc agacacttca gaaaagggag tcagatcttg ttacagatgg ttgtgagcca   9660
ccatgtggtt gctgggattt gaactctgga ccttcggaag agcagtcggg tgctcttacc   9720
cactgagcca tctcaccagc ccccctttttt tatcttttaa gatttctttt ttatttatat   9780
gagtacatcg tagctgcctt cagacacacc agaagagggc attggatccc cattatagat   9840
ggttgtgagc gagccactaa gtagttgctg ggaattggac tctggaagat ctctccagtc   9900
cttgtttgtt tgtttggttg gttggttggt ttttcaagac agggtttctc tgtgttcccc   9960
tggctgtcct ggaactcact ctgtagacta ggctggcctt gaactaagaa atcagcctgc  10020
ctctgcctcc caagtgctgg gattaaaggt gtgtgccacc acttcccagc ccttgtttgt  10080
tttttttgttt gtttgcttta agactattgc tgggatcaaa ggtgtatgtc actaattctg  10140
gctcctcaat tacttttata aagtgttttt caataaacag acaacttatt ttgataagtt  10200
gaatctattt aaaagggaaa ggctggaagt ggtagggcag gacattaacc ctagccccca  10260
gcagtaaaga taggttggtc tctgtaagtt agaatccagt ctggtctgta tcgtgacttc  10320
```

```
cagtttagtt agggctacgc agtcgaaccc tttctagaca taaccaagta ttttaaaggg  10380
aaaccttcca aatagctatg aactcactgt tggtactggg ttcctgggag tccgtgggcc  10440
tcagagctca gagctctgat cagggagctc tggacctaag agcagttggc ttaatttgaa  10500
atgagacgac tgggaggcac ccaggggcca gatcgtctgc agaacaggta tcagaatggc  10560
tgggacctcc agggcggcca actattggcc tggagagaga gagagagaga gagaaagaga  10620
gagagagaga gagagagaga gagagttggg gagcagagcc aaacaaagct gctggctttt  10680
gatgaccccg agagccacct acccaagtcc tctacccagg tggatctcta tgtcacctcc  10740
atttttacta accaggcagg gaccgagctt tgtctggagg cccaaggagg aaagggcagt  10800
atccacctct atccacttgc cattgcataa tactgctaag acagacatgg accccaggct  10860
tgggccccta gctgtctctc aggttcatgg gtaaaatgga gtgatcttgt aaagatgtgt  10920
tatgcaaggt ggcagagtgt atgcgcagct cactgctaga ttccagcttt ccctgataaa  10980
ttgcccccct agttgcaggt tgaccttatc tgattgagaa catctgggag gctgcatcag  11040
aatctattgc tcctaggatt ctactggagg acccagtaaa gcatggggca aggtttgctg  11100
agcctttaaa acagtggtcc tcagtgatcc tttggtgcca aatgatcttt tcacaggatg  11160
gcccaagact gttggaaata tctgagagtt gggattcgta acagtagcac aattacagtt  11220
acaaagtagc aacaaaaata atgttatggt ggggggggt gtcatcacat catgaggaac  11280
tgtattaaag ggttgaagca ttgggaagat tgagaaccac tgtcctagag tctagccaca  11340
aacagtgaaa gtcacttcta gaatgaagac gaggattgag caatggggcc tccactggct  11400
tcactgtgaa ctcctgacag agcctgccac tccctgactg gagctctgtc actatggcca  11460
gggcaggtcc aactaagttc agctcatgtg actagtgaaa gcagagagac actggctggg  11520
tgctagccac cgggtctctt taggggctac agggaatata taggacagat tgttgccctc  11580
agcctgcctg tgtccccagc ctgaggtact aggtgtgagt ctgctctgtg gtggagtaca  11640
gtctactgcc ccaagtcctg cgtctggtcc ctagcctgct gctaggttgg gttgactatt  11700
gattctctgc tttggttcca ggtaggggac gactctgcta gtcacgaccc tgttctacat  11760
agggacgacc tggagtccct cctcaatgag gtaatctgtc acctagtctg ggctgtgctc  11820
acagattctt tgctgcccct agtaggcagc accagcagac cagtgttacc ctgcccccat  11880
agctgctctt cctagaagag cttgtttcca tgtagggtgc tggcctcctc caggaacctc  11940
acatctggga tcctcacatc aagacctcag agccaggggg tttaagccct tgacttttca  12000
gggaaagctg ggagggtctt ccaggggcct ctctcttacc cctcccaact cagttttctg  12060
tttcttgagg tggataggtg gcccaggtct ttgattccca gtgcttgagg tagatgtagg  12120
aggactgtga ggtggatact aatctggact acattataaa accctatctc aaaaacctga  12180
ggggctacag aaatgcaaga gcattgttct ttcagaggac ccaagtttgg gggggggggg  12240
tcccagcagc catgtcaggt gacttttaac tgtttatcat tccactccag gggatctgaa  12300
acctctggcc tcctcgggca tctgtacaca catcacgcac acacacatac ttatacacac  12360
agacacacat atacacatag gtgcatacac acatgtacat acccactttt tttttttttt  12420
tttttttggt ttttcgagac agggtttctc tgtgtagccc tggctgtcct agaactcact  12480
ctgtagacca ggctggcctc aaactcagaa atccacctgc ctctgcctcc caagtactgg  12540
gattaaaggt gtgtgccacc actgcccagc atacatacat acttaaaagt agtaaattcc  12600
cagaaaccac atggtggctc acaatcatct gtaatagaat ctgatgccct cttctggtgt  12660
```

```
gtctgaagac agctacagtg tgtgtgtgtg tgtgtgtgtg tgtgtgtgtg tgtgtgtgtg  12720

tgaatattat gtgtatatgc atatatataa attaaaaaat agtaagaatg aatttcttct  12780

agaaaatgaa atagggcccc atctattgca agggcacaaa ctcctttggt cattcccata  12840

ccccagggag cccacatgcc ttcttcagtg tccactgaca tttagggaga ctcaactggc  12900

tgagggacag agacctgccc tgggcagagg gccatgcaca ggcagatctg cagaagcacg  12960

agagagagag agagagagag agagagagag agagagagag agaggatcca gcatgggtgg  13020

acactggaaa aactgaggac cttctccagg acttcccagt cctgttggca gagaagaagg  13080

acccagcaga ggaagccaca cccagggccc acaggctgct ctagaggagg actggatcaa  13140

gagacctccc ttcactggca tgtcccatgg gccctagctc tcagtccccc tccttgaact  13200

agcgggtcag gttgggtgat accttcatgt caagatggct ctatggaggt gcgactgctc  13260

taacctcccg tgtcactctc tctcagcact catttgacgg catcctgcag tgggccatcc  13320

agagcatgtc acgcccgctg gccgagacac cacccttctc ttcctgatga caggtggccc  13380

aggaaggggt gggcagcaca gcattggctc cctccccacc cagccccatc ggatgaggca  13440

ctctgttctg agaggcctgg gctgattagg accaagagct ggcaggttct ggcctgctgg  13500

actcagcttg cagatggccc tgatctttgt agagatgcaa ggccacccca tatcctggaa  13560

ttaaagtcac ttctatgtac tttgaggta                                    13589
```

<210> SEQ ID NO 5
<211> LENGTH: 203
<212> TYPE: PRT
<213> ORGANISM: Homo sapiens

<400> SEQUENCE: 5

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200
```

<210> SEQ ID NO 6
<211> LENGTH: 11504
<212> TYPE: DNA
<213> ORGANISM: Homo sapiens

<400> SEQUENCE: 6
agaccccgcc cctttcctgg gcggggccaa ggctggggca ggggagtcag cagaggcctc 60
gctcgggcgc ccagtggtcc tgccgcctgg tctcacctcg ctatggttcg tctgcctctg 120
cagtgcgtcc tctggggctg cttgctgacc gctgtgagtt gtttttgccc cgaccagacg 180
ggagttggga gtggggaatg agaaggaaag ggaaggaaga cttcggggaa gaggccttcc 240
tggctgattt ttgtgggggc aggagggtgg gtgggagctg ggcaaggtgc cccccgctcct 300 ggctgaatgg ggtgggctgc ctctctcttc tcccgggctg gggtcccggg agcggcctac 360
aggggccgct cagggaaggc actggctgcc caagcgtgcc tagacggcct ggacgggttt 420
agggagcctc agaggctggc cacacagaga ctggtagggg gttcagaggg cgggaagtga 480
ggcggaccaa gggaaggggc gggtctggcc cgtttcctgt ccccttctta ttgtggacag 540
atgccagcct ctgtaagtag ttatcatctc cttgccagct ggggctgcct tcttccaggg 600
catcttgtgg gaacaagaga tgggtgcaga ggcccaggta cttttgtgag aaggcaagga 660
gcttttaaca tcgccttcca ccccgaaccg tatcttgggt gttccaacct aggaggaatc 720
cccagggctt tgccttttttc tcctgaattt aagatgacat aggagacccc tggggagatg 780
aacagtttat gggacacaat aaagggttag gagaccagag ttctggttgg ctctgacagg 840
gctggtgatc agagggctgg agaaaccagg ggtttctcca ggcaccagag gggctcagag 900
ccaaccaagc atatctccgg gattttcaga agcctacact tgactcactt tttgtttaaa 960
tgtatttttg tagttcctca ttctggaggc tgggaatccc ccaagtacct ggctccttca 1020
tcccagcccc tctggcctcc ccctacttta gagggctgta gattcctgcc tgaagcctgg 1080
gcaggaatga cccatggtat caaggaaagc aagggaagca gcaagggaag agagggagtg 1140
gggaggctgc tttggtccca cagctttcac tttcacctga agcaatggct cttagggaac 1200
agggaggcag ggggagggcg gagctggaaa gaggtaaagg ggggcccttg tggtaggagt 1260
ggagaaagag ccagaggagg tggggtgaag ggtgtgatcc aggcttctca agagcagagt 1320
ttgccctcat aactcccaac tttggctcca ggtagaggct gggctgtgac aacaatgtca 1380
gaagctatct attgagggct tcttgtgtgt caggctctga gccaaacact gcctgttttc 1440
tttgtctgat ttctcacaac tcccccatta tacagatggg caaattgagg ctcagaaagg 1500
gggattgtct tgccaaaggt ctcatagcta gctaatggaa gaacctggtt gtgaatctac 1560
atctgcatga ttcccgagcc tgcctctcag atagtgagag tctccaagct ctggtcctga 1620
gctgttttgt ggcagaagga ccagaactat ggggagtgag aactggagat tgacagactt 1680
ttaggggagc gttttatttc tcatgtgttt gaagatggta tcaaggactt tcctatcttt 1740
gggagtgtgg gagctccacg ttcacaggat ggtgtcttgc aatgagctgg tggggggcag 1800
tagccttttc tacttccttt cccattttgg gtaagacaca tttctgtaag taatttgctg 1860
agatacccag gttgaatgag agccaccagt taggtaggat tctggacagc cagccaggta 1920
gccgggctgc ttgccatata tcatgcaagc agaaacaaat gaatgatgat taaaattgcc 1980
atttaatgag cacctactat gttcctgaca ctgtgctagg ccatatacat gtattctttc 2040
ttatcttcgt aatccaacct gcagggcagg cattattact cccattttag agatagagaa 2100
actgaggcta agagaagcaa aataactagt aagtgttaca aagtcaggac tggagtctaa 2160

```
agctgtctga ctctcaaact tgtgttcttt tcactggctg ttcccaaact gtgggacagt   2220
tttaaggagc acatggacat agaattaaac atacacttac tttacagttc ttttaaaaat   2280
ccttctcatt ttttcaaaga ggaagtctct ggagctagaa tagagttaat gcctctcaaa   2340
ggcttgctaa tccttctttt aaaacaaaaa tcaagagcag gcctgggagg gccttcaaca   2400
agcaaacaac cagctgggtt ttaataacct tgttttgttt ccccagaatt tatttttagg   2460
gttacctttt atttatgaga agtgatactg gttcttgtct cttggcaatg atgtgaggtt   2520
tacatttaaa gtaaatgtac cggccaggca cggtggcttg tgcctgtaat cccagcactt   2580
tgggaggcca aggcagtcag atcacttgag gtcaggagtt ttagatcagc ctggccaaca   2640
tggtgaaacc ctgtctctac taaaaataca taaattagcc gggcatagtg gtacacacct   2700
gtaatcccag ctactcagga ggctgaggct ggagaattgc ttgaacccag gagatagagg   2760
ttgcagtggg ctgagatgat gccactgcac tccagcctgg gcgatggagc gagactctgt   2820
ctcaaaaaat aaaataaaag tattgaaatt aacaataagt aattaatagc atgggtggta   2880
cctggatgta gtaaaatggt gaagatgaaa cacaagttga tggagagagg agcattgaga   2940
cctgagttct catttggact ctgtcactgt gagactctgg gcaagtgacc ctcctctttg   3000
gtgctcagtc tcaactatct gtaaaatgaa agtgtgagtt tacccttcca gctttacatt   3060
ctagcatttt atgagggaag ggctggatga acagatgatg aggagttgga ggaagaaaac   3120
atgatgggct ttggaaagga gcaggaaggg aagcagaaga ataggaggaa gaggccaagt   3180
gctaaacata gccccaaaca gcactgggac cagctgaagt cagccagctt caggactcca   3240
ggggagctgc tggagtcccc atatcctatg ggatctttgg gaagaggaat gactcaggca   3300
tcaagcccca aggaattctg ttctgttcag agaatattgt gagtttacag taccattgct   3360
ttgtaaaaat accagaatga ttctctgggt gcgattataa tcagctcagt tgacaattta   3420
cttgaaaaca aacatgccaa atatcatgca ggttccactt tctgttttga cttgcacttc   3480
agtttgcagc ctctgtcctg gatgactttt acctttctgc tgaagaagtt gcaacggaga   3540
tttcaagatc ccttcaaatt gcacaattct gtttttaggt ccatccagaa ccacccactg   3600
catgcagaga aaaacagtac ctaataaaca gtcagtgctg ttctttgtgc cagccaggtg   3660
agatgccaac cctctagccc catcatggag tccccctttg ctttggtggc agacgcagac   3720
cccatatgtt aactgtaaac tcaaatctga aacgacccat ttcccagccc tgcttcactg   3780
tcagaatgtt ctggttccct ctctaccagg taaaactctg tctaccctga actagggatc   3840
ccagcttctc catcttcctc gcctgattat gaaggatcca agactttcat ctttgaatcc   3900
cctaccctaa agcctggcct gatcattgtg tggttagtgt ctgactcatg gagttggcca   3960
gagccctccc tcatttcctg atgttttcca ggacagaaac tggtgagtga ctgcacagag   4020
ttcactgaaa cggaatgcct tccttgcggt gaaagcgaat tcctagacac ctggaacaga   4080
gagacacact gccaccagca caaatactgc gaccccagtg cgtgcgctgt tgggaaaggg   4140
acgcttggga accgggctga tattcccgac aatgcagcca ttctaatttt atgtagccag   4200
ggtctgctct gattggttgg agtccgggct gtactgatca ttaaatgatt tgattgccat   4260
ctctacttgg aagagggtct gaggaagaaa gagcaggcaa tgtggggagt gaggctcaga   4320
gcatggccca gcaggggggtt cccatccttc ctgcccttct cttctcagac ctagggcttc   4380
gggtccagca gaagggcacc tcagaaacag acaccatctg cacctgtgaa gaaggctggc   4440
actgtacgag tgaggcctgt gagagctgtg tcctgcaccg ctcatgctcg cccggctttg   4500
```

```
gggtcaagca gattggtaag tggctcatct gggaatcagt tttggagggg gacagaggag   4560
cttagggccc aaggtgaggg gctgggcagt gggcacttag ccccagaggc agaggaagca   4620
gaggctccaa cctatgtcgg tatccccact ggagtgagct gcagacggga ccttgttcat   4680
tctgccttct gccatgggga tctgcctttg aagggcaatg ggagaagtcc tcctggggac   4740
tgcagctgtc gggggcagta ccacatcggg ggaagagtgc tcaaggcagg agctcttccc   4800
gtcctgcctg gccactggct gccttgtgag ccggacaggt ggtccactgt gatggttaat   4860
gtccccctcc ccacccactc ccagctacag ggtttctga  taccatctgc gagccctgcc   4920
cagtcggctt cttctccaat gtgtcatctg ctttcgaaaa atgtcaccct tggacaaggt   4980
ataagcactc atcccttgtg tttcctgctc taagagtggc atggagctgc ctccattctc   5040
tccagccacc tgtcctgtcc ctgctcccag aggtccacac acactcatgt acttgtgaag   5100
catctgcaga gtggcctcat ggccaaccag acaggcacat ttccacattt tttttgcctg   5160
ctgtctcttt gaggtaatag acactgttga tctctcgctt catgagagcc tcctatcttg   5220
ggggtattgg gacacttatt ttagctttcc ttctgcccct cctgcttctc ctcagttttc   5280
ctcgtcttgc tttcacctta cctggctttc tagggctttc tgggctctgg gtgctcaccc   5340
tgagggcctc cctctcttac ctccaactcc aaacccacac caggtcctgc cactggctgt   5400
ctacgtgttt tgggaactta ctgtctccac tgttgtcact ttagtttggg cctcatcact   5460
gtggtctggg tgatgccttt tctgcctcct ggcctccctg cctctgtctc tcccctcctg   5520
ctggttctgt ctccatcctc ttgccaacat gagcgttcga cagtttcttt caaatcatga   5580
cactctccta tttgagatgc ttcctgtctc tctgttggaa ctaagactcc ttagcatggc   5640
acccaacctt cctgttgcat ttcctgctct ctttcctgca tcgcatagct tcatgctact   5700
tgcaatcctc tgaacacact gttcattctc ttccatcaaa ctcatctgcc tggaatacct   5760
taaacatggg ccccaggcca ggcgcggtgg ctcttgcctg taatctcagc actttggatg   5820
ccaaggcggg tggatcactt gaggtcagga gttcaagacc agccagcaca acatggtaaa   5880
aacccatctc tactaaaaat accaaaaaat tagctgggtg tggtggtggg cgcctgtaat   5940
cccagctcct cgggaggctg aggcaggaga atcacttgaa cccggaaggt ggagtttgca   6000
gtgagccaag atagcgccac tgcactccag cctgggcaac agagcgacat tctgtctcaa   6060
aaaacaaaca cctgccccat taacttttttg catttgattt ttaaaaatgg gcaagatagg   6120
cacatgggac agaaggcaca aaagagccaa agtgatgtct ttctcccatc cctgcccctt   6180
aggctcccag ttctttctgg agggagccat tgttccttgc atatccttcc agagattcta   6240
catataaaca aaccaacaca cacacacaca cacacaaaca cacacaaaat ttccctcctt   6300
ttacttttgc acaaatagga gtatacattt tatttgttaa ctgtctgcct ttccctaata   6360
gattgaaaat tccttaaatg tagaaacttg gccttttttt tttcttccat tgatacatcc   6420
cctatacctg gaacagtacc tgacgcatgg taggtgctta aatttttact gataaatgtt   6480
gactgataac tggaggcacc actggtatag tttttttttt tttttttttt tttttttttt   6540
tttgagacag agtctcactc tgtcgcccag gctggagtgc agtggcgcaa tctcggctca   6600
ctgcaagctc tgcctcccag gttcacgcca ttctcctgcc tcagcctcct gagtagctgg   6660
gactataggc gcccgccacc acacccggct aatttttttg tatttttagt agagacggcg   6720
tttcaccgtg ttagccagga tggtcttgat ctcctgacct cgtgatccgt ctgccttggc   6780
ctcccaaagt gctgggatta caggcgtgag ccaccgtgcc cggccaccag tggtatagta   6840
ttaatggaat cagtgcattg gcttacgtat ctgattacag ctcagtaagt gtgtgaccct   6900
```

```
cactgagcct cagtctcctc atctgaaaaa tgggaatgac cttcatttca caaggcttga   6960
gctaaaaaca tgtaaagtgt attgtaaatt cctgaatgct ctactcatgt aagactaaag   7020
taggccgggc gtggtggctc acacctgtaa ttgcagcact ttgggaggcc gaggagggca   7080
gatcatgagg tcaagagatc gagaccatcc tggctaatat ggtaaaaccc tgtctctact   7140
aaaaatacaa aaattagctg ggcgtggtgg cgcacatctg tagtcccagc tactcaggag   7200
gcggaggcag gagaattgct tgaacctggg aggtggaggt tgcagtgagc tgagatcgcg   7260
ccactgcatt ccagccagtc tggcgaaaga gcaagactct gtctcaaaaa aaaaaaaaaa   7320
aaaaaaaaaa gactaaagta catggtttct tcaaagcttc tctctctttc tcccacctta   7380
gatgattttt cctttgcaat gtcctgtgtc cattccgccc cactcctcct ggggccacct   7440
ggaccaggtc ttcatcatct catatctata tgtttgctgt gtctcctggc tggccactct   7500
tctgtaattt ctcctcctct gagctctctg ggcagctgaa tcttctcact agtgaagtcg   7560
cctggttgga tgctgatgag actgaccagc tgaatccagt tgaaaacttc acacttggca   7620
gtgatctggt tctaaagaca caattttcca tagtttccta acaccatcct gcatgccacc   7680
tgccttattt ccccacatca catcgtccca cttagcggga ctgcactgct gatccaaatt   7740
ttacatcctt tagggcccac tcaggtcata tgtcctcagg gaagtctttc tggaagaacc   7800
ttaaaccaga ggttctcaac agggggcagt tttgctccct gtggaacgtt tgccaatgtc   7860
tggacacatt tcattcgtca caaacggaga gggggatgct acagggatct ggcggataga   7920
ggccagggat gctgctgaac atctgcaatg cataggacag cccaccccca cccccacacc   7980
cccagtaaat aatgatccag cccaagtgtc actggtgctg acgttgagta accctatctt   8040
aagctgaact catcatctct ccattccagc cttggtggat tctgtctcct ctgaaccatt   8100
cccatctcac tttagcctac ctagatcaca aagcttggca ctcattatag actcccctat   8160
ttattactcc ttcaagatgt gcaagaatct tttctctgca cttttaagtt ctgtaagaag   8220
agtctgtgtc gttcctataa taaccagcat aggacgttgc acgtgttgtg tgctcagtga   8280
acctggattt gttgattgtt gactgactca ctctagagtt ggaaatctta tgcttgggga   8340
aacttaatat ctctttcttt ctctgtgtgt gtgcatttgt gcacgtgtct gtgcatagct   8400
gtgagaccaa agacctggtt gtgcaacagg caggcacaaa caagactgat gttgtctgtg   8460
gtgagtcctg gacaatgggc cctggagaaa gcctaggaag gtgggaactg aagggggaga   8520
tgaggcacac aggaacactg gatgggaaaa aggggagggg aggcagtttg gggtgtggt    8580
atcacagctc tgccacttat cttgggagtc tgggcaaatc acttcccctc tcttagcctc   8640
agtttcttca tctgtaaaat gggatgataa cagcacttcc ttagtaggtt ttgattttag   8700
agtgagaagg ttggcctaca gtaaagatca gataatgtaa atcagtgaaa aaggtcaggg   8760
gtaagaaaat tacattctct ttacctaacg ctaaatgacc agttaatggg tgcagcacac   8820
caacatggta catgtataca tatgtaacaa acctgcacat tatgcacatg taccctaaag   8880
cttaaagtat aataataata aaatttaaaa aaacgaaaaa tacattctct ttgctttttc   8940
tcaaaatgta ctttcctctt tgtagggctg ggactagaat gaggtgagca aggcacttgc   9000
cctcgggcgc aatatttaag aaggtgccat aaaagtgtag taatcaaggt aaattcattt   9060
tgatgcaata tttttaaaaa taaaaattaa tgcaaagaaa tccatgatga gcaagatagc   9120
aacattttaa ataaagaaca ggatccgacc ctgtgtttgc atgaccctgc ctcactcacc   9180
tcaccctaat cctggccctg gttccagtaa aaggaatagg cagccagcct gcaggccgta   9240
```

```
gtttgctgac ttggtgtccg cctgatgatt ttcaaaatat ggcattaaaa gaatgtttac   9300
cttgatgact gagtgttttg gacatccttt tcaattttgt cctgaaacaa tttcatccct   9360
tgcctcacgc tagtctccgc cctgcctttt ggtctttctt ttattttccc actttgaaaa   9420
aaaaattcgg catgagaaat actttacctt tcccctccac tcttctatac caaaagcaac   9480
atgcagacat gaatcatgct agacctcggc attgggcaga gagcagggag tggcggggag   9540
catggtgagc aggtggtgac agccactgcc accactcgct tctagatggt tcccaggtgg   9600
ggaggctgcc aactggaacc cagtcttccc agtttgtaag agaaatcaga tgtctaggtt   9660
tgaatatgtg atctcccagt ttaaaaatgt cggcaaatat ttccaaacgt taagaaaatg   9720
ttctggctcc tttaaagaca tctgccagcc acatttcccc aaggaccgcg gtttgaacct   9780
tctgatgtag atgagctctg acattggaag attctggagt ctgacaagtc acagcaggtt   9840
gagggtaggg agaaactgca ggtgaggggt gcatgctgaa gtcctgattt ctccaggtcc   9900
ccaggatcgg ctgagagccc tggtggtgat ccccatcatc ttcgggatcc tgtttgccat   9960
cctcttggtg ctggtcttta tcagtgagtc ctcaggtggg gaggtgttgg gggagggagg  10020
ggagaccacc tgtttcttat ctggcctctc caactcccca tccttttttt tttttttttt  10080
tttttagaa aaggtggcca agaagccaac caataaggta ggtcacccct gagaacccgg  10140
gacagagttt tgacaaactg ggaagatggc ctcacggttg cctatggggc agtaaaactg  10200
attcagagtc tgtctctgca gccagtgggg tggcagcaga attggggact gtcatcccca  10260
cccaccatgc tccttccatc cagagctcaa tcccccacag aactgcccct ggcaccactg  10320
gcagagccta acactggctg ttcttcactc ctttcctggc attcaacgcg tggggagctg  10380
catctttggg ccttggggct gggtcaaatg ggtgggagca aatgtggcag ccccttaagc  10440
ccactggctc ccactctgga agctcttcgt cgcccttggt gtggccagca gggggcagga  10500
ggcacccgag gaatcagcac tgacccgccg tctgggaaag gggggagggc ttggggaagg  10560
gatccgcttc ccagggaggg gctcctcaga ggcacagctg cccctgctgc tgggggtgac  10620
ctcacacctt gcctctccag gccccccacc ccaagcagga accccaggag atcaattttc  10680
ccgacgatct tcctggctcc aacactgctg ctccagtgca ggagacttta catggatgcc  10740
aaccggtcac ccaggaggat ggcaaagaga gtcgcatctc agtgcaggag agacagtgag  10800
gctgcaccca cccaggagtg tggccacgtg ggcaaacagg cagttggcca gagagcctgg  10860
tgctgctgct gctgtggcgt gagggtgagg ggctggcact gactgggcat agctccccgc  10920
ttctgcctgc accccctgcag tttgagacag gagacctggc actggatgca gaaacagttc  10980
accttgaaga acctctcact tcaccctgga gcccatccag tctcccaact tgtattaaag  11040
acagaggcag aagtttggtg gtggtggtgt tggggtatgg tttagtaata tccaccagac  11100
cttccgatcc agcagtttgg tgcccagaga ggcatcatgg tggcttccct gcgcccagga  11160
agccatatac acagatgccc attgcagcat tgtttgtgat agtgaacaac tggaagctgc  11220
ttaactgtcc atcagcagga gactggctaa ataaaattag aatatattta tacaacagaa  11280
tctcaaaaac actgttgagt aaggaaaaaa aggcatgctg ctgaatgatg ggtatggaac  11340
tttttaaaaa agtacatgct tttatgtatg tatattgcct atggatatat gtataaatac  11400
aatatgcatc atatattgat ataacaaggg ttctggaagg gtacacagaa aacccacagc  11460
tcgaagagtg gtgacgtctg gggtggggaa gaagggtctg gggg                   11504
```

<210> SEQ ID NO 7
<211> LENGTH: 289

```
<212> TYPE: PRT
<213> ORGANISM: Mus musculus

<400> SEQUENCE: 7

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
    210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
        275                 280                 285

Val


<210> SEQ ID NO 8
<211> LENGTH: 16047
<212> TYPE: DNA
<213> ORGANISM: Mus musculus

<400> SEQUENCE: 8

ccccgccctc ttcctgggcg ggactcctag cagggacttt ggagtgactt gtggcttcag      60

caggagccct gtgatttggc tcttctgatc tcgccctgcg atggtgtctt tgcctcggct     120

gtgcgcgcta tggggctgct tgttgacagc ggtgagtggc ttgtgttcta acctccaagg     180

gagttagggc ttagagagtg agagatggaa agaggaaaga ggagacaaga ctttggagat     240

gagagatctt cctactggaa gcggcggtta gtaggatggg caagatctct cgcgtcttga     300
```

```
cacacacaca cacacacaca aatgaggtgg gctgctcctc tttccttcca gaaggtcggg    360
gttctgttcc acgaagccca caggggaacc ttagggaggg cattcctcca cagcggtgcc    420
tggacagctt tgtctgaccc aagccttggc tccggagctg actgcagaga ctggaaaggg    480
ttagcagaca ggaaagcctg gctaggggga agggcgggtc tggcctgttt cctgtcactt    540
tcccattgtg gacagatgtc tgccacctgt ggttatcttc tccttgccag ttggggccac    600
tttgtctagg gaatcttgtg cgaacaagac cccaggtact ttttagggaa gaggtaattt    660
actaaccacc atacccgtat catagctgag ccaatctaga gaaatcccca agtttgtgcc    720
tctgcctcat gagcttaagg tggtacagga gacacccaga ggatgaggag gaagaagagg    780
aggaggggga ggaagaggag gagggatagc tttagaaccc aagaaaggat aagagaccag    840
actaggtttc tccaggcacc agcagggctc agacccaatc aagcgcatct tggggatttc    900
tagaagccgg cacttgattc gcttttggtt taaatgtatt tctgcagttc ctcattctgg    960
aacctgggaa tcccctgact acctgagtct cagcccctct cctctggcga ggctccccta   1020
gctttcaggc agggtagatt ctttccggtt ggtgacaggg acttcggtaa cttcatgggt   1080
tctgaattgt ccacccagga aggtgtcgtg gttcaggact ggctttctgc agctgggaca   1140
gtcagtgccc taagcacatc cctgtccatc agccaatgtc acctgtccat cagccaatgt   1200
cacctatccc aggttggtct agttgagaat gacctttcac attcttcttt ttcttctgtt   1260
cacgcatggt ttgtgtatat gcgtacatct gtgtgggaac acacgtgtgc ttgcatgcgg   1320
tagcctgaag ttcatctcat gagtcatcct tggacacggt cccttcttag tcatccacac   1380
agggtctcaa gcaaacccag agctccccat agggcgagtc tcacacgtca gctggctctg   1440
gggaccctct gcttctgccc tctgaagctg gagttacagg gaggccacta caaagacctg   1500
gtgtttgcac gtgtttctgg agatcagaat tctggcccac ccatttatat ggcaaacacc   1560
ttgagagctc agtcatctct cttgtccttg aatctctgat cctcctgcct tcacctccct   1620
agtgcataca ccaccatgcc cagttttatg tggcacttag aatagaatct agggcttcat   1680
gcatgctagg caagacacta tacttactga gacacacccc cagccaaagg acatagactc   1740
tgacatgtgg cctgccaaga atcaccatgg aggttagccg caggaaagga gcagaagcga   1800
gacagttgct ttactagttt tcatttttta ccccaggcca gtggttcctt tcgcagaggt   1860
ggtctaagac catcagaaaa cacagatatt tacattagga ttcagaacag taacaaaatt   1920
acaattatga ggtagcaaca aaaataatgt tttggttggg ggggggtca gcaccacatg    1980
aggaactgta atgggcccca gcgttaggac agttgagaac cactgctcta aataagactt   2040
ttagggagac tggatgcagg aagacggtga ggtgagagag aagtggatga gggcctttgg   2100
gagggatgga ggaagaaaca gaggtgtgat gaaggctagt ctggaccact caagaacaaa   2160
gtctgccctt gtaagcccca atctgggctc cagggagggg ctgggccctg agagaaatag   2220
caggtgttct ttactgacct cttcctgtgc agggggctgt gagggagact gcatgtcacc   2280
ttcctgtgtg agggagactg catgtcacct tcatttgatg tctcccaacg tctctgttac   2340
acggatgacc aagatgaggc tcagaaaggg gaggggtttt acccaaagcc tcttgacatg   2400
gatatgaagc tatgtctgcc tgacttctga gcctgccact cacgcggcaa ggggtcttca   2460
agctgtggcc ctgagaccta ttgtggagga aggaacaatg ctctgggggc tggaaactgg   2520
ggctgactgg ccatcagagg gaaagtgtct tttccaaagg tgccattgag gatgtctact   2580
gttctagaag gaaggaagga aggaaggaag gaaggaagga aggaaggaag gaaggaaagg   2640
agggagggag ggagggaggt gggaagtctc agggaagata aaactcaggg atgatgccct   2700
```

```
gctgggggca ggtgctttca ggtacatttc attaagtgat ttgctcagat acccagtttg   2760
agtgagagtt ctcaatttcc tggattctgg acagtcagac agctactagg gtgcaggaca   2820
ccagggcaga cccccatcat ctatgtgtgc tgattaaagc tgccattttc tgaatactac   2880
cttgctatac tgccaggcca tgggcaagtg ttacaatctc attttaaagg tgagaacaca   2940
gggctagaga gatggcttag tgggtaagag cgcacgctgg ctgccatagc cacattgggc   3000
tggtacataa attcaacaag aataataaaa acaaaggaaa cacagtctta gagaagcaaa   3060
ataattagga tggtgtactg gctagttttg tgtgtcaact tgacacaggc tggagttatc   3120
acaaagaaag gggcttcagt tggggaaatg cctccatgag atccagctgt aaggcatttt   3180
ctcaaatagt gatcaagtgg ggaggtcccc ttgtgggtgg tgccatctct gggctggtag   3240
tcttggttct ataagagagc aggctgagca agccagggga ggcaagccag taaagaacat   3300
ccctccatgg cctctgcatc agctcctgat tcctgacctg cttgaattcc agtcctggct   3360
tccttagtga tgaacagcag catgaaagtg taagctgaat aaactctttc ctccccaagt   3420
gcttcttgat cgtgatgttt gtgcaggaat agaagccctg actacacaga tgggatacag   3480
agtggtttgt cccgttctca aatgtgggct ccacgcaatc ggtagctgtg gttgtttcta   3540
aaatgtaacc tggcttcaag gagcacacga gcaagccgga gggcttagct ctgcagttaa   3600
gagcatgtgc tgcccttgca gagagctgga atccgattcc cagctcccac attccacagc   3660
ccccagatat ctgatcccct cttccgaggg tacttacacc cacacatgtt catattcata   3720
tatctaccta taatcaaaca tgaaataaat cttgtggcta gagagatgct cagaatattg   3780
ttgctctggg agaggaccca ggttcagttt tctagcaccc acgtgtggcc cacaatcatc   3840
ctcaacacca gttccaggga acccagtgcc ctcttctgac ctccaagggc accaggcacg   3900
catgtggagc atattcaggc tacacttgta cacataaaat aaataaatct aattattttt   3960
aaagtcttaa aaaacaaaca aacaaacccc caaacaccgt cgcctaaaac ctcaaggata   4020
gggttgtgac tgaaggcact tgtcatataa gcctgaggcc ctgggttcat ttcctggaac   4080
ccatgtaagg tagtgtgtgg tggcagaagt ccaagtctga catcctaagg ctcctactgt   4140
gagacaggag gtgggaacag gagaaccccg gaaactttca gcacatgcaa ccaagaacaa   4200
caaaatgatg gtggcttaag cacagtagga gatagcactg agagcagtgt tggccactga   4260
cctccgtaca cttccagtta tggcaagagc acgctccaag ctgcagacag ggcagtgggc   4320
gttgcgtgtg cacacacacc aaaacacggg cccactttat ggttcttaaa aaaagtttct   4380
acacttaaaa aaatgtagtt ttcgttatac ttatttattt atatattatt tgtatgcatg   4440
catgcatgca tgcgtgcttg agtaccaaag cgtgtgtgtg gtcagaggac aagttaggga   4500
agctggctct tcctaccatg tgattctaag gaactgaact caggctgtca ggcttggcag   4560
caagagcctt caccagctga gccatctctc cggcacctct ctctctctct ctctctctct   4620
ctctctctct ctctctctct ctctctctcc tgtttgtatt tttctttttt aaaaatattt   4680
tttcaagttt tttttttttt taaagatgta tttattttat gtgagtacac tgtcactgtc   4740
ttcagacaca ccagaagagg gcatcagatt ccattacaga tggttgtgag ctaccctgtg   4800
cttgctggga tttgaactca ggacctttgg tcagtgttct taactgctga cccatctctc   4860
cagccctgtt tgtatttttc aacacaaggt ttctctgtgt agccctggcc gttctagacc   4920
aggttggcct cgaactcaga gatccacctg cctctgccgc ctgagcgctg ggattaaagg   4980
tgtgcgccac cactgctcag ctgactgttt ctggaagtgt tacagctccg ctctgaggga   5040
```

```
aacttttctc tgagtgttgt agatgtgagg agaaatcccg aaaggcttcc ctgtggaggt   5100
gttgcatctc tgaaaggaaa agcggagtat cacaaagtcc cactgctgga caaacctcag   5160
agagtggctg cctccgccca ggggcgaagc agcagagagc tgagctgcag gcagcttagg   5220
cagttctcca gggtggagtc cttctgggca gggattggtg agacttcatg ctcaaggatt   5280
ggtgggttcg catagttctt ttattttttc ccaactagga agtgggctca ggcctttccc   5340
ccagctagag tttcactgtt ctttaaaaaa catcattttg tttttatttc atgtgaattg   5400
gtgttttgcc ctgcatgttt ctctgtgtga gggtgtcaga ttccctggat ctggagttac   5460
aactggtggt tgtgagttgc catgtggatg ctgggaactg aacttgggtc ctctgaaaga   5520
gtaaccagtg ctcttagcca ttgagccatc tctccagctc ctccaaatcc ttttcttatt   5580
catttaaaaa attacatgta tgtatgtatg tatgtatgta tgtatgcatg tttgtacgca   5640
cacacacaca cacacacaca cacacggaga ttagatgcta acttttgaga gttggttctc   5700
tccttccatt tctgggcctt gaaattctgg ttatcagtct tggcagcaag cgccttgatt   5760
ggctgagcca tctcgctcct tggttcttca aggagtaagt ctctggcgct agctagatca   5820
tagttaatgc cttttttttt tctttttctt ttttttgaga cagggtttct ctgtgtagct   5880
ttggctgtct tggaactcac tctgtagacc aggctggact cacagagatc tgcctgcctc   5940
tgcctctgga gtgctgggat tagaggctta tgccaccaca gttggccagt taacacctct   6000
gaaagacttg ctaccaaccc accccaggct taaaagtaaa atcaagagca gacagagcga   6060
aggatctcag caaagaaagc tacgcatcga ggcttaataa ccctgttatg aatctgttga   6120
gtgtattttt agggtttctt ttaatttata ggaagtgata cttgctgacc tcttgatgca   6180
gcagtagaag atttacagtt aaaagaagtg tgcttaaatt agcaagaagc agctcatagc   6240
atgggtggtc cccggatgtt gtagaaacac atgttgagag tcccgcccct gtggactctg   6300
ttcagtgttg ccctctgtgg ggtgattctt atctctttgg tggcagggag ctggggacag   6360
aaaccgggag aagggctgag gccagcttga gccagcagtc tcgggactct ggaggaagaa   6420
ctggagttct ccctacctgc tgcgtctttg ggagcactga agagtcctgt gcatctgttc   6480
ggattagagg gttctgcgtt cttgctttgg tagatggcag taagacgatg tgacaacaga   6540
gtaaaaaaaa aaatagacct cacactctgg gggctcactt ttctgctttg gatttccaca   6600
tcagctacag cctgcgtctt ggctaacttt caacatgccg gtggaagatc ccttccagct   6660
gtccacttct gtttttaggt ccatctaggg cagtgtgtta cgtgcagtga caaacagtac   6720
ctccacgatg gccagtgctg tgatttgtgc cagccaggtg agatgctagc cctcctgccc   6780
cgtaccaaga ccctttccct cttggattgc tggtggatgc agaccccata tatagactgt   6840
gaactcaagt ctaaaatgac ccatttctcc ctcttccttg atgccagaat accccaagct   6900
gtcccgtctc ttccatcttc cttactcgtg tagggtctga gatatccatt cccaaactcc   6960
aaccctctca cctccagtcc tggctccctg ggttgtgaca cagtctgtgt cacaggattg   7020
gcccaacctg cctcatatcc tcctgttttt caggaagccg actgacaagc cactgcacag   7080
ctcttgagaa gacccaatgc cacccatgtg actcaggcga attctcagcc cagtggaaca   7140
gggagattcg ctgtcaccag cacagacact gtgaacccag tgcgtggggc tgcctgggaa   7200
ggggtacttg agaaccgggt tgatgttcct aatgctgaaa tccctctgtt gtcagtggcc   7260
agggtctttc ctgtgagcta gagtctgggt tgaaggggct agttgactga catctgtact   7320
gggaagagcg agaaaaccag cagatgacgt gaggagtggg gtcctggctg cggcccagcg   7380
ggttttccca ttcttccttc tcatctccgc tcagatcaag ggcttcgggt taagaaggag   7440
```

```
ggcaccgcag aatcagacac tgtctgtacc tgtaaggaag gacaacactg caccagcaag   7500
gattgcgagg catgtgctca gcacacgccc tgtatccctg gctttggagt tatggagatg   7560
ggtgagtggc ctgcctgggg aaacagctct gtgggtggga gagctggggt gagctttggg   7620
tctctggcct ccagaagctg agggcagaga aagtcccacc tgggctggga tctttcattt   7680
ggatttggac ctgggctctg ggcagcttcc tgcggggttg tggccttcag ggctgtgtt    7740
gccttggggt aagaagctga gggcaggtgt tctgtcctgc cctgcttgtc tgctggctcc   7800
cttgggagtc agacactgtg gcccaggtgt ctgctcatgc atctttccgc atccttccag   7860
ccactgagac cactgatacc gtctgtcatc cctgcccagt cggcttcttc tccaatcagt   7920
catcactttt cgaaaagtgt tatccctgga caaggtataa gggtcacctc tccctaacca   7980
atgacagggt gggtcttgtc tcagtctctt tagccacctg ctgttcagtc cctgactttc   8040
cccaccccca tggtgggtca cttactggtg aatgtgacct tgtggctggc ttaagggaca   8100
ctttgtgcag ttcttttagc ttgcttctgc ttagttaata gaagcctgtt ggtctccata   8160
tcctcttgaa gtctcttctt aaagcatcat gacactcgta ctccccttt cagttcactt    8220
tcttggtggg tatgtgtatg tgtgcatgtg tatgcatgtg catgcatgca tgtgtgtgtg   8280
catgcatgta tgagcatata tatgcatgtg catgcatgga tgcatgtgca cacatgcatg   8340
tatgtgcatg tatgtgcatg tgcattcatg catgtgtgca tgcatgtgta tgcatgcatg   8400
tgcattcatg catgtgcatt catgcatgtg tgtgcatgtg tcagctatca gtttggtgtg   8460
ttcctcctca ggtactgtcc actgtttttt gtttttgttt gtttgtttgt tttgttttgt   8520
tttgttttga gagtcccaac actgggacta taaccacttg ctaccaagca tggatttttt   8580
ttttttttt atcgtgggtt ccagggcttg aactcgggcc cttgggttca cagtgctttc    8640
ctgagtgagt tatcaatgcc cccagccctt ctggactctt acttgtgttt gttgggcttt   8700
gtctgggttc tctgaccact tctttccacc tctccttggc tgtcttatct acatctatgg   8760
ctccatctcc ccctggatct gtccttcagc ccccagatgg tcaagtccca ctgctgagtg   8820
ttatggatca ccagcacctc agactctgtg catccaaaat gggcccctag ccaatccctg   8880
agccccagct gacaggcagg ttctggctcc aggcagtcac acagtgagct gcccaccctt   8940
gccttcaact ccctgtcagt caggcccata tgactgtctt gggaatccac ctcctcactc   9000
tctagagtgg tcacgtgagt tcgcacctcc tcactgtggt gtggtgatgg ctctgtctcc   9060
tcataggctc cctgcctctg gtgtctccct tggcagcttt gcaccatgct gctgttggga   9120
gcttccgtag cccctttgg atcatgtcgc ttcatgattt aaagcactcc acgtctccct    9180
gctgcctttg ggaggaagcc cagactcccg ggactggggc tgggccttcc agctacagtt   9240
cctgtctctc cccccacacc tcgcaccctg cacttgcacc ccgggcacac tgtttattct   9300
tttgcttcaa agtctcctgt ttgggagaaa acaatatata tgccctattc tgtttttat    9360
agttcacatt taatgttttt taaatgggca aacctgtcac ctcaggctgt ttcctcacta   9420
ctccttcaga gagagagaga cagagagaga cagagacaga gagagacaga gacagagaga   9480
gacagagaga gacagagaca gagactcaga gacagtcaga gagacaaaga tagagacaga   9540
gaaagagaca atcagtgaga gacagaggga tagagagaga cagagagtca gagagacaga   9600
gacagataga gagacagaaa gacagagaca gagaggtggg gggaggagat agggggagac   9660
agagggacag agagacagaa ggacagagaa actgctaata aacaaacaca ttgacatacc   9720
actcccctct gccatgatac acatatgcac acacacacat acacacacac acacacacac   9780
```

```
acacacacac acacacacac acacacacac acacacacca cagtggtttc tcttgtggtt   9840
atagtgcttg cttgcaggtc acactcaccg tcctcactgg tgggtttagt tgttcataga   9900
agttcccgtc ccggagtcaa atgtgcaact gccgcactgc cccacttagc tggttcatgc   9960
tgctgtttca acttttatcc cctttggaga cccttcggat cttctctggg gacccccaaa  10020
tctgcctcag tttgtgtgag accctcaggg atgcccctaa tctcgggagg cttcagccaa  10080
cttgtaaagg tgctgagggc ctttctcaca caaggctaga gcacgcacgc attttctctg  10140
aagcctctct tccaccacat cccggttttc cttcgccatg tcccttgcca tgtcccctct  10200
gtcccctcct cccaggacct tccatccaca ccacacatct ccactcctgt cctgcctctg  10260
gctgcccact ctgctgcaac ggtcctctca ccagtcaggt cactccctag ctgcctgcct  10320
gcagctgccc tgcctgcagc tgctcatcac cgcacttgtc accatgtgac tcccctcctg  10380
tcacactgtt cctacttagc tgggtcccac tttcccatcc ttcaatgcct tctgatgccc  10440
cccttcatgg ggaagtcttc ccagaagacc ctgaaagcag agcttcttaa cggggaccag  10500
tttggctctc tgtgggggcg ttggccacat ctgatcatct tttggatgct gtacttggcg  10560
gggaggctgt ttctggcatt tggttagtgg aggcaaaggt gctgctaaat agtctgtgaa  10620
acaaaggcca tttcccagca caaaatacct gcagattggc catttccatt tcaatatgac  10680
cgtaaccttt cctttctgtg gtttctgttc ttcacttaat gatcatcttg ggatgctgca  10740
ctctaagtca cgtgctcagt gaacaaggac ttgctgcttg ctgggggact cccctgggct  10800
tggaagtctt atggcgggga gccctgtttc tgtctgtctg tctgcatgtg tgtgtgtaca  10860
tgcacataca tgtgtacaca tgtgtctttg tgcagctgtg aggataagaa cttggaggtc  10920
ctacagaaag gaacgagtca gactaatgtc atctgtggtg agtccagggg agaatggcct  10980
tgccaagtct ttgggaagca gggaactggg gagagactga ggcacgcagg aacactgact  11040
gggataggag tgagaccaag aggcagtttg gggtacagta ccttagctcc cgtcttggga  11100
gctgggtaag tcacatccct tgtctgagcc tcagtttctt caattgtgaa ataggcccac  11160
agcagctcct tcctccctta cctgggtcgt gtaagtggca ttggaatttt gcagtttgga  11220
agctgctgcc ccttgcttga ggttcaggtt cactgtgaca gtgtcacctg gtaaccccag  11280
tttggatgct aggatgtaaa acttgaccat cccctaatgg atcacaatct cagataacaa  11340
tagagaccag gccacttttg aatgagtgaa gacagagaag ggtaagagag ctaggtctga  11400
tgagcgggcc tgtcagcgca gctaattaga ggcaagagct ttgtaagttc aaggctagcc  11460
tgggcagctt agaaagatac tggttcaaca tagaaaaggg ctgctgagat gggtcagtaa  11520
gttaagctct tgcctgatgg cccagcttcc atccccagca tccatggaaa ggtagaagga  11580
gaggatcagc tcctaaaagt tgtcctctga ccgctgcatg tacagcacaa cacagcacag  11640
cacatgtgag tgtgcataca tcatgcacac acatcataca tacatcatgt gcacatatca  11700
tgcacacaca tcatgtgcac acatcataca cacatcatgc acacacatca tgtgcacaca  11760
tcatgcacac acatcataca tacatcatgt gcacatatta tgcacacaca tcatgtgcac  11820
acatcatgca tacacatcat acacacacat catgcacaca catcatgtgc acatatcata  11880
cacacatcac gtacacacat catgcacaca catcatacac acatatcatg tgcacccatc  11940
atgtgcacac atcatacaca catcatgtac atgcacaccc acaatagtga taaataaaag  12000
tttaaatatg tttctagggc tggggaggtg gcacttgctg ttctgacaga ggacctgggt  12060
tcagtttcct gagcccatgt cattgcagta taaaactgtc catgactcca gctcctggtg  12120
atctgatatc tctgctggcg ctaggcacat acatgatgca cgtacatacc tctagcactt  12180
```

```
tctgatatac ataaataaaa atagatacaa attaaaagac attaaaaaaa aaagtaagaa  12240
gatagctggg ggtggggctc agtggtggag cagttgtcca gcatgctgag gtcctgggtt  12300
agacccccac acttgcctag catatgtgag gtcctgggtt agacccccac acttgcctag  12360
catatgtaag gtcctgggtt agacccccac acttgtccag gatatatgag gtcctgggtt  12420
agacccccac acttgcctag tatatgtgag gtcctgggtt agacccccac acttgtccag  12480
gatatgtgag gtcctgggtt agaccagtgc cacaaagtaa aaaagaaaat aaaagtgcag  12540
tctctttgct ttttctcaag attgcctttt tgtcttggaa aggcgtgagt ggatggagtg  12600
tgaaaagcac ttgagttcat gtgtaacatt taagaagaca tcgagaaggg acagtaagca  12660
agagaaaaca ttttgagatg atgctagaaa aaccaaaaac acttttaata aatctgaaac  12720
caaaaaacat gttgatgcac aacatagcaa aattttaaat taagtaagag ctgggctggc  12780
gagatggctc agcgggtaag agcactgact gctcttccag aggtcctgag ttcaaatccc  12840
agcaaccaca tggtggctca caaccaccca taatgagatc tgatgccctc ttctggtgtg  12900
tctgaagtca gctacagtgt acttacatat aataataaat aaatctttaa aaagtaagag  12960
ctgaccttgc cagactcgag accctgccta ccttcttcat cctaaccttg gccctggttc  13020
caatacaagt ttatctaaaa gccaggtagc cacctatgga cctgtgtttg tttcactggt  13080
gtctgcctcc cgacccatga gctgggtgtg gtggtacagg catgagagcc ccaagtttaa  13140
ggccagcctg aaccacttag tgagaccctg tctcaaagaa gacttacctt catgacagtg  13200
tgtgtgtgtg tgtgtgtgtg tgtgtgtata cacacccctt gcctctaaga gtacctgcct  13260
tttggtcttt tcatttgtca cttagaatag cagtgcagac acagagatac tttgtttctc  13320
tccgccatac ttccatagca gatgtaacaa tttgggggct agtgtaggga ggggtaaagc  13380
aggcaggcag gctgtccctt caagacacag ctgacgaaca caccagatgg gaagttggct  13440
cactgggggc ttctcattcc aactgcaatc tcccagagct agagactgct caaagggtag  13500
gagtatttac tatgcaagca tgagctaggt gtggccacac cacatgtgac tgtgacctta  13560
ataccatgtg taggggggtg gcactagaag gagaattgta gggtgttgcc tcccagacta  13620
gctccaggct caagagactc tgtctcagca gaaggtgcaa tatggtggat caggacacca  13680
gcaccctcct ttggcctctg catgtgtgca cagatgcaca catctaaaca cataccaggc  13740
ccacatacac cgtaccccac caccacacaa agatggactc tctcaattta taaacactgg  13800
caaataccat aaagcgtttt aaaagttccc ctagtgacca cattacccac aatgctactg  13860
cttaaaagct ctgacctgga ttctgggagt gtacagatgc tttgggcaag gagtgggagc  13920
acctgccagt gagagcacct gccagtggga gcacactcca ttgggagcac ccgccagtgg  13980
gagcatctgc cagtggggtc cactcaagtc tgtttctcca ggtttaaagt cccggatgcg  14040
agccctgctg gtcattcctg tcgtgatggg catcctcatc accattttcg gggtgtttct  14100
ctatatcagt gagtgctcag gagaggaaag ggagggaggg ttcagccctg tcgaaccagc  14160
ctcctgactc accctcgcaa tgtcccacac cccttcttct tctcactaga aaaggtggtc  14220
aagaaaccaa aggataatga ggtaagccat ccctgaggga gagatgctgg aaagagtgac  14280
tggtgggcag ggagggaggc tcacggcgta gggagacaga ctcagtaagc agagagcttg  14340
tattggatcc ttgagtgtgg acccatggaa aaggcccatt acacccacgc tggtgggggc  14400
ggggagaggg ggggaggatg gacacaggga tcttaggagc ttgctagcca accatgggct  14460
actccaggtt ccaagagaaa ccctgactcg gaaaataagg gttaagagtg caagaagaca  14520
```

```
caagatgttg acctctagcc tctaataatg tgtacatggg tgtgtggacc ctctacgcca  14580
tgagcataca cccaatacca cgccacactc cgcgcgcgca catgcgcgca cacacatgcc  14640
caaacaggtt tagggtccgt tccctggaac atataggtgg gctactcgca cccccaccca  14700
gccctgctct cagtctccat cgcttcctcc tactcaacta cttcccctta gggcagagct  14760
gggcaccact ggcagagaaa ctctggctgt gctttcctcc agccttgaat gctggggatg  14820
ggagtcggcg gcggggggtg ggggtggggg gtgggggtgg gtggatcccg ccttcagggg  14880
ccagtaggtg gaaccaaagg ggcagtttct cctgctggtc tgcagtggct ctggaaattt  14940
cctgccaaat ttcatgtgtc cagcaggggg cagaaggcat ccaagaaatc agttttggta  15000
cacccccatc ctcccacccc attggaaagg acttgaagga gggattctat tcctcagagg  15060
cagggtggct ctgtggctag aggtgacatt ggaccttata ccttgactcc ccagatctta  15120
ccccctgcgg ctcgacggca agatccccag gagatggaag attatcccgg tcataacacc  15180
gctgctccag tgcaggagac gctgcacggg tgtcagcctg tcacacagga ggatggtaaa  15240
gagagtcgca tctcagtgca ggagcggcag gtgacagaca gcatagcctt gaggcccctg  15300
gtctgaaccc tggaactgct ttggaggcga tggctcggct cgggagcagg ggcctggctc  15360
tgaggactgc ttgctgacct ttgaagtttg agatgagcca agacagagcc cagtgcagct  15420
aactctcatg cctgcccccct atcatttctc aacttgcttt ttaaggatgg agggagagct  15480
cgggcatcgg gggtccacag tgatacctac caagtgcagc agtgcaggac ccagagtcgt  15540
cttgctgcgg cgttcactgt aaggagtcat ggacacagga gtccgtggcc cacagcttgt  15600
gctgctagag ggcacctggt tgcccatcag cagggtactg gctaaataaa tctgtaatta  15660
tttatacaat gacatctcag aaactctagc aggtggggca gaaaacaggt agtagaatga  15720
tgggtagaga aatagctttt aaaacacatt ccaaggcagg taagatggct tttgtgagta  15780
aaggagcttg ctgcccaaac ccggttacct gattttgatc cctgggactt catggtaaaa  15840
gggagagaac caaatccaga gggttgtcat ttgacctcca tgtgtgctct gtggtaatgt  15900
accccgtgtg tgcacatgtg cacatatcct aaaatggatg tggtggtgta ttgtagaaat  15960
tatttaatcc cgccctgggg tttctacctg tgtgttacca tttagttctt gaataaaaga  16020
cacactcaac ctttatattt acaataa                                       16047
```

```
<210> SEQ ID NO 9
<211> LENGTH: 23
<212> TYPE: DNA
<213> ORGANISM: Artificial Sequence
<220> FEATURE:
<223> OTHER INFORMATION: single guide RNA (sgRNA) for Exon 1 of AIRE

<400> SEQUENCE: 9

gcaccgcacc gagatcgcgg tgg                                              23


<210> SEQ ID NO 10
<211> LENGTH: 23
<212> TYPE: DNA
<213> ORGANISM: Artificial Sequence
<220> FEATURE:
<223> OTHER INFORMATION: single guide RNA (sgRNA) for Exon 3 of AIRE

<400> SEQUENCE: 10

acctaaacca gtcccggaaa ggg                                              23


<210> SEQ ID NO 11
<211> LENGTH: 15
```

```
<212> TYPE: PRT
<213> ORGANISM: Artificial Seqeunce
<220> FEATURE:
<223> OTHER INFORMATION: Peptide tag

<400> SEQUENCE: 11

Gly Leu Asn Asp Ile Phe Glu Ala Gln Lys Ile Glu Trp His Glu
1               5                   10                  15


<210> SEQ ID NO 12
<211> LENGTH: 6
<212> TYPE: PRT
<213> ORGANISM: Artificial Sequence
<220> FEATURE:
<223> OTHER INFORMATION: Peptide tag

<400> SEQUENCE: 12

His His His His His His
1               5


<210> SEQ ID NO 13
<211> LENGTH: 198
<212> TYPE: PRT
<213> ORGANISM: Homo sapiens

<400> SEQUENCE: 13

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Pro Arg Gln Leu
                165                 170                 175

Arg Arg Ile Leu Leu Pro Leu Tyr Glu Val Asp Asp Leu Arg Asp Ala
            180                 185                 190

Phe Arg Thr Trp Gly Arg
        195
```